US012275687B2

(12) United States Patent
Yokoyama et al.

(10) Patent No.: US 12,275,687 B2
(45) Date of Patent: Apr. 15, 2025

(54) CLASS A GPCR-BINDING COMPOUND MODIFIER

(71) Applicant: RIKEN, Wako (JP)

(72) Inventors: Shigeyuki Yokoyama, Yokohama (JP); Tetsuya Hori, Yokohama (JP)

(73) Assignee: RIKEN, Wako (JP)

( * ) Notice: Subject to any disclaimer, the term of this patent is extended or adjusted under 35 U.S.C. 154(b) by 269 days.

(21) Appl. No.: 16/613,049

(22) PCT Filed: May 14, 2018

(86) PCT No.: PCT/JP2018/018621
§ 371 (c)(1),
(2) Date: Nov. 12, 2019

(87) PCT Pub. No.: WO2018/207950
PCT Pub. Date: Nov. 15, 2018

(65) Prior Publication Data
US 2020/0199168 A1 Jun. 25, 2020

(30) Foreign Application Priority Data
May 12, 2017 (JP) ................................. 2017-096017

(51) Int. Cl.
C07C 257/18 (2006.01)
C07C 211/33 (2006.01)
C07C 211/34 (2006.01)
C07C 211/39 (2006.01)
C07C 211/44 (2006.01)
C07C 233/57 (2006.01)
C07C 233/64 (2006.01)
C07C 257/16 (2006.01)
C07C 259/16 (2006.01)
C07C 259/18 (2006.01)
C07C 279/16 (2006.01)
C07C 279/18 (2006.01)
C07C 279/26 (2006.01)
C07D 403/12 (2006.01)
C07H 19/167 (2006.01)
C07K 16/28 (2006.01)
C12N 15/115 (2010.01)

(52) U.S. Cl.
CPC .......... C07C 257/18 (2013.01); C07C 211/33 (2013.01); C07C 211/34 (2013.01); C07C 211/39 (2013.01); C07C 211/44 (2013.01); C07C 233/57 (2013.01); C07C 233/64 (2013.01); C07C 257/16 (2013.01); C07C 259/16 (2013.01); C07C 259/18 (2013.01); C07C 279/16 (2013.01); C07C 279/18 (2013.01); C07C 279/26 (2013.01); C07D 403/12 (2013.01); C07H 19/167 (2013.01); C07K 16/28 (2013.01); C12N 15/115 (2013.01)

(58) Field of Classification Search
None
See application file for complete search history.

(56) References Cited

U.S. PATENT DOCUMENTS

| 5,731,332 | A | 3/1998 | Anderskewitz et al. |
|---|---|---|---|
| 5,939,418 | A | 8/1999 | Quan et al. |
| 6,127,423 | A | 10/2000 | Anderskewitz et al. |
| 6,197,753 | B1 | 3/2001 | Anderskewitz et al. |
| 6,197,824 | B1 | 3/2001 | Schromm et al. |
| 6,265,612 | B1 | 7/2001 | Schromm et al. |
| 2002/0128209 | A1 | 9/2002 | Anderskewitz et al. |
| 2002/0161043 | A1 | 10/2002 | Anderskewitz et al. |
| 2003/0119901 | A1 | 6/2003 | Becker et al. |
| 2003/0140431 | A1* | 7/2003 | Chassot ............... C07C 237/20 548/530 |
| 2003/0225004 | A1 | 12/2003 | Birke et al. |
| 2004/0116516 | A1 | 6/2004 | Birke et al. |
| 2004/0186150 | A1 | 9/2004 | Suh et al. |
| 2005/0070562 | A1 | 3/2005 | Jones et al. |
| 2005/0129768 | A1 | 6/2005 | Bock et al. |
| 2007/0155763 | A1 | 7/2007 | Jones et al. |
| 2007/0237823 | A1 | 10/2007 | Bock et al. |

(Continued)

FOREIGN PATENT DOCUMENTS

| JP | 2931410 B2 | 8/1999 |
|---|---|---|
| JP | 2000502333 A | 2/2000 |

(Continued)

OTHER PUBLICATIONS

Aiglstorfer et al. (Regulatory Peptides (1998), 75-76, 9-21) (Year: 1998).*
STN abstract for Aiglstorfer et al. (Regulatory Peptides (1998), 75-76, 9-21) (Year: 1998).*
STN abstract for Chassot et al. (US 20030140431) (Year: 2003).*
Adams et al., "PHENIX: A Comprehensive Python-based System for Macromolecular Structure Solution," Acta Crystallogr D Biol Crystallogr. 66 (Pt 2):213-21 (2010).
Aiglstorfer et al., "NPY Y1 Antagonists: Structure-Activity Relationships of Arginine Derivatives and Hybrid Compounds With Arpromidine-Like Partial Structures," Regul Pept. 75-76:9-21 (1998).

(Continued)

Primary Examiner — Sudhakar Katakam
Assistant Examiner — Jennifer C Sawyer
(74) Attorney, Agent, or Firm — Clark & Elbing LLP

(57) ABSTRACT

To provide a novel class-A GPCR antagonist, a production method therefor, or a novel compound that interacts with a Na$^+$-water cluster binding site of a class-A GPCR.
Used is a compound or a salt thereof comprising a structure comprising a class-A GPCR-binding compound linked to a functional group that can bind to a Na$^+$-water cluster binding site of the class-A GPCR. Also used is a method for producing a class-A GPCR antagonist, comprising the step of linking one compound with another compound that can bind to a Na$^+$-water cluster binding site of the class-A GPCR.

14 Claims, 67 Drawing Sheets

(56) References Cited

U.S. PATENT DOCUMENTS

| | | |
|---|---|---|
| 2010/0120875 A1 | 5/2010 | Suh et al. |
| 2010/0160394 A1 | 6/2010 | Suh et al. |
| 2011/0112060 A1 | 5/2011 | Jones et al. |
| 2013/0137856 A1 | 5/2013 | Steyaert et al. |
| 2013/0183287 A1 | 7/2013 | Steyaert et al. |
| 2014/0079632 A1 | 3/2014 | Augustyns et al. |
| 2016/0068512 A1 | 3/2016 | Macielag et al. |
| 2016/0347842 A1 | 12/2016 | Steyaert et al. |
| 2017/0153245 A1 | 6/2017 | Steyaert et al. |
| 2018/0067126 A1 | 3/2018 | Steyaert et al. |
| 2018/0100865 A1 | 4/2018 | Steyaert et al. |
| 2019/0041400 A1 | 2/2019 | Steyaert et al. |
| 2019/0049463 A1 | 2/2019 | Steyaert et al. |
| 2019/0383825 A1 | 12/2019 | Steyaert et al. |
| 2019/0383826 A1 | 12/2019 | Steyaert et al. |
| 2019/0383827 A1 | 12/2019 | Steyaert et al. |
| 2019/0383828 A1 | 12/2019 | Steyaert et al. |
| 2019/0383829 A1 | 12/2019 | Steyaert et al. |
| 2020/0199168 A1 | 6/2020 | Yokoyama et al. |

FOREIGN PATENT DOCUMENTS

| | | |
|---|---|---|
| JP | 2001500146 A | 1/2001 |
| JP | 2001502655 A | 2/2001 |
| JP | 2001509787 A | 7/2001 |
| JP | 2004513100 A | 4/2004 |
| JP | 2005502630 A | 1/2005 |
| JP | 2005529085 A | 9/2005 |
| JP | 2006508992 A | 3/2006 |
| JP | 3917516 B2 | 5/2007 |
| JP | 2007513068 A | 5/2007 |
| JP | 2007528856 A | 10/2007 |
| JP | 2007536299 A | 12/2007 |
| JP | 4047275 B2 | 2/2008 |
| JP | 4215278 B2 | 1/2009 |
| JP | 4288299 B2 | 7/2009 |
| JP | 4334016 B2 | 9/2009 |
| JP | 2013536173 A | 9/2013 |
| JP | 2014-518859 A | 8/2014 |
| WO | WO-98/04537 A1 | 2/1998 |
| WO | WO-2018/207950 A1 | 11/2018 |

OTHER PUBLICATIONS

Ardati et al., "Interaction of [3H]orphanin FQ and 125I-Tyr14-orphanin FQ With the Orphanin FQ Receptor: Kinetics and Modulation by Cations and Guanine Nucleotides," Mol Pharmacol. 51(5):816-24 (1997).

Ballesteros et al., "Integrated methods for the construction of three-dimensional models and computational probing of structure-function relations in G protein-coupled receptors," Methods in Neurosciences. 25:366-428 (1995).

Basu et al., "Critical Role for Polar Residues in Coupling Leukotriene B4 Binding to Signal Transduction in BLT1," J Biol Chem. 282(13):10005-17 (2007) (14 pages).

Birke et al., "In Vitro and in Vivo Pharmacological Characterization of BIIL 284, a Novel and Potent Leukotriene B(4) Receptor Antagonist," J Pharmacol Exp Ther. 297(1):458-66 (2001).

Bonnet et al., "A Rapid and Versatile Method to Label Receptor Ligands Using "Click" Chemistry: Validation with the Muscarinic M1 Antagonist Pirenzepine," Bioconjugate Chem. 17(6):1618-23 (2006).

Brunger et al., "Crystallography & NMR System: A New Software Suite for Macromolecular Structure Determination," Acta Crystallogr D Biol Crystallogr. 54(Pt 5):905-21 (1998).

Brunger, "Version 1.2 of the Crystallography and NMR system," Nat Protoc. 2(11):2728-33 (2007).

Canals et al., "Allostery in GPCRs: 'MWC' Revisited," Trends Biochem Sci. 36(12):663-72 (2011).

Carpenter et al., "Structure of the Adenosine A(2A) Receptor Bound to an Engineered G Protein," available in PMC Feb. 4, 2017, published in final edited form as: Nature. 536(7614):104-7 (2016) (25 pages).

Ceresa et al., "Mutation of an Aspartate Residue Highly Conserved Among G-protein-coupled Receptors Results in Nonreciprocal Disruption of Alpha 2-adrenergic receptor-G-protein Interactions. A Negative Charge at Amino Acid Residue 79 Forecasts Alpha 2A-adrenergic Receptor Sensitivity to Allosteric Modulation by Monovalent Cations and Fully Effective receptor/G-protein Coupling," J Biol Chem. 269(47):29557-64 (1994).

Chen et al., "MolProbity: all-atom structure validation for macromolecular crystallography," Acta Crystallogr D Biol Crystallogr. 66 (Pt 1):12-21 (2010).

Christopoulos et al., "G Protein-Coupled Receptor Allosterism and Complexing," Pharmacol Rev. 54(2):323-74 (2002).

Emsley et al., "Features and development of Coot," Acta Crystallogr D Biol Crystallogr. 66(Pt 4):486-501 (2010).

Evans et al., "How Good Are My Data and What Is the Resolution?" Acta Crystallogr D Biol Crystallogr. 69 (Pt 7):1204-14 (2013).

Evans, "An Introduction to Data Reduction: Space-Group Determination, Scaling and Intensity Statistics," Acta Crystallogr D Biol Crystallogr. 67(Pt 4):282-92 (2011).

Fenalti et al., "Molecular Control of delta-Opioid Receptor Signaling," available in PMC Feb. 13, 2015, published in final edited form as: Nature. 506(7487):191-6 (2014) (17 pages).

Foadi et al., "Clustering procedures for the optimal selection of data sets from multiple crystals in macromolecular crystallography," Acta Crystallogr D Biol Crystallogr. 69(Pt 8):1617-32 (2013).

Fredriksson et al., "The G-protein-coupled Receptors in the Human Genome Form Five Main Families. Phylogenetic Analysis, Paralogon Groups, and Fingerprints," Mol Pharmacol. 63(6):1256-72 (2003).

Gao et al., "Differential Allosteric Modulation by Amiloride Analogues of Agonist and Antagonist Binding at A(1) and A(3) Adenosine Receptors," Biochem Pharmacol. 65(4):525-34 (2003).

Gao et al., "Identification of Essential Residues Involved in the Allosteric Modulation of the Human A(3) Adenosine Receptor," available in PMC Mar. 20, 2015, published in final edited form as: Mol Pharmacol. 63(5):1021-31 (2003) (24 pages).

Gutiérrez-de-Terán et al., "The Role of a Sodium Ion Binding Site in the Allosteric Modulation of the A(2A) Adenosine G Protein-Coupled Receptor," Structure. 21(12):2175-85 (2013).

Hato et al., "A New Manual Dispensing System for in Meso Membrane Protein Crystallization With Using a Stepping Motor-Based Dispenser," J Struct Funct Genomics. 15(3):165-71 (2014).

Hato et al., "Aqueous Phase Behavior of Lipids With Isoprenoid Type Hydrophobic Chains," J Phys Chem B. 113(30):10196-209 (2009).

Hicks et al., "Leukotriene B4 Receptor Antagonists as Therapeutics for Inflammatory Disease: Preclinical and Clinical Developments," Expert Opin Investig Drugs. 16(12):1909-20 (2007).

Hori et al., "Expression, Purification and Characterization of Leukotriene B(4) Receptor, BLT1 in Pichia Pastoris," Protein Expr Purif. 72(1):66-74 (2010).

Hori et al., "Na +-mimicking Ligands Stabilize the Inactive State of Leukotriene B 4 Receptor BLT1," Nat Chem Biol. 14(3):262-9 (2018) (11 pages).

Hori et al., "The Leukotriene B 4 Receptor BLT1 Is Stabilized by Transmembrane Helix Capping Mutations," Biochem Biophys Rep. 4:243-9 (2015).

Horstman et al., "An Aspartate Conserved Among G-protein Receptors Confers Allosteric Regulation of Alpha 2-adrenergic Receptors by Sodium," J Biol Chem. 265(35):21590-5 (1990).

Hou et al., "The Impact of Click Chemistry in Medicinal Chemistry," Expert Opin Drug Discov. 7(6):489-501 (2012).

Huang et al., "Structural Insights Into mu-Opioid Receptor Activation," available in PMC Feb. 20, 2016, published in final edited form as: Nature. 524(7565):315-21 (2015) (32 pages).

Inoue et al., "TGF-alpha Shedding Assay: An Accurate and Versatile Method for Detecting GPCR Activation," Nat Methods. 9(10):1021-9 (2012).

International Search Report and Written Opinion, mailed Aug. 14, 2018 for International Application No. PCT/JP2018/018621, Yokoyama et al., "Class A GPCR-Binding Compound Modifier," filed May 14, 2018 (36 pages).

Kabsch, "XDS," Acta Crystallogr D Biol Crystallogr. 66(Pt 2):125-32 (2010).

(56) References Cited

OTHER PUBLICATIONS

Karplus et al., "Linking crystallographic model and data quality," available in PMC Nov. 25, 2012, published in final edited form as: Science. 336(6084):1030-33 (2012) (9 pages).

Katritch et al., "Allosteric sodium in class A GPCR signaling," available in PMC May 1, 2015, published in final edited form as: Trends Biochem Sci. 39(5):233-44 (2014) (26 pages).

Katritch et al., "Allosteric sodium in class A GPCR signaling," Trends Biochem Sci. 39(5):233-44 (2014).

Khilnani et al., "Inverse Agonism and Its Therapeutic Significance," Indian J Pharmacol. 43(5):492- 501 (2011).

Kleemann et al., "Functional Reconstitution of the Human Chemokine Receptor CXCR4 With G(i)/G (O)-Proteins in Sf9 Insect Cells," available in PMC Sep. 1, 2009, published in final edited form as: Naunyn Schmiedebergs Arch Pharmacol. 378(3):261-74 (2008) (22 pages).

Kruse et al., "Activation and Allosteric Modulation of a Muscarinic Acetylcholine Receptor," available in PMC Jun. 5, 2014, published in final edited form as: Nature. 504(7478):101-6 (2013) (34 pages).

Kruse et al., "Muscarinic Receptors as Model Targets and Antitargets for Structure-Based Ligand Discovery," Mol Pharmacol. 84(4):528-40 (2013).

Kruse et al., "Structure and Dynamics of the M3 Muscarinic Acetylcholine Receptor," available in PMC Dec. 25, 2012, published in final edited form as: Nature. 482(7386):552-6 (2012) (20 pages).

Lam et al., "Structure-based Design of Novel Guanidine/Benzamidine Mimics: Potent and Orally Bioavailable Factor Xa Inhibitors as Novel Anticoagulants," J Med Chem. 46(21):4405-18 (2003).

Leach et al., "Allosteric GPCR Modulators: Taking Advantage of Permissive Receptor Pharmacology," Trends Pharmacol Sci. 28(8):382-9 (2007).

Levit et al., "Modeling of Human Prokineticin Receptors: Interactions With Novel Small-Molecule Binders and Potential Off-Target Drugs," PLoS One. 6(11):e27990 (2011) (17 pages).

Liu et al., "Structural Basis for Allosteric Regulation of GPCRs by Sodium Ions," Science. 337(6091):232-6 (2012) (34 pages).

Lupala et al., "New Insights Into the Stereochemical Requirements of the Bradykinin B2 Receptor Antagonists Binding," J Comput Aided Mol Des. 30(1):85-101 (2016).

Mahoney et al., "Mechanistic Insights Into GPCR-G Protein Interactions," available in PMC Dec. 1, 2017, published in final edited form as: Curr Opin Struct Biol. 41:247-254 (2016) (14 pages).

Manglik et al., "Structural insights into the dynamic process of beta2-adrenergic receptor signaling," available in PMC May 21, 2016, published in final edited form as: Cell. 161(5):1101-11 (2015) (23 pages).

Marie et al., "Control of Conformational Equilibria in the Human B2 Bradykinin Receptor. Modeling of Nonpeptidic Ligand Action and Comparison to the Rhodopsin Structure," J Biol Chem. 276(44):41100-41111 (2001) (13 pages).

Massink et al., "Sodium Ion Binding Pocket Mutations and Adenosine A2A Receptor Function," Mol Pharmacol. 87(2):305-13 (2015).

Michielan et al., "Exploring Potency and Selectivity Receptor Antagonist Profiles Using a Multilabel Classification Approach: The Human Adenosine Receptors as a Key Study," J Chem Inf Model. 49(12):2820-36 (2009).

Miller-Gallacher et al., "The 2.1 Å Resolution Structure of Cyanopindolol-Bound beta-1-adrenoceptor Identifies an Intramembrane Na+ Ion That Stabilises the Ligand-Free Receptor," PLoS One. 9(3):e92727 (2014) (9 pages).

Nakayama et al., "New Serine Protease Inhibitors With Leukotriene B4 (LTB4) Receptor Binding Affinity," Bioorg Med Chem. 5(5):971-85 (1997).

Neve et al., "Modeling and Mutational Analysis of a Putative Sodium-Binding Pocket on the Dopamine D2 Receptor," Mol Pharmacol. 60(2):373-81 (2001).

Nickl et al., "Differential Coupling of the Human Cannabinoid Receptors hCB1R and hCB2R to the G-protein G(alpha)i2beta1gamma2," Neurosci Lett. 447(1):68-72 (2008).

Rasmussen et al., "Crystal Structure of the beta-2 Adrenergic receptor-Gs Protein Complex," available in PMC Mar. 29, 2012, published in final edited form as: Nature. 477(7366):549-55 (2011) (23 pages).

Rosenbaum et al., "GPCR Engineering Yields High-Resolution Structural Insights Into beta2-adrenergic Receptor Function," Science. 318(5854):1266-73 (2007).

Rosenbaum et al., "Structure and Function of an Irreversible Agonist-beta-2 Adrenoceptor complex," available in PMC Jul. 13, 2011, published in final edited form as: Nature. 469(7329):236-40 (2011) (16 pages).

Sabirsh et al., "Residues From Transmembrane Helices 3 and 5 Participate in Leukotriene B4 Binding to BLT1," Biochemistry. 45(18):5733-44 (2006).

Schnell et al., "Modulation of Histamine H(3) Receptor Function by Monovalent Ions," Neurosci Lett. 472(2):114-8 (2010).

Seifert et al., "Constitutive Activity of G-protein-coupled Receptors: Cause of Disease and Common Property of Wild-Type Receptors," Naunyn Schmiedeberg's Arch Pharmacol. 366(5):381-416 (2002).

Selley et al., "Effects of Sodium on Agonist Efficacy for G-protein Activation in Mu-Opioid Receptor-Transfected CHO Cells and Rat Thalamus," Br J Pharmacol. 130(5):987-996 (2000).

Stoy et al., "How Genetic Errors in GPCRs Affect Their Function: Possible Therapeutic Strategies," Genes Dis. 2(2):108-32 (2015).

Tan et al., "Structure of the CCR5 Chemokine receptor-HIV Entry Inhibitor Maraviroc Complex," available in PMC Sep. 20, 2014, published in final edited form as: Science. 341(6152):1387-90 (2013) (9 pages).

Thal et al., "Crystal Structures of the M1 and M4 Muscarinic Acetylcholine Receptors," available in PMC Sep. 17, 2016, published in final edited form as: Nature. 531(7594):335-40 (2016) (30 pages).

Thompson et al., "Structure of the Nociceptin/Orphanin FQ Receptor in Complex with a Peptide Mimetic," available in PMC Nov. 16, 2012, published in final edited form as: Nature. 485(7398):395-9 (2012) (13 pages).

Vošahlíková et al., "High- And Low-Affinity Sites for Sodium in delta-OR-Gi1-alpha (Cys (351)-Ile (351)) Fusion Protein Stably Expressed in HEK293 Cells; Functional Significance and Correlation With Biophysical State of Plasma Membrane," Naunyn Schimiedebergs Arch Pharmacol. 387(5):487-502 (2014).

Wilson et al., "The Role of a Conserved Inter-Transmembrane Domain Interface in Regulating alpha(2a)-adrenergic Receptor Conformational Stability and Cell-Surface Turnover," Mol Pharmacol. 59(4):929-38 (2001).

Wu et al., "Structures of the CXCR4 Chemokine GPCR With Small-Molecule and Cyclic Peptide Antagonists," available in PMC Nov. 19, 2011, published in final edited form as: Science. 330(6007):1066-71 (2010) (16 pages).

Yokomizo et al., "A G-protein-coupled Receptor for Leukotriene B4 That Mediates Chemotaxis," Nature. 387(6633):620-4 (1997).

Zhang et al., "High-resolution Crystal Structure of Human Protease-Activated Receptor 1 Bound to the Antagonist Vorapaxer," available in PMC Jun. 20, 2013, published in final edited form as: Nature. 492(7429):387-92 (2012) (24 pages).

Zhang et al., "Structure of the Angiotensin Receptor Revealed by Serial Femtosecond Crystallography," available in PMC May 7, 2016, published in final edited form as: Cell. 161(4):833-44 (2015) (24 pages).

Database Registry [online], [retrieved on Jul. 23, 2018], American Chemical Society, Retrieved from: STN, Entered STN: Mar. 5, 2014, RN: 1562462-15-0, CN: Benzeneacetamide, 4-[(hydroxyamino)iminomethyl]-N-[2-(1H-imidazol-5-yl)ethyl]—(CA Index Name) (1 page).

Database Registry [online], [retrieved on Jul. 23, 2018], American Chemical Society, Retrieved from: STN, Entered STN: Mar. 6, 2014, RN: 1563162-34-4, CN: Benzamide, 3-[(hydroxyamino) iminomethyl]-N-[2-(1H-imidazol-5-yl)ethyl]—(CA Index Name),

(56) References Cited

OTHER PUBLICATIONS

RN: 1563101-45-0, CN: Benzamide, 4-[(hydroxyamino)iminomethyl]-N-[2-(1H-imidazol-5-yl)ethyl]—(CA Index Name) (1 page).

Office Action dated Apr. 19, 2022, for Japanese Patent Application No. 2019-517741, Yokoyama et al., "Class A GPCR-Coupled Compound Variant," filed May 14, 2018 (18 pages) (English translation).

Berger et al., "Synthesis and antimalarial activities of a diverse set of triazole-containing furamidine analogues," ChemMedChem. 6(11):2094-108 (Epub Sep. 2011).

Office Action dated Apr. 23, 2024, for Japanese Patent Application No. 2023-017433, Yokoyama et al., "Class A GPCR-Binding Compound Modifier," filed Feb. 8, 2023 (English translation) (19 pages).

Rechenmacher et al., "A molecular toolkit for the functionalization of titanium-based biomaterials that selectively control integrin-mediated cell adhesion," Chemistry. 19(28):9218-23 (Epub Jun. 2013).

Sánchez et al., "Straightforward access to bisbenzamidine DNA binders and their use as versatile adaptors for DNA-promoted processes," Chem Sci. 3(7):2383-7 (May 2012).

* cited by examiner

[Figure 1]
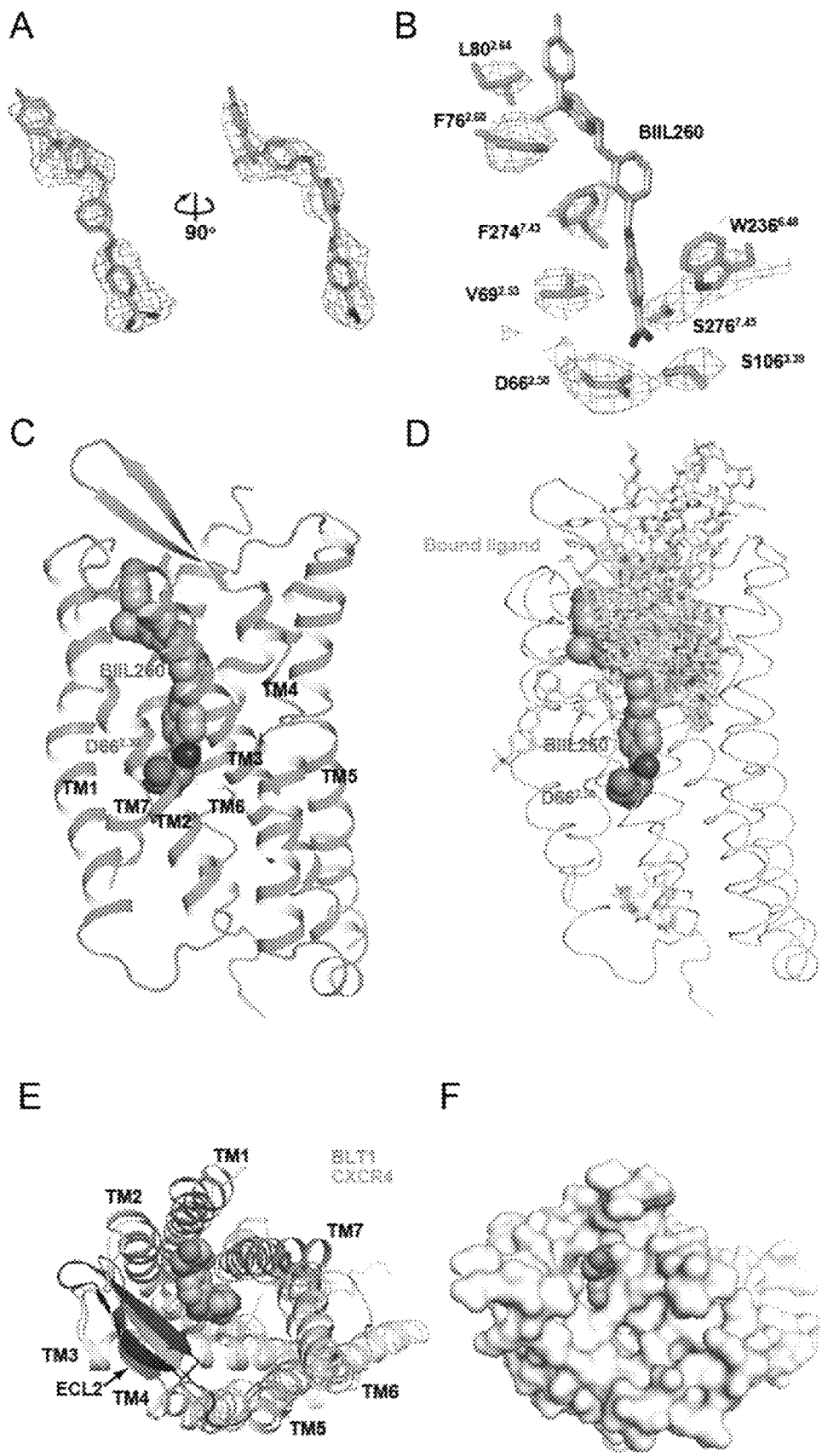

[Figure 2]
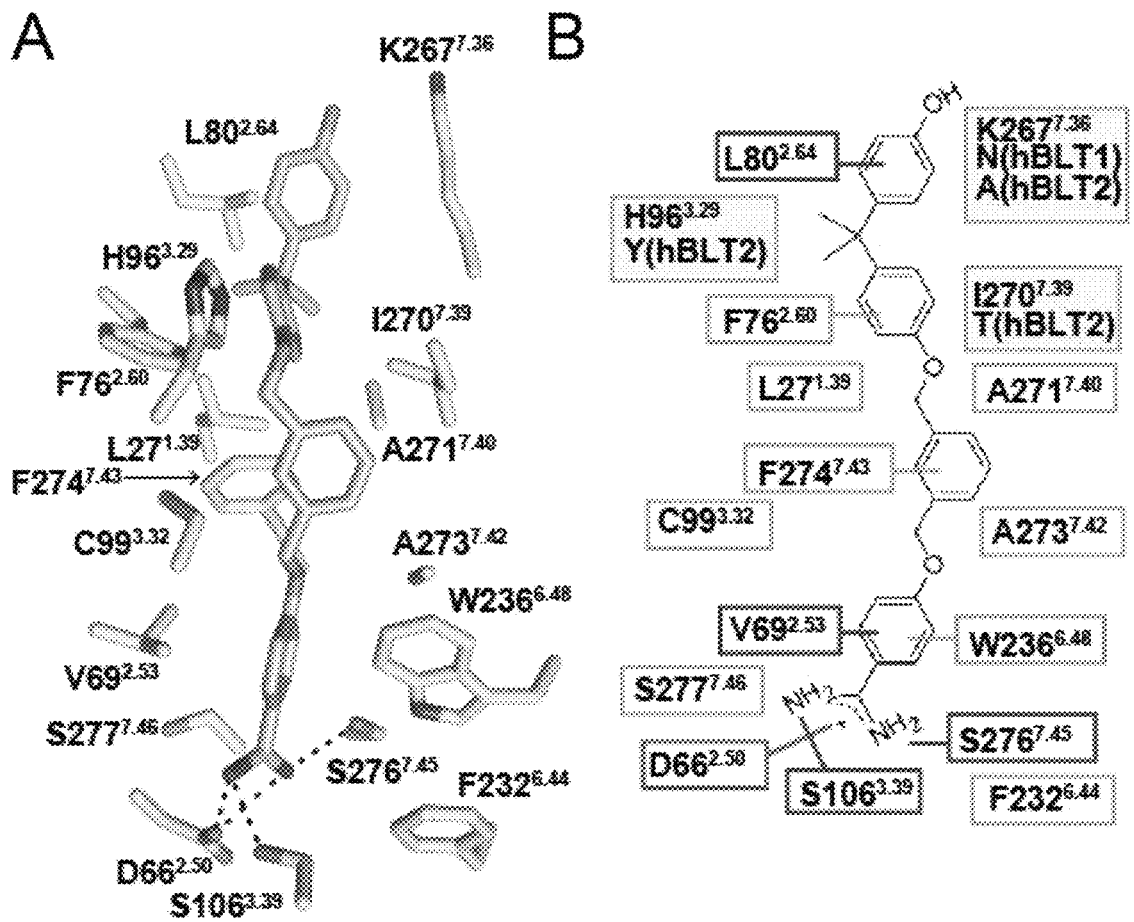
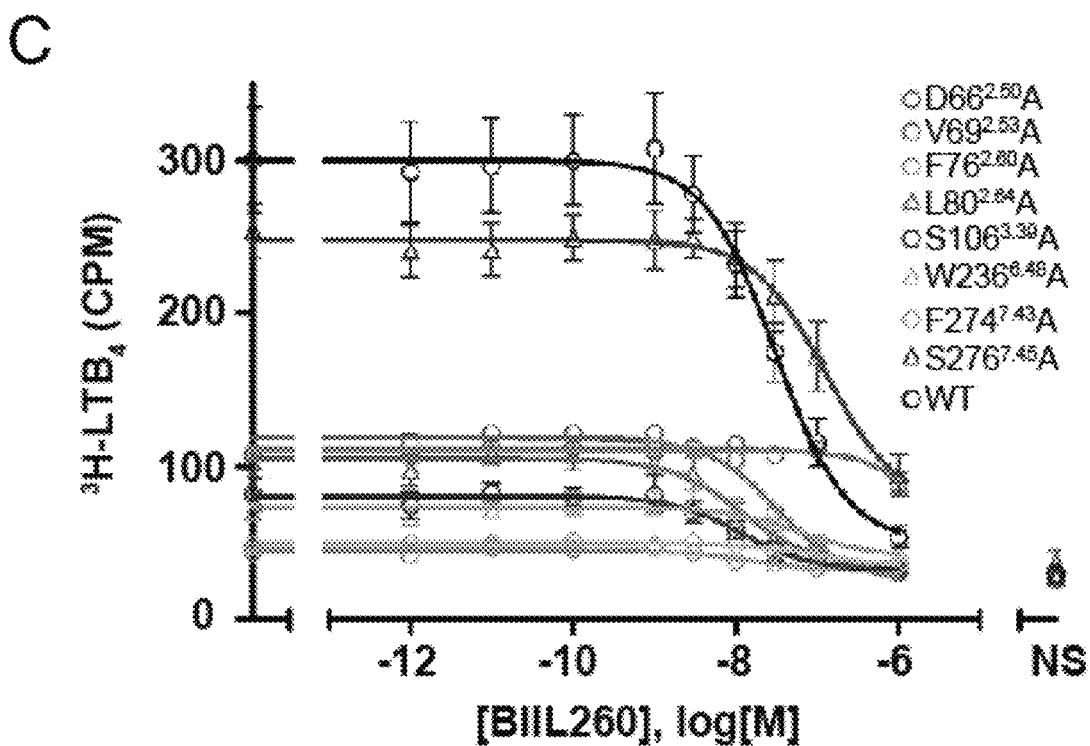

[Figure 3]
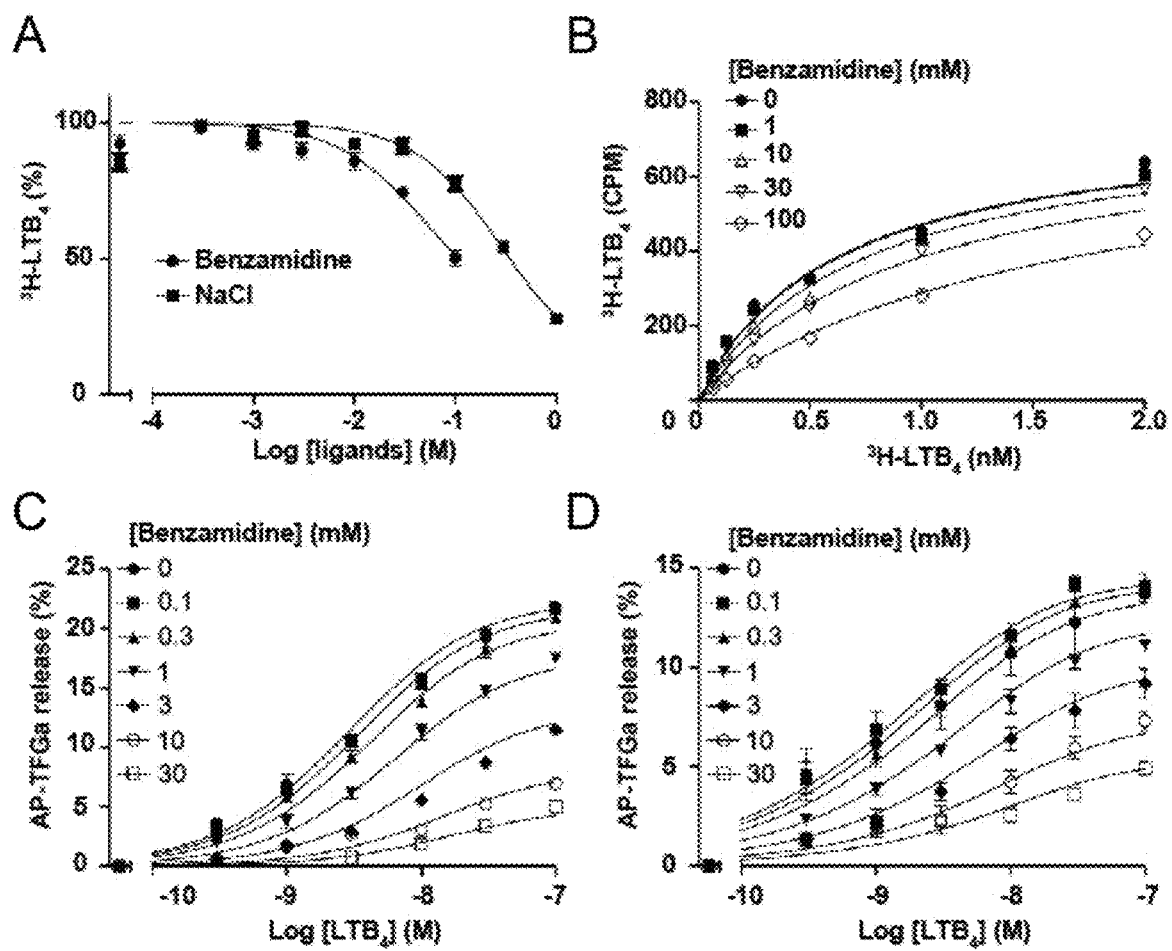

[Figure 4]
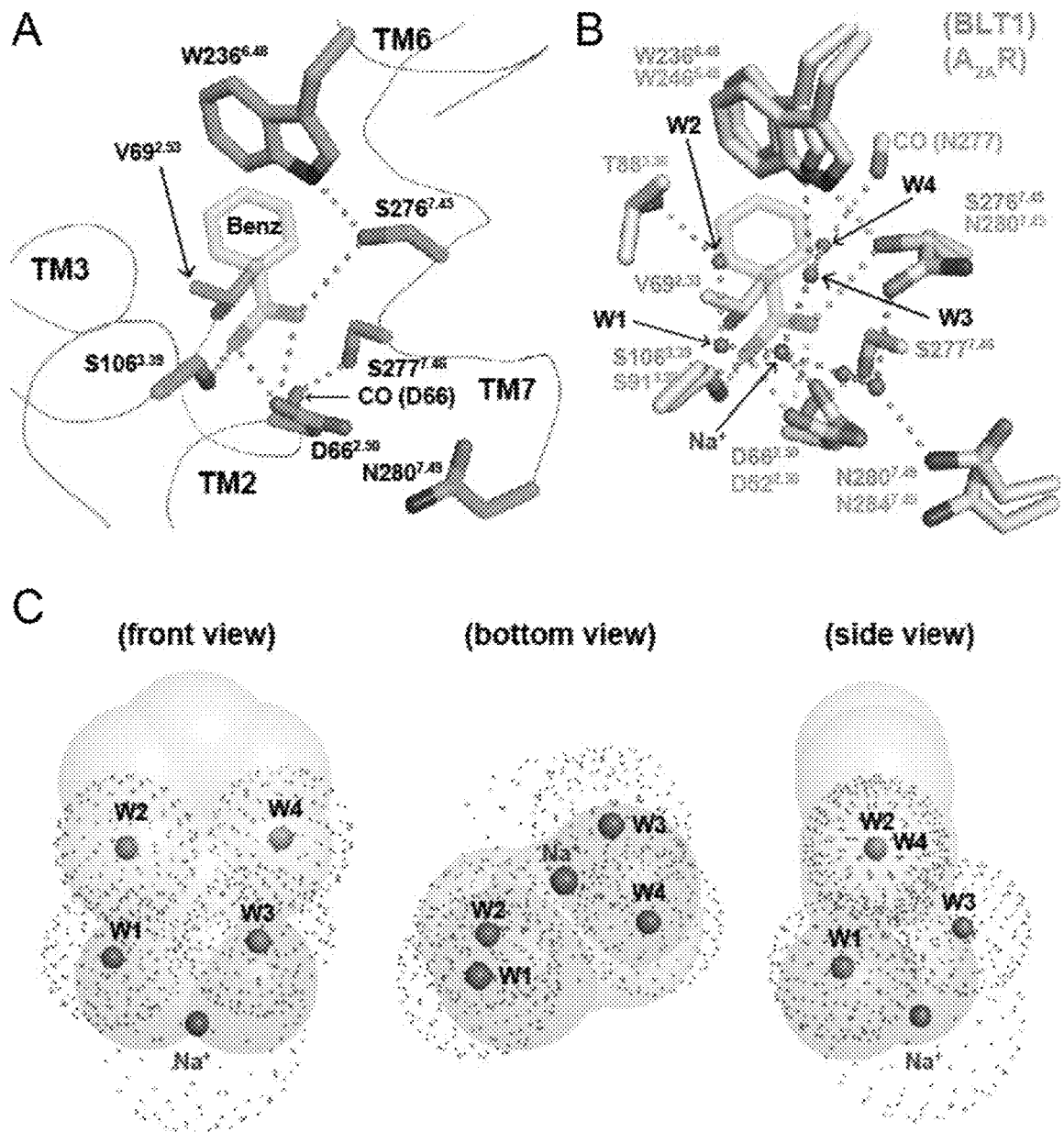

[Figure 5]
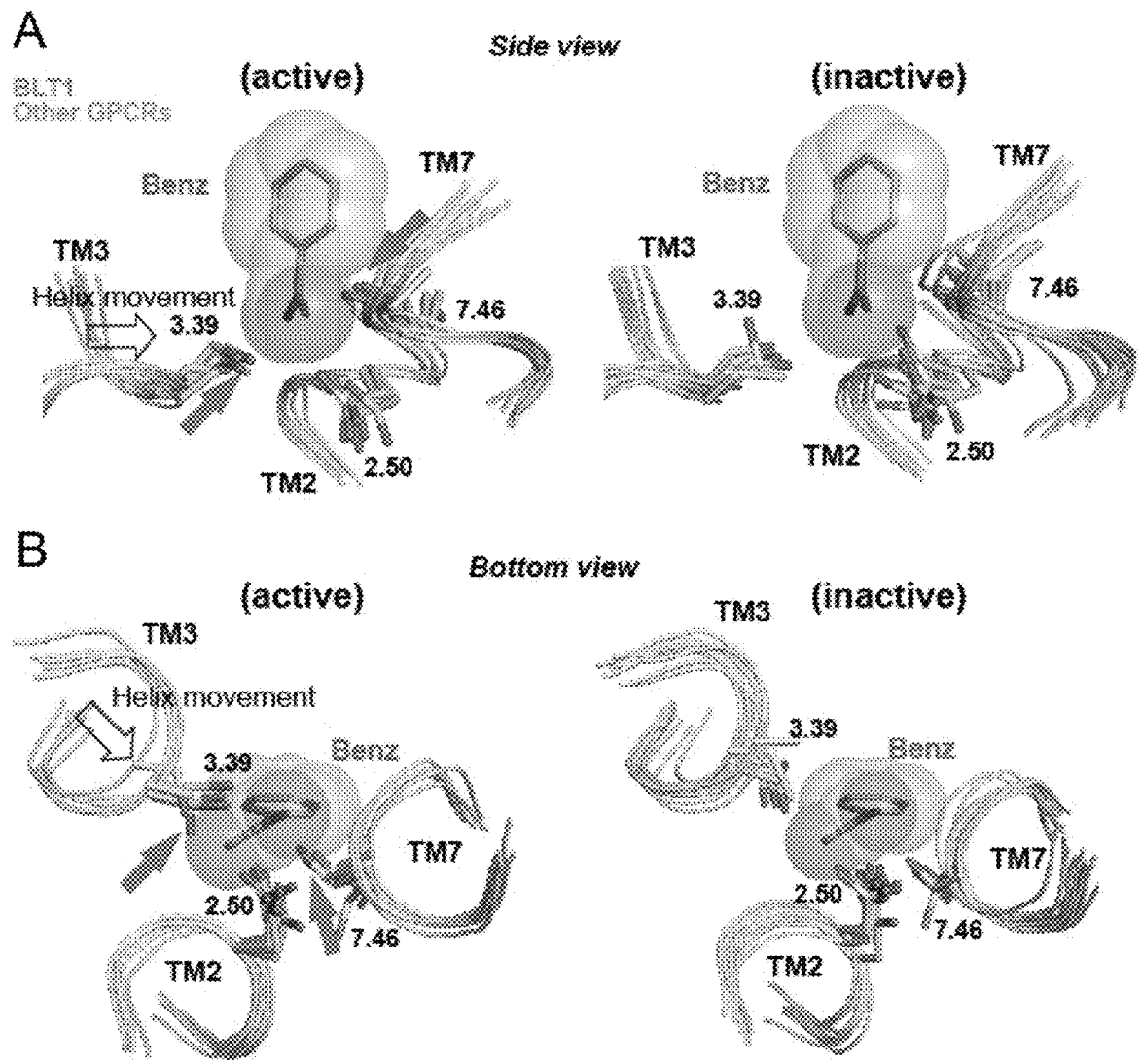

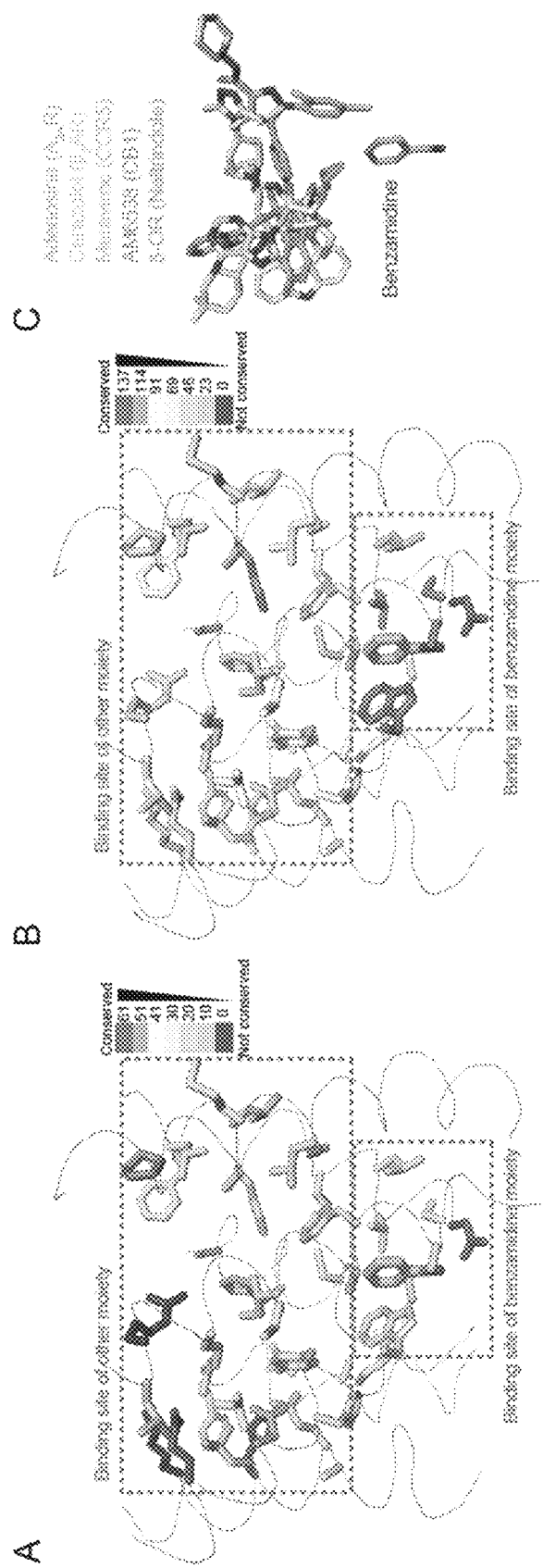
[Figure 6]

[Figure 7]
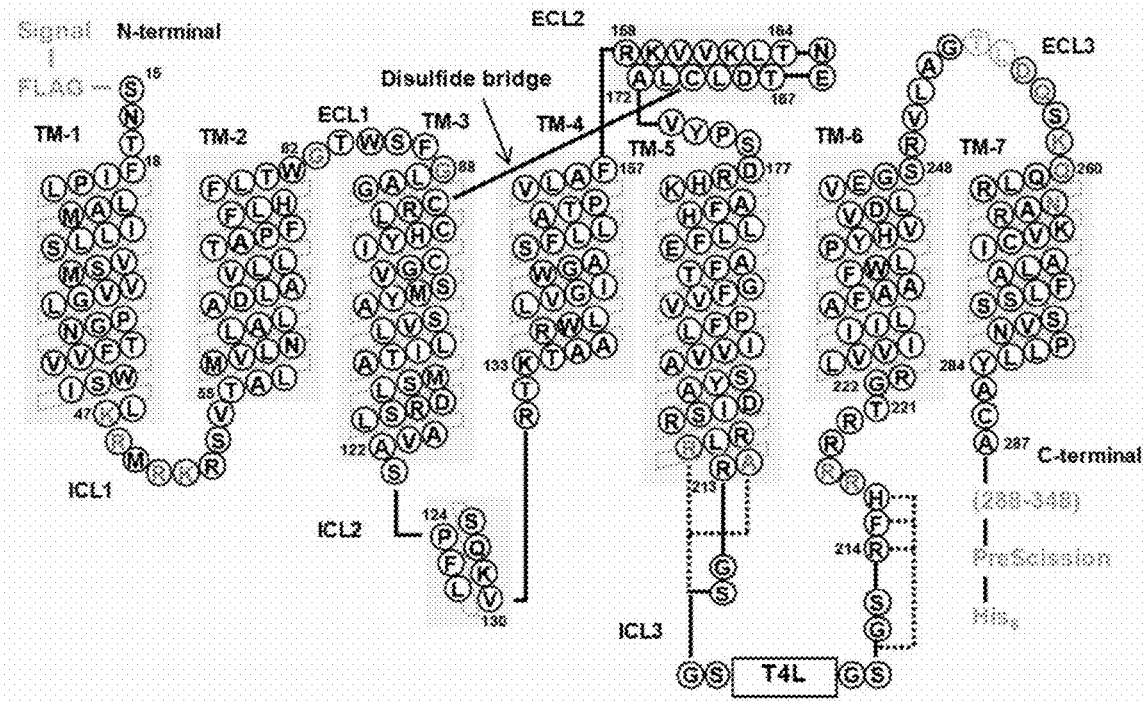

[Figure 8]
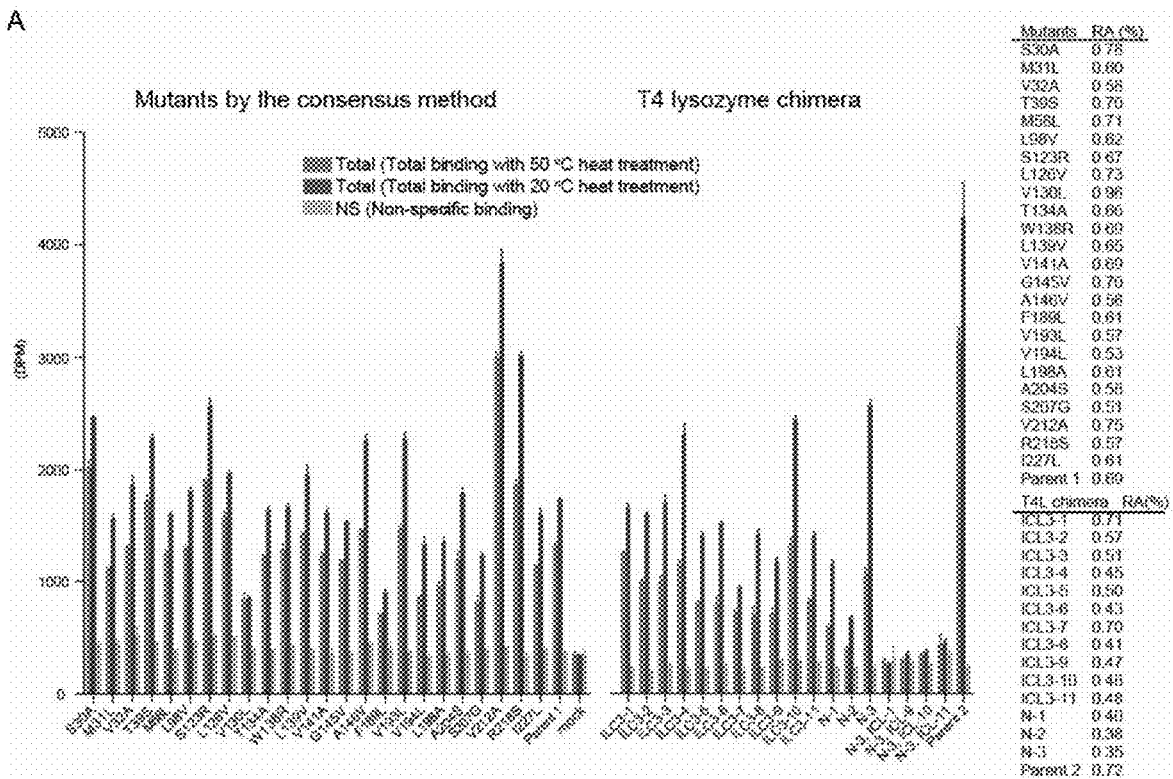
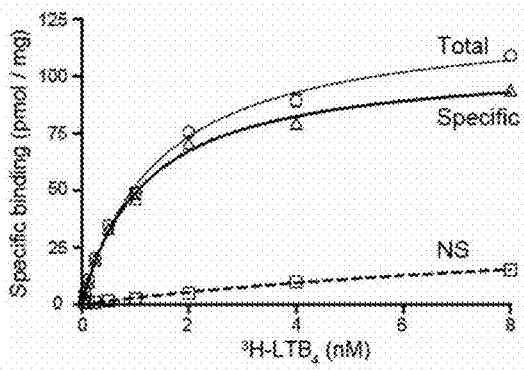
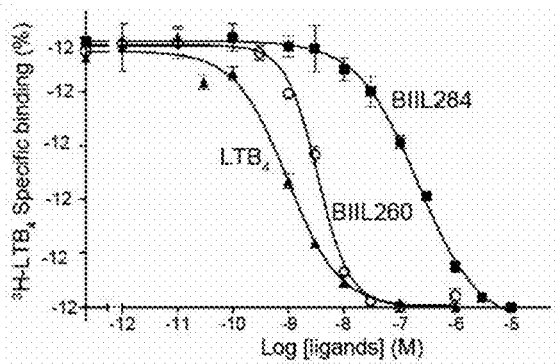

[Figure 9]
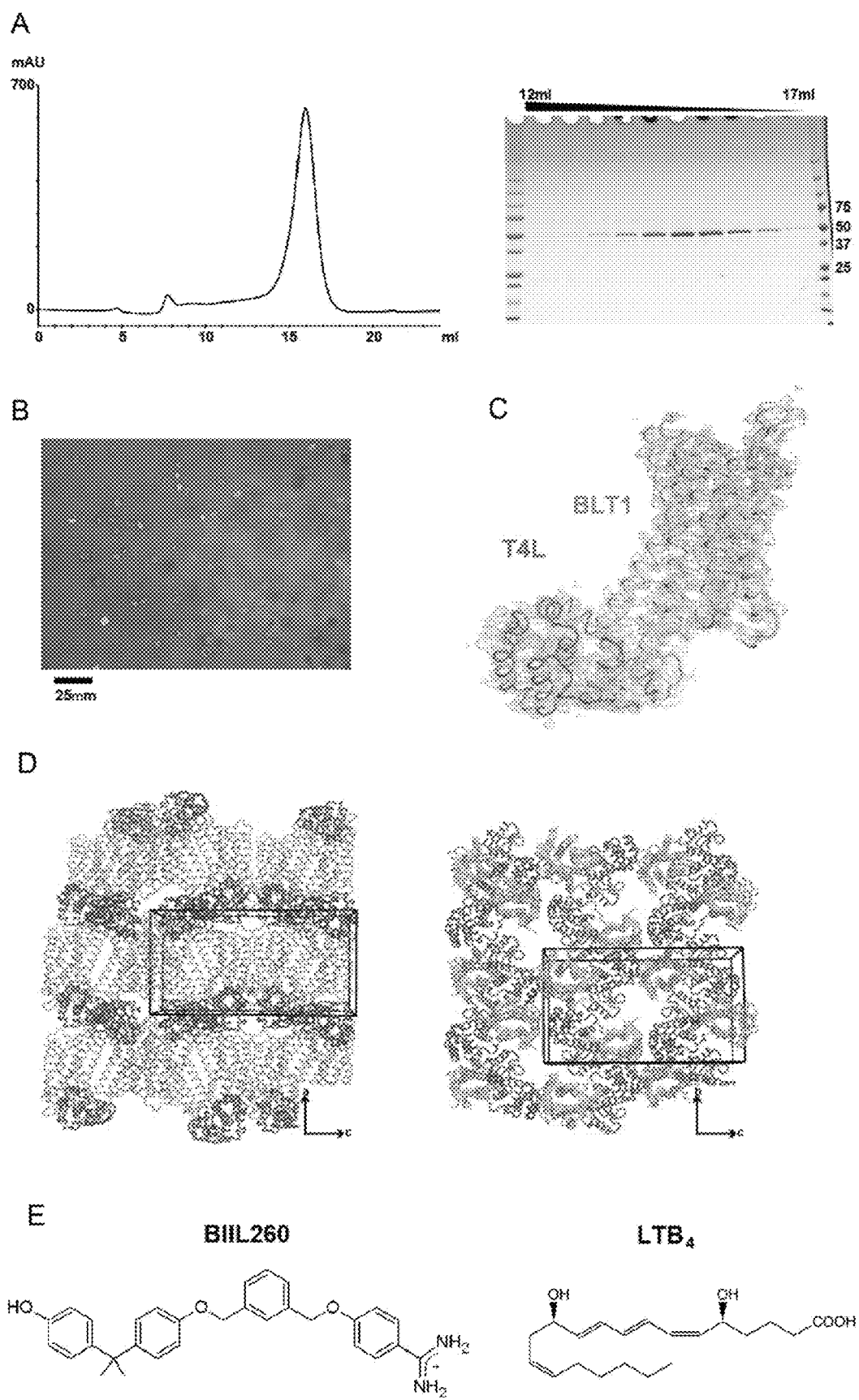

[Figure 10]
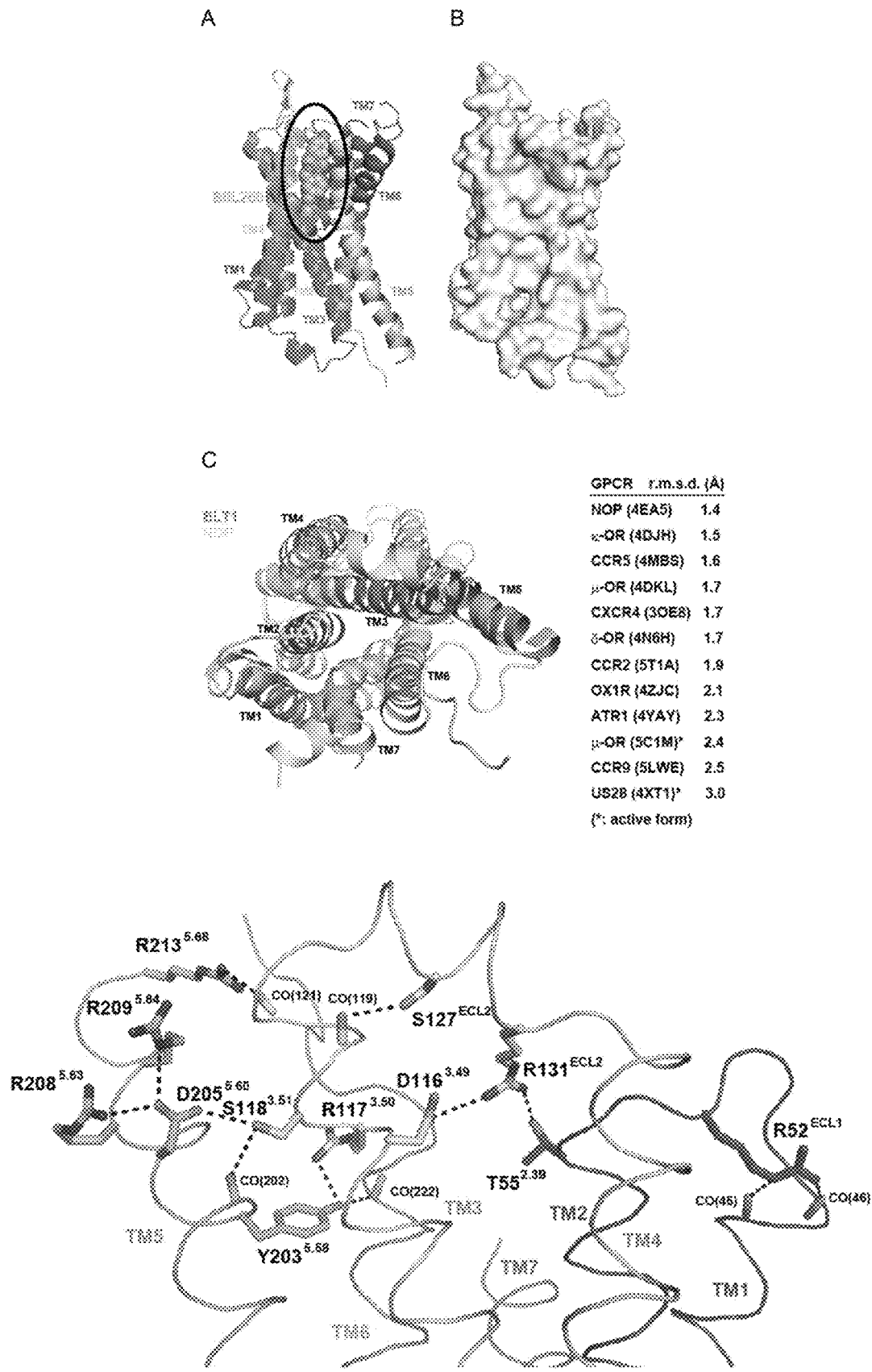

[Figure 11]
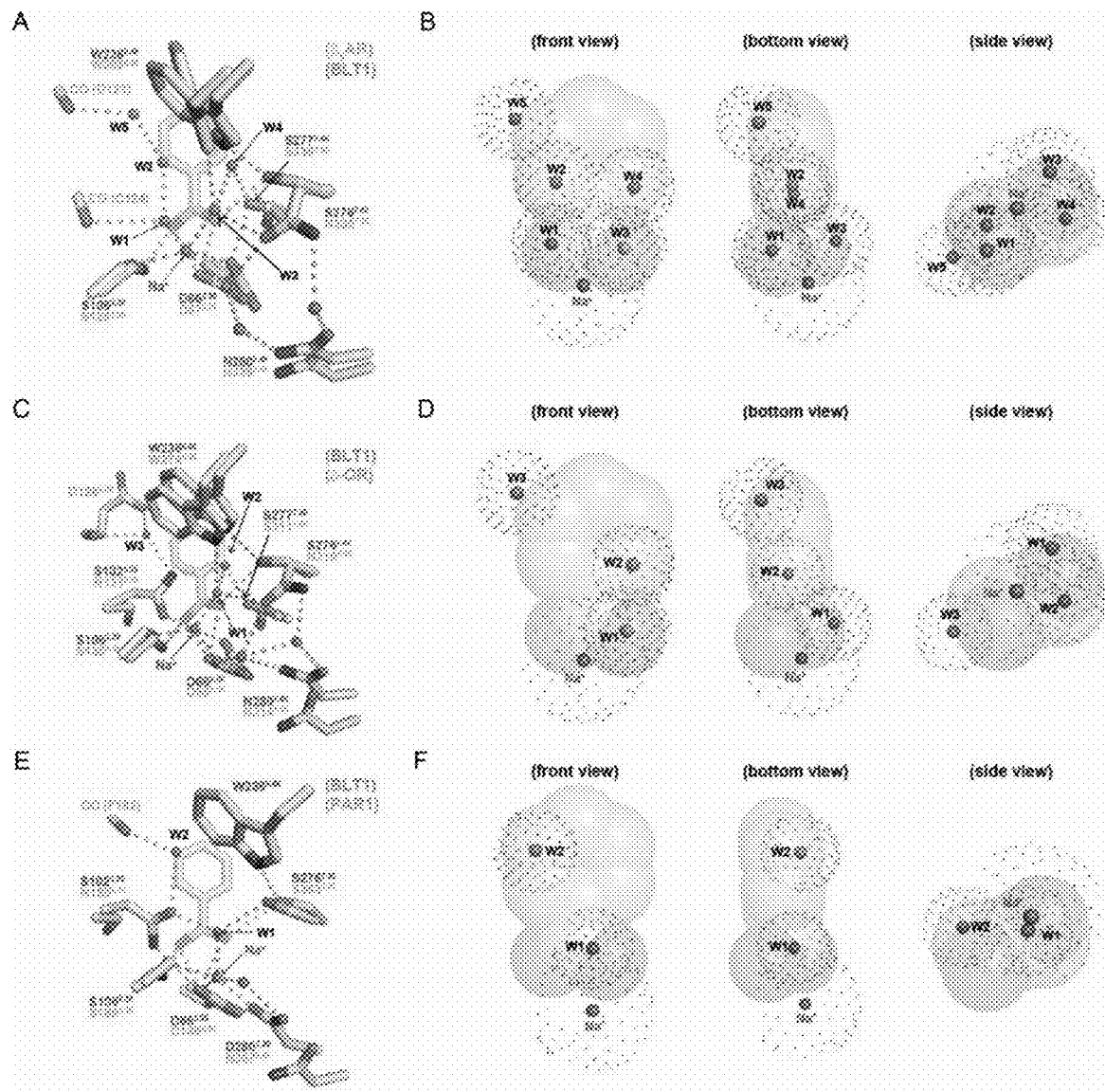

[Figure 12(A)]
(A)
(1) adenosine-benzamidine 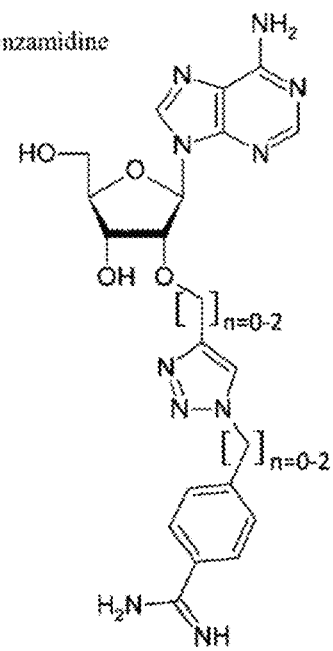
(2) histamine-benzamidine 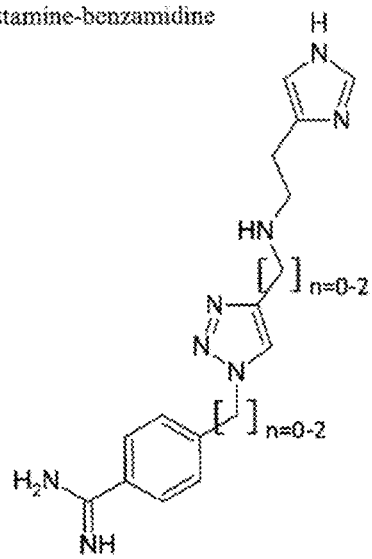
(3) TIPP-benzamidine
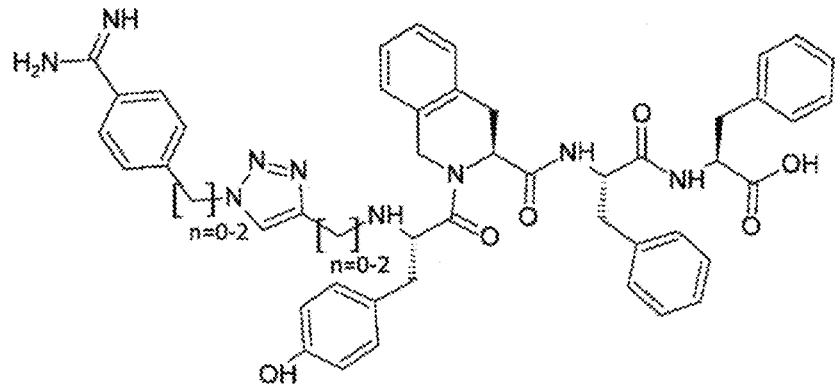
(4) Carazolol-benzamidine
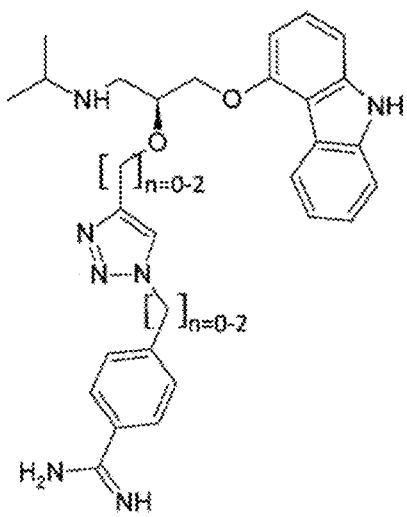

[Figure 12(B)]
(B)
(5) TIPP-benzamidine
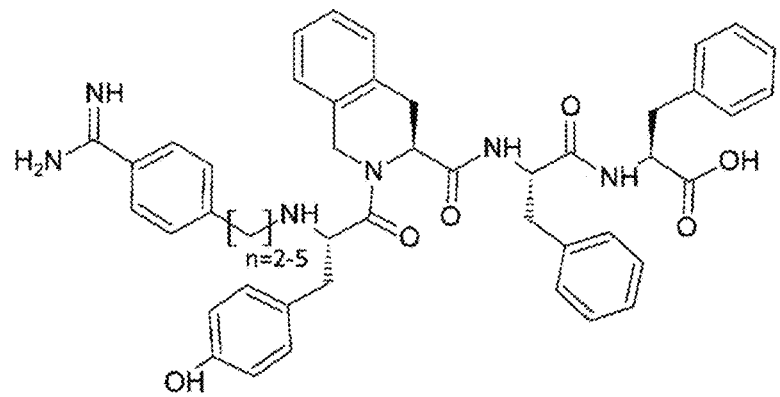
(6) TIPP-CO-benzamidine
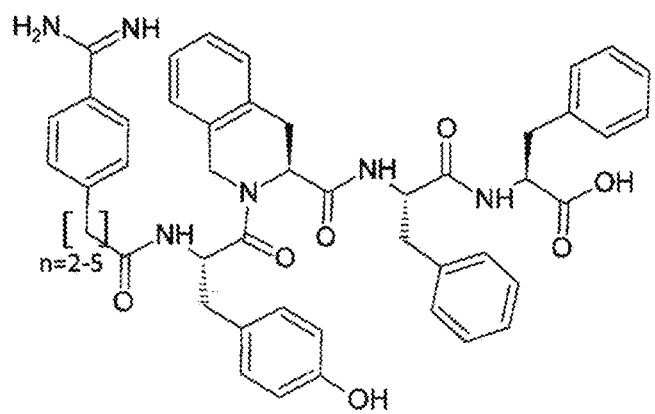
(7) Adenosine-benzamidine
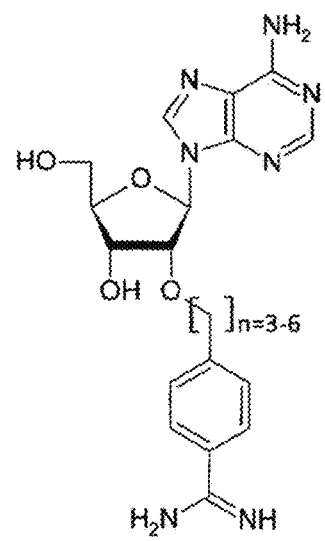
(8) Carazolol-benzamidine
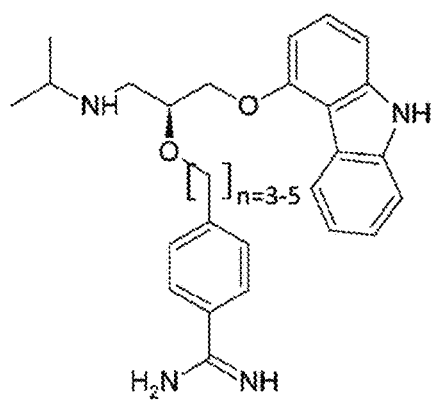

[Figure 13(A)]
(A) Modeling of $A_{2A}$ adenosine receptor ($A_{2A}AR$)
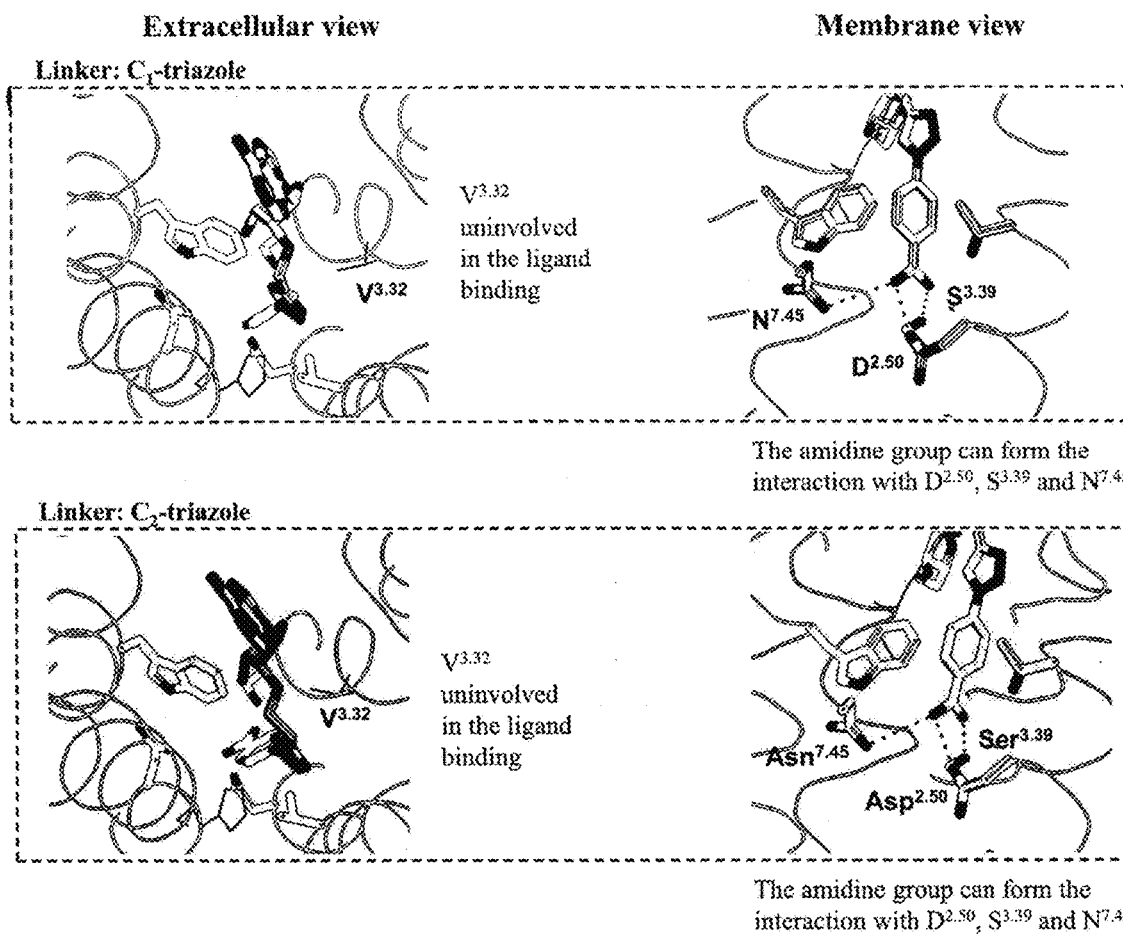
(b) Adenoside-linker-benzamidine
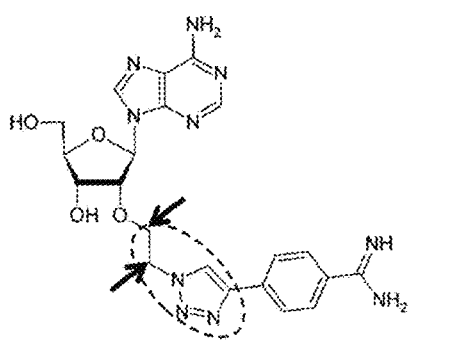
Linker: alkyl chain ($C_1$ or $C_2$) and triazole
(c) Structure before the energy minimization procedure
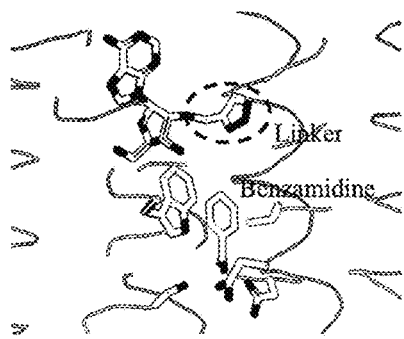
The linker is arbitrary position in before energy minimization procedure.

[Figure 13(B)]

(B) Modeling of $\beta_1$ adrenergic receptor ($\beta_1$AR)

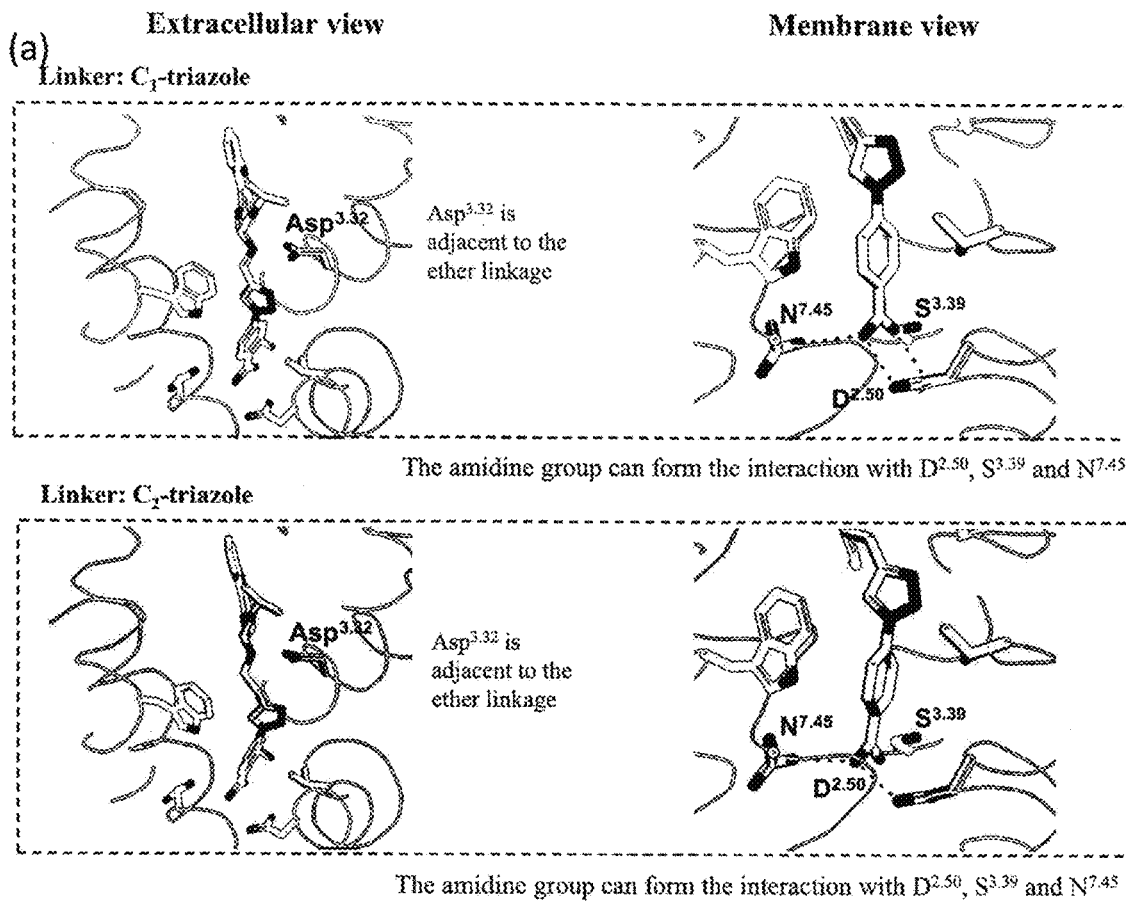

(a) Extracellular view / Membrane view

Linker: $C_1$-triazole — Asp$^{3.32}$ is adjacent to the ether linkage. The amidine group can form the interaction with D$^{2.50}$, S$^{3.39}$ and N$^{7.45}$ Linker: $C_2$-triazole — Asp$^{3.32}$ is adjacent to the ether linkage. The amidine group can form the interaction with D$^{2.50}$, S$^{3.39}$ and N$^{7.45}$ (b) Carazolol-linker-benzamidine

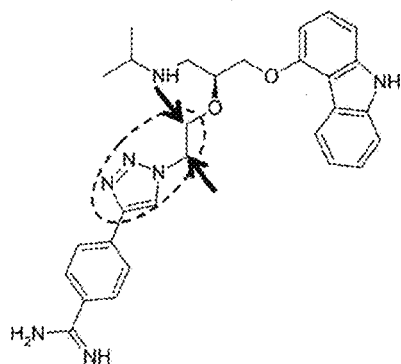

Linker: alkyl chain ($C_1$ or $C_2$) and triazole (c) Structure before the energy minimization procedure

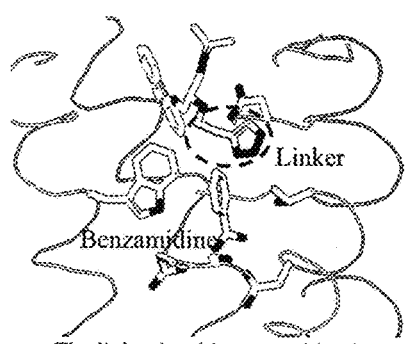

The linker is arbitrary position in before energy minimization procedure.

[Figure 13(C)]

(C) Modeling of δ-opioid receptor (δ-OR)

(a) Linker: $C_1$-triazole

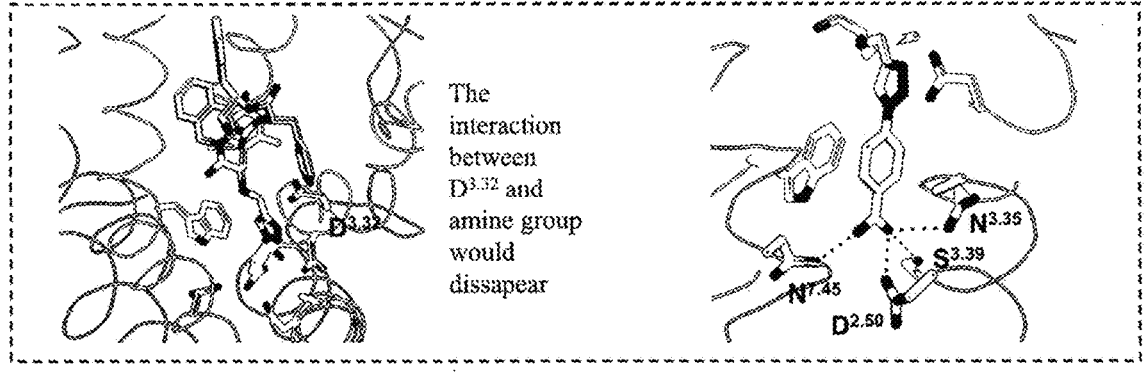

The amidine group can form the interaction with $D^{2.50}$, $N^{3.35}$, $S^{3.39}$ and $N^{7.45}$ Linker: $C_2$-triazole

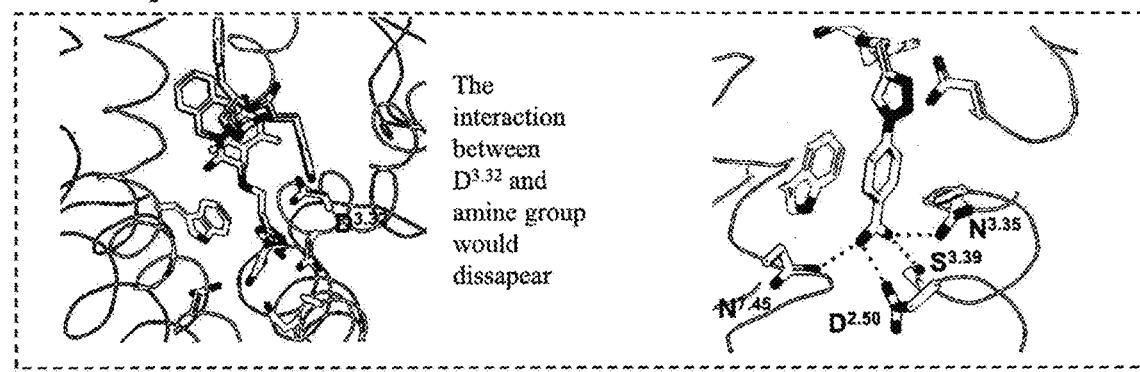

The amidine group can form the interaction with $D^{2.50}$, $N^{3.35}$, $S^{3.39}$ and $N^{7.45}$

(b) TIPP-linker-benzamidine

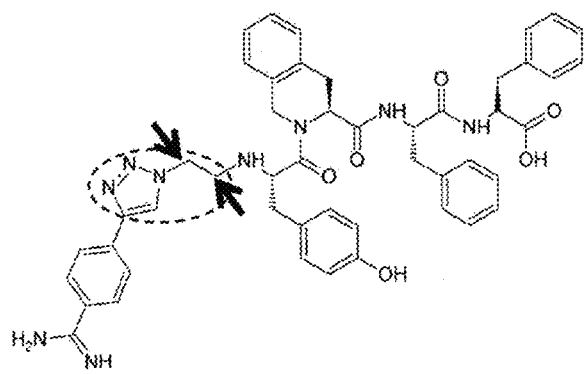

Linker: alkyl chain ($C_1$ or $C_2$) and triazole

(c) Structure before the energy minimization procedure

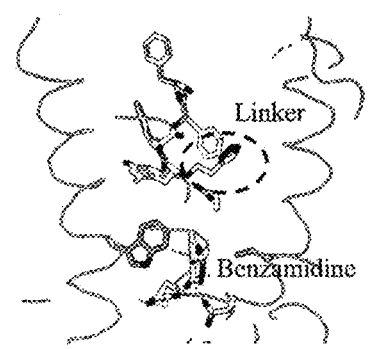

The linker is arbitrary position in before energy minimization procedure.

[Figure 13(D)]
(D) Modeling of $H_1$ histamine receptor ($H_1HR$)
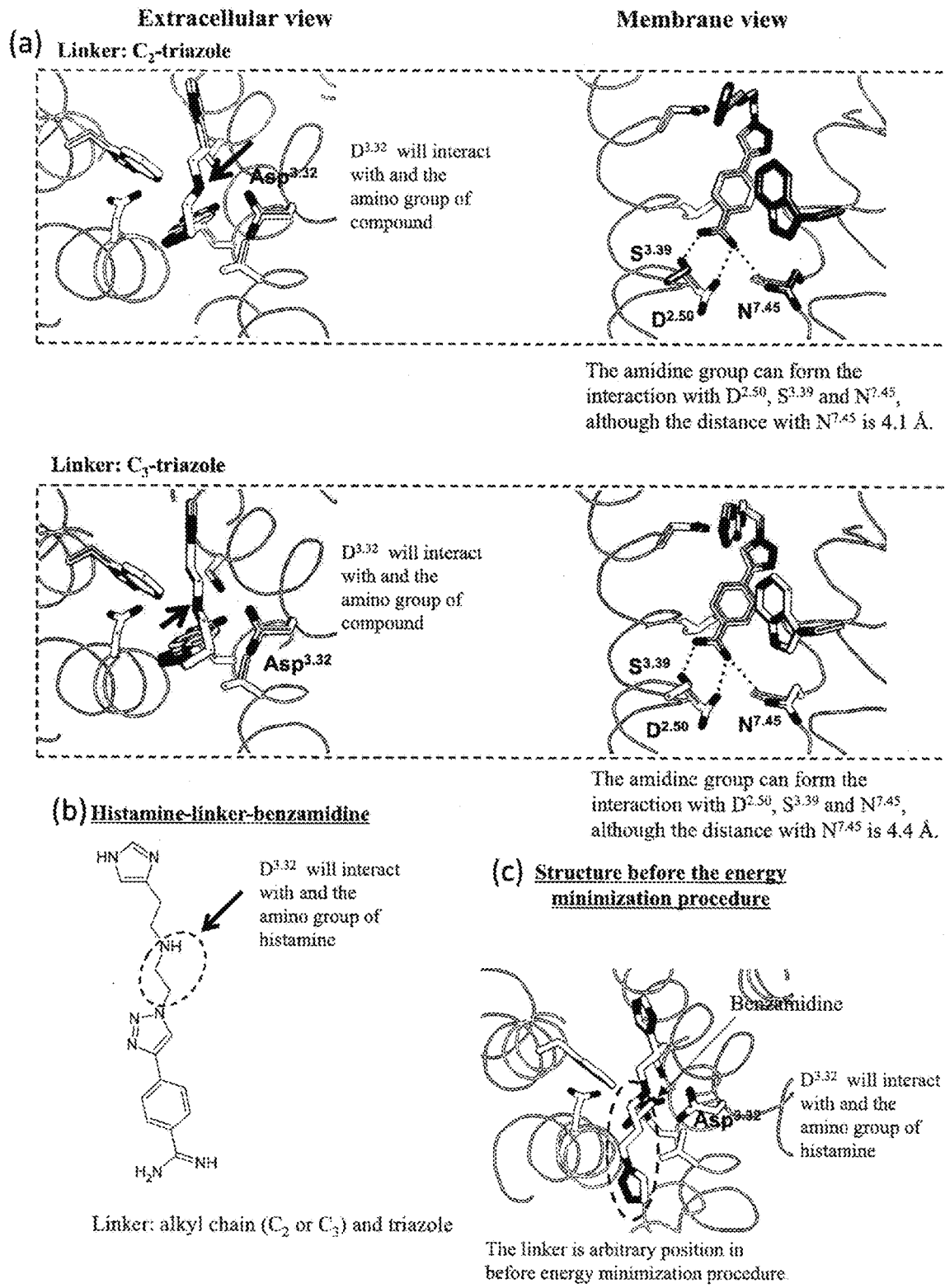

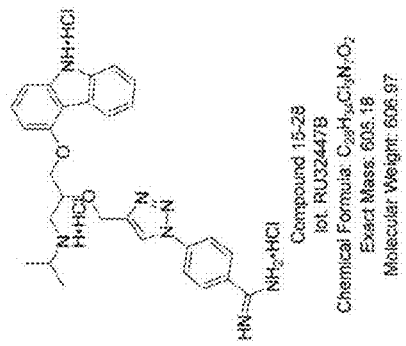
[Figure 14(A)]

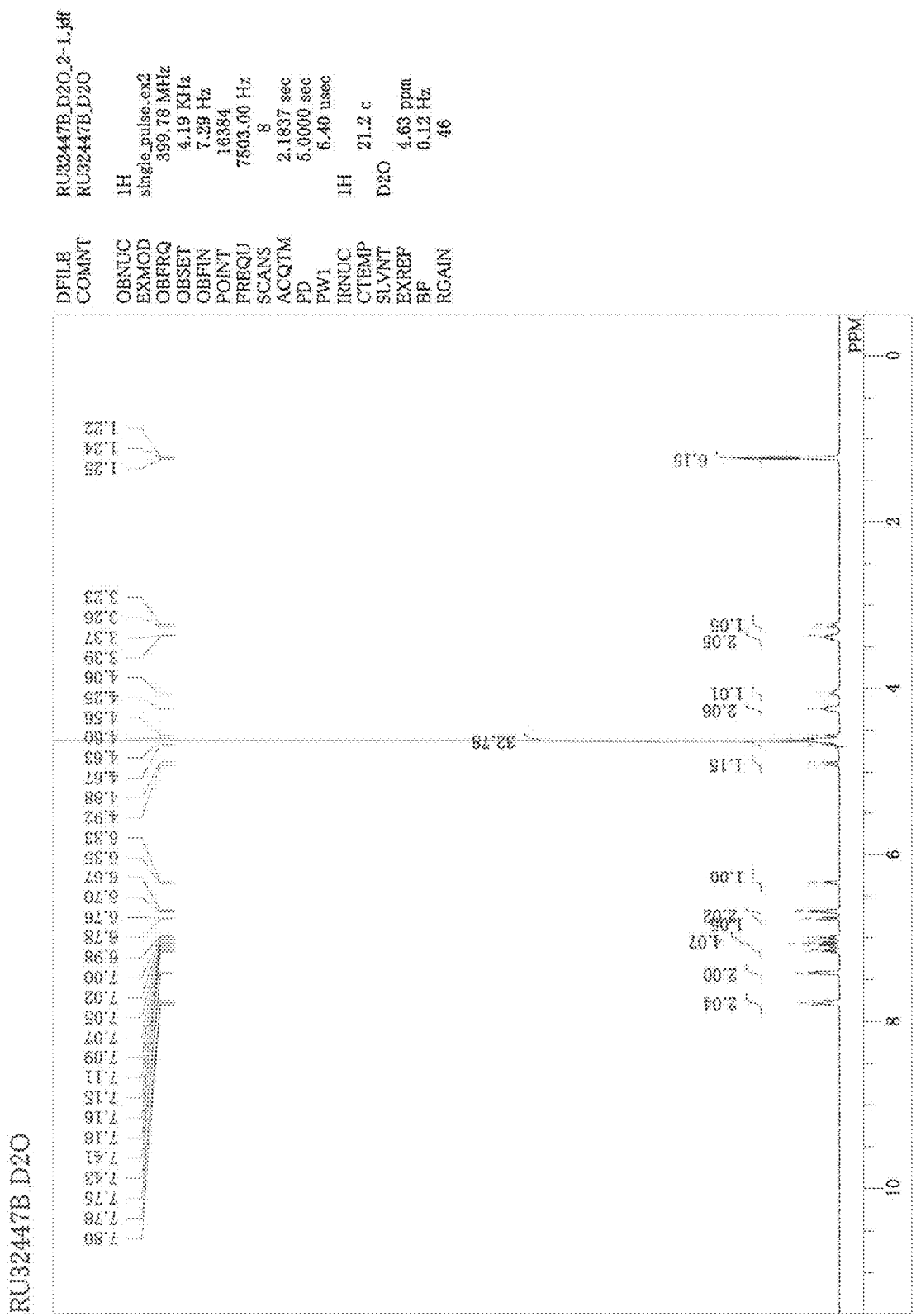
[Figure 14(B)]

[Figure 14(C)]
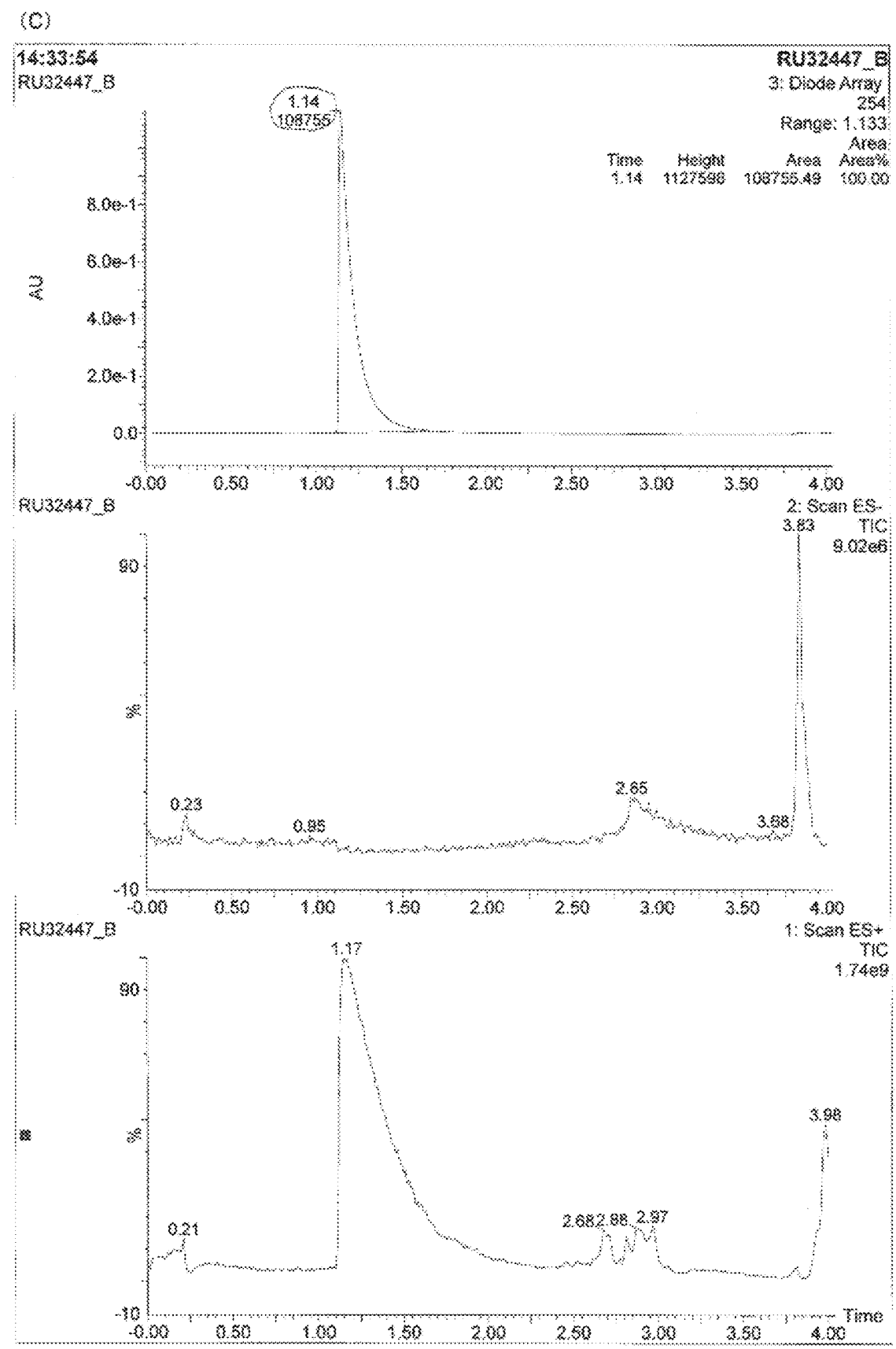

[Figure 14(D)]
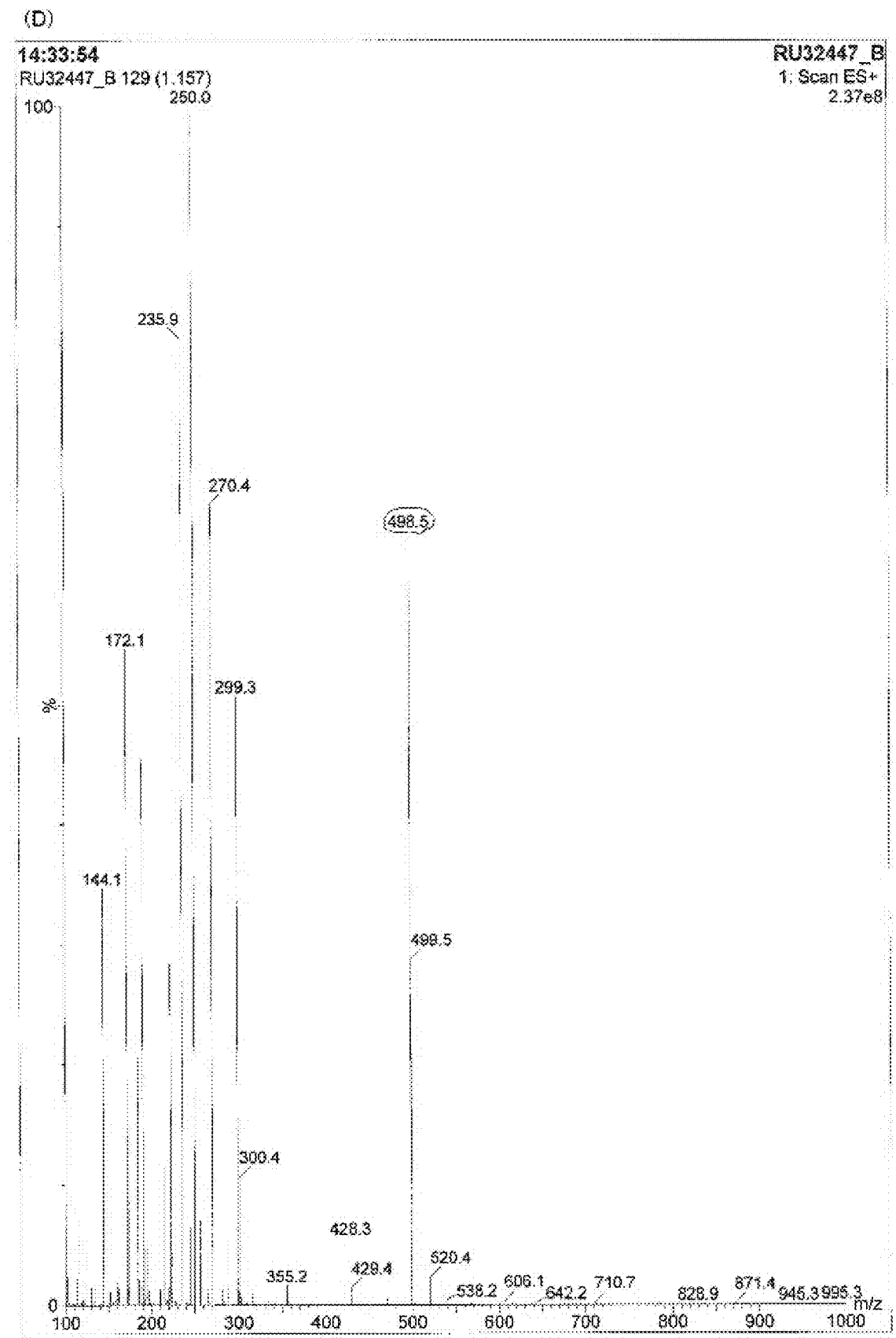

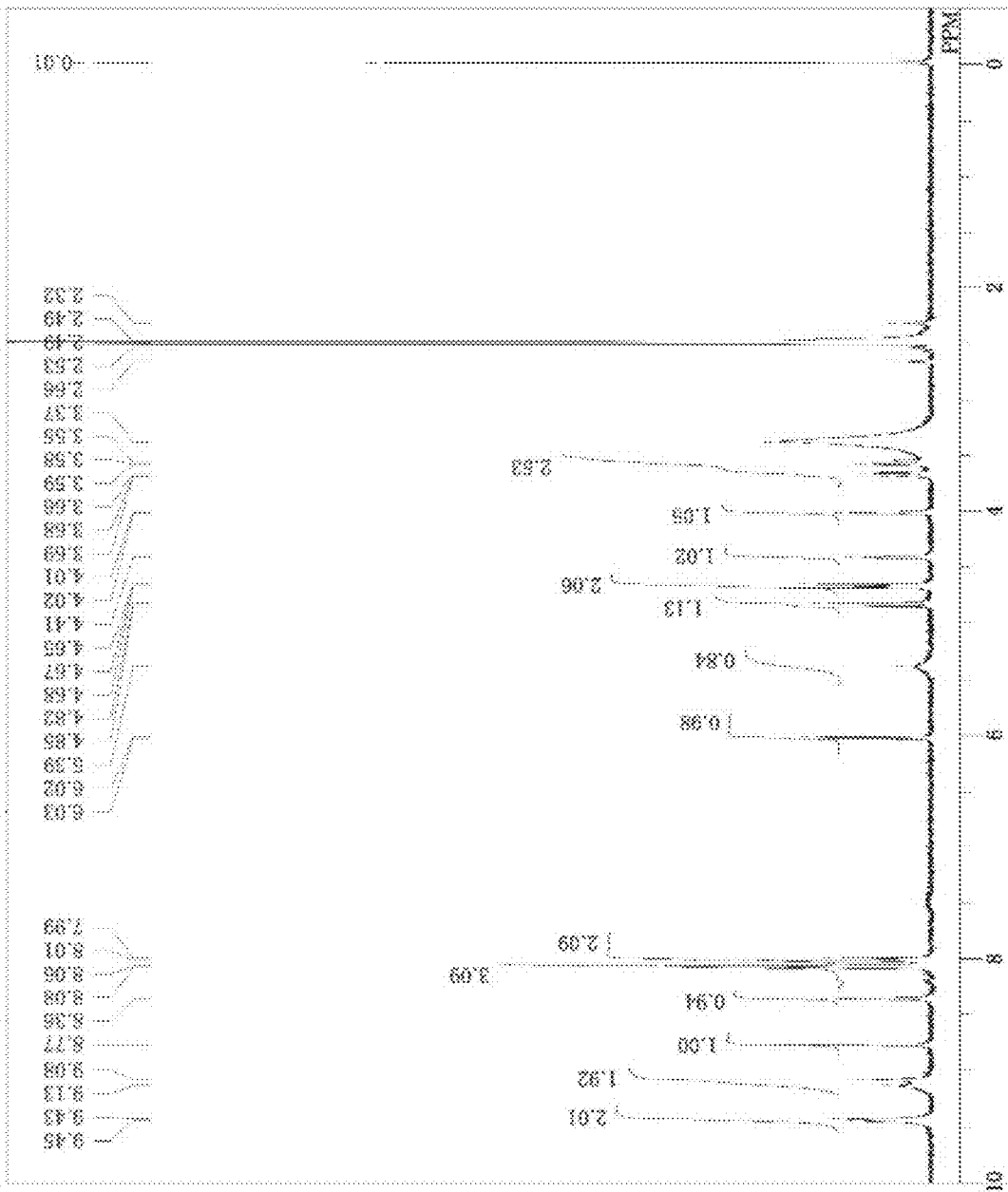
[Figure 15(A)]

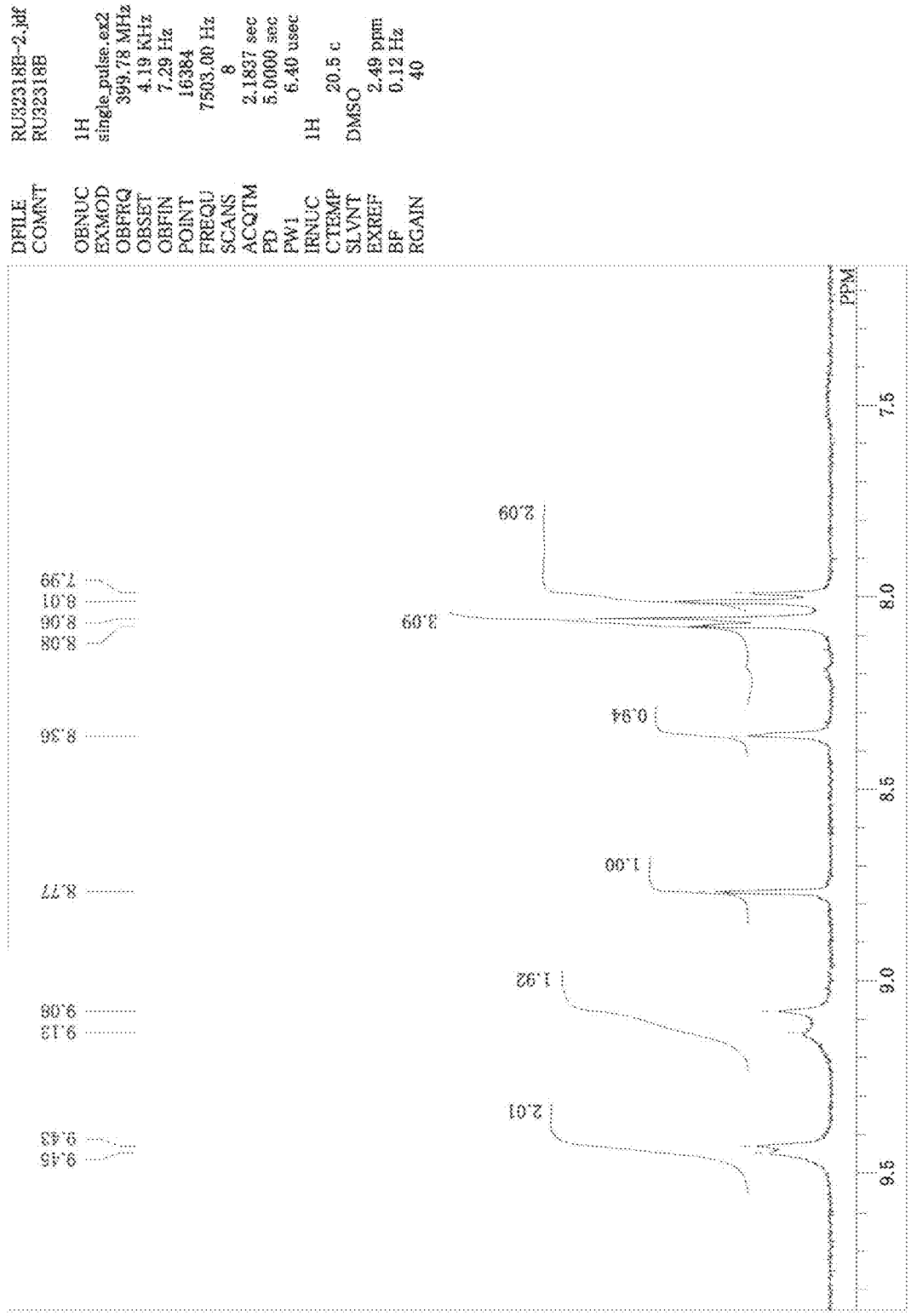
[Figure 15(B)]

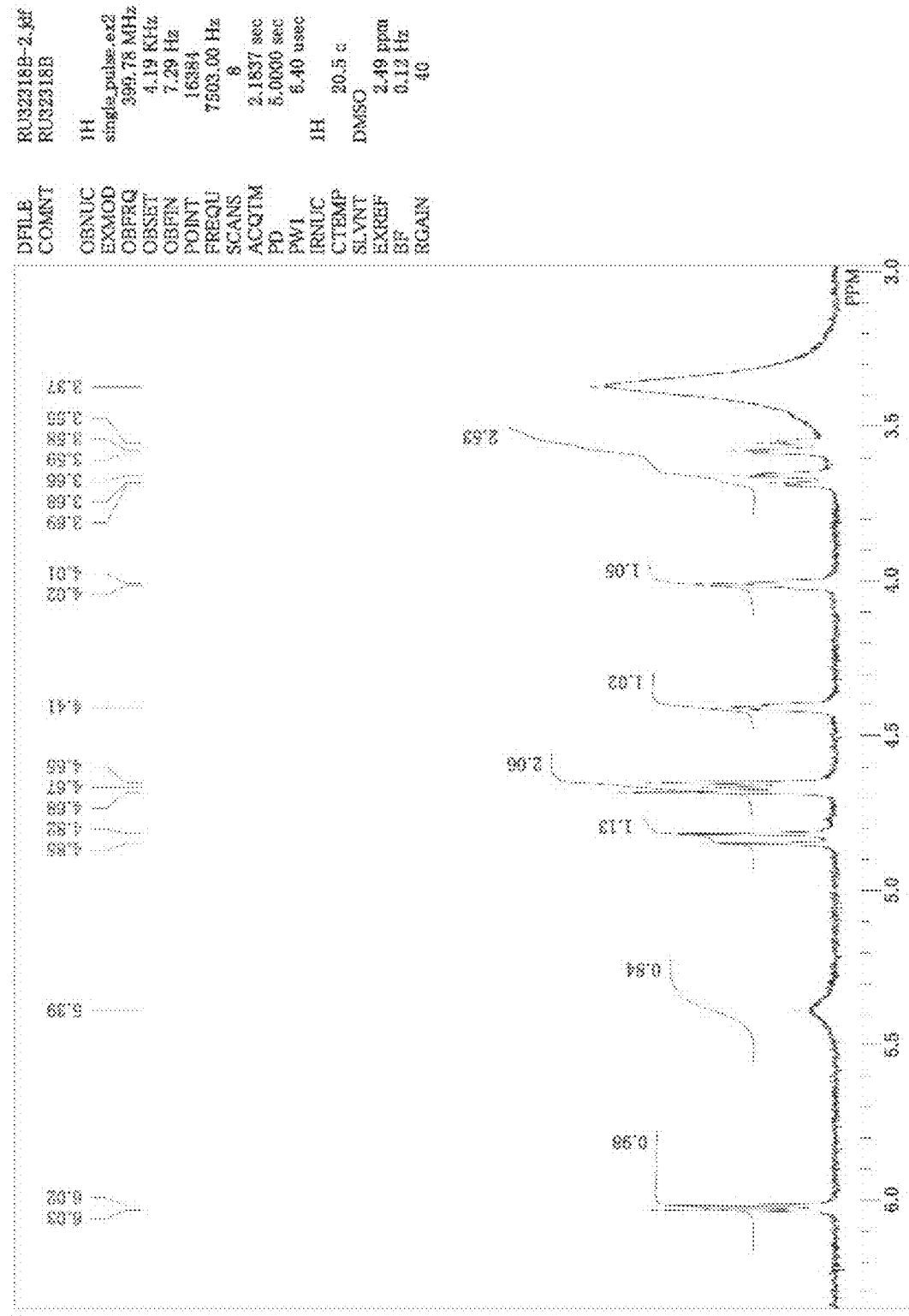
[Figure 15(C)]

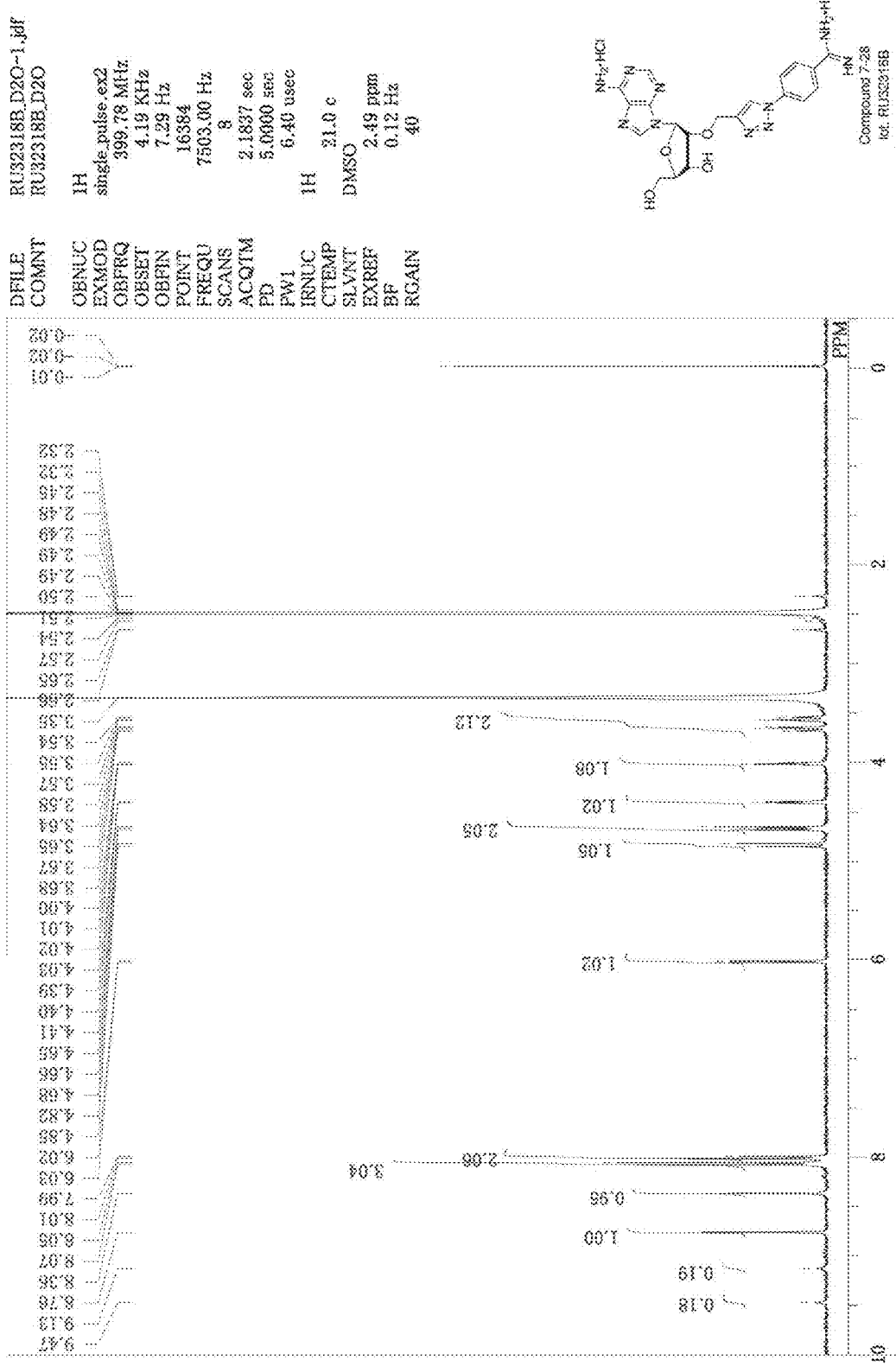
[Figure 15(D)]

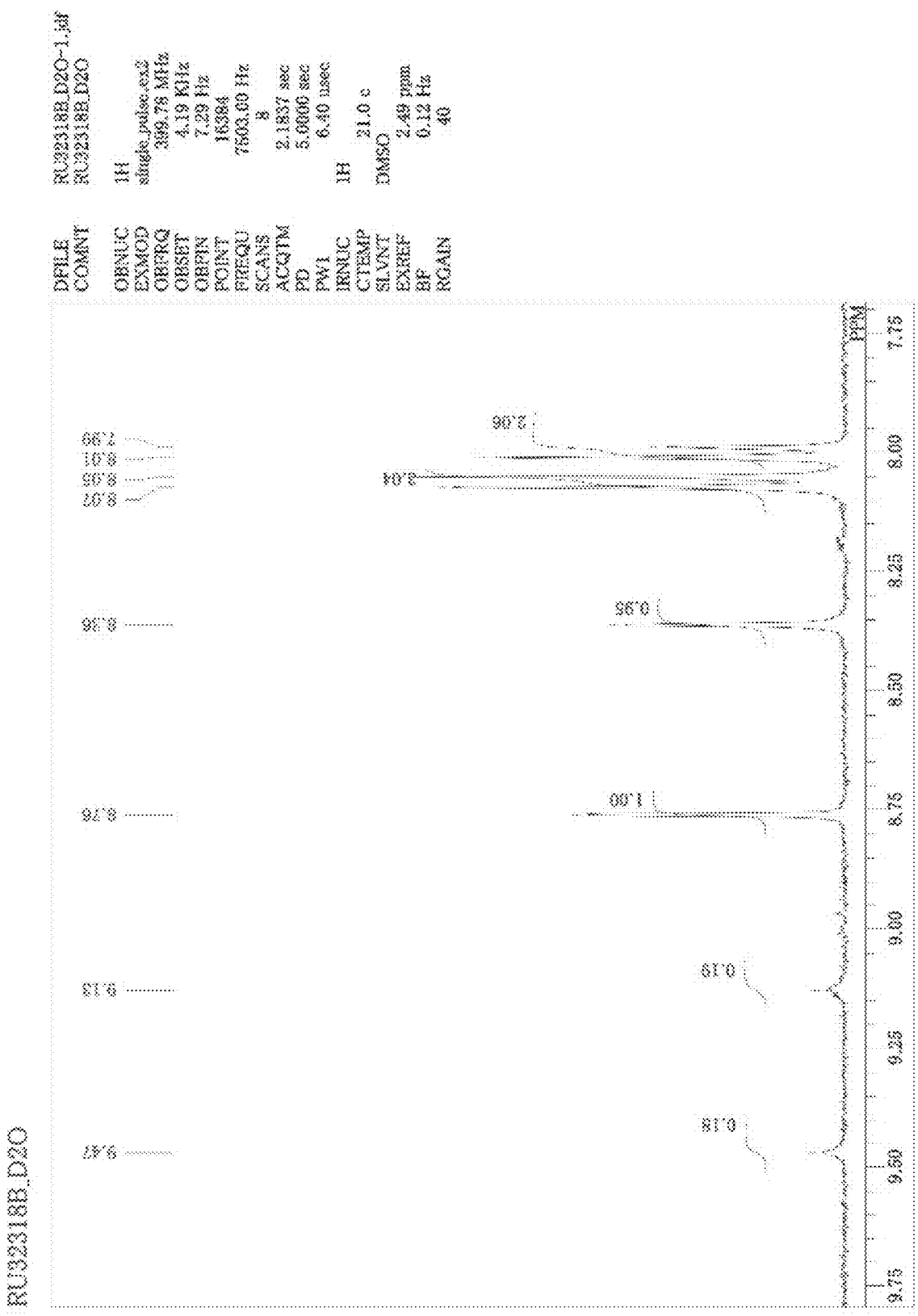
[Figure 15(E)]

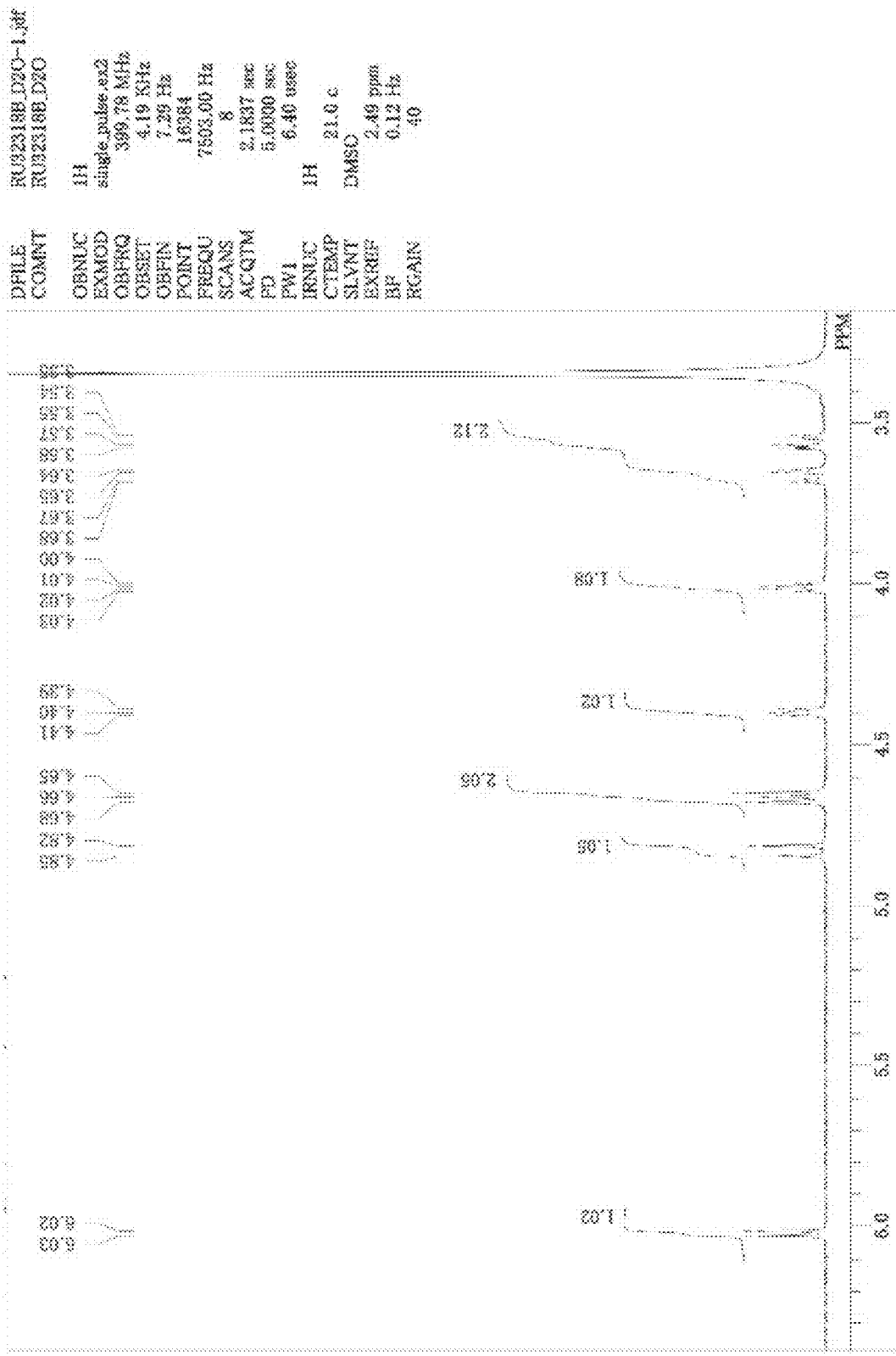
[Figure 15(F)]

[Figure 15(G)]
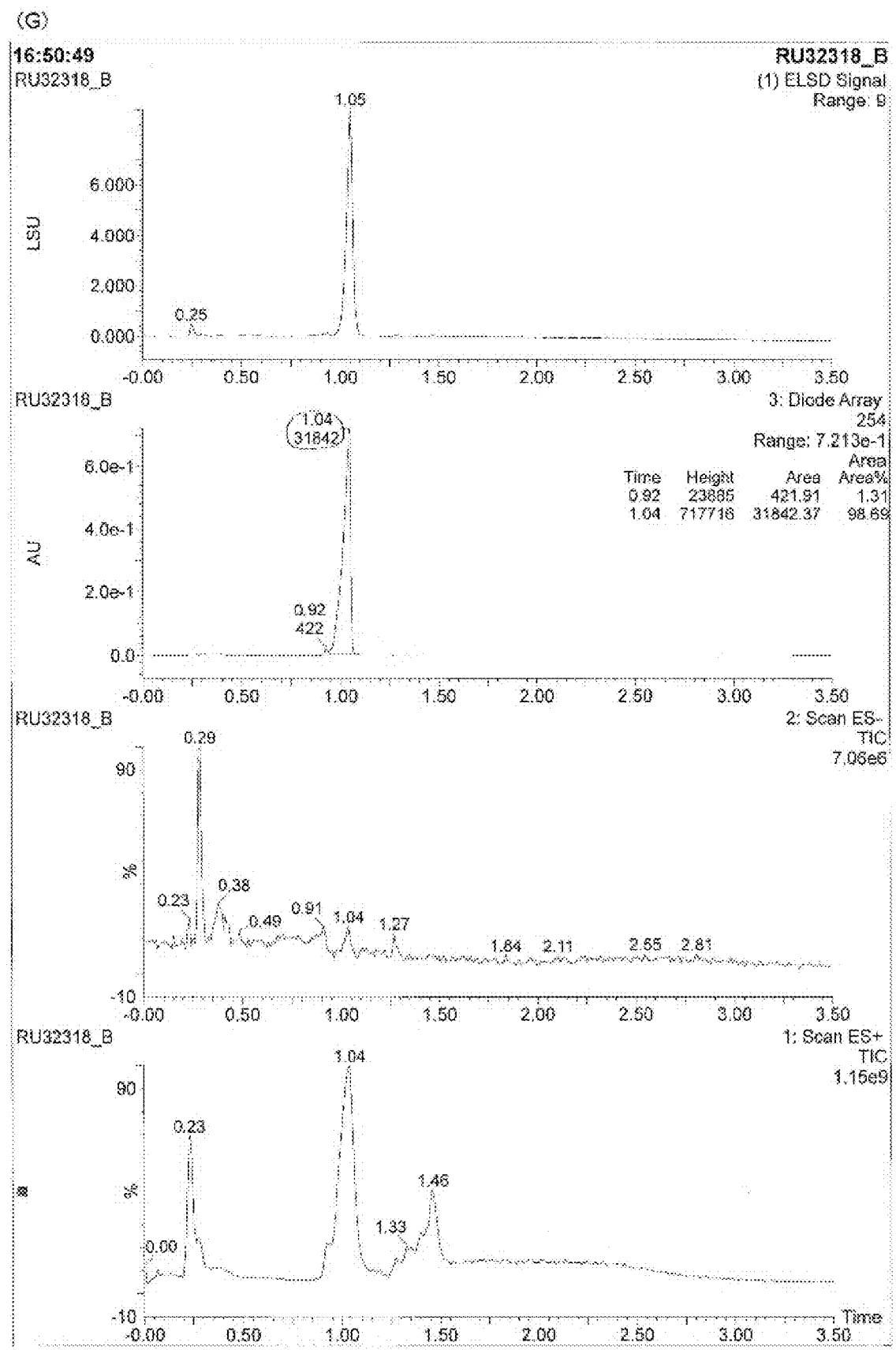

[Figure 15(H)]
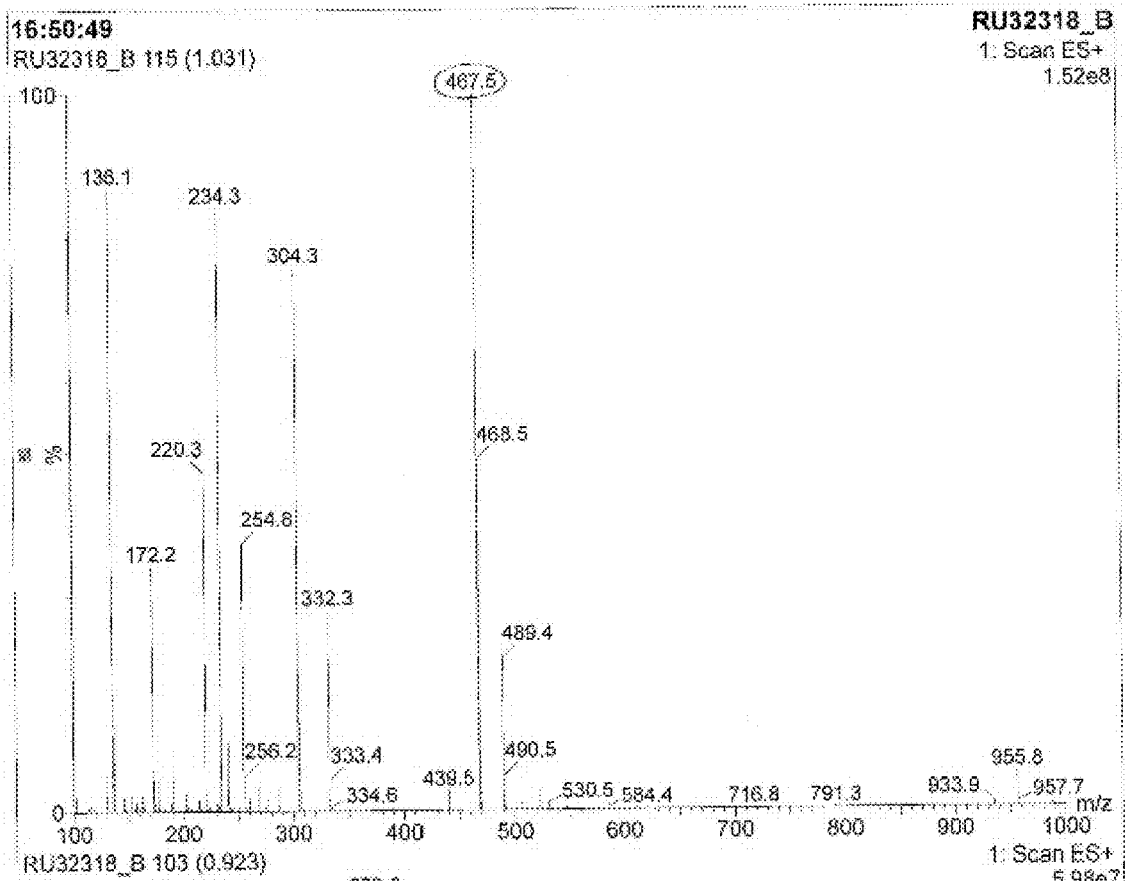
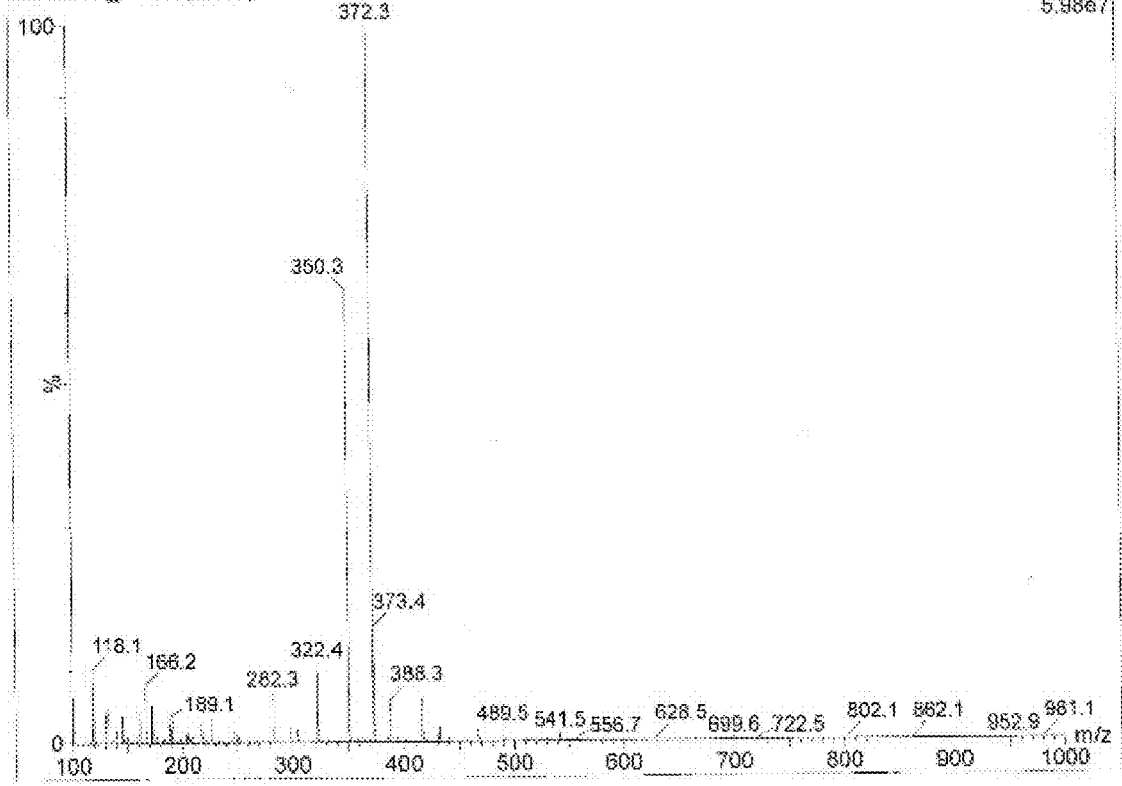

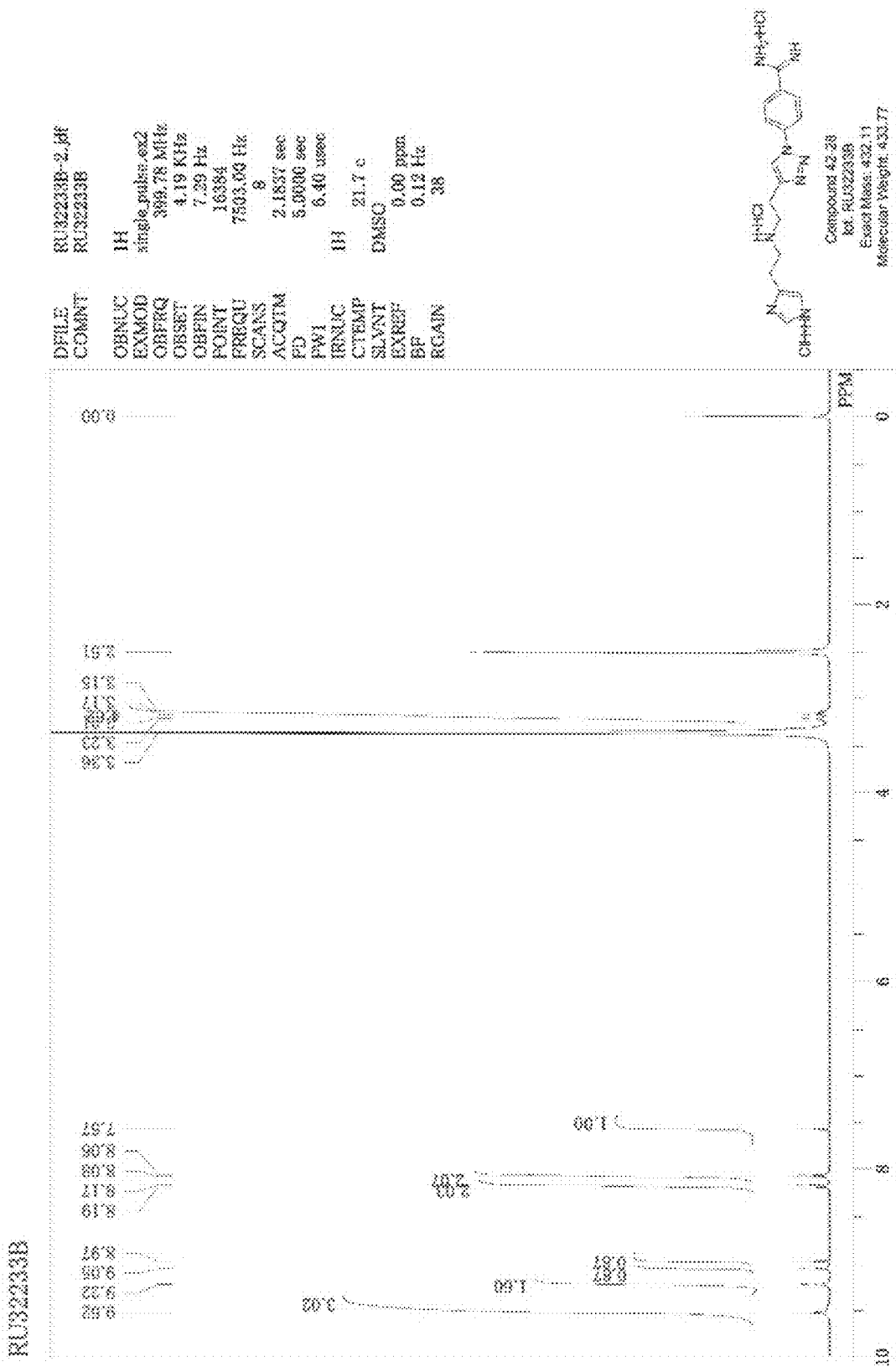
[Figure 16(A)]

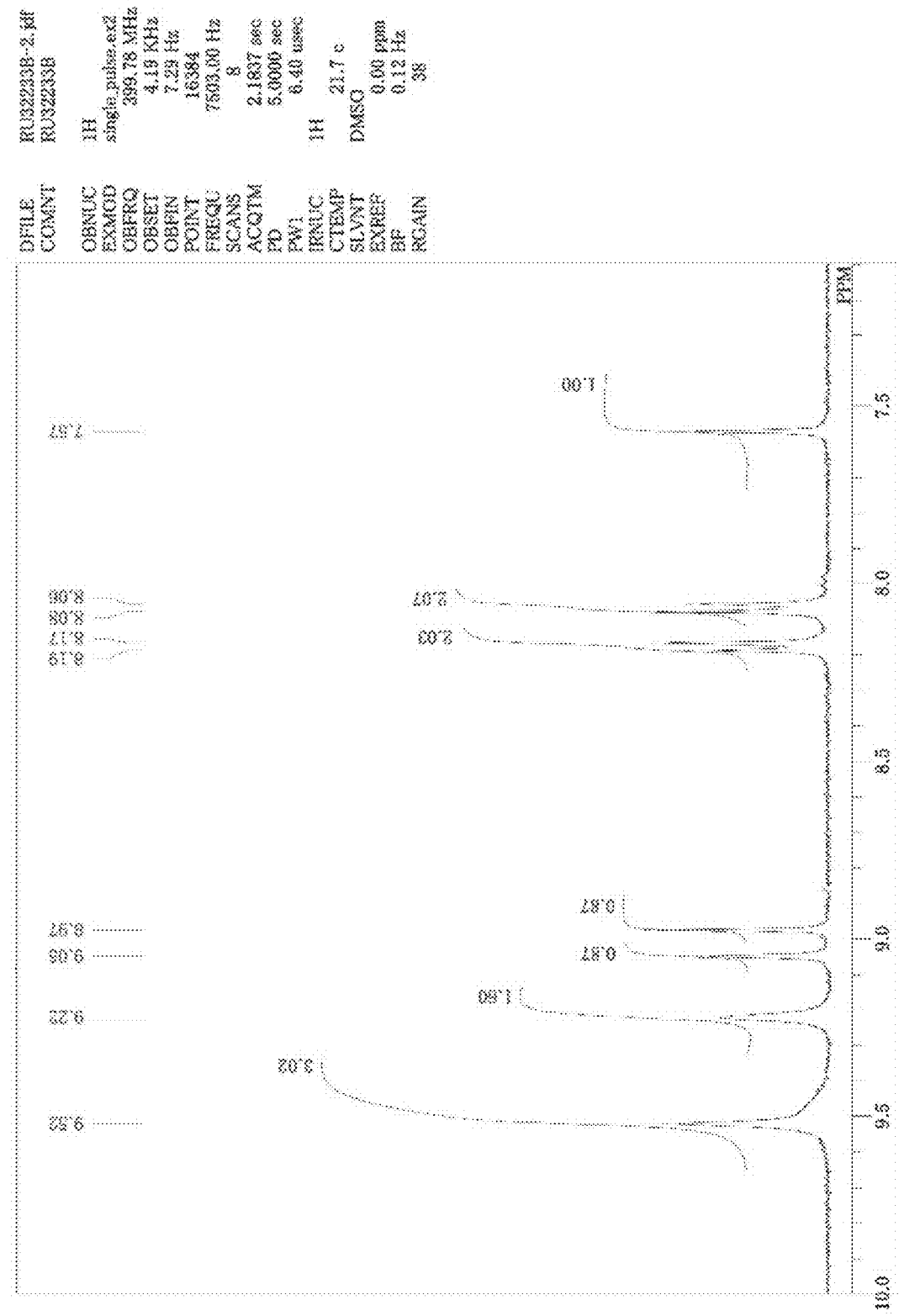
[Figure 16(B)]

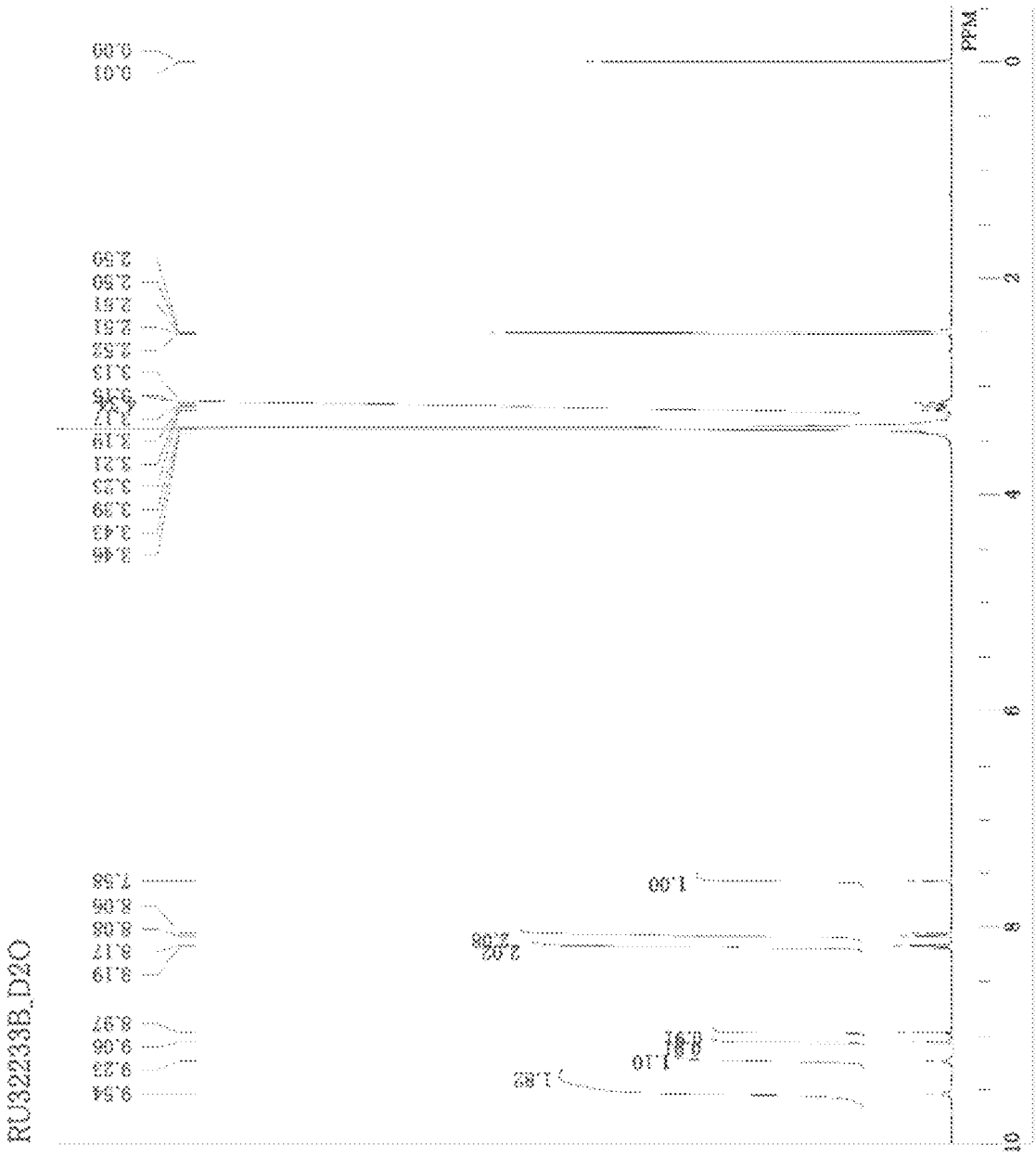
[Figure 16(C)]

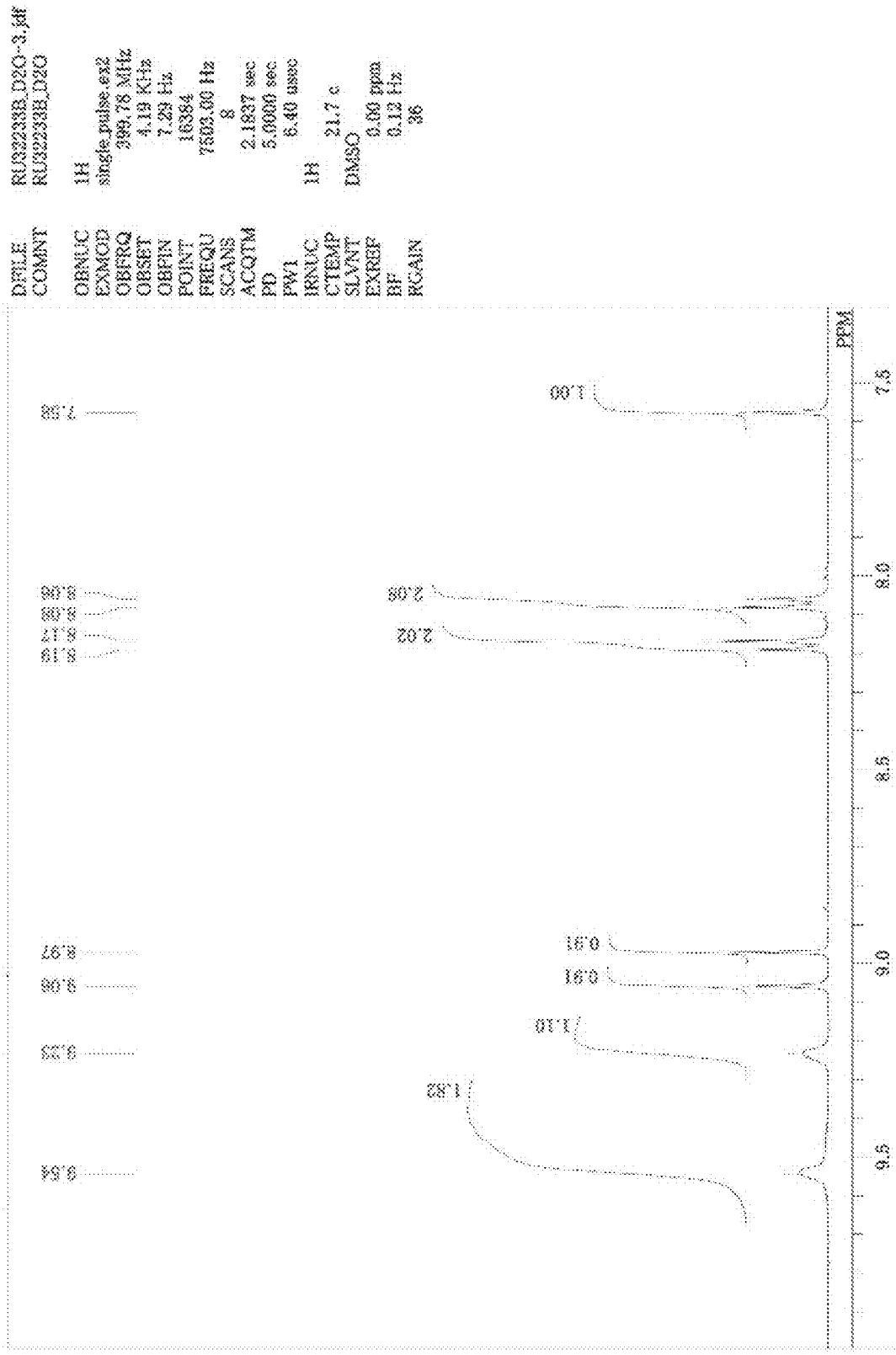
[Figure 16(D)]

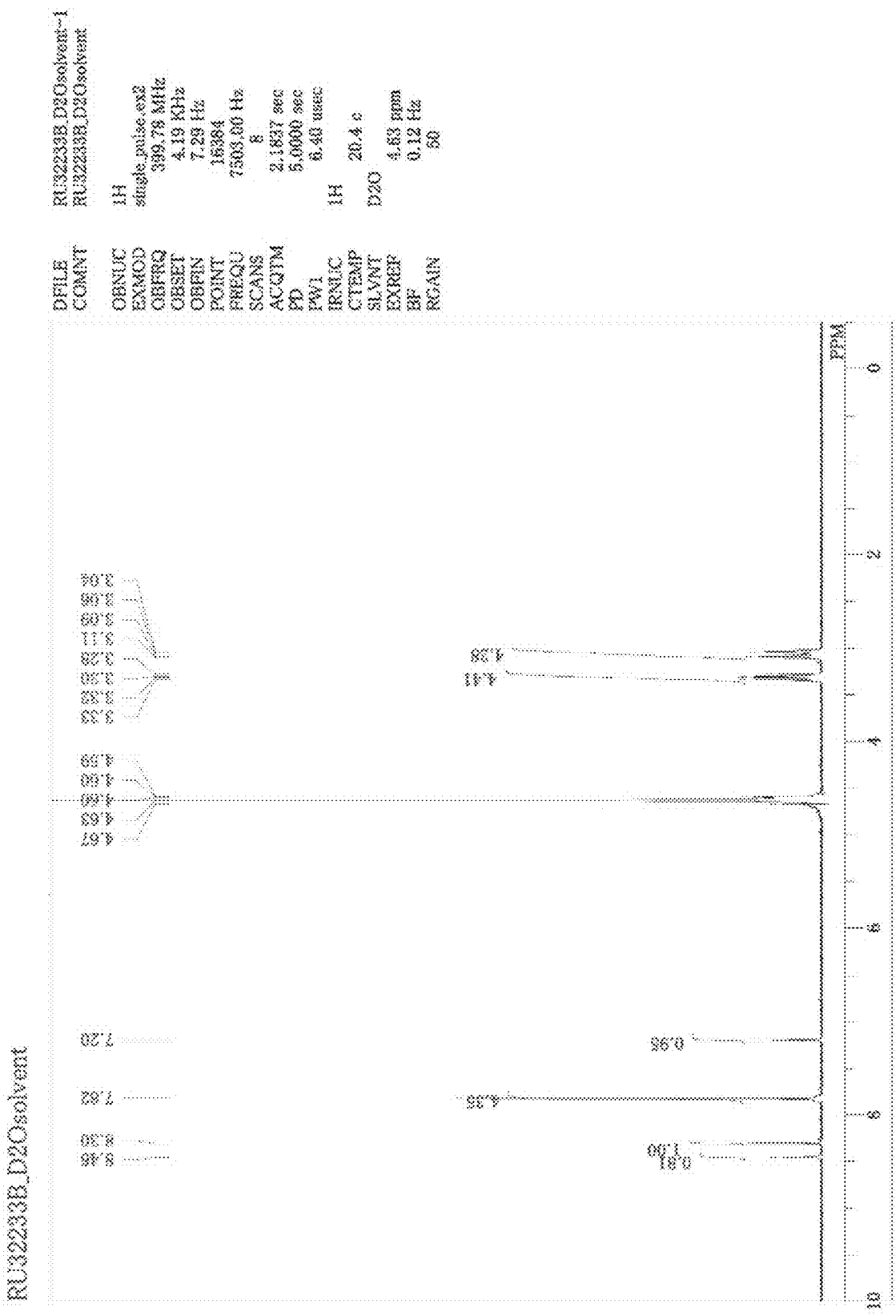
[Figure 16(E)]

[Figure 16(F)]
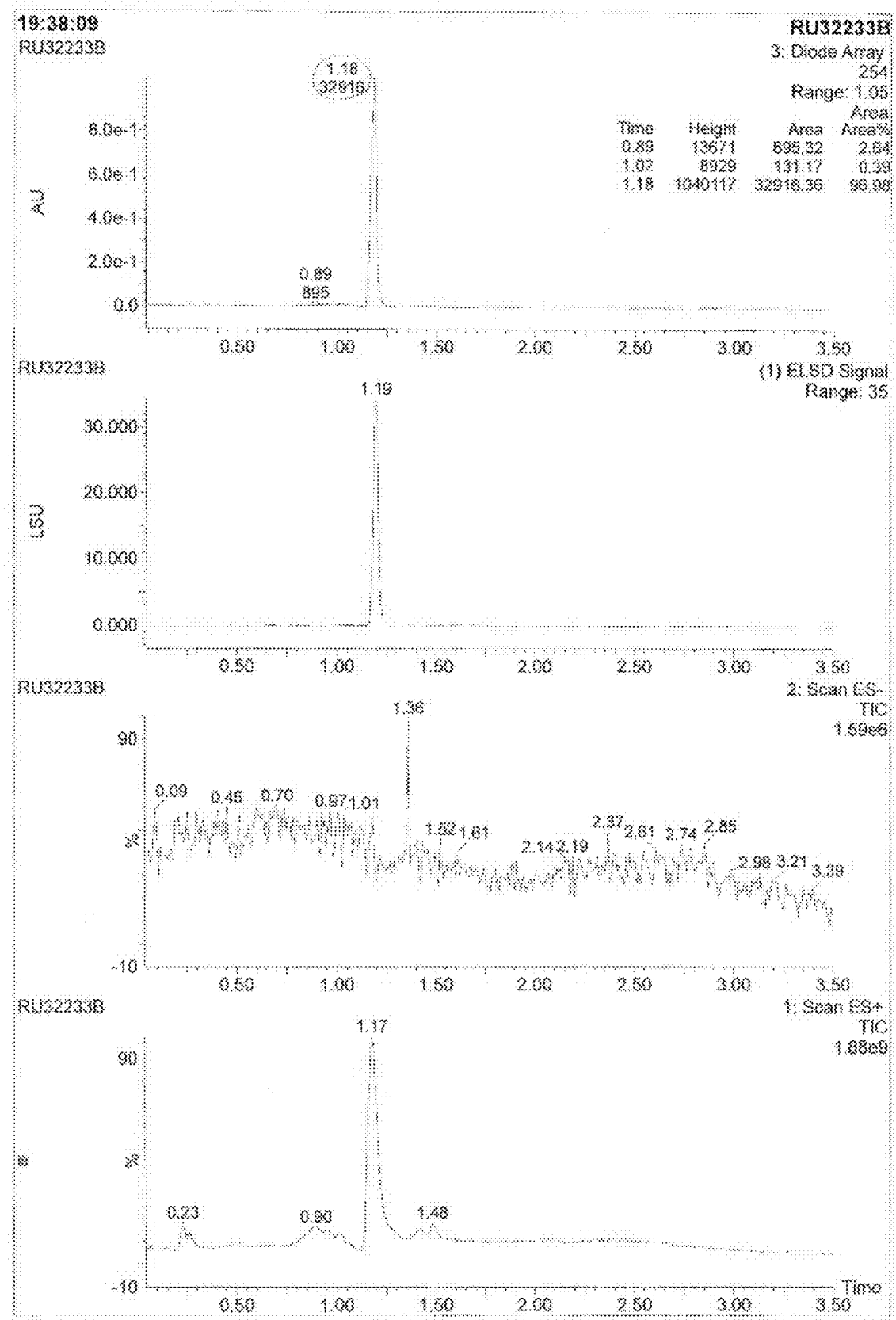

[Figure 16(G)]
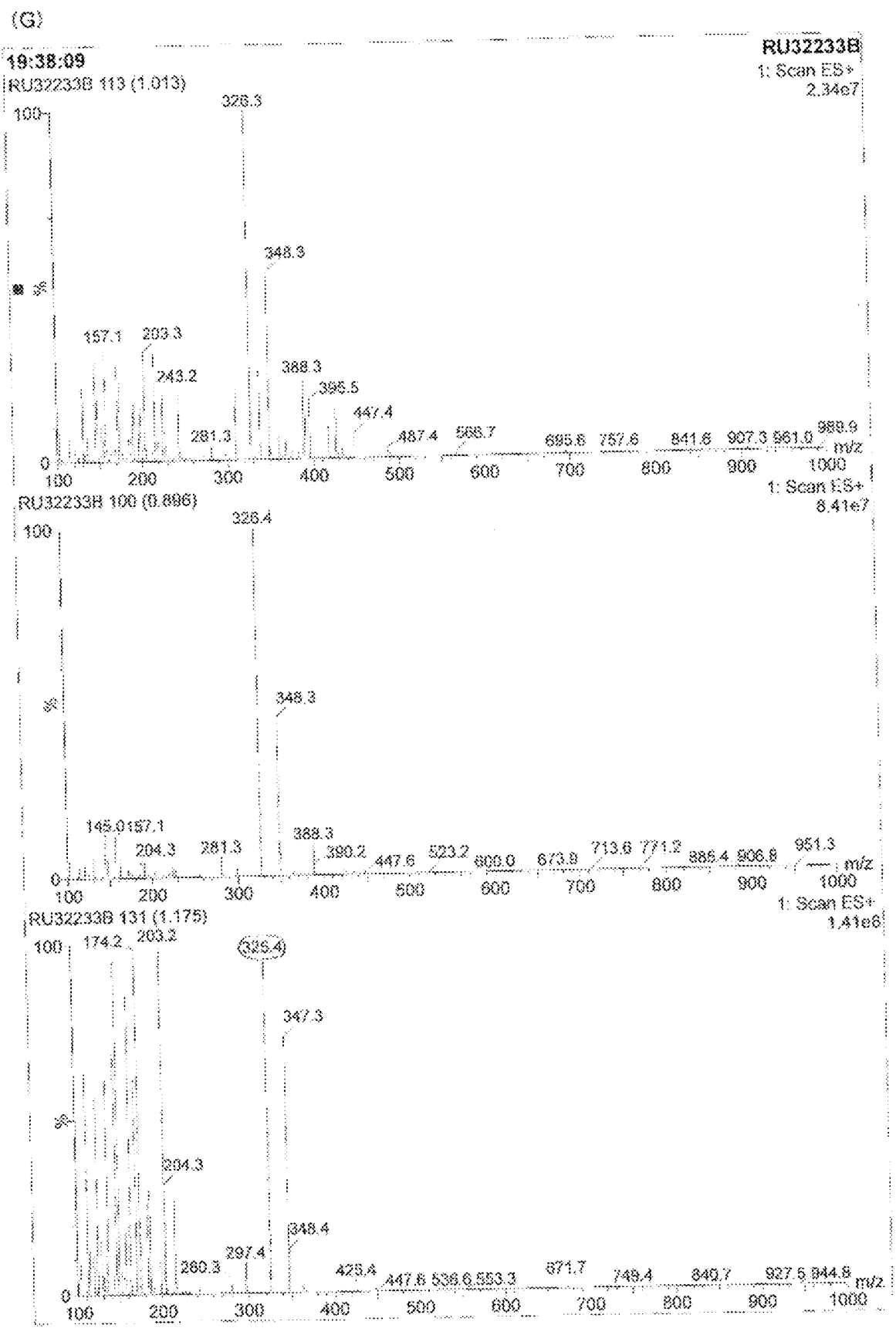

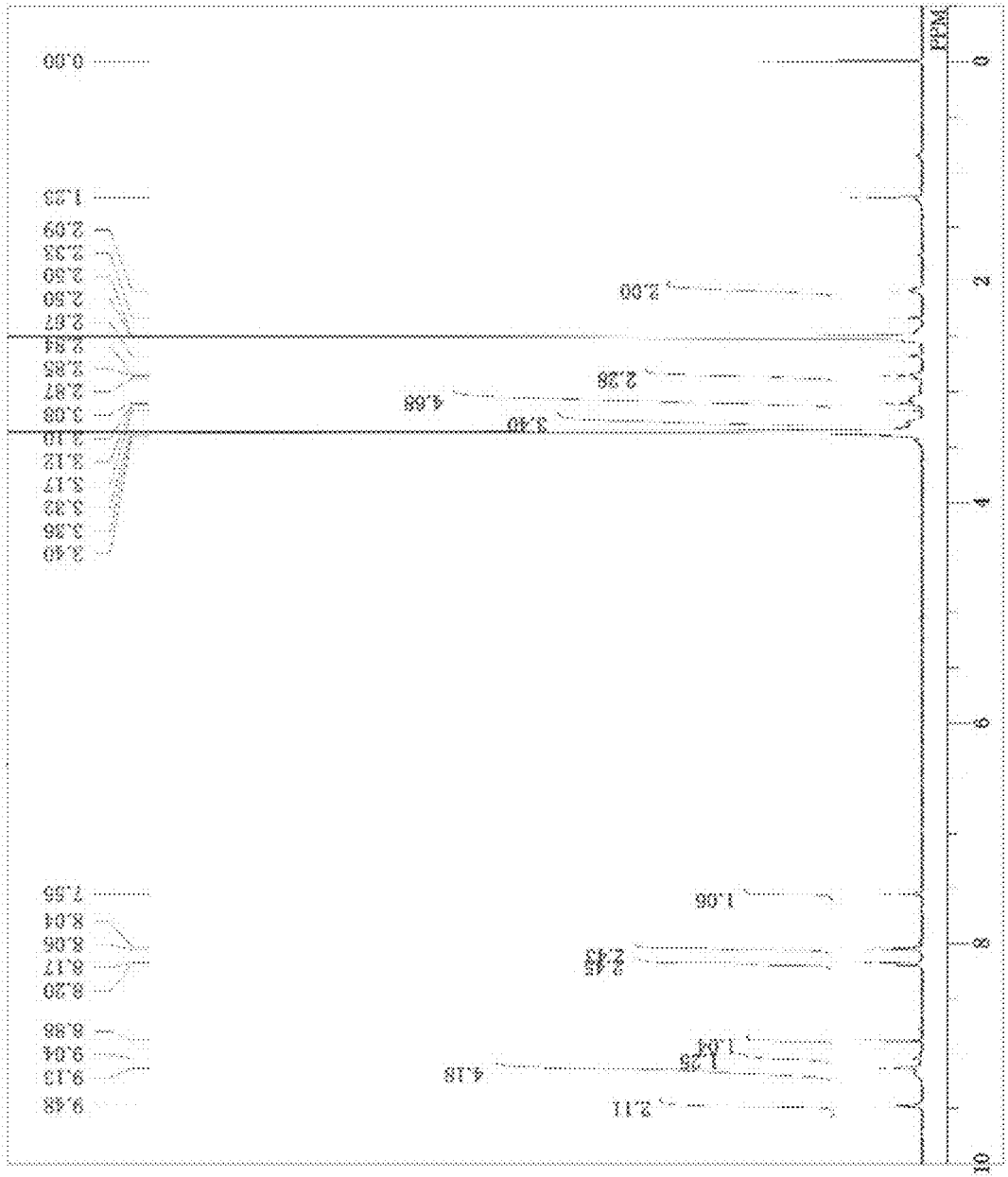
[Figure 17(A)]

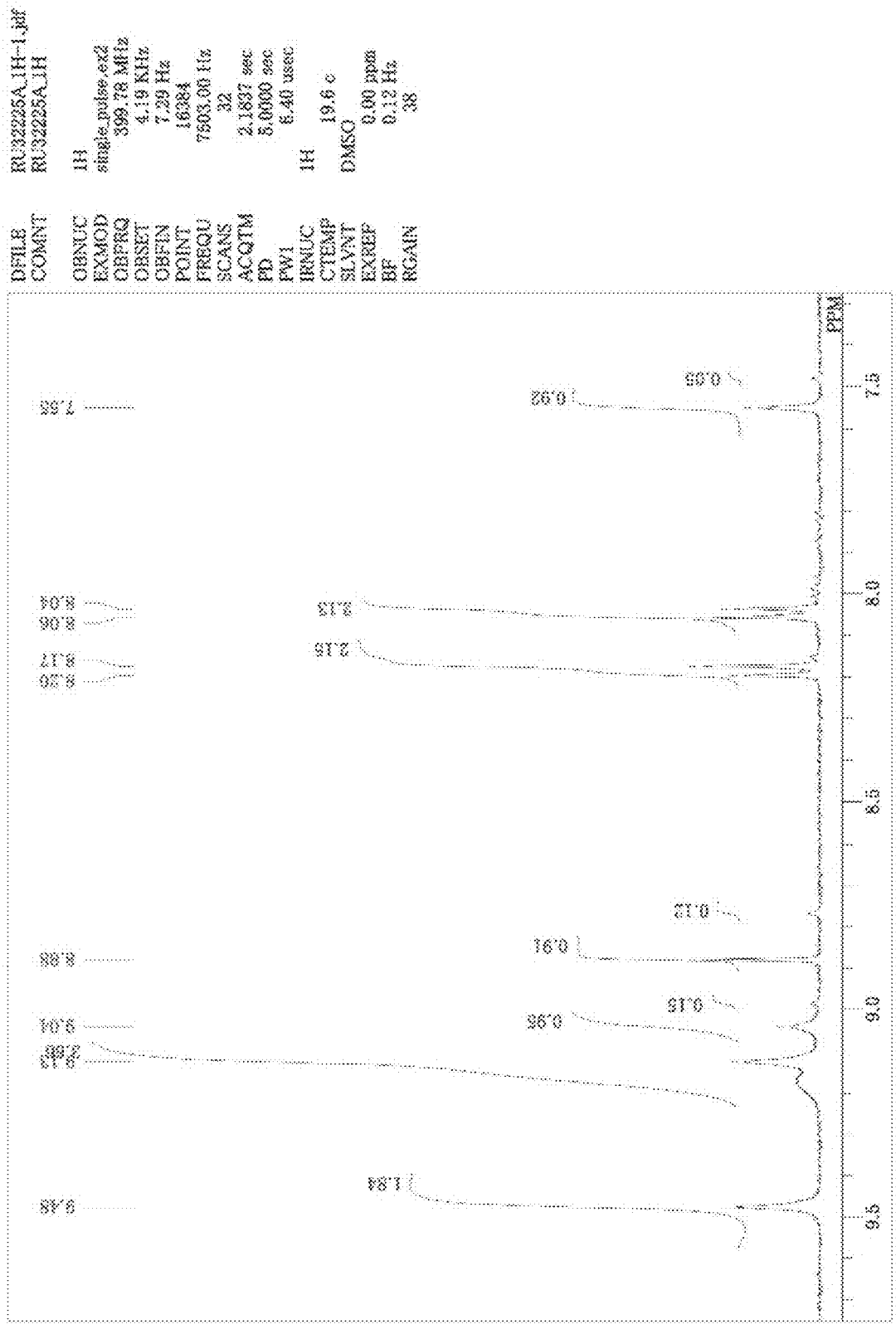
[Figure 17(B)]

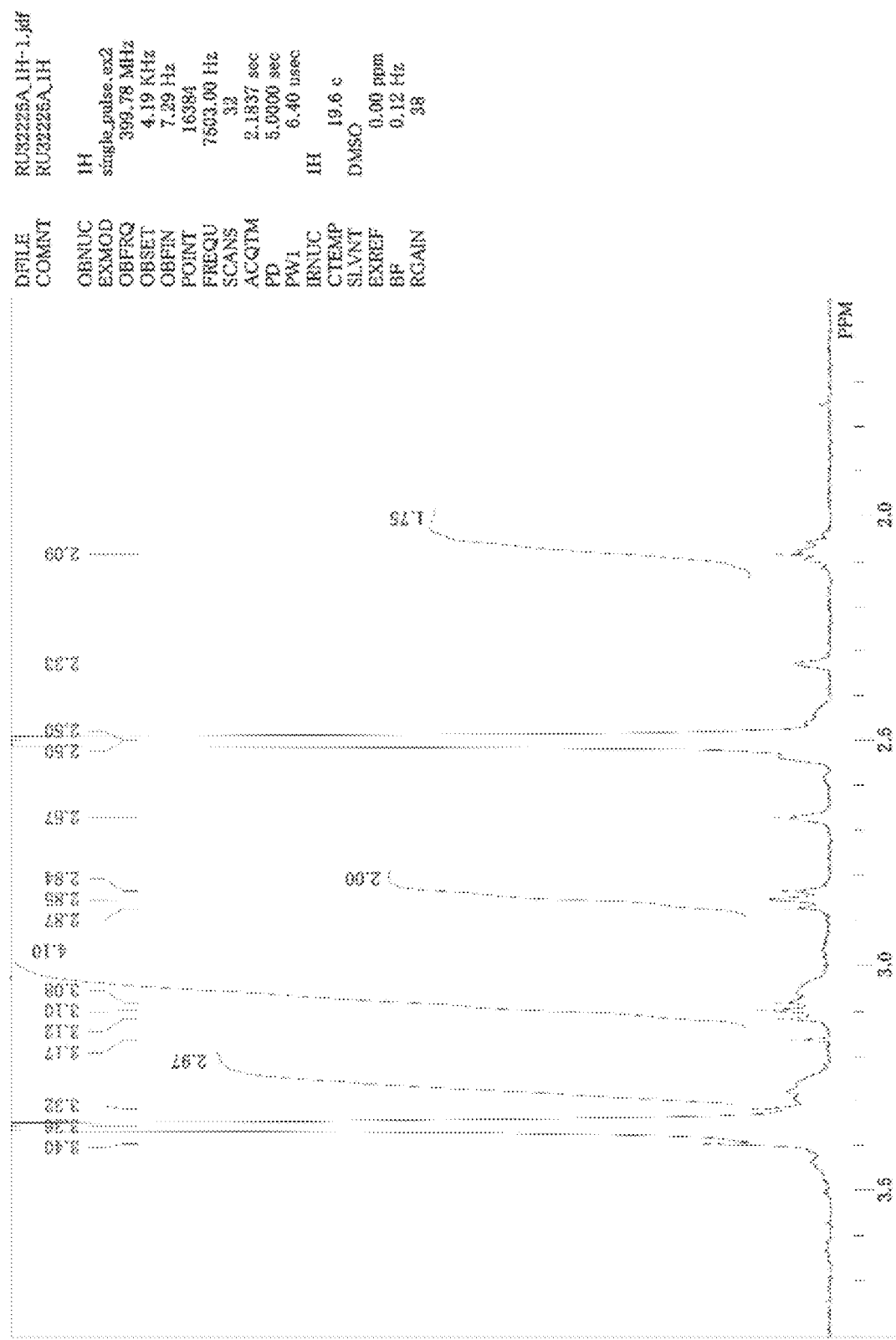
[Figure 17(C)]

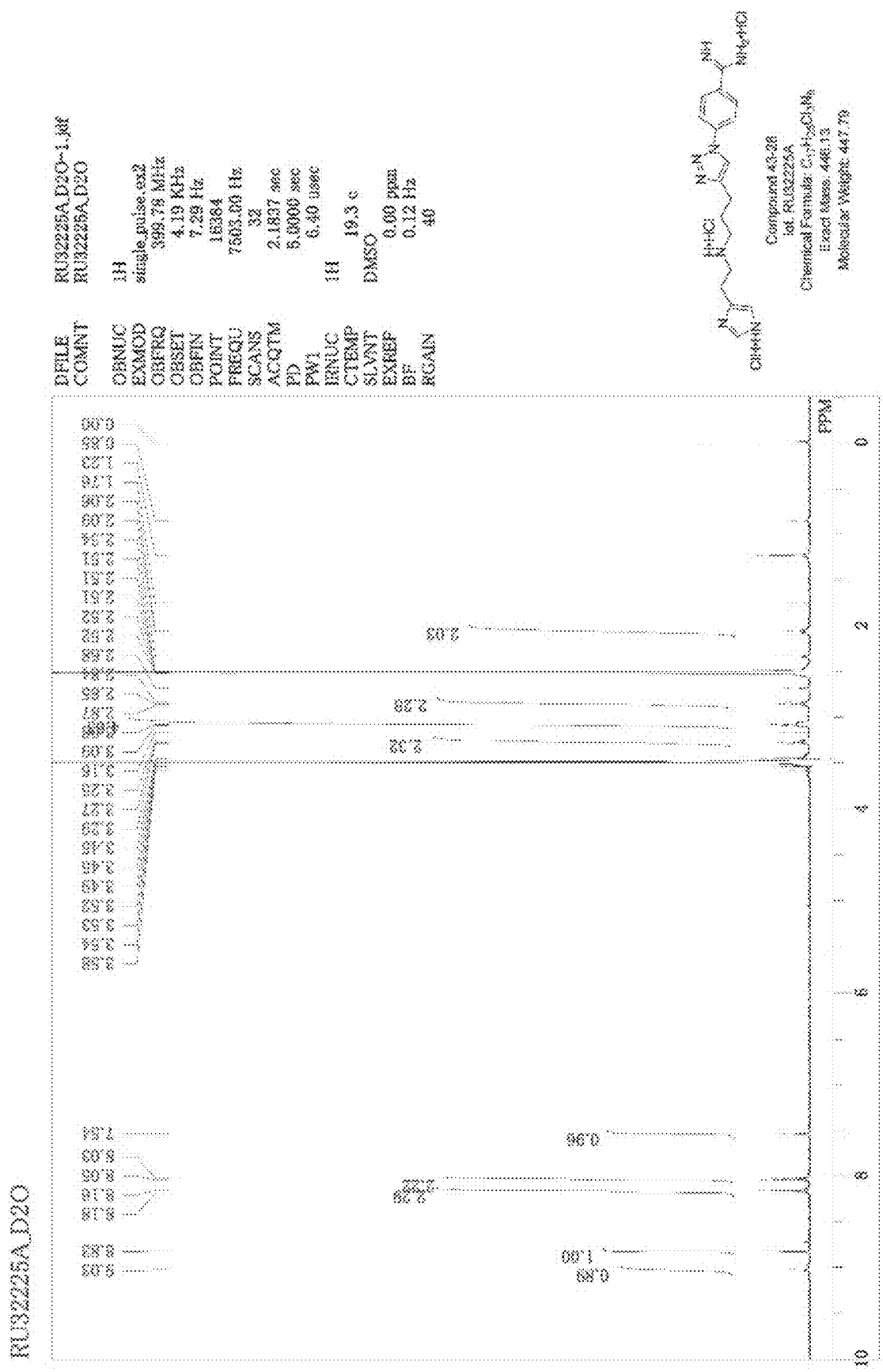
[Figure 17(D)]

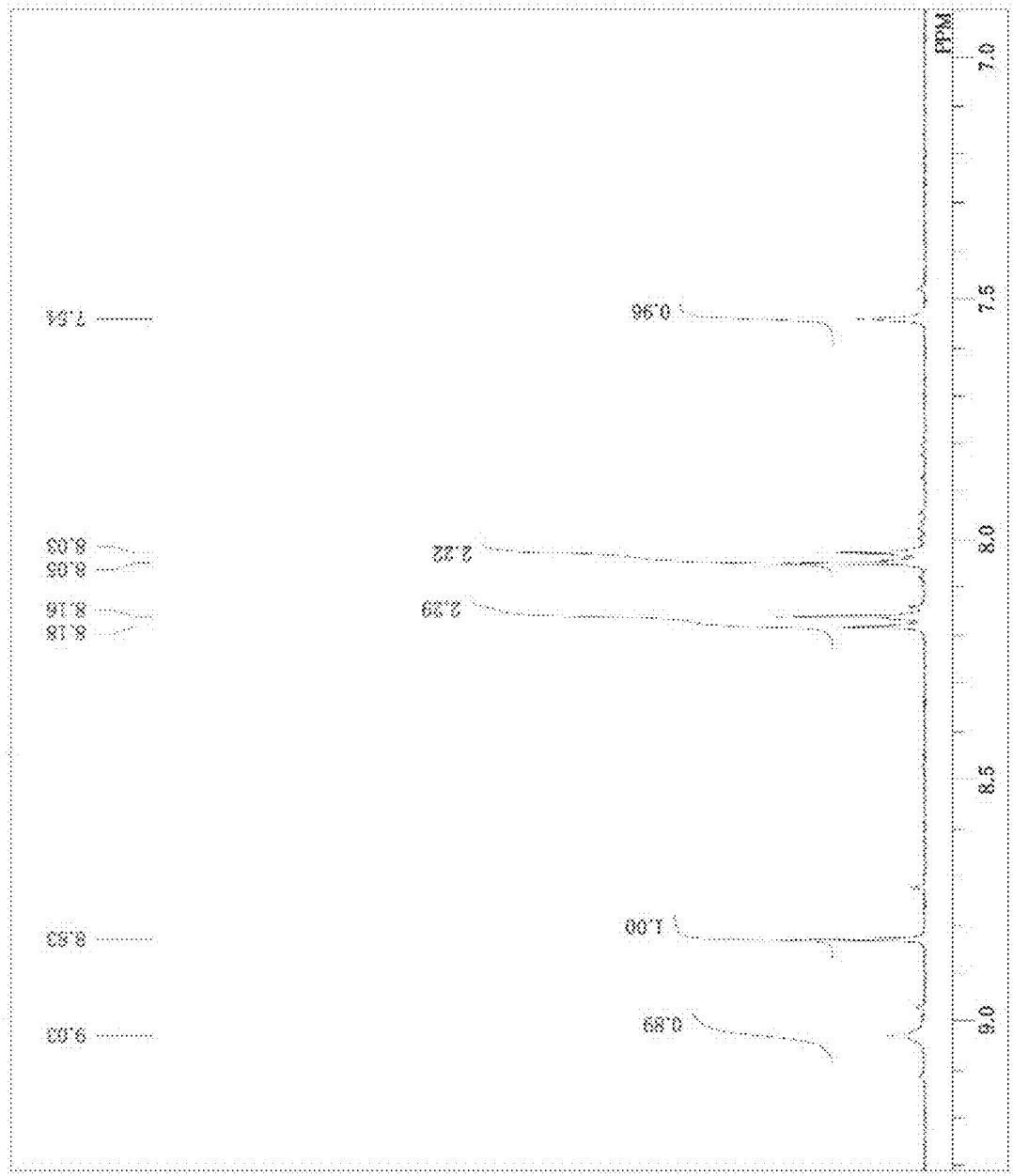
[Figure 17(E)]

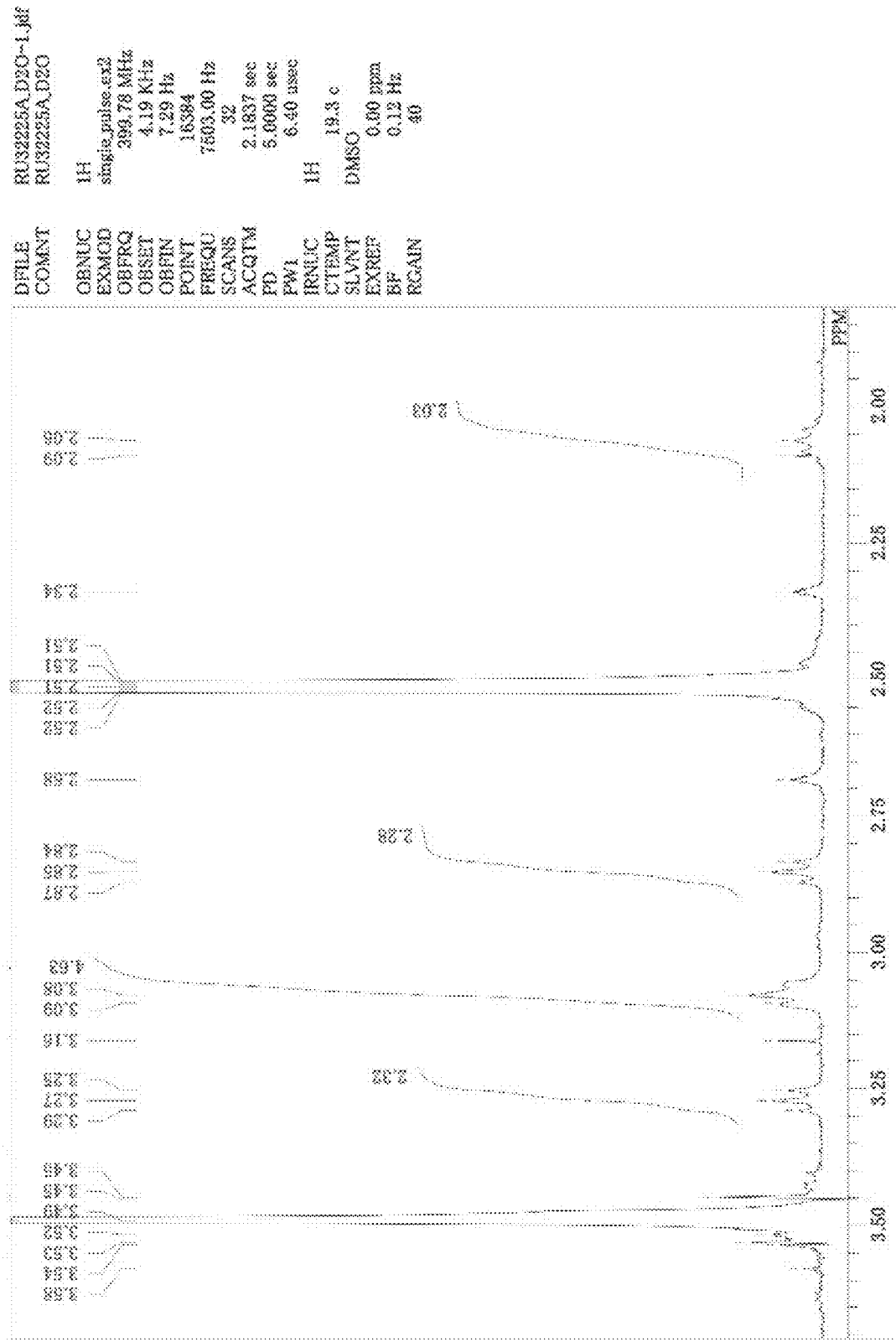
[Figure 17(F)]

[Figure 17(G)]
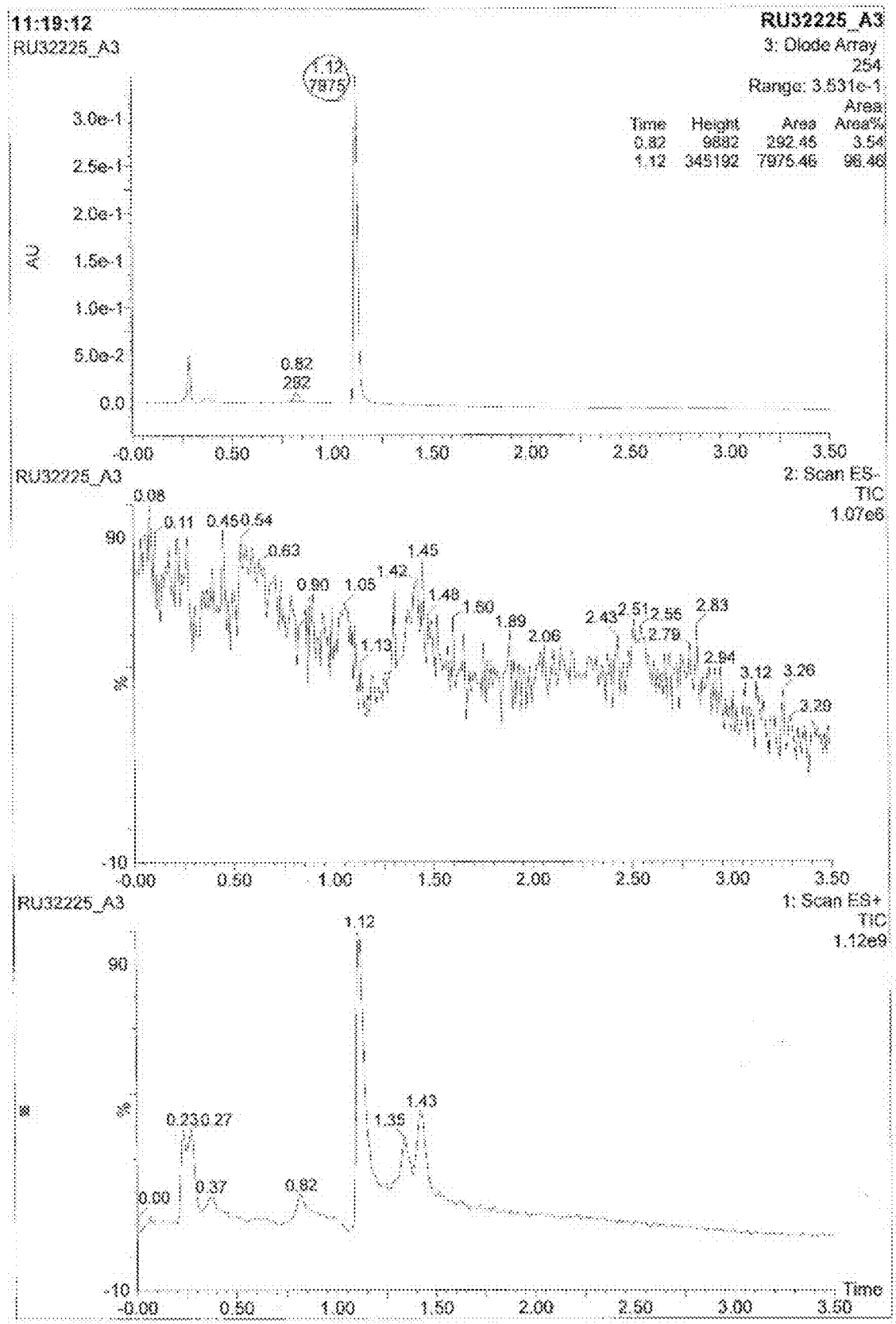

[Figure 17(H)]
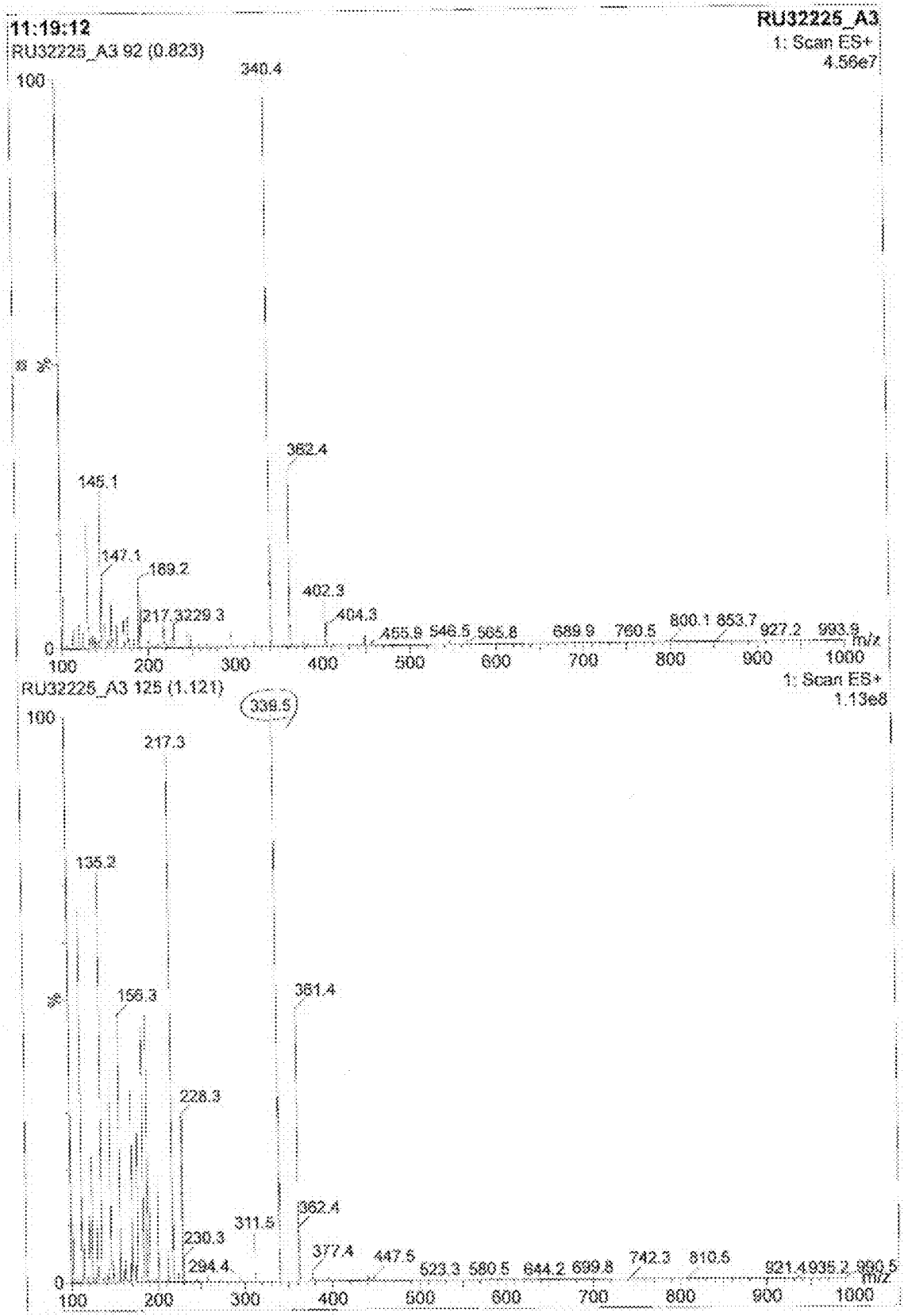

[Figure 18(A)]
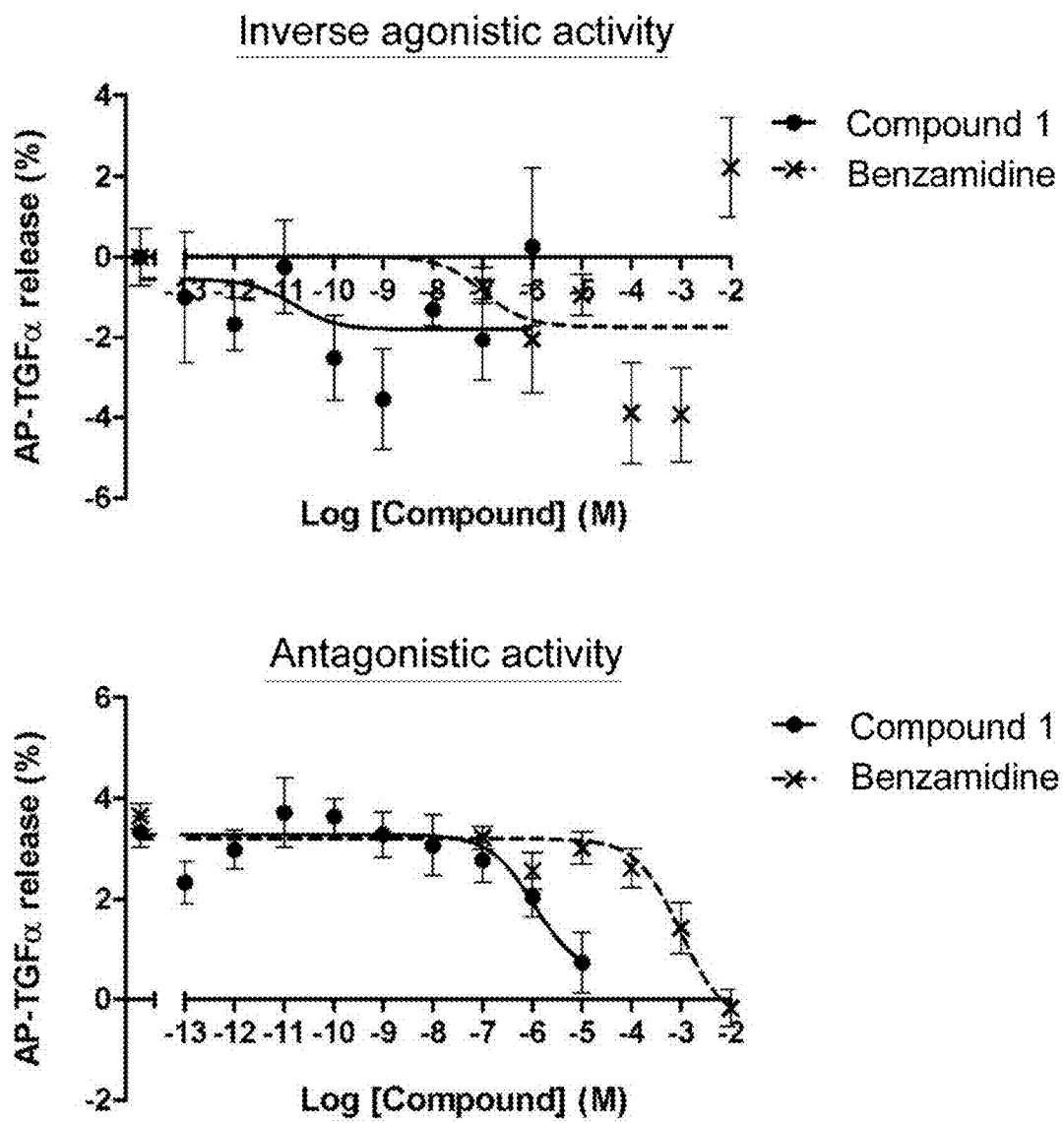

[Figure 18(B)]
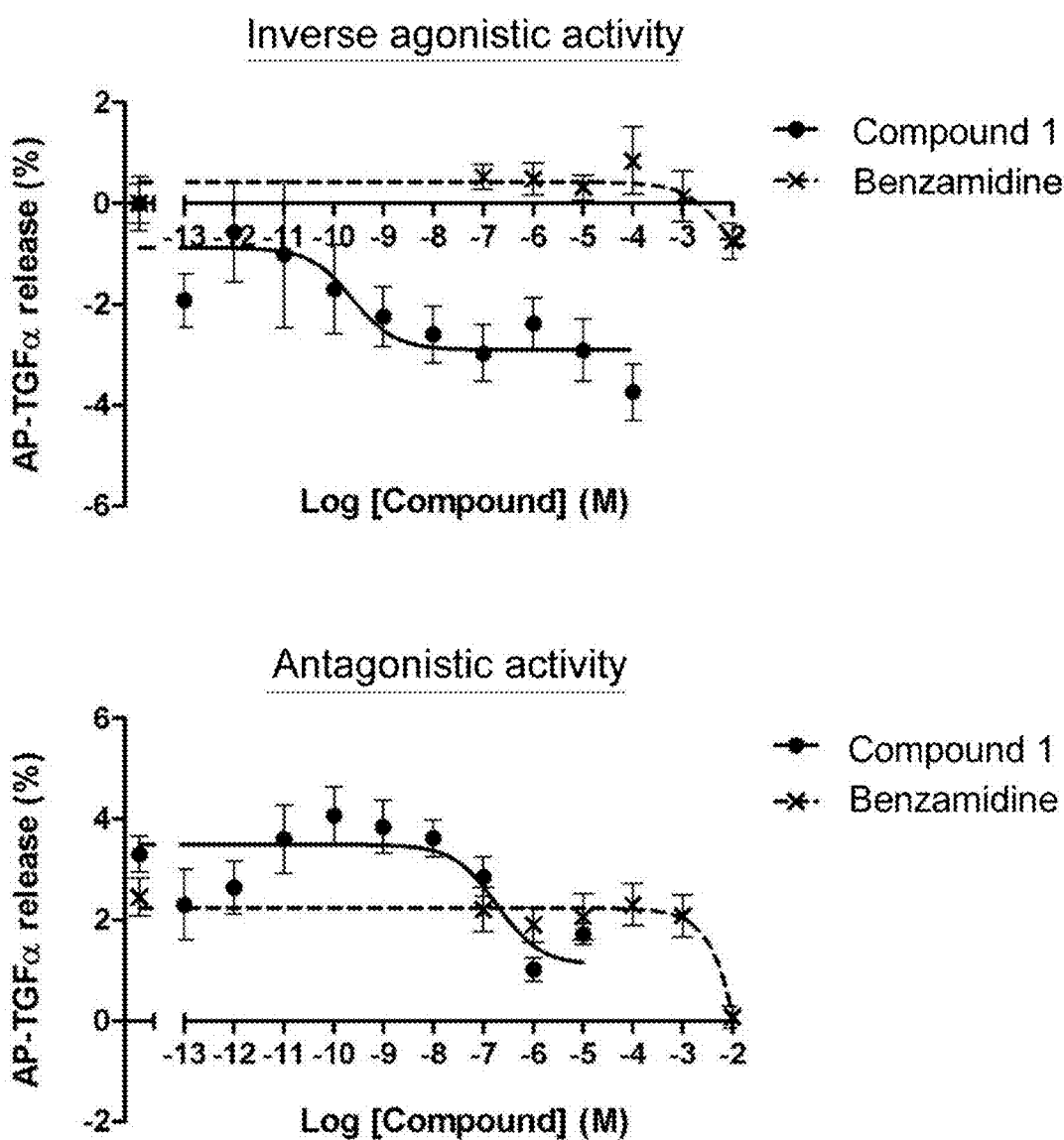

[Figure 18(C)]
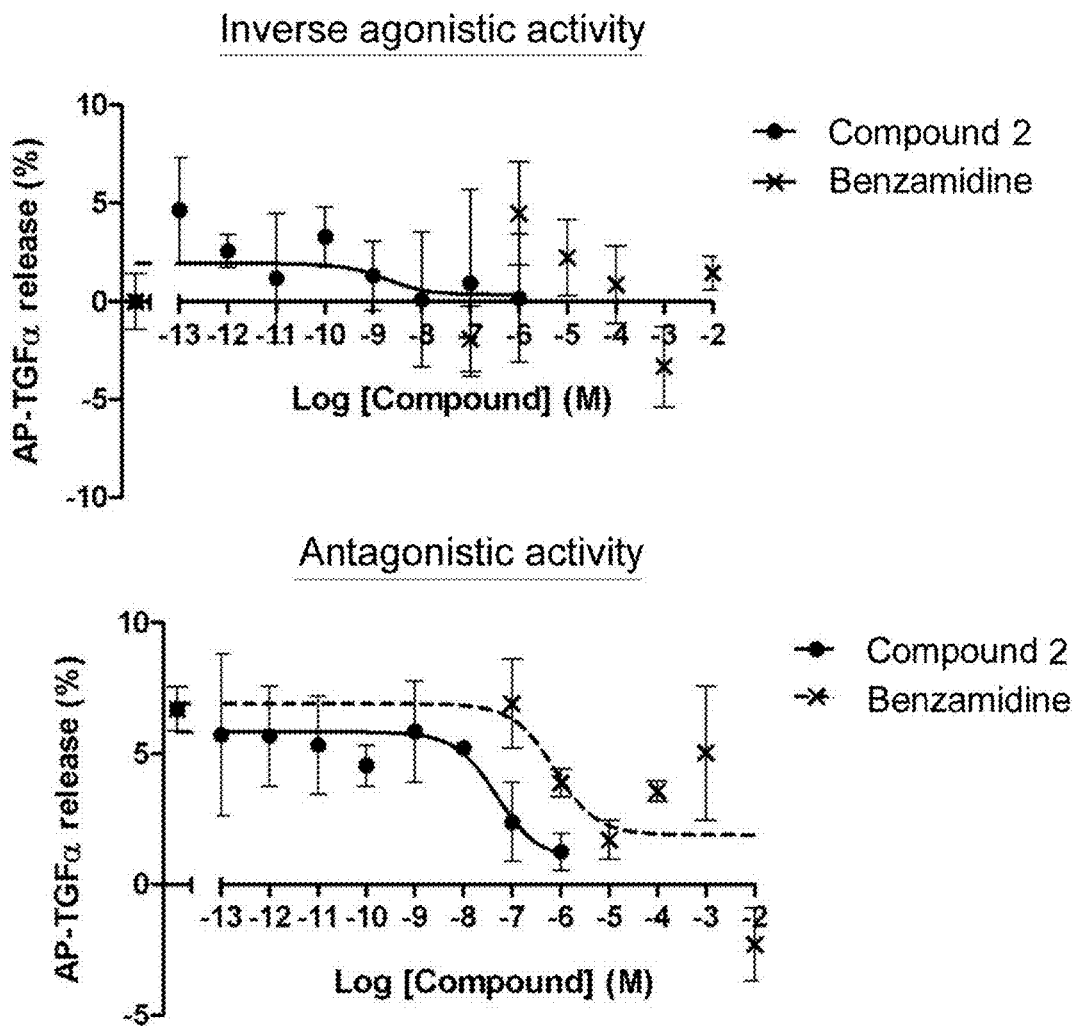

[Figure 18(D)]
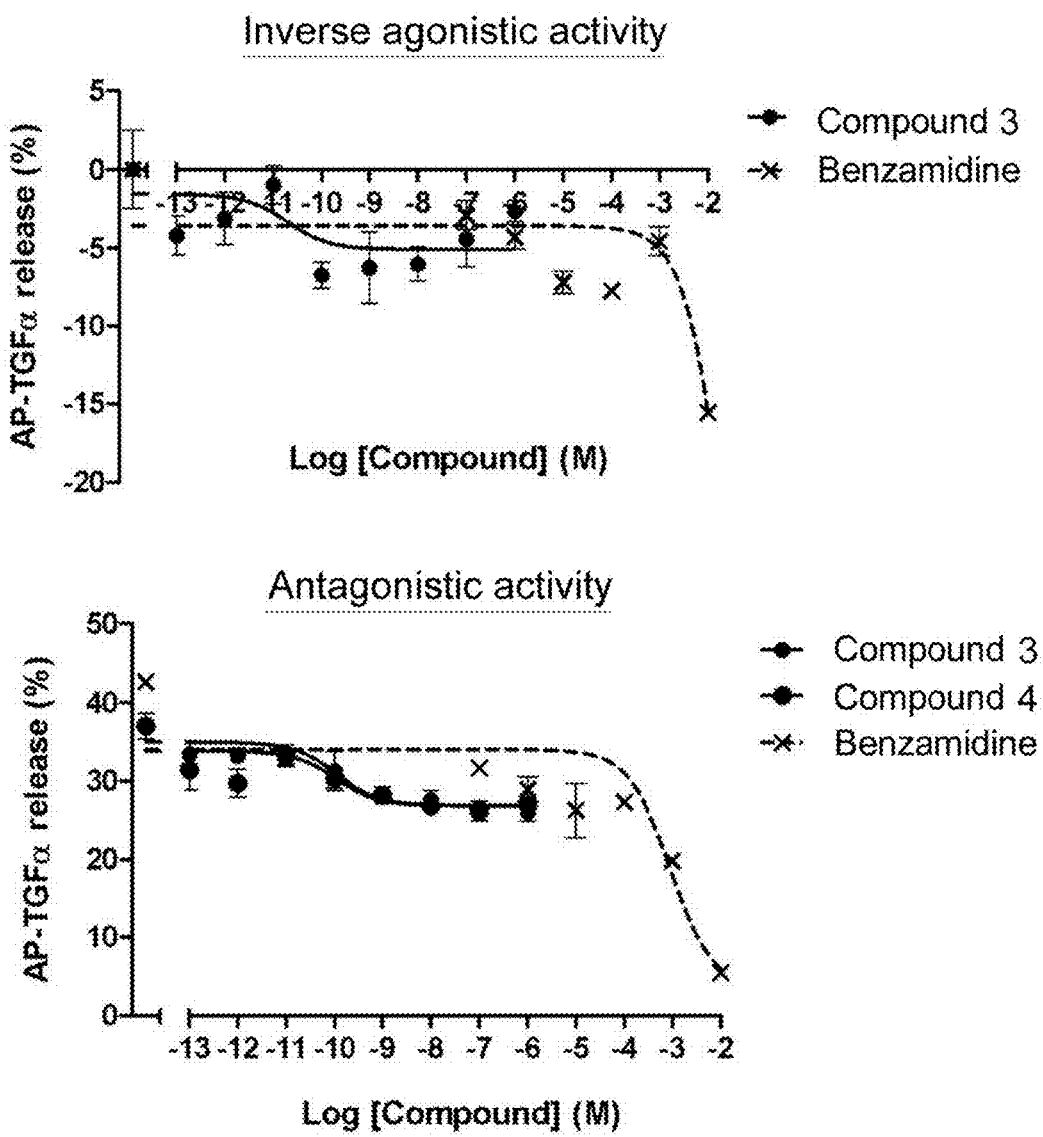

[Figure 18(E)]
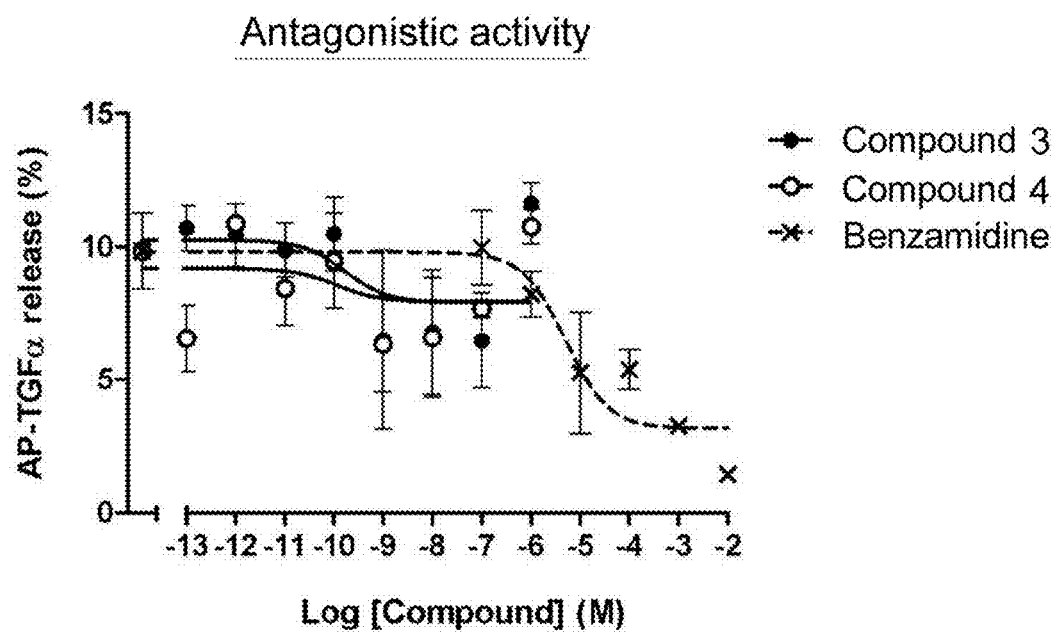

[Figure 18(F)]
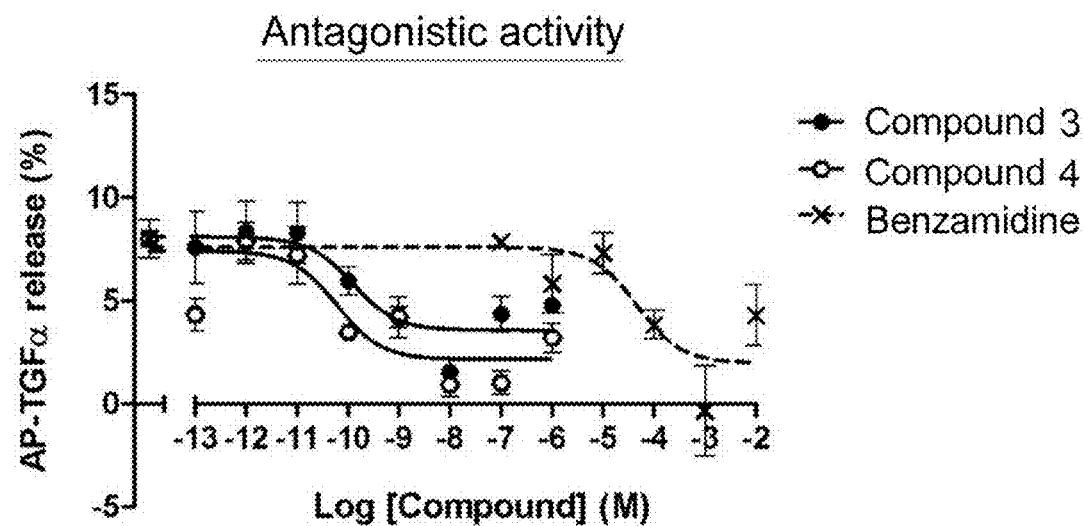

[Figure 19]
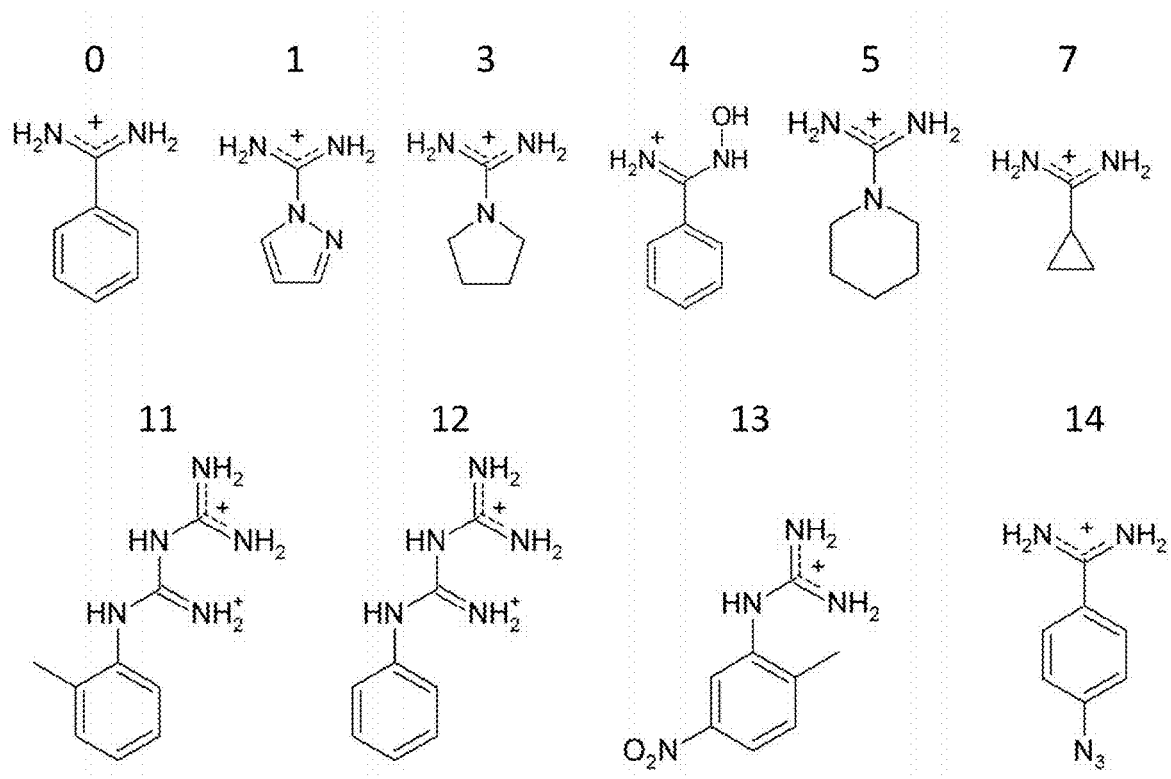

| Serial No | 1 | | | |
|---|---|---|---|---|
| Protein name | Prostaglandin E2 receptor (EP1) | | | |
| | AP-TGFa release (%) | | Normalized to control | |
| Compound | 1 mM | 1 μM | 1 mM | 1 μM |
| 0 | 73.1 ± 1.9 * | 78 ± 1.8 | 0.92 | 0.99 |
| 1 | 74.4 ± 1.2 * | 74.2 ± 0.5 * | 0.94 | 0.94 |
| 3 | 72.5 ± 2.4 * | 75.6 ± 1 | 0.92 | 0.96 |
| 5 | 69 ± 5.9 | 73.2 ± 2.4 * | 0.87 | 0.93 |
| 7 | 72.6 ± 4.3 * | 73.8 ± 2.3 * | 0.92 | 0.93 |
| control | 79.1 ± 2.9 | | 1 | |

| Serial No | 2 | | | |
|---|---|---|---|---|
| Protein name | Oxoglutarate receptor (OXGR1) | | | |
| | AP-TGFa release (%) | | Normalized to control | |
| Compound | 1 mM | 1 μM | 1 mM | 1 μM |
| 0 | 74.9 ± 0.9 * | 83.1 ± 1.3 | 0.92 | 1.02 |
| 1 | 74.3 ± 1.2 * | 81.8 ± 1.2 | 0.91 | 1 |
| 3 | 68.9 ± 2 * | 78 ± 0.5 | 0.85 | 0.96 |
| 5 | 71.3 ± 4.9 | 76.8 ± 0.8 * | 0.88 | 0.94 |
| 7 | 72.6 ± 3.5 * | 75.1 ± 1 * | 0.89 | 0.92 |
| control | 81.4 ± 2.8 | | 1 | |

| Serial No | 3 | | | |
|---|---|---|---|---|
| Protein name | Orphan receptor (GPR119) | | | |
| | AP-TGFa release (%) | | Normalized to control | |
| Compound | 1 mM | 1 μM | 1 mM | 1 μM |
| 1 | 81.5 ± 2.5 * | 86.2 ± 1.3 * | 0.91 | 0.96 |
| control | 89.5 ± 1 | | 1 | |

| Serial No | 4 | | | |
|---|---|---|---|---|
| Protein name | Leukotriene receptors (CysLT1) | | | |
| | AP-TGFa release (%) | | Normalized to control | |
| Compound | 1 mM | 1 μM | 1 mM | 1 μM |
| 0 | 63 ± 2.5 * | 71.3 ± 1.5 | 0.92 | 1.04 |
| 3 | 54.7 ± 2.7 * | 62.7 ± 1.4 * | 0.8 | 0.92 |
| 4 | 63.9 ± 0.9 * | 63.3 ± 1.7 * | 0.93 | 0.92 |
| 5 | 58.5 ± 4.1 * | 65.6 ± 1.4 | 0.85 | 0.96 |
| control | 68.5 ± 2.7 | | 1 | |

| Serial No | 5 | | | |
|---|---|---|---|---|
| Protein name | Free fatty acid receptors (FFAT2) | | | |
| | AP-TGFa release (%) | | Normalized to control | |
| Compound | 1 mM | 1 μM | 1 mM | 1 μM |
| 5 | 77 ± 0.8 * | 80.6 ± 2.7 | 0.88 | 0.93 |
| control | 87.1 ± 4.7 | | 1 | |

| Serial No | 6 | | | |
|---|---|---|---|---|
| Protein name | Orphan receptor (G2A) | | | |
| | AP-TGFa release (%) | | Normalized to control | |
| Compound | 1 mM | 1 μM | 1 mM | 1 μM |
| 5 | 70.3 ± 5.4 | 74.9 ± 4.7 | 0.92 | 0.98 |
| 7 | 72.2 ± 0.6 * | 73.6 ± 0.3 | 0.95 | 0.97 |
| control | 76.2 ± 2 | | 1 | |

| Serial No | 7 | | | |
|---|---|---|---|---|
| Protein name | P2Y receptors (P2Y2) | | | |
| | AP-TGFa release (%) | | Normalized to control | |
| Compound | 1 mM | 1 μM | 1 mM | 1 μM |
| 3 | 68.3 ± 0.9 * | 78.2 ± 4.2 | 0.92 | 1.05 |
| 5 | 63.6 ± 5 | 72.7 ± 0.7 | 0.85 | 0.98 |
| 7 | 69 ± 1.6 * | 71.8 ± 0.9 | 0.93 | 0.96 |
| control | 74.5 ± 2.9 | | 1 | |

| Serial No | 8 | | | |
|---|---|---|---|---|
| Protein name | P2Y receptors (P2Y4) | | | |
| | AP-TGFa release (%) | | Normalized to control | |
| Compound | 1 mM | 1 μM | 1 mM | 1 μM |
| 0 | 56.8 ± 1 * | 66.5 ± 1.7 | 0.83 | 0.97 |
| 3 | 57.2 ± 3.6 * | 65.7 ± 2.8 | 0.84 | 0.96 |
| 7 | 58.7 ± 4 * | 61.7 ± 2.8 | 0.86 | 0.9 |
| control | 68.4 ± 4.4 | | 1 | |

| Serial No | 9 | | | |
|---|---|---|---|---|
| Protein name | Tachykinin receptors (NK2) | | | |
| | AP-TGFa release (%) | | Normalized to control | |
| Compound | 1 mM | 1 μM | 1 mM | 1 μM |
| 3 | 59.2 ± 3.9 * | 66.7 ± 0.5 | 0.83 | 0.94 |
| 5 | 62.6 ± 5.8 * | 64.5 ± 3.9 * | 0.88 | 0.91 |
| 7 | 64.2 ± 3.3 * | 68.5 ± 6.6 | 0.9 | 0.96 |
| control | 71.2 ± 3.6 | | 1 | |

| Serial No | 10 | | | |
|---|---|---|---|---|
| Protein name | P2Y receptors (P2Y6) | | | |
| | AP-TGFa release (%) | | Normalized to control | |
| Compound | 1 mM | 1 μM | 1 mM | 1 μM |
| 0 | 75.5 ± 0.4 * | 83.9 ± 3 | 0.92 | 1.03 |
| 1 | 73.2 ± 2.4 | 76 ± 1.9 * | 0.89 | 0.93 |
| 3 | 68.6 ± 3.8 * | 76.3 ± 1.7 * | 0.84 | 0.93 |
| 5 | 68.1 ± 4 * | 72.9 ± 1.1 * | 0.83 | 0.89 |
| 7 | 76.1 ± 1.4 * | 76.2 ± 0.7 * | 0.93 | 0.93 |
| control | 81.9 ± 3.4 | | 1 | |

| Serial No | 11 | | | |
|---|---|---|---|---|
| Protein name | Proteinase-activated receptors (PAR1) | | | |
| | AP-TGFa release (%) | | Normalized to control | |
| Compound | 1 mM | 1 μM | 1 mM | 1 μM |
| 3 | 52.8 ± 0.6 * | 56.9 ± 4.8 | 0.94 | 1.01 |
| 5 | 51.4 ± 0.6 * | 57.7 ± 1.5 | 0.91 | 1.03 |
| control | 56.2 ± 1.6 | | 1 | |

| Serial No | 12 | | | |
|---|---|---|---|---|
| Protein name | Vasopressin receptors (V2) | | | |
| | AP-TGFa release (%) | | Normalized to control | |
| Compound | 1 mM | 1 μM | 1 mM | 1 μM |
| 0 | 38.4 ± 1.2 * | 45.7 ± 2.5 * | 0.76 | 0.91 |
| 1 | 38.8 ± 1.6 * | 41.3 ± 1.2 * | 0.77 | 0.82 |
| 3 | 34.9 ± 1.2 * | 45.4 ± 0.8 * | 0.69 | 0.9 |
| 5 | 35.2 ± 1.4 * | 45.8 ± 1.5 * | 0.7 | 0.91 |
| 7 | 39.5 ± 1.4 * | 44.6 ± 1.6 * | 0.79 | 0.89 |
| control | 50.3 ± 2.1 | | 1 | |

| Serial No | 13 | | | |
|---|---|---|---|---|
| Protein name | Prostanoid receptors (DP) | | | |
| | AP-TGFa release (%) | | Normalized to control | |
| Compound | 1 mM | 1 μM | 1 mM | 1 μM |
| 0 | 59.9 ± 1.9 * | 66 ± 3.6 | 0.88 | 0.97 |
| 1 | 61.6 ± 0.5 * | 66.4 ± 1.8 | 0.9 | 0.98 |
| 3 | 59.9 ± 2.1 * | 68.1 ± 0.6 | 0.88 | 1 |
| 5 | 55.5 ± 3.1 * | 61.9 ± 4.4 * | 0.82 | 0.91 |
| 7 | 63.1 ± 0.3 * | 64.6 ± 0.7 * | 0.93 | 0.95 |
| control | 66.1 ± 1.9 | | 1 | |

| Serial No | 14 | | | |
|---|---|---|---|---|
| Protein name | Prostanoid receptors (FP) | | | |
| | AP-TGFa release (%) | | Normalized to control | |
| Compound | 1 mM | 1 μM | 1 mM | 1 μM |
| 1 | 47.9 ± 2.6 * | 53 ± 1.3 | 0.91 | 1.01 |
| 3 | 40.4 ± 2.1 * | 47.3 ± 3.5 * | 0.77 | 0.9 |
| 5 | 41.1 ± 1.9 * | 50.7 ± 1.2 | 0.78 | 0.97 |
| 7 | 46.1 ± 3.2 * | 49.9 ± 1.9 | 0.88 | 0.95 |
| control | 52.5 ± 2.1 | | 1 | |

| Serial No | 15 | | | |
|---|---|---|---|---|
| Protein name | 5-Hydroxytryptamine receptors (5-HT2A) | | | |
| | AP-TGFa release (%) | | Normalized to control | |
| Compound | 1 mM | 1 μM | 1 mM | 1 μM |
| 1 | 59.2 ± 0.4 * | 63.5 ± 1.1 | 0.95 | 1.01 |
| 3 | 53.5 ± 1.3 * | 63.5 ± 1.5 | 0.85 | 1.01 |
| 5 | 57.9 ± 0.4 * | 61.6 ± 1.5 | 0.93 | 0.98 |
| 7 | 56.5 ± 1.4 * | 57.6 ± 2.3 * | 0.9 | 0.92 |
| control | 62.6 ± 1.8 | | 1 | |

| Serial No | 16 | | | |
|---|---|---|---|---|
| Protein name | Prostanoid receptors (EP2) | | | |
| | AP-TGFa release (%) | | Normalized to control | |
| Compound | 1 mM | 1 μM | 1 mM | 1 μM |
| 3 | 35.6 ± 1.1 * | 49.2 ± 1.3 | 0.79 | 1.09 |
| 5 | 36.8 ± 2.3 * | 45.4 ± 2.2 | 0.81 | 1 |
| control | 45.2 ± 3.8 | | 1 | |

| Serial No | 17 | | | |
|---|---|---|---|---|
| Protein name | Prostanoid receptors (EP4) | | | |
| | AP-TGFa release (%) | | Normalized to control | |
| Compound | 1 mM | 1 μM | 1 mM | 1 μM |
| 0 | 47.2 ± 0.6 * | 54.9 ± 0.4 | 0.86 | 1 |
| 1 | 47.6 ± 0.7 * | 55.6 ± 0.6 | 0.87 | 1.02 |
| 3 | 45.7 ± 1.3 * | 54.7 ± 1.5 | 0.84 | 1 |
| 5 | 46.3 ± 0.8 * | 52.5 ± 1.2 | 0.85 | 0.96 |
| 7 | 49.3 ± 3.5 * | 51.9 ± 1.6 | 0.9 | 0.95 |
| control | 54.7 ± 2.6 | | 1 | |

| Serial No | 18 | | | |
|---|---|---|---|---|
| Protein name | Vasopressin receptors (V1B) | | | |
| | AP-TGFa release (%) | | Normalized to control | |
| Compound | 1 mM | 1 μM | 1 mM | 1 μM |
| 3 | 39.4 ± 1.6 * | 48.8 ± 1.4 * | 0.8 | 0.99 |
| 5 | 40.4 ± 2.2 * | 47.4 ± 1.3 * | 0.82 | 0.96 |
| control | 49.4 ± 1.4 | | 1 | |

| Serial No | 19 | | | |
|---|---|---|---|---|
| Protein name | Vasopressin receptors (V1A) | | | |
| | AP-TGFa release (%) | | Normalized to control | |
| Compound | 1 mM | 1 μM | 1 mM | 1 μM |
| 1 | 42.7 ± 0.5 * | 46.8 ± 1.1 | 0.92 | 1.01 |
| 3 | 35.5 ± 2 * | 45 ± 0.7 | 0.76 | 0.97 |
| 5 | 36.2 ± 1.5 * | 43.6 ± 1.4 | 0.78 | 0.94 |
| control | 46.5 ± 2.3 | | 1 | |

| Serial No | 20 | | | |
|---|---|---|---|---|
| Protein name | Adrenergic receptors (α1A) | | | |
| | AP-TGFa release (%) | | Normalized to control | |
| Compound | 1 mM | 1 μM | 1 mM | 1 μM |
| 3 | 40.1 ± 2 * | 45.9 ± 1.1 | 0.84 | 0.97 |
| 5 | 39.1 ± 2.6 * | 44.6 ± 2.9 | 0.82 | 0.94 |
| control | 47.5 ± 1.4 | | 1 | |

| Serial No | 21 | | | |
|---|---|---|---|---|
| Protein name | 5-Hydroxytryptamine receptors (5-HT4) | | | |
| | AP-TGFa release (%) | | Normalized to control | |
| Compound | 1 mM | 1 μM | 1 mM | 1 μM |
| 0 | 44.8 ± 0.9 * | 46.9 ± 0.3 | 0.93 | 0.98 |
| 3 | 35.4 ± 1.5 * | 46.9 ± 2.5 | 0.74 | 0.98 |
| 5 | 37.8 ± 0.8 * | 46.2 ± 1.4 | 0.79 | 0.96 |
| 7 | 43.5 ± 0.3 * | 46.9 ± 0.2 | 0.91 | 0.98 |
| control | 48 ± 1.9 | | 1 | |

| Serial No | 22 | | | |
|---|---|---|---|---|
| Protein name | Cannabinoid receptors (CB2) | | | |
| | AP-TGFa release (%) | | Normalized to control | |
| Compound | 1 mM | 1 μM | 1 mM | 1 μM |
| 0 | 62.8 ± 1.1 * | 65.9 ± 0.4 * | 0.89 | 0.93 |
| 1 | 62.4 ± 0.9 * | 67.6 ± 0.7 | 0.88 | 0.96 |
| 3 | 63.2 ± 1.6 * | 67.9 ± 2.2 | 0.89 | 0.96 |
| 5 | 64.3 ± 1.7 * | 67.7 ± 1 | 0.91 | 0.96 |
| 7 | 64.7 ± 2.1 * | 69.9 ± 1.4 | 0.92 | 0.99 |
| control | 70.7 ± 0.9 | | 1 | |

| Serial No | 23 | | | |
|---|---|---|---|---|
| Protein name | Class A Orphans (EBI2) | | | |
| | AP-TGFa release (%) | | Normalized to control | |
| Compound | 1 mM | 1 μM | 1 mM | 1 μM |
| 0 | 63.1 ± 0.5 * | 71.1 ± 1.7 * | 0.81 | 0.91 |
| 1 | 67.6 ± 0.6 * | 72.5 ± 2.4 * | 0.87 | 0.93 |
| 3 | 62.8 ± 1 * | 73.3 ± 2.3 * | 0.8 | 0.94 |
| 5 | 64.5 ± 0.9 * | 73.1 ± 1 * | 0.83 | 0.94 |
| 7 | 68.6 ± 0.8 * | 74.4 ± 1.3 * | 0.88 | 0.95 |
| control | 78.1 ± 1.6 | | 1 | |

| Serial No | 24 | | | |
|---|---|---|---|---|
| Protein name | Leukotriene receptors (BLT2) | | | |
| | AP-TGFa release (%) | | Normalized to control | |
| Compound | 1 mM | 1 μM | 1 mM | 1 μM |
| 0 | 56.2 ± 0.9 * | 57.1 ± 0.7 * | 0.89 | 0.91 |
| 1 | 54.7 ± 1 * | 60 ± 0.6 | 0.87 | 0.95 |
| 3 | 49.2 ± 0.9 * | 59.9 ± 3 | 0.78 | 0.95 |
| 5 | 51.6 ± 1.4 * | 58.2 ± 1.7 * | 0.82 | 0.92 |
| 7 | 54.8 ± 0.7 * | 58.8 ± 0.8 * | 0.87 | 0.93 |
| control | 63 ± 2.4 | | 1 | |

| Serial No | 25 | | | |
|---|---|---|---|---|
| Protein name | 5-Hydroxytryptamine receptors (5-HT1A) | | | |
| | AP-TGFa release (%) | | Normalized to control | |
| Compound | 1 mM | 1 μM | 1 mM | 1 μM |
| 0 | 43.1 ± 0.2 * | 50.1 ± 0.3 | 0.87 | 1.01 |
| 3 | 43.2 ± 0.4 * | 51.5 ± 0.3 | 0.87 | 1.04 |
| 5 | 42.3 ± 0.2 * | 50.3 ± 2.6 | 0.86 | 1.02 |
| 7 | 41.7 ± 1.5 * | 47.8 ± 1.8 | 0.85 | 0.97 |
| control | 49.4 ± 2.2 | | 1 | |

| Serial No | 26 | | | |
|---|---|---|---|---|
| Protein name | 5-Hydroxytryptamine receptors (5-HT1D) | | | |
| | AP-TGFa release (%) | | Normalized to control | |
| Compound | 1 mM | 1 μM | 1 mM | 1 μM |
| 0 | 70.2 ± 1.1 * | 72.6 ± 1.6 * | 0.88 | 0.91 |
| 1 | 71.9 ± 1.5 * | 78.3 ± 2.3 | 0.9 | 0.98 |
| 3 | 71 ± 2.5 * | 75.6 ± 1 * | 0.89 | 0.94 |
| 4 | 76.2 ± 1.1 * | 76.1 ± 1.5 * | 0.95 | 0.95 |
| 5 | 70.5 ± 2.1 * | 76.5 ± 1.3 * | 0.88 | 0.95 |
| 7 | 75.5 ± 0.6 * | 75.6 ± 0.3 * | 0.94 | 0.94 |
| control | 80.1 ± 1.5 | | 1 | |

| Serial No | 27 | | | |
|---|---|---|---|---|
| Protein name | Adrenergic receptors (α1D) | | | |
| | AP-TGFa release (%) | | Normalized to control | |
| Compound | 1 mM | 1 μM | 1 mM | 1 μM |
| 0 | 47.3 ± 0.3 * | 50.7 ± 1.7 | 0.94 | 1 |
| 1 | 46.4 ± 0.7 * | 53.3 ± 0.3 * | 0.92 | 1.05 |
| 3 | 40.2 ± 1.5 * | 52.2 ± 0.8 | 0.79 | 1.03 |
| 5 | 40.4 ± 0.6 * | 51.2 ± 1.3 | 0.8 | 1.01 |
| 7 | 47.2 ± 1 * | 51.9 ± 1.2 | 0.93 | 1.03 |
| control | 50.6 ± 1.4 | | 1 | |

| Serial No | 28 | | | |
|---|---|---|---|---|
| Protein name | Proteinase-activated receptors (PAR3) | | | |
| | AP-TGFa release (%) | | Normalized to control | |
| Compound | 1 mM | 1 μM | 1 mM | 1 μM |
| 1 | 57.1 ± 3 * | 61.6 ± 2.1 * | 0.93 | 1 |
| 3 | 52.3 ± 1.5 * | 62.6 ± 1 * | 0.85 | 1.02 |
| 5 | 56.3 ± 2 * | 59.6 ± 1.3 * | 0.92 | 0.97 |
| 7 | 55.7 ± 2.4 * | 59.4 ± 0.6 * | 0.91 | 0.97 |
| control | 61.3 ± 2.1 | | 1 | |

| Serial No | 29 | | | |
|---|---|---|---|---|
| Protein name | P2Y receptors (P2Y13) | | | |
| | AP-TGFa release (%) | | Normalized to control | |
| Compound | 1 mM | 1 μM | 1 mM | 1 μM |
| 0 | 48 ± 1.1 * | 58.6 ± 1.8 | 0.79 | 0.97 |
| 1 | 53 ± 1.7 * | 59.1 ± 1.2 | 0.87 | 0.97 |
| 3 | 45 ± 1 * | 61.8 ± 2.8 | 0.74 | 1.02 |
| 5 | 46.9 ± 2.2 * | 58.5 ± 1 | 0.77 | 0.96 |
| control | 60.6 ± 1.8 | | 1 | |

| Serial No | 30 | | | |
|---|---|---|---|---|
| Protein name | P2Y receptors (P2Y12) | | | |
| | AP-TGFa release (%) | | Normalized to control | |
| Compound | 1 mM | 1 μM | 1 mM | 1 μM |
| 0 | 53.3 ± 2.2 * | 60.5 ± 0.8 | 0.87 | 0.98 |
| 3 | 49 ± 1.6 * | 61.8 ± 1.6 | 0.8 | 1.01 |
| 5 | 51 ± 1.8 * | 61.2 ± 0.3 | 0.83 | 1 |
| 7 | 53.2 ± 0.6 * | 61.3 ± 2.4 | 0.87 | 1 |
| control | 61.4 ± 2.6 | | 1 | |

| Serial No | 31 | | | |
|---|---|---|---|---|
| Protein name | P2Y receptors (P2Y14) | | | |
| | AP-TGFa release (%) | | Normalized to control | |
| Compound | 1 mM | 1 μM | 1 mM | 1 μM |
| 0 | 61.3 ± 0.7 * | 68.6 ± 2 * | 0.81 | 0.91 |
| 1 | 62.9 ± 1.4 * | 70.2 ± 1.2 | 0.83 | 0.93 |
| 3 | 59.8 ± 0.7 * | 70.5 ± 2 | 0.79 | 0.93 |
| 5 | 59.7 ± 0.4 * | 74.2 ± 1.2 | 0.79 | 0.98 |
| 7 | 66.4 ± 0.7 * | 70.3 ± 2.6 * | 0.88 | 0.93 |
| control | 75.5 ± 1.7 | | 1 | |

| Serial No | 32 | | | |
|---|---|---|---|---|
| Protein name | Free fatty acid receptors (FFA3) | | | |
| | AP-TGFa release (%) | | Normalized to control | |
| Compound | 1 mM | 1 μM | 1 mM | 1 μM |
| 0 | 34.8 ± 0.6 * | 41.4 ± 0.9 * | 0.75 | 0.9 |
| 1 | 38.8 ± 0.9 * | 43.3 ± 3 | 0.84 | 0.94 |
| 3 | 35.5 ± 2.1 * | 42.8 ± 0.3 * | 0.77 | 0.93 |
| 5 | 36.1 ± 2.9 * | 41.8 ± 0.7 * | 0.78 | 0.91 |
| 7 | 36.6 ± 0.8 * | 43.7 ± 0.8 * | 0.79 | 0.95 |
| control | 46.2 ± 1.5 | | 1 | |

| Serial No | 33 | | | |
|---|---|---|---|---|
| Protein name | Opioid receptors (NOP) | | | |
| | AP-TGFa release (%) | | Normalized to control | |
| Compound | 1 mM | 1 μM | 1 mM | 1 μM |
| 0 | 56.6 ± 1.4 * | 59.8 ± 1 * | 0.88 | 0.93 |
| 1 | 58.7 ± 2.6 * | 60.3 ± 1.9 | 0.91 | 0.94 |
| 3 | 58.4 ± 0.7 * | 61.1 ± 1.3 | 0.91 | 0.95 |
| 5 | 59.1 ± 1.1 * | 61.9 ± 2.8 | 0.92 | 0.96 |
| control | 64.4 ± 2.7 | | 1 | |

| Serial No | 34 | | | |
|---|---|---|---|---|
| Protein name | 5-Hydroxytryptamine receptors (5-HT1E) | | | |
| | AP-TGFa release (%) | | Normalized to control | |
| Compound | 1 mM | 1 μM | 1 mM | 1 μM |
| 0 | 52.3 ± 1.5 * | 57.9 ± 0.9 | 0.89 | 0.98 |
| 1 | 54.9 ± 0.8 * | 56.5 ± 0.6 * | 0.93 | 0.96 |
| 3 | 51.7 ± 1.6 * | 55 ± 2.7 * | 0.88 | 0.93 |
| 5 | 49.8 ± 1.3 * | 56.5 ± 1.9 * | 0.85 | 0.96 |
| 7 | 51.7 ± 0.1 * | 56.8 ± 0.6 * | 0.88 | 0.96 |
| control | 58.9 ± 0.7 | | 1 | |

| Serial No | 35 | | | |
|---|---|---|---|---|
| Protein name | Class A Orphans (GPR84) | | | |
| | AP-TGFa release (%) | | Normalized to control | |
| Compound | 1 mM | 1 μM | 1 mM | 1 μM |
| 0 | 52.8 ± 0.5 * | 57 ± 1.4 * | 0.83 | 0.9 |
| 1 | 54 ± 0.6 * | 56.3 ± 1.9 * | 0.85 | 0.89 |
| 3 | 48.4 ± 0.2 * | 56.1 ± 2.4 * | 0.76 | 0.89 |
| 5 | 51.5 ± 1 * | 59.1 ± 1.6 * | 0.81 | 0.93 |
| 7 | 56.6 ± 1 * | 62.1 ± 1.6 * | 0.89 | 0.98 |
| control | 63.4 ± 1.2 | | 1 | |

| Serial No | 36 | | | |
|---|---|---|---|---|
| Protein name | Proteinase-activated receptors (PAR4) | | | |
| | AP-TGFa release (%) | | Normalized to control | |
| Compound | 1 mM | 1 μM | 1 mM | 1 μM |
| 0 | 63.3 ± 1.3 * | 63.7 ± 0 * | 0.89 | 0.9 |
| 1 | 65.7 ± 1.6 * | 67.2 ± 2.6 | 0.92 | 0.94 |
| 3 | 63.1 ± 0.7 * | 68.8 ± 2.3 | 0.89 | 0.97 |
| 5 | 62.5 ± 2.2 * | 64.7 ± 0.3 * | 0.88 | 0.91 |
| 7 | 67.2 ± 0.2 * | 68.1 ± 1.2 | 0.94 | 0.96 |
| control | 71.2 ± 1.9 | | 1 | |

| Serial No | 37 | | | |
|---|---|---|---|---|
| Protein name | Opioid receptors (κ OR) | | | |
| | AP-TGFa release (%) | | Normalized to control | |
| Compound | 1 mM | 1 μM | 1 mM | 1 μM |
| 0 | 49.9 ± 1.3 * | 53.3 ± 3.2 | 0.92 | 0.98 |
| 1 | 48.9 ± 0.9 * | 54.3 ± 2.1 | 0.9 | 1 |
| 3 | 42.5 ± 0.9 * | 52.9 ± 1.6 | 0.78 | 0.97 |
| 5 | 41.7 ± 1.6 * | 53.6 ± 1.3 | 0.77 | 0.99 |
| 7 | 46 ± 0.9 * | 53.3 ± 2.1 | 0.85 | 0.98 |
| control | 54.3 ± 1.6 | | 1 | |

| Serial No | 38 | | | |
|---|---|---|---|---|
| Protein name | Dopamine receptors (D5) | | | |
| | AP-TGFa release (%) | | Normalized to control | |
| Compound | 1 mM | 1 μM | 1 mM | 1 μM |
| 0 | 70.5 ± 2.1 * | 76.1 ± 2 | 0.93 | 1 |
| 1 | 70.7 ± 0.6 * | 75.3 ± 0.6 | 0.93 | 0.99 |
| 3 | 67.4 ± 1.1 * | 73.9 ± 1.9 | 0.89 | 0.98 |
| 5 | 66.3 ± 3.2 * | 74.2 ± 1.5 | 0.88 | 0.98 |
| 7 | 71.3 ± 1.2 * | 76.5 ± 0.5 | 0.94 | 1.01 |
| control | 75.7 ± 1.7 | | 1 | |

| Serial No | 39 | | | |
|---|---|---|---|---|
| Protein name | Adenosine receptors (A3) | | | |
| | AP-TGFa release (%) | | Normalized to control | |
| Compound | 1 mM | 1 μM | 1 mM | 1 μM |
| 3 | 77.8 ± 2.1 * | 84.1 ± 1.4 | 0.94 | 1.01 |
| 5 | 77.1 ± 0.8 * | 82.5 ± 0.4 | 0.93 | 0.99 |
| control | 83.2 ± 1.9 | | 1 | |

| Serial No | 40 | | | |
|---|---|---|---|---|
| Protein name | Histamine receptors (H2) | | | |
| | AP-TGFa release (%) | | Normalized to control | |
| Compound | 1 mM | 1 μM | 1 mM | 1 μM |
| 3 | 59 ± 0.4 * | 68.7 ± 3.8 | 0.89 | 1.04 |
| 5 | 58 ± 0.4 * | 68.3 ± 2.1 | 0.88 | 1.03 |
| control | 66 ± 2.9 | | 1 | |

| Serial No | 41 | | | |
|---|---|---|---|---|
| Protein name | Formylpeptide receptors (FPR1) | | | |
| | AP-TGFa release (%) | | Normalized to control | |
| Compound | 1 mM | 1 μM | 1 mM | 1 μM |
| 3 | 48.5 ± 0.9 * | 60.5 ± 0.7 | 0.82 | 1.02 |
| 5 | 48.6 ± 1.1 * | 60.1 ± 1 | 0.82 | 1.01 |
| 7 | 53.6 ± 1 * | 60.1 ± 0.4 | 0.91 | 1.02 |
| control | 59.2 ± 3.5 | | 1 | |

| Serial No | 42 | | | |
|---|---|---|---|---|
| Protein name | Dopamine receptors (D1) | | | |
| | AP-TGFa release (%) | | Normalized to control | |
| Compound | 1 mM | 1 μM | 1 mM | 1 μM |
| 0 | 59.8 ± 1 * | 65.4 ± 1 | 0.9 | 0.99 |
| 1 | 60.4 ± 0.8 * | 64.2 ± 2.1 | 0.91 | 0.97 |
| 3 | 57.6 ± 1.7 * | 63 ± 0.9 * | 0.87 | 0.95 |
| 5 | 57.4 ± 2.6 * | 63.5 ± 1 | 0.87 | 0.96 |
| 7 | 58.9 ± 1.4 * | 64.7 ± 0.4 | 0.89 | 0.98 |
| control | 66.3 ± 1.5 | | 1 | |

| Serial No | 43 | | | |
|---|---|---|---|---|
| Protein name | Free fatty acid receptors (FFA4) | | | |
| | AP-TGFa release (%) | | Normalized to control | |
| Compound | 1 mM | 1 μM | 1 mM | 1 μM |
| 1 | 80.6 ± 0.5 * | 87 ± 1.2 | 0.92 | 0.99 |
| 3 | 73.3 ± 3.3 * | 87.2 ± 1.9 | 0.84 | 0.99 |
| 5 | 71.8 ± 0.8 * | 87 ± 0.3 | 0.82 | 0.99 |
| 7 | 79.2 ± 1.3 * | 86.6 ± 0.2 | 0.9 | 0.99 |
| control | 87.8 ± 1.8 | | 1 | |

| Serial No | 44 | | | |
|---|---|---|---|---|
| Protein name | Prostanoid receptors (EP3 (iso8)) | | | |
| | AP-TGFa release (%) | | Normalized to control | |
| Compound | 1 mM | 1 μM | 1 mM | 1 μM |
| 7 | 75.1 ± 2.2 * | 81.6 ± 1.5 | 0.91 | 0.99 |
| control | 82.3 ± 1.8 | | 1 | |

| Serial No | 45 | | | |
|---|---|---|---|---|
| Protein name | Angiotensin receptors (AGTR2) | | | |
| | AP-TGFa release (%) | | Normalized to control | |
| Compound | 1 mM | 1 μM | 1 mM | 1 μM |
| 0 | 60.7 ± 1.4 * | 69 ± 4 | 0.91 | 1.04 |
| 3 | 60.4 ± 0.8 * | 67.2 ± 2 | 0.91 | 1.01 |
| 5 | 59.7 ± 1.6 * | 67.3 ± 0.9 | 0.9 | 1.01 |
| 7 | 58.2 ± 0.7 * | 66.1 ± 1.5 | 0.88 | 1 |
| control | 66.4 ± 2.2 | | 1 | |

| Serial No | 46 | | | |
|---|---|---|---|---|
| Protein name | 5-Hydroxytryptamine receptors (5-HT1F) | | | |
| | AP-TGFa release (%) | | Normalized to control | |
| Compound | 1 mM | 1 μM | 1 mM | 1 μM |
| 0 | 55.6 ± 3.7 * | 66.8 ± 2.5 * | 0.89 | 1.07 |
| 1 | 58.2 ± 2.9 * | 64.9 ± 2.9 | 0.93 | 1.04 |
| 3 | 53.8 ± 6.4 * | 66.3 ± 1 * | 0.86 | 1.06 |
| 5 | 54.4 ± 3.4 * | 63.1 ± 0.7 | 0.87 | 1.01 |
| 7 | 56.3 ± 2.1 * | 65.4 ± 3.4 | 0.9 | 1.05 |
| control | 62.4 ± 2.3 | | 1 | |

| Serial No | 47 | | | |
|---|---|---|---|---|
| Protein name | Adrenergic receptors (β1) | | | |
| | AP-TGFa release (%) | | Normalized to control | |
| Compound | 1 mM | 1 μM | 1 mM | 1 μM |
| 0 | 71.9 ± 3.3 * | 79.1 ± 4.4 * | 0.92 | 1.01 |
| 3 | 73.7 ± 1.7 * | 81.2 ± 4.3 * | 0.94 | 1.04 |
| 5 | 67.1 ± 0.4 * | 76 ± 4.6 * | 0.86 | 0.97 |
| 7 | 69.7 ± 0.8 * | 78.4 ± 3.5 * | 0.89 | 1 |
| control | 78.1 ± 2.7 | | 1 | |

| Serial No | 48 | | | |
|---|---|---|---|---|
| Protein name | Chemokine receptors (CCR1) | | | |
| | AP-TGFa release (%) | | Normalized to control | |
| Compound | 1 mM | 1 μM | 1 mM | 1 μM |
| 0 | 71.2 ± 5.5 * | 77.7 ± 2.3 | 0.91 | 1 |
| 1 | 72.4 ± 0.7 * | 78 ± 2.5 | 0.93 | 1 |
| control | 77.8 ± 2 | | 1 | |

| Serial No | 49 | | | |
|---|---|---|---|---|
| Protein name | Chemokine receptors (CCR8) | | | |
| | AP-TGFa release (%) | | Normalized to control | |
| Compound | 1 mM | 1 μM | 1 mM | 1 μM |
| 0 | 58.8 ± 2.4 * | 67.6 ± 0.4 * | 0.81 | 0.94 |
| 1 | 63.1 ± 2.9 * | 66.2 ± 2.1 * | 0.87 | 0.92 |
| 3 | 62.3 ± 5.5 * | 67.6 ± 0.7 * | 0.86 | 0.94 |
| 5 | 65.2 ± 0.9 * | 72.2 ± 0.7 | 0.9 | 1 |
| 7 | 64.8 ± 1.3 * | 72.7 ± 1.6 | 0.9 | 1.01 |
| control | 72.2 ± 1.8 | | 1 | |

| Serial No | 50 | | | |
|---|---|---|---|---|
| Protein name | Chemokine receptors (CCR6) | | | |
| | AP-TGFa release (%) | | Normalized to control | |
| Compound | 1 mM | 1 μM | 1 mM | 1 μM |
| 0 | 76.8 ± 3.1 * | 75.2 ± 7.4 | 0.94 | 0.92 |
| 7 | 76.4 ± 1.9 * | 83.1 ± 2.5 | 0.94 | 1.02 |
| control | 81.6 ± 2.5 | | 1 | |

| Serial No | 51 | | | |
|---|---|---|---|---|
| Protein name | Chemokine receptors (CCR5) | | | |
| | AP-TGFa release (%) | | Normalized to control | |
| Compound | 1 mM | 1 μM | 1 mM | 1 μM |
| 0 | 61.7 ± 0.4 * | 80.1 ± 11.3 | 0.88 | 1.14 |
| 3 | 66.9 ± 1.9 * | 69.9 ± 3.6 | 0.95 | 1 |
| control | 70.2 ± 1.9 | | 1 | |

| Serial No | 52 | | | |
|---|---|---|---|---|
| Protein name | Orexin receptors (HCRTR2(OX2R)) | | | |
| | AP-TGFa release (%) | | Normalized to control | |
| Compound | 1 mM | 1 μM | 1 mM | 1 μM |
| 1 | 51.5 ± 0.9 * | 54.5 ± 0.5 | 0.92 | 0.97 |
| 5 | 50.7 ± 1.7 * | 52.7 ± 3.2 | 0.9 | 0.94 |
| 7 | 50.7 ± 3 * | 53.6 ± 1.8 | 0.91 | 0.96 |
| control | 56 ± 2.7 | | 1 | |

| Serial No | 53 | | | |
|---|---|---|---|---|
| Protein name | Hydroxycarboxylic acid receptors (GPR81) | | | |
| | AP-TGFa release (%) | | Normalized to control | |
| Compound | 1 mM | 1 μM | 1 mM | 1 μM |
| 0 | 49.3 ± 2.1 * | 75.4 ± 20.3 | 0.87 | 1.32 |
| 1 | 51.8 ± 3.7 * | 57.1 ± 0.8 | 0.91 | 1 |
| 7 | 51.8 ± 2.8 * | 62.7 ± 5.8 | 0.91 | 1.1 |
| control | 56.9 ± 2.5 | | 1 | |

| Serial No | 54 | | | |
|---|---|---|---|---|
| Protein name | Class A Orphans (GPR85) | | | |
| | AP-TGFa release (%) | | Normalized to control | |
| Compound | 1 mM | 1 μM | 1 mM | 1 μM |
| 0 | 48 ± 2 * | 56.2 ± 1.8 | 0.89 | 1.04 |
| 1 | 48.2 ± 2.6 * | 53.7 ± 1.5 | 0.89 | 0.99 |
| 7 | 48 ± 1.8 * | 54 ± 0.4 | 0.89 | 1 |
| control | 54.2 ± 1.9 | | 1 | |

| Serial No | 55 | | | |
|---|---|---|---|---|
| Protein name | Gonadotrophin-releasing hormone receptors (GNRHR) | | | |
| | AP-TGFa release (%) | | Normalized to control | |
| Compound | 1 mM | 1 μM | 1 mM | 1 μM |
| 0 | 56.4 ± 3.8 * | 62.2 ± 0.1 | 0.93 | 1.02 |
| 1 | 56.3 ± 2.2 * | 60.8 ± 2.2 | 0.93 | 1 |
| 5 | 56.7 ± 2.2 * | 60.2 ± 1.2 | 0.93 | 0.99 |
| 7 | 52.7 ± 1.9 * | 58.8 ± 0.8 | 0.87 | 0.97 |
| control | 60.8 ± 1.5 | | 1 | |

| Serial No | 56 | | | |
|---|---|---|---|---|
| Protein name | Class A Orphans (GPR149) | | | |
| | AP-TGFa release (%) | | Normalized to control | |
| Compound | 1 mM | 1 μM | 1 mM | 1 μM |
| 0 | 50.8 ± 0.9 * | 58.9 ± 0.4 * | 0.94 | 1.09 |
| 1 | 50.9 ± 1.6 * | 55.4 ± 0.9 | 0.94 | 1.03 |
| 3 | 48.7 ± 3.3 * | 50.7 ± 0.7 * | 0.9 | 0.94 |
| 5 | 47.5 ± 3.9 * | 50.3 ± 0.9 * | 0.88 | 0.93 |
| 7 | 45.5 ± 2.3 * | 49.4 ± 1 * | 0.84 | 0.92 |
| control | 54 ± 1.7 | | 1 | |

| Serial No | 57 | | | |
|---|---|---|---|---|
| Protein name | Class A Orphans (GPR17) | | | |
| | AP-TGFa release (%) | | Normalized to control | |
| Compound | 1 mM | 1 μM | 1 mM | 1 μM |
| 0 | 55.4 ± 1.7 * | 63.5 ± 0.5 | 0.89 | 1.01 |
| control | 62.6 ± 3.8 | | 1 | |

| Serial No | 58 | | | |
|---|---|---|---|---|
| Protein name | Class A Orphans (GPR61) | | | |
| | AP-TGFa release (%) | | Normalized to control | |
| Compound | 1 mM | 1 μM | 1 mM | 1 μM |
| 0 | 49.4 ± 1.9 * | 56.8 ± 2.3 | 0.88 | 1.01 |
| 5 | 49.7 ± 2 * | 54.8 ± 1.1 | 0.89 | 0.98 |
| 7 | 47 ± 2.2 * | 55 ± 1 | 0.84 | 0.98 |
| control | 56.1 ± 2.6 | | 1 | |

| Serial No | 59 | | | |
|---|---|---|---|---|
| Protein name | Galanin receptors (GALR3) | | | |
| | AP-TGFa release (%) | | Normalized to control | |
| Compound | 1 mM | 1 μM | 1 mM | 1 μM |
| 0 | 48.7 ± 0.4 * | 58.7 ± 1.6 | 0.85 | 1.02 |
| 1 | 52.5 ± 1.9 * | 59.8 ± 1 | 0.91 | 1.04 |
| 7 | 51.4 ± 3.2 * | 55.7 ± 1.1 | 0.89 | 0.97 |
| control | 57.6 ± 2.9 | | 1 | |

| Serial No | 60 | | | |
|---|---|---|---|---|
| Protein name | Galanin receptors (GALR2) | | | |
| | AP-TGFa release (%) | | Normalized to control | |
| Compound | 1 mM | 1 μM | 1 mM | 1 μM |
| 0 | 57.7 ± 1 * | 64.2 ± 2 | 0.92 | 1.02 |
| 1 | 55.7 ± 1.7 * | 63.1 ± 0.7 | 0.88 | 1 |
| 4 | 59.1 ± 1.9 * | 60.6 ± 0.6 | 0.94 | 0.96 |
| 5 | 56.1 ± 2.1 * | 60.3 ± 3.4 | 0.89 | 0.96 |
| 7 | 54 ± 2.1 * | 61.3 ± 2.3 | 0.86 | 0.97 |
| control | 63 ± 2 | | 1 | |

| Serial No | 61 | | | |
|---|---|---|---|---|
| Protein name | Chemerin receptors (GPR1) | | | |
| | AP-TGFa release (%) | | Normalized to control | |
| Compound | 1 mM | 1 μM | 1 mM | 1 μM |
| 1 | 42.75126 * | 44.9 ± 3 | 0.88 | 0.92 |
| 3 | 42.92088 * | 41.7 ± 2.3 * | 0.88 | 0.86 |
| 5 | 42.76833 * | 44.6 ± 1.3 | 0.88 | 0.92 |
| 7 | 42.73596 * | 42.7 ± 2.3 * | 0.88 | 0.88 |
| control | 48.6 ± 2.8 | | 1 | |

| Serial No | 62 | | | |
|---|---|---|---|---|
| Protein name | Class A Orphans (GPR62) | | | |
| | AP-TGFa release (%) | | Normalized to control | |
| Compound | 1 mM | 1 μM | 1 mM | 1 μM |
| 0 | 53.05829 * | 63.5 ± 1.9 * | 0.87 | 1.04 |
| 1 | 53.9176 * | 60.3 ± 1.8 | 0.89 | 0.99 |
| 5 | 57.95231 * | 61.8 ± 4.9 | 0.95 | 1.02 |
| 7 | 54.54393 * | 62 ± 0.6 | 0.9 | 1.02 |
| control | 60.9 ± 1.1 | | 1 | |

| Serial No | 63 | | | |
|---|---|---|---|---|
| Protein name | Class A Orphans (GPR52) | | | |
| | AP-TGFa release (%) | | Normalized to control | |
| Compound | 1 mM | 1 μM | 1 mM | 1 μM |
| 0 | 44.26752 * | 51.2 ± 1.9 | 0.85 | 0.98 |
| 1 | 44.07512 * | 50.6 ± 1.3 | 0.84 | 0.97 |
| 3 | 45.66714 * | 50.8 ± 2.2 | 0.87 | 0.97 |
| 5 | 44.82798 * | 50.9 ± 0.4 | 0.86 | 0.97 |
| 7 | 40.50064 * | 50.5 ± 2.4 | 0.77 | 0.96 |
| control | 52.31505 | | 1 | |

| Serial No | 64 | | | |
|---|---|---|---|---|
| Protein name | Class A Orphans (GPR37) | | | |
| | AP-TGFa release (%) | | Normalized to control | |
| Compound | 1 mM | 1 μM | 1 mM | 1 μM |
| 0 | 40.47533 * | 51.1 ± 5.7 | 0.81 | 1.03 |
| 1 | 39.0583 * | 45.8 ± 0.5 * | 0.79 | 0.92 |
| 3 | 44.71315 * | 48.6 ± 5.8 | 0.9 | 0.98 |
| 4 | 44.97631 * | 43 ± 0.6 * | 0.91 | 0.87 |
| 5 | 43.70953 * | 44.3 ± 3.1 * | 0.88 | 0.89 |
| 7 | 39.19653 * | 45.2 ± 1.2 * | 0.79 | 0.91 |
| control | 49.69017 | | 1 | |

| Serial No | 65 | | | |
|---|---|---|---|---|
| Protein name | Class A Orphans (GPR32) | | | |
| | AP-TGFa release (%) | | Normalized to control | |
| Compound | 1 mM | 1 µM | 1 mM | 1 µM |
| 1 | 52.74887 * | 61.9 ± 2.3 | 0.87 | 1.02 |
| control | 60.65523 | | 1 | |

| Serial No | 66 | | | |
|---|---|---|---|---|
| Protein name | Muscarinic receptors (M5) | | | |
| | AP-TGFa release (%) | | Normalized to control | |
| Compound | 1 mM | 1 µM | 1 mM | 1 µM |
| 0 | 50.2 ± 0.6 * | 56.5 ± 1.3 | 0.89 | 1 |
| 5 | 48.2 ± 0.7 * | 51.3 ± 1.8 | 0.86 | 0.91 |
| control | 56.2 ± 3.8 | | 1 | |

| Serial No | 67 | | | |
|---|---|---|---|---|
| Protein name | Class A Orphans (GPR55) | | | |
| | AP-TGFa release (%) | | Normalized to control | |
| Compound | 1 mM | 1 µM | 1 mM | 1 µM |
| 0 | 72.6 ± 1.1 * | 81.7 ± 3.7 | 0.88 | 0.99 |
| 1 | 75.5 ± 2.4 | 79.3 ± 4.4 | 0.92 | 0.96 |
| 3 | 70.9 ± 0.9 * | 78.2 ± 1.1 * | 0.86 | 0.95 |
| 5 | 70.8 ± 1.8 * | 75.6 ± 1.4 * | 0.86 | 0.92 |
| 7 | 67.7 ± 0.4 * | 67 ± 8 * | 0.82 | 0.81 |
| control | 82.4 ± 1.8 | | 1 | |

| Serial No | 68 | | | |
|---|---|---|---|---|
| Protein name | Platelet-activating factor receptors (PAFR) | | | |
| | AP-TGFa release (%) | | Normalized to control | |
| Compound | 1 mM | 1 µM | 1 mM | 1 µM |
| 0 | 69 ± 1 * | 72.1 ± 0.9 * | 0.91 | 0.95 |
| 1 | 69.3 ± 0.9 * | 74 ± 1.5 | 0.91 | 0.98 |
| 3 | 61.2 ± 1.4 * | 71.5 ± 1.1 * | 0.81 | 0.94 |
| 5 | 64.7 ± 0.2 * | 72.3 ± 1.3 * | 0.85 | 0.95 |
| control | 75.8 ± 1.7 | | 1 | |

| Serial No | 69 | | | |
|---|---|---|---|---|
| Protein name | Bradykinin receptors (B1) | | | |
| | AP-TGFa release (%) | | Normalized to control | |
| Compound | 1 mM | 1 µM | 1 mM | 1 µM |
| 0 | 44.4 ± 0.7 * | 47.7 ± 1.2 * | 0.85 | 0.91 |
| 1 | 45.6 ± 0.9 * | 48.6 ± 0.4 | 0.87 | 0.93 |
| 3 | 38.9 ± 2.9 * | 46.6 ± 2 * | 0.74 | 0.89 |
| 5 | 38.7 ± 2.1 * | 45.7 ± 2 * | 0.74 | 0.87 |
| control | 52.3 ± 2.7 | | 1 | |

| Serial No | 70 | | | |
|---|---|---|---|---|
| Protein name | Oxytocin receptors (OT) | | | |
| | AP-TGFa release (%) | | Normalized to control | |
| Compound | 1 mM | 1 µM | 1 mM | 1 µM |
| 0 | 41.1 ± 1.3 * | 46.7 ± 0.7 | 0.83 | 0.95 |
| 1 | 42 ± 1 * | 45.1 ± 1.9 * | 0.85 | 0.92 |
| 3 | 36.1 ± 0.3 * | 48.5 ± 0.8 | 0.73 | 0.98 |
| 5 | 36.4 ± 0.8 * | 46.5 ± 0.7 * | 0.74 | 0.94 |
| 7 | 44.7 ± 0.4 * | 45.6 ± 1.6 * | 0.91 | 0.93 |
| control | 49.3 ± 1.8 | | 1 | |

| Serial No | 71 | | | |
|---|---|---|---|---|
| Protein name | Leukotriene receptors (CysLT2) | | | |
| | AP-TGFa release (%) | | Normalized to control | |
| Compound | 1 mM | 1 µM | 1 mM | 1 µM |
| 0 | 60.5 ± 0.6 * | 64.3 ± 1.3 | 0.94 | 1 |
| 1 | 60 ± 0.9 * | 61.5 ± 1.8 * | 0.93 | 0.95 |
| 3 | 54.3 ± 0.7 * | 61.8 ± 2.2 | 0.84 | 0.96 |
| 5 | 53.4 ± 0.9 * | 61.6 ± 3.7 | 0.83 | 0.96 |
| 7 | 58.2 ± 0.9 * | 62.7 ± 2.1 | 0.9 | 0.97 |
| control | 64.5 ± 1.3 | | 1 | |

| Serial No | 72 | | | |
|---|---|---|---|---|
| Protein name | Free fatty acid receptors (FFA1) | | | |
| | AP-TGFa release (%) | | Normalized to control | |
| Compound | 1 mM | 1 µM | 1 mM | 1 µM |
| 0 | 68.5 ± 1.8 * | 78.3 ± 1.5 * | 0.89 | 1.01 |
| 1 | 68.8 ± 1.1 * | 75.4 ± 2.9 * | 0.89 | 0.97 |
| 3 | 66.7 ± 0.7 * | 71.7 ± 1.2 * | 0.86 | 0.93 |
| 5 | 68.1 ± 0.6 * | 73.7 ± 2.4 * | 0.88 | 0.95 |
| 7 | 68.7 ± 0.9 * | 73.5 ± 1.2 * | 0.89 | 0.95 |
| control | 77.4 ± 4 | | 1 | |

| Serial No | 73 | | | |
|---|---|---|---|---|
| Protein name | Angiotensin receptors (AT1) | | | |
| | AP-TGFa release (%) | | Normalized to control | |
| Compound | 1 mM | 1 µM | 1 mM | 1 µM |
| 3 | 53.8 ± 0.4 * | 59.5 ± 1 | 0.88 | 0.97 |
| 5 | 56.6 ± 2.2 * | 55.9 ± 2 * | 0.93 | 0.91 |
| control | 61.1 ± 2 | | 1 | |

| Serial No | 74 | | | |
|---|---|---|---|---|
| Protein name | Bradykinin receptors (B2) | | | |
| | AP-TGFa release (%) | | Normalized to control | |
| Compound | 1 mM | 1 µM | 1 mM | 1 µM |
| 3 | 42 ± 2.2 * | 52.4 ± 1 | 0.77 | 0.96 |
| 5 | 44.1 ± 1.5 * | 54.7 ± 0.7 | 0.81 | 1 |
| control | 54.5 ± 3.7 | | 1 | |

| Serial No | 75 | | | |
|---|---|---|---|---|
| Protein name | Muscarinic receptors (M1) | | | |
| | AP-TGFa release (%) | | Normalized to control | |
| Compound | 1 mM | 1 µM | 1 mM | 1 µM |
| 0 | 60.1 ± 0.8 * | 67.4 ± 3.7 | 0.92 | 1.03 |
| 3 | 61.6 ± 0.5 * | 64.6 ± 0.7 | 0.94 | 0.99 |
| 5 | 49.7 ± 1.4 * | 57.4 ± 1.6 * | 0.76 | 0.88 |
| control | 65.3 ± 1.7 | | 1 | |

| Serial No | 76 | | | |
|---|---|---|---|---|
| Protein name | P2Y receptors (P2Y11) | | | |
| | AP-TGFa release (%) | | Normalized to control | |
| Compound | 1 mM | 1 µM | 1 mM | 1 µM |
| 0 | 74.1 ± 1.1 * | 83.7 ± 1.6 | 0.87 | 0.98 |
| 1 | 76.6 ± 2.1 * | 85.7 ± 4.4 | 0.9 | 1 |
| 3 | 76.8 ± 4.8 * | 79.6 ± 2.7 * | 0.9 | 0.93 |
| 5 | 75.1 ± 5 * | 78.4 ± 0.4 * | 0.88 | 0.92 |
| 7 | 77.8 ± 0.9 * | 78.1 ± 1.7 * | 0.91 | 0.91 |
| control | 85.5 ± 1.9 | | 1 | |

| Serial No | 77 | | | |
|---|---|---|---|---|
| Protein name | Tachykinin receptors (NK3) | | | |
| | AP-TGFa release (%) | | Normalized to control | |
| Compound | 1 mM | 1 μM | 1 mM | 1 μM |
| 3 | 42.3 ± 1.7 * | 54.6 ± 0.9 | 0.78 | 1 |
| 5 | 37.7 ± 1.8 * | 53.3 ± 1.8 | 0.69 | 0.98 |
| 7 | 44.5 ± 3.4 * | 52 ± 4.2 | 0.82 | 0.96 |
| control | 54.3 ± 3.8 | | 1 | |

| Serial No | 78 | | | |
|---|---|---|---|---|
| Protein name | P2Y receptors (P2Y1) | | | |
| | AP-TGFa release (%) | | Normalized to control | |
| Compound | 1 mM | 1 μM | 1 mM | 1 μM |
| 0 | 49.5 ± 1.9 * | 57.9 ± 2 * | 0.76 | 0.88 |
| 1 | 54.3 ± 2.6 * | 60.6 ± 1.3 * | 0.83 | 0.93 |
| 3 | 44.9 ± 7.5 * | 64.8 ± 1.9 | 0.69 | 0.99 |
| 5 | 54.1 ± 1 * | 63.6 ± 1.4 | 0.83 | 0.97 |
| 7 | 57 ± 2.6 * | 67.3 ± 1.1 | 0.87 | 1.03 |
| control | 65.5 ± 1.8 | | 1 | |

| Serial No | 79 | | | |
|---|---|---|---|---|
| Protein name | Adenosine receptors (A2B) | | | |
| | AP-TGFa release (%) | | Normalized to control | |
| Compound | 1 mM | 1 μM | 1 mM | 1 μM |
| 0 | 44.7 ± 0.6 * | 57 ± 1.7 | 0.76 | 0.97 |
| 1 | 50.5 ± 1.3 * | 53.7 ± 1.4 | 0.86 | 0.92 |
| 3 | 41.2 ± 1.3 * | 54.7 ± 1.9 | 0.7 | 0.94 |
| 5 | 43.2 ± 0.4 * | 54 ± 0.9 | 0.74 | 0.92 |
| 7 | 42.7 ± 0.7 * | 55.4 ± 2.9 | 0.73 | 0.95 |
| control | 58.5 ± 4.7 | | 1 | |

| Serial No | 80 | | | |
|---|---|---|---|---|
| Protein name | Adenosine receptors (A2A) | | | |
| | AP-TGFa release (%) | | Normalized to control | |
| Compound | 1 mM | 1 μM | 1 mM | 1 μM |
| 3 | 75 ± 0.7 * | 82.1 ± 2 | 0.93 | 1.01 |
| 7 | 73.6 ± 1.3 * | 82.3 ± 3.8 | 0.91 | 1.01 |
| control | 81.1 ± 3.1 | | 1 | |

| Serial No | 81 | | | |
|---|---|---|---|---|
| Protein name | Lysophospholipid (S1P) receptors (S1P5) | | | |
| | AP-TGFa release (%) | | Normalized to control | |
| Compound | 1 mM | 1 μM | 1 mM | 1 μM |
| 0 | 42.2 ± 0.9 * | 49.4 ± 1.7 * | 0.91 | 1.07 |
| 1 | 42.1 ± 1.3 * | 45.8 ± 4.1 | 0.91 | 0.99 |
| 3 | 38.6 ± 1 * | 45.6 ± 4.1 | 0.83 | 0.98 |
| 5 | 37 ± 2.1 * | 42.6 ± 3 * | 0.8 | 0.92 |
| 7 | 43.3 ± 1.2 * | 44.8 ± 1.6 | 0.93 | 0.97 |
| control | 46.3 ± 1.8 | | 1 | |

| Serial No | 82 | | | |
|---|---|---|---|---|
| Protein name | Prostanoid receptors (IP) | | | |
| | AP-TGFa release (%) | | Normalized to control | |
| Compound | 1 mM | 1 μM | 1 mM | 1 μM |
| 0 | 53 ± 2.1 * | 62.3 ± 2 * | 0.91 | 1.07 |
| 3 | 49 ± 2 * | 58.2 ± 1 | 0.84 | 1 |
| 5 | 50 ± 2 * | 57.1 ± 1.9 | 0.86 | 0.98 |
| 7 | 52.5 ± 1.5 * | 58 ± 3.4 | 0.9 | 0.99 |
| control | 58.4 ± 2 | | 1 | |

| Serial No | 83 | | | |
|---|---|---|---|---|
| Protein name | 5-Hydroxytryptamine receptors (5-HT6) | | | |
| | AP-TGFa release (%) | | Normalized to control | |
| Compound | 1 mM | 1 μM | 1 mM | 1 μM |
| 0 | 55.9 ± 1.1 * | 63.3 ± 0.9 | 0.84 | 0.96 |
| 1 | 58.5 ± 0.8 * | 63.5 ± 1.5 | 0.88 | 0.96 |
| 3 | 47.3 ± 1.1 * | 64.8 ± 3.5 | 0.72 | 0.98 |
| 5 | 48.8 ± 0.6 * | 62.3 ± 2.9 | 0.74 | 0.94 |
| 7 | 52.7 ± 1.1 * | 61.9 ± 2.9 | 0.8 | 0.94 |
| control | 66.2 ± 2.8 | | 1 | |

| Serial No | 84 | | | |
|---|---|---|---|---|
| Protein name | 5-Hydroxytryptamine receptors (5-HT2B) | | | |
| | AP-TGFa release (%) | | Normalized to control | |
| Compound | 1 mM | 1 μM | 1 mM | 1 μM |
| 0 | 57.5 ± 0.7 * | 63.4 ± 3 | 0.9 | 0.99 |
| 1 | 57.3 ± 0.8 * | 62.6 ± 1.9 | 0.89 | 0.97 |
| 3 | 45.5 ± 1.7 * | 63.5 ± 2.6 | 0.71 | 0.99 |
| 5 | 48.5 ± 0.3 * | 62.2 ± 1.8 | 0.75 | 0.97 |
| 7 | 56.4 ± 2.7 * | 62.1 ± 0.5 * | 0.88 | 0.97 |
| control | 64.3 ± 1 | | 1 | |

| Serial No | 85 | | | |
|---|---|---|---|---|
| Protein name | Lysophospholipid (S1P) receptors (S1P3) | | | |
| | AP-TGFa release (%) | | Normalized to control | |
| Compound | 1 mM | 1 μM | 1 mM | 1 μM |
| 0 | 56.4 ± 0.6 * | 68.3 ± 1.1 | 0.82 | 0.99 |
| 1 | 57.4 ± 1.2 * | 70.5 ± 1 | 0.83 | 1.02 |
| 3 | 53.7 ± 1.7 * | 68.1 ± 1.1 | 0.78 | 0.99 |
| 5 | 57.1 ± 0.9 * | 69.6 ± 2.6 | 0.83 | 1.01 |
| 7 | 59.2 ± 0.7 * | 69 ± 1.6 | 0.86 | 1 |
| control | 69 ± 1 | | 1 | |

| Serial No | 86 | | | |
|---|---|---|---|---|
| Protein name | Adrenergic receptor (α1B) | | | |
| | AP-TGFa release (%) | | Normalized to control | |
| Compound | 1 mM | 1 μM | 1 mM | 1 μM |
| 0 | 42 ± 0.7 * | 43 ± 0.9 * | 0.89 | 0.91 |
| 1 | 39.4 ± 0.1 * | 43.6 ± 0.9 * | 0.84 | 0.92 |
| 3 | 26.6 ± 1.1 * | 43.8 ± 0.9 * | 0.56 | 0.93 |
| 5 | 26.8 ± 1.1 * | 42.3 ± 1 * | 0.57 | 0.9 |
| 7 | 37 ± 0.3 * | 42.9 ± 0.4 * | 0.79 | 0.91 |
| control | 47.1 ± 2.1 | | 1 | |

| Serial No | 87 | | | |
|---|---|---|---|---|
| Protein name | Prostanoid receptors (TP) | | | |
| | AP-TGFa release (%) | | Normalized to control | |
| Compound | 1 mM | 1 μM | 1 mM | 1 μM |
| 0 | 38.8 ± 0.7 * | 47.2 ± 2.2 | 0.82 | 1 |
| 1 | 43.1 ± 1.1 * | 45.3 ± 1.3 | 0.91 | 0.96 |
| 3 | 38.5 ± 2.4 * | 50.4 ± 3.4 | 0.82 | 1.07 |
| 5 | 38.1 ± 2.3 * | 49.5 ± 2.2 | 0.81 | 1.05 |
| 7 | 40.7 ± 0.8 * | 47.3 ± 3.2 | 0.86 | 1 |
| control | 47.1 ± 1.3 | | 1 | |

| Serial No | 88 | | | |
|---|---|---|---|---|
| Protein name | Dopamine receptors (D3) | | | |
| | AP-TGFa release (%) | | Normalized to control | |
| Compound | 1 mM | 1 μM | 1 mM | 1 μM |
| 0 | 57.9 ± 0.9 * | 61.3 ± 0.7 | 0.91 | 0.96 |
| 1 | 57.4 ± 1.1 * | 60.5 ± 2.4 | 0.9 | 0.95 |
| 3 | 59.9 ± 0.8 * | 59.8 ± 1 * | 0.94 | 0.94 |
| 5 | 59.3 ± 1.8 * | 62.4 ± 2 | 0.93 | 0.98 |
| 7 | 60.3 ± 1.8 * | 62.9 ± 1.1 | 0.95 | 0.99 |
| control | 63.5 ± 1.6 | | 1 | |

| Serial No | 89 | | | |
|---|---|---|---|---|
| Protein name | Lysophospholipid (S1P) receptors (S1P1) | | | |
| | AP-TGFa release (%) | | Normalized to control | |
| Compound | 1 mM | 1 µM | 1 mM | 1 µM |
| 0 | 57.8 ± 0.7 * | 63.9 ± 1.4 * | 0.85 | 0.94 |
| 1 | 60.4 ± 2 * | 63.7 ± 1.4 * | 0.89 | 0.94 |
| 3 | 56.5 ± 2.4 * | 63.1 ± 2.4 * | 0.83 | 0.93 |
| 5 | 61 ± 1.4 * | 65.1 ± 1.9 | 0.9 | 0.96 |
| 7 | 61.3 ± 2 * | 65.9 ± 0.7 | 0.9 | 0.97 |
| control | 68.1 ± 2.1 | | 1 | |

| Serial No | 90 | | | |
|---|---|---|---|---|
| Protein name | Histamine receptors (H4) | | | |
| | AP-TGFa release (%) | | Normalized to control | |
| Compound | 1 mM | 1 µM | 1 mM | 1 µM |
| 0 | 61.7 ± 0.8 * | 70.8 ± 3.9 | 0.82 | 0.94 |
| 1 | 67.1 ± 2.4 * | 68.4 ± 3 * | 0.89 | 0.91 |
| 3 | 63.2 ± 1.3 * | 67.7 ± 2.8 * | 0.84 | 0.9 |
| 5 | 67 ± 1.2 * | 71.6 ± 0.3 * | 0.89 | 0.95 |
| 7 | 68 ± 2 * | 72.4 ± 0.8 * | 0.91 | 0.96 |
| control | 75.2 ± 1.9 | | 1 | |

| Serial No | 91 | | | |
|---|---|---|---|---|
| Protein name | Lysophospholipid (S1P) receptors (S1P2) | | | |
| | AP-TGFa release (%) | | Normalized to control | |
| Compound | 1 mM | 1 µM | 1 mM | 1 µM |
| 0 | 69.8 ± 1 * | 72.6 ± 1.3 * | 0.91 | 0.95 |
| 3 | 70.8 ± 1.3 * | 74.8 ± 1.4 | 0.92 | 0.98 |
| 5 | 70.4 ± 1.2 * | 76.5 ± 1 | 0.92 | 1 |
| 7 | 71.8 ± 1.1 * | 76.1 ± 0.5 | 0.94 | 0.99 |
| control | 76.7 ± 1.9 | | 1 | |

| Serial No | 92 | | | |
|---|---|---|---|---|
| Protein name | 5-Hydroxytryptamine receptors (5-HT1B) | | | |
| | AP-TGFa release (%) | | Normalized to control | |
| Compound | 1 mM | 1 µM | 1 mM | 1 µM |
| 1 | 50.5 ± 0.9 * | 54.6 ± 2.7 | 0.88 | 0.95 |
| 3 | 44.8 ± 2.4 * | 56.6 ± 0.5 | 0.78 | 0.99 |
| 5 | 46.7 ± 2.4 * | 53.8 ± 1.2 * | 0.82 | 0.94 |
| 7 | 52.2 ± 1.6 * | 54.3 ± 0.3 * | 0.91 | 0.95 |
| control | 57.2 ± 1.3 | | 1 | |

| Serial No | 93 | | | |
|---|---|---|---|---|
| Protein name | Endothelin receptors (ETB) | | | |
| | AP-TGFa release (%) | | Normalized to control | |
| Compound | 1 mM | 1 µM | 1 mM | 1 µM |
| 0 | 53.1 ± 1.5 * | 56.3 ± 2.1 * | 0.87 | 0.92 |
| 1 | 54.7 ± 0.6 * | 57.8 ± 1.4 | 0.9 | 0.95 |
| 3 | 47.5 ± 3.1 * | 58.5 ± 1 | 0.78 | 0.96 |
| 5 | 48 ± 1.5 * | 58.7 ± 2.5 | 0.78 | 0.96 |
| 7 | 54 ± 0.6 * | 59.3 ± 0.9 | 0.88 | 0.97 |
| control | 61.1 ± 1.8 | | 1 | |

| Serial No | 94 | | | |
|---|---|---|---|---|
| Protein name | Muscarinic receptor (M4) | | | |
| | AP-TGFa release (%) | | Normalized to control | |
| Compound | 1 mM | 1 µM | 1 mM | 1 µM |
| 0 | 54.2 ± 1.1 * | 61.8 ± 2.3 | 0.88 | 1 |
| 1 | 56.9 ± 0.6 * | 57.2 ± 2 * | 0.92 | 0.93 |
| control | 61.7 ± 1.9 | | 1 | |

| Serial No | 95 | | | |
|---|---|---|---|---|
| Protein name | Prostanoid receptors (EP3) | | | |
| | AP-TGFa release (%) | | Normalized to control | |
| Compound | 1 mM | 1 µM | 1 mM | 1 µM |
| 0 | 54.5 ± 0.2 * | 61.6 ± 2.3 | 0.87 | 0.99 |
| 3 | 53.3 ± 1 * | 63.9 ± 3.2 | 0.85 | 1.02 |
| 5 | 53.6 ± 1 * | 62.2 ± 0.4 | 0.86 | 0.99 |
| 7 | 55.7 ± 1.4 * | 60.7 ± 1.8 | 0.89 | 0.97 |
| control | 62.5 ± 3.1 | | 1 | |

| Serial No | 96 | | | |
|---|---|---|---|---|
| Protein name | Muscarinic receptor (M2) | | | |
| | AP-TGFa release (%) | | Normalized to control | |
| Compound | 1 mM | 1 µM | 1 mM | 1 µM |
| 0 | 54.7 ± 1.3 * | 56.1 ± 0.8 * | 0.93 | 0.95 |
| 1 | 54.1 ± 0.7 * | 56 ± 0.3 * | 0.92 | 0.95 |
| 3 | 53.7 ± 0 * | 59.1 ± 1.2 | 0.91 | 1 |
| 5 | 53.9 ± 0.9 * | 56.7 ± 2 * | 0.91 | 0.96 |
| control | 59.1 ± 1.1 | | 1 | |

| Serial No | 97 | | | |
|---|---|---|---|---|
| Protein name | Histamine receptors (H3) | | | |
| | AP-TGFa release (%) | | Normalized to control | |
| Compound | 1 mM | 1 µM | 1 mM | 1 µM |
| 0 | 49.5 ± 3.2 * | 55.6 ± 0.4 * | 0.81 | 0.91 |
| 1 | 57.3 ± 1 | 55.4 ± 1.2 * | 0.94 | 0.91 |
| 3 | 51.6 ± 0.6 * | 53.7 ± 3.5 * | 0.84 | 0.88 |
| 5 | 52.2 ± 0.9 * | 58.3 ± 5.3 | 0.85 | 0.95 |
| control | 61.2 ± 1.9 | | 1 | |

| Serial No | 98 | | | |
|---|---|---|---|---|
| Protein name | 5-Hydroxytryptamine receptors (5-HT7) | | | |
| | AP-TGFa release (%) | | Normalized to control | |
| Compound | 1 mM | 1 µM | 1 mM | 1 µM |
| 0 | 36.5 ± 1.5 * | 50.6 ± 1.8 * | 0.63 | 0.88 |
| 1 | 49.9 ± 0.2 * | 50.8 ± 2.7 * | 0.87 | 0.88 |
| 3 | 39.1 ± 1.1 * | 53.7 ± 1.4 * | 0.68 | 0.93 |
| 5 | 38.2 ± 1.7 * | 55.2 ± 1.2 | 0.66 | 0.96 |
| 7 | 44.4 ± 1.6 * | 56.6 ± 1.4 | 0.77 | 0.98 |
| control | 57.7 ± 2 | | 1 | |

| Serial No | 99 | | | |
|---|---|---|---|---|
| Protein name | Dopamine receptors (D2) | | | |
| | AP-TGFa release (%) | | Normalized to control | |
| Compound | 1 mM | 1 µM | 1 mM | 1 µM |
| 0 | 46.8 ± 1.5 * | 50.9 ± 1.5 | 0.87 | 0.95 |
| 3 | 44.3 ± 1.2 * | 52.7 ± 2.7 | 0.83 | 0.98 |
| 5 | 47.2 ± 1.9 * | 53.3 ± 7.1 | 0.88 | 0.99 |
| control | 53.6 ± 2.7 | | 1 | |

| Serial No | 100 | | | |
|---|---|---|---|---|
| Protein name | Dopamine receptors (D4) | | | |
| | AP-TGFa release (%) | | Normalized to control | |
| Compound | 1 mM | 1 µM | 1 mM | 1 µM |
| 0 | 43.9 ± 1.4 * | 48.4 ± 0.3 | 0.9 | 0.99 |
| 3 | 41.7 ± 0.8 * | 49.8 ± 1.2 | 0.85 | 1.02 |
| 5 | 44 ± 1.7 * | 51.2 ± 0.7 * | 0.9 | 1.05 |
| control | 48.9 ± 1.3 | | 1 | |

| Serial No | 101 | | | |
|---|---|---|---|---|
| Protein name | Cannabinoid receptor (CB1) | | | |
| | AP-TGFa release (%) | | Normalized to control | |
| Compound | 1 mM | 1 µM | 1 mM | 1 µM |
| 0 | 64.4 ± 2.7 * | 75.9 ± 1.9 * | 0.77 | 0.91 |
| 1 | 67.2 ± 3.2 * | 77.2 ± 0.4 * | 0.81 | 0.92 |
| 3 | 63.4 ± 1.7 * | 76.9 ± 1 * | 0.76 | 0.92 |
| 4 | 76.7 ± 1.7 * | 79.3 ± 1.5 * | 0.92 | 0.95 |
| 5 | 68.1 ± 0.8 * | 78.6 ± 0.4 * | 0.82 | 0.94 |
| 7 | 74 ± 0.3 * | 81.9 ± 2 | 0.89 | 0.98 |
| control | 83.5 ± 1.2 | | 1 | |

| Serial No | 102 | | | |
|---|---|---|---|---|
| Protein name | Endothelin receptors (ETA) | | | |
| | AP-TGFa release (%) | | Normalized to control | |
| Compound | 1 mM | 1 µM | 1 mM | 1 µM |
| 0 | 39.9 ± 1.6 * | 42.2 ± 1.2 * | 0.88 | 0.93 |
| 1 | 39.6 ± 2.1 * | 41.5 ± 1.2 * | 0.87 | 0.92 |
| 3 | 36.5 ± 1.3 * | 43.4 ± 1.1 | 0.81 | 0.96 |
| 5 | 37.3 ± 0.8 * | 43.6 ± 0.7 | 0.82 | 0.96 |
| 7 | 40.9 ± 0.4 * | 40.8 ± 1.7 * | 0.9 | 0.9 |
| control | 45.3 ± 1.4 | | 1 | |

| Serial No | 103 | | | |
|---|---|---|---|---|
| Protein name | Opioid receptors (δ-OR) | | | |
| | AP-TGFa release (%) | | Normalized to control | |
| Compound | 1 mM | 1 µM | 1 mM | 1 µM |
| 3 | 63.4 ± 1.5 * | 71.8 ± 3.3 | 0.87 | 0.98 |
| 5 | 64.8 ± 2.8 * | 73.2 ± 2.5 | 0.89 | 1 |
| control | 73.2 ± 3.7 | | 1 | |

| Serial No | 104 | | | |
|---|---|---|---|---|
| Protein name | Adenosine receptors (A1) | | | |
| | AP-TGFa release (%) | | Normalized to control | |
| Compound | 1 mM | 1 µM | 1 mM | 1 µM |
| 5 | 63.9 ± 4 * | 79.9 ± 0.6 | 0.86 | 1.08 |
| control | 73.9 ± 4.4 | | 1 | |

| Serial No | 105 | | | |
|---|---|---|---|---|
| Protein name | Formylpeptide receptors (FPR2) | | | |
| | AP-TGFa release (%) | | Normalized to control | |
| Compound | 1 mM | 1 µM | 1 mM | 1 µM |
| 0 | 61.8 ± 0.4 * | 67 ± 1.4 | 0.94 | 1.02 |
| 1 | 62 ± 0.6 * | 64.8 ± 2.3 | 0.95 | 0.99 |
| 3 | 58.4 ± 1 * | 65.6 ± 0.4 | 0.89 | 1 |
| 5 | 59.1 ± 1.3 * | 65.2 ± 0.9 | 0.9 | 1 |
| 7 | 61.2 ± 0.7 * | 64.8 ± 0.9 | 0.93 | 0.99 |
| control | 65.5 ± 0.9 | | 1 | |

| Serial No | 106 | | | |
|---|---|---|---|---|
| Protein name | Adrenergic receptors (α2C) | | | |
| | AP-TGFa release (%) | | Normalized to control | |
| Compound | 1 mM | 1 µM | 1 mM | 1 µM |
| 0 | 56.2 ± 0.9 | 65.5 ± 0.6 | 0.87 | 1.01 |
| 3 | 50.5 ± 1.9 * | 60.5 ± 1.3 * | 0.78 | 0.93 |
| 5 | 50.6 ± 1.1 * | 61.6 ± 0.7 | 0.78 | 0.95 |
| 7 | 58 ± 2.1 | 59.8 ± 1.3 * | 0.89 | 0.92 |
| control | 64.9 ± 2.9 | | 1 | |

| Serial No | 107 | | | |
|---|---|---|---|---|
| Protein name | Adrenergic receptors (α2A) | | | |
| | AP-TGFa release (%) | | Normalized to control | |
| Compound | 1 mM | 1 µM | 1 mM | 1 µM |
| 3 | 54.2 ± 1.6 * | 65.4 ± 0.9 | 0.81 | 0.98 |
| 5 | 54.4 ± 2.8 * | 64.8 ± 0.9 | 0.81 | 0.97 |
| 7 | 61.2 ± 2.3 * | 64.9 ± 0.2 | 0.91 | 0.97 |
| control | 66.9 ± 3.2 | | 1 | |

| Serial No | 108 | | | |
|---|---|---|---|---|
| Protein name | Adrenergic receptors (α2B) | | | |
| | AP-TGFa release (%) | | Normalized to control | |
| Compound | 1 mM | 1 µM | 1 mM | 1 µM |
| 1 | 56.8 ± 0.5 | 60 ± 0.5 | 0.95 | 1.01 |
| 3 | 53.4 ± 0.5 | 59.6 ± 0.8 | 0.9 | 1 |
| 5 | 53.6 ± 0.1 | 60 ± 1 | 0.9 | 1.01 |
| control | 59.6 ± 1 | | 1 | |

| Serial No | 109 | | | |
|---|---|---|---|---|
| Protein name | leukotriene receptors (BLT1) | | | |
| | AP-TGFa release (%) | | Normalized to control | |
| Compound | 1 mM | 1 µM | 1 mM | 1 µM |
| 0 | 50.9 ± 1.2 * | 56.6 ± 1.5 * | 0.9 | 1 |
| 1 | 52 ± 1.2 * | 55.1 ± 1.1 * | 0.92 | 0.97 |
| 3 | 45.3 ± 1.5 * | 55.7 ± 1 * | 0.8 | 0.98 |
| 5 | 45.3 ± 1 * | 55.5 ± 0.9 * | 0.8 | 0.98 |
| 7 | 52.1 ± 0.4 * | 54.4 ± 1 * | 0.92 | 0.96 |
| control | 56.6 ± 0.5 | | 1 | |

| Serial No | 110 | | | |
|---|---|---|---|---|
| Protein name | Formylpeptide receptors (FPR3) | | | |
| | AP-TGFa release (%) | | Normalized to control | |
| Compound | 1 mM | 1 µM | 1 mM | 1 µM |
| 0 | 55.1 ± 1.2 * | 64.4 ± 3.6 | 0.92 | 1.08 |
| 5 | 53.9 ± 0.9 * | 61.5 ± 0.8 | 0.9 | 1.03 |
| 7 | 54.4 ± 1.2 * | 60.7 ± 2.1 | 0.91 | 1.02 |
| control | 59.8 ± 1.8 | | 1 | |

| Serial No | 111 | | | |
|---|---|---|---|---|
| Protein name | Complement peptide receptors (C3AR1) | | | |
| | AP-TGFa release (%) | | Normalized to control | |
| Compound | 1 mM | 1 µM | 1 mM | 1 µM |
| 0 | 58.7 ± 2.6 * | 67.8 ± 0.4 | 0.89 | 1.02 |
| 1 | 62.6 ± 1.4 * | 69.6 ± 1.5 * | 0.95 | 1.05 |
| 7 | 55.2 ± 2.7 * | 68.7 ± 2.5 | 0.83 | 1.04 |
| control | 66.2 ± 2.1 | | 1 | |

| Serial No | 112 | | | |
|---|---|---|---|---|
| Protein name | Chemokine receptors (CCR3) | | | |
| | AP-TGFa release (%) | | Normalized to control | |
| Compound | 1 mM | 1 µM | 1 mM | 1 µM |
| 0 | 54.3 ± 3.4 * | 65 ± 2.9 | 0.84 | 1.01 |
| 1 | 60.1 ± 0.9 * | 77 ± 13.4 | 0.93 | 1.19 |
| 3 | 59.3 ± 1.3 * | 67.6 ± 4.1 | 0.92 | 1.05 |
| 5 | 58.3 ± 2.2 * | 68.2 ± 4.4 | 0.9 | 1.05 |
| 7 | 55.9 ± 2.7 * | 67.8 ± 3 | 0.86 | 1.05 |
| control | 64.7 ± 2.4 | | 1 | |

| Serial No | 113 | | | |
|---|---|---|---|---|
| Protein name | Chemerin receptors (CMKLR1) | | | |
| | AP-TGFa release (%) | | Normalized to control | |
| Compound | 1 mM | 1 µM | 1 mM | 1 µM |
| 0 | 50.7 ± 0.7 * | 59.9 ± 0.4 | 0.87 | 1.02 |
| 3 | 47.9 ± 0.6 * | 56.9 ± 2.9 | 0.82 | 0.97 |
| 5 | 59 ± 0.7 * | 59.3 ± 1.9 | 0.86 | 1.01 |
| 7 | 52.1 ± 1 * | 59.5 ± 1 | 0.89 | 1.02 |
| control | 58.4 ± 1.4 | | 1 | |

| Serial No | 114 | | | |
|---|---|---|---|---|
| Protein name | Complement peptide receptors (C5AR1) | | | |
| | AP-TGFa release (%) | | Normalized to control | |
| Compound | 1 mM | 1 µM | 1 mM | 1 µM |
| 0 | 50.3 ± 0.5 * | 59.8 ± 0.8 | 0.87 | 1.03 |
| 1 | 52.9 ± 2.1 * | 59.1 ± 1.5 | 0.91 | 1.02 |
| 3 | 48.3 ± 1.6 * | 56.9 ± 1 | 0.83 | 0.98 |
| 5 | 49.9 ± 2.2 * | 54.8 ± 2.8 * | 0.86 | 0.95 |
| 7 | 46.9 ± 0.1 * | 56 ± 0.8 * | 0.81 | 0.97 |
| control | 57.9 ± 2.3 | | 1 | |

| Serial No | 115 | | | |
|---|---|---|---|---|
| Protein name | Adrenergic receptors (β3) | | | |
| | AP-TGFa release (%) | | Normalized to control | |
| Compound | 1 mM | 1 μM | 1 mM | 1 μM |
| 3 | 86 ± 4 * | 92.1 ± 1.5 | 0.92 | 0.99 |
| 5 | 81.5 ± 3.8 * | 90.8 ± 2.5 | 0.88 | 0.98 |
| 7 | 86.5 ± 2.7 * | 92.9 ± 2.5 | 0.93 | 1 |
| control | 93.1 ± 4.1 | | 1 | |

| Serial No | 116 | | | |
|---|---|---|---|---|
| Protein name | Chemokine receptors (CCR7) | | | |
| | AP-TGFa release (%) | | Normalized to control | |
| Compound | 1 mM | 1 μM | 1 mM | 1 μM |
| 0 | 60.7 ± 2.3 * | 69.7 ± 1.6 * | 0.78 | 0.9 |
| 1 | 68.9 ± 1.5 * | 69.1 ± 1.9 * | 0.89 | 0.89 |
| 3 | 67.2 ± 0.9 * | 71.1 ± 4.1 | 0.87 | 0.92 |
| 7 | 70.9 ± 1.5 * | 75.6 ± 4 | 0.91 | 0.98 |
| control | 77.5 ± 4.1 | | 1 | |

| Serial No | 117 | | | |
|---|---|---|---|---|
| Protein name | Prostanoid receptors (EP3 (iso6)) | | | |
| | AP-TGFa release (%) | | Normalized to control | |
| Compound | 1 mM | 1 μM | 1 mM | 1 μM |
| 0 | 77.4 ± 2.6 * | 83.7 ± 1.6 | 0.94 | 1.02 |
| 5 | 77.6 ± 1 * | 83.2 ± 3.4 | 0.94 | 1.01 |
| 7 | 76.2 ± 1.4 * | 82.9 ± 3.4 | 0.92 | 1.01 |
| control | 82.4 ± 2.5 | | 1 | |

| Serial No | 118 | | | |
|---|---|---|---|---|
| Protein name | Chemokine receptors (CCR4) | | | |
| | AP-TGFa release (%) | | Normalized to control | |
| Compound | 1 mM | 1 μM | 1 mM | 1 μM |
| 0 | 57.2 ± 0.7 * | 69.3 ± 0.9 | 0.82 | 0.99 |
| 3 | 63.8 ± 4.1 | 70.5 ± 4.2 | 0.91 | 1.01 |
| 5 | 62.8 ± 2.2 * | 72.8 ± 1.1 | 0.9 | 1.04 |
| 7 | 60.9 ± 1.6 * | 71 ± 2.7 | 0.87 | 1.02 |
| control | 69.8 ± 3 | | 1 | |

| Serial No | 119 | | | |
|---|---|---|---|---|
| Protein name | Chemokine receptors (CXCR5) | | | |
| | AP-TGFa release (%) | | Normalized to control | |
| Compound | 1 mM | 1 μM | 1 mM | 1 μM |
| 0 | 59.5 ± 2.5 * | 70.1 ± 0.9 | 0.84 | 0.98 |
| 7 | 61.2 ± 2.9 * | 71.8 ± 5.9 | 0.86 | 1.01 |
| control | 71.2 ± 6.1 | | 1 | |

| Serial No | 120 | | | |
|---|---|---|---|---|
| Protein name | Chemokine receptors (DARC) | | | |
| | AP-TGFa release (%) | | Normalized to control | |
| Compound | 1 mM | 1 μM | 1 mM | 1 μM |
| 0 | 53.8 ± 2 * | 67.1 ± 0.6 * | 0.88 | 1.09 |
| 1 | 56.2 ± 4.2 * | 64 ± 0.8 | 0.92 | 1.04 |
| 3 | 47.6 ± 2.1 * | 64.7 ± 2.5 | 0.78 | 1.06 |
| 5 | 53.1 ± 2.7 * | 64.6 ± 1.4 | 0.87 | 1.05 |
| 7 | 53.4 ± 4.4 * | 67.1 ± 2.2 * | 0.87 | 1.1 |
| control | 61.3 ± 2.4 | | 1 | |

| Serial No | 121 | | | |
|---|---|---|---|---|
| Protein name | Cholecystokinin receptors (CCKBR) | | | |
| | AP-TGFa release (%) | | Normalized to control | |
| Compound | 1 mM | 1 μM | 1 mM | 1 μM |
| 7 | 59.2 ± 1.5 * | 72.2 ± 3.5 | 0.89 | 1.09 |
| control | 66.3 ± 4.2 | | 1 | |

| Serial No | 122 | | | |
|---|---|---|---|---|
| Protein name | Hydroxycarboxylic acid receptors (GPR109A) | | | |
| | AP-TGFa release (%) | | Normalized to control | |
| Compound | 1 mM | 1 μM | 1 mM | 1 μM |
| 0 | 53 ± 1 * | 61.5 ± 3 | 0.87 | 1.01 |
| 1 | 54.2 ± 1 * | 56.8 ± 1.8 * | 0.89 | 0.93 |
| 5 | 58.2 ± 0.8 * | 59.2 ± 1.2 * | 0.95 | 0.97 |
| 7 | 54.2 ± 0.7 * | 60.2 ± 1.6 | 0.89 | 0.99 |
| control | 61 ± 1.1 | | 1 | |

| Serial No | 123 | | | |
|---|---|---|---|---|
| Protein name | Bombesin receptors (GRPR) | | | |
| | AP-TGFa release (%) | | Normalized to control | |
| Compound | 1 mM | 1 μM | 1 mM | 1 μM |
| 0 | 63.7 ± 0.2 * | 68.9 ± 1.7 | 0.95 | 1.03 |
| 1 | 61.7 ± 1.4 * | 68.8 ± 2.9 | 0.92 | 1.03 |
| 7 | 61.1 ± 0.4 * | 65.2 ± 2.2 | 0.91 | 0.97 |
| control | 67 ± 1 | | 1 | |

| Serial No | 124 | | | |
|---|---|---|---|---|
| Protein name | Class A Orphans (GPR75) | | | |
| | AP-TGFa release (%) | | Normalized to control | |
| Compound | 1 mM | 1 μM | 1 mM | 1 μM |
| 0 | 55.5 ± 1.6 * | 61.6 ± 0.8 | 0.91 | 1.01 |
| 1 | 56.8 ± 0.7 * | 58.1 ± 0.8 | 0.93 | 0.95 |
| 7 | 54.1 ± 0.8 * | 58.7 ± 1.1 | 0.88 | 0.96 |
| control | 61.2 ± 2.2 | | 1 | |

| Serial No | 125 | | | |
|---|---|---|---|---|
| Protein name | G protein-coupled estrogen receptors (GPER) | | | |
| | AP-TGFa release (%) | | Normalized to control | |
| Compound | 1 mM | 1 μM | 1 mM | 1 μM |
| 0 | 59 ± 1.1 * | 62.7 ± 0.5 | 0.94 | 1 |
| 1 | 57 ± 1.1 * | 61.6 ± 0.6 | 0.91 | 0.98 |
| 3 | 58.4 ± 2.6 * | 63 ± 0.6 | 0.93 | 1 |
| 5 | 57.8 ± 1.1 * | 63 ± 1.1 | 0.92 | 1 |
| 7 | 56.6 ± 0.5 * | 63.8 ± 1.2 | 0.9 | 1.02 |
| control | 62.8 ± 0.8 | | 1 | |

| Serial No | 126 | | | |
|---|---|---|---|---|
| Protein name | Class A Orphans (GPR173) | | | |
| | AP-TGFa release (%) | | Normalized to control | |
| Compound | 1 mM | 1 μM | 1 mM | 1 μM |
| 5 | 52 ± 1.8 * | 56 ± 0.6 * | 0.87 | 0.94 |
| 7 | 51.3 ± 1.7 * | 54.9 ± 0.9 * | 0.86 | 0.92 |
| control | 59.8 ± 1.9 | | 1 | |

| Serial No | 127 | | | |
|---|---|---|---|---|
| Protein name | Class A Orphans (GPR18) | | | |
| | AP-TGFa release (%) | | Normalized to control | |
| Compound | 1 mM | 1 μM | 1 mM | 1 μM |
| 1 | 55.5 ± 1.6 * | 60 ± 2.7 | 0.91 | 0.99 |
| 3 | 53.2 ± 1.2 * | 56.7 ± 0.4 * | 0.88 | 0.93 |
| 5 | 52.2 ± 1.9 * | 57.7 ± 0.2 | 0.86 | 0.95 |
| 7 | 52 ± 0.8 * | 58.4 ± 0.7 | 0.86 | 0.96 |
| control | 60.7 ± 2.1 | | 1 | |

| Serial No | 128 | | | |
|---|---|---|---|---|
| Protein name | Class A Orphans (GPR101) | | | |
| | AP-TGFa release (%) | | Normalized to control | |
| Compound | 1 mM | 1 μM | 1 mM | 1 μM |
| 3 | 59.4 ± 1.2 * | 63.7 ± 2.1 | 0.89 | 0.95 |
| control | 66.8 ± 4.7 | | 1 | |

Serial No 129
Protein name: Class A Orphans (LGR5)

| Compound | AP-TGFa release (%) 1 mM | 1 μM | Normalized to control 1 mM | 1 μM |
|---|---|---|---|---|
| 0 | 72 ± 1.2 * | 75 ± 0.4 | 0.95 | 0.99 |
| 1 | 68.7 ± 0.9 * | 74.5 ± 1.7 | 0.9 | 0.98 |
| 3 | 67.7 ± 1.9 * | 75.3 ± 0.6 | 0.89 | 0.99 |
| 5 | 66.4 ± 0.7 * | 75.4 ± 3 | 0.87 | 0.99 |
| 7 | 70.9 ± 1.6 * | 74.2 ± 1.7 | 0.93 | 0.98 |
| control | 76 ± 0.8 | | 1 | |

Serial No 130
Protein name: Class A Orphans (GPR142)

| Compound | AP-TGFa release (%) 1 mM | 1 μM | Normalized to control 1 mM | 1 μM |
|---|---|---|---|---|
| 0 | 48 ± 1.2 * | 54.9 ± 1.8 | 0.84 | 0.96 |
| 1 | 47.3 ± 1.1 * | 54.9 ± 2.4 | 0.82 | 0.96 |
| 3 | 52.6 ± 1.8 * | 55.1 ± 1.1 | 0.92 | 0.96 |
| 5 | 53 ± 0.9 * | 54.8 ± 1.4 | 0.92 | 0.95 |
| 7 | 47.6 ± 2.1 * | 55.7 ± 0.8 | 0.83 | 0.97 |
| control | 57.5 ± 2.2 | | 1 | |

Serial No 131
Protein name: Class A Orphans (GPR146)

| Compound | AP-TGFa release (%) 1 mM | 1 μM | Normalized to control 1 mM | 1 μM |
|---|---|---|---|---|
| 0 | 54.3 ± 2 * | 62.2 ± 2.2 | 0.87 | 0.99 |
| 1 | 54.2 ± 4.1 * | 59.6 ± 1.8 | 0.86 | 0.95 |
| 7 | 52.3 ± 1.6 * | 60.4 ± 2 | 0.83 | 0.96 |
| control | 62.7 ± 2.6 | | 1 | |

Serial No 132
Protein name: Ghrelin receptors (GHSR)

| Compound | AP-TGFa release (%) 1 mM | 1 μM | Normalized to control 1 mM | 1 μM |
|---|---|---|---|---|
| 0 | 63.9 ± 1.7 * | 72.9 ± 2.3 | 0.91 | 1.04 |
| 1 | 63.7 ± 2.7 * | 69.2 ± 4.5 | 0.91 | 0.99 |
| 5 | 62.8 ± 1.5 * | 68.2 ± 2.3 | 0.9 | 0.97 |
| 7 | 63.6 ± 2.5 * | 70.5 ± 0.8 | 0.91 | 1.01 |
| control | 70 ± 3 | | 1 | |

Serial No 133
Protein name: Galanin receptors (GALR1)

| Compound | AP-TGFa release (%) 1 mM | 1 μM | Normalized to control 1 mM | 1 μM |
|---|---|---|---|---|
| 0 | 40.3 ± 1.6 * | 54.8 ± 4.1 * | 0.86 | 1.16 |
| 1 | 41.9 ± 1.8 * | 50.9 ± 5.5 | 0.89 | 1.08 |
| 5 | 40.7 ± 1.1 * | 45.5 ± 0.8 | 0.87 | 0.97 |
| 7 | 38.5 ± 1.4 * | 45.8 ± 3.7 | 0.82 | 0.97 |
| control | 47.1 ± 2.5 | | 1 | |

Serial No 134
Protein name: Class A Orphans (GPR161)

| Compound | AP-TGFa release (%) 1 mM | 1 μM | Normalized to control 1 mM | 1 μM |
|---|---|---|---|---|
| 0 | 56.3 ± 1.7 * | 57.5 ± 2.5 | 0.95 | 0.98 |
| 1 | 51.5 ± 0.8 * | 56.7 ± 2.2 | 0.87 | 0.96 |
| 3 | 50.2 ± 2 * | 54 ± 1 | 0.85 | 0.92 |
| 5 | 49.5 ± 0.4 * | 55.7 ± 1.9 * | 0.84 | 0.94 |
| 7 | 47.9 ± 1.9 * | 54.7 ± 1.7 * | 0.81 | 0.93 |
| control | 58.9 ± 1.4 | | 1 | |

Serial No 135
Protein name: Prostanoid receptors (GPR44 (DP2))

| Compound | AP-TGFa release (%) 1 mM | 1 μM | Normalized to control 1 mM | 1 μM |
|---|---|---|---|---|
| 0 | 54.5 ± 1.3 * | 62.6 ± 3.1 | 0.84 | 0.96 |
| 1 | 59 ± 1.9 * | 61.6 ± 3.9 | 0.91 | 0.95 |
| 5 | 60.1 ± 2.3 * | 64.6 ± 2 | 0.92 | 0.99 |
| 7 | 54.3 ± 1.3 * | 63.3 ± 2.6 | 0.83 | 0.97 |
| control | 65.1 ± 1.2 | | 1 | |

Serial No 136
Protein name: Class A Orphans (GPR139)

| Compound | AP-TGFa release (%) 1 mM | 1 μM | Normalized to control 1 mM | 1 μM |
|---|---|---|---|---|
| 0 | 72.8 ± 1 * | 78.2 ± 1.4 | 0.91 | 0.98 |
| 1 | 69.2 ± 2.9 * | 77.2 ± 2.6 | 0.86 | 0.97 |
| 3 | 73.3 ± 2.6 * | 76.7 ± 1.7 * | 0.92 | 0.96 |
| 4 | 74.2 ± 0.9 * | 78.1 ± 0.9 | 0.93 | 0.98 |
| 5 | 74.7 ± 0.3 * | 78.4 ± 1.9 | 0.93 | 0.98 |
| 7 | 74.4 ± 0.8 * | 79 ± 0.7 | 0.93 | 0.99 |
| control | 80 ± 2 | | 1 | |

Serial No 137
Protein name: Class A Orphans (GPR182)

| Compound | AP-TGFa release (%) 1 mM | 1 μM | Normalized to control 1 mM | 1 μM |
|---|---|---|---|---|
| 3 | 51.2 ± 1.5 * | 61.3 ± 3.7 | 0.86 | 1.03 |
| 5 | 52.4 ± 0.9 * | 68.1 ± 9.2 | 0.88 | 1.15 |
| 7 | 50.9 ± 2.3 * | 60.1 ± 3.3 | 0.86 | 1.02 |
| control | 59.3 ± 4.1 | | 1 | |

Serial No 138
Protein name: Class A Orphans (MRGX2)

| Compound | AP-TGFa release (%) 1 mM | 1 μM | Normalized to control 1 mM | 1 μM |
|---|---|---|---|---|
| 1 | 62 ± 1.5 * | 66.6 ± 1.7 | 0.94 | 1.01 |
| control | 66 ± 0.9 | | 1 | |

Serial No 139
Protein name: Neuropeptide FF receptors (NPFFR2)

| Compound | AP-TGFa release (%) 1 mM | 1 μM | Normalized to control 1 mM | 1 μM |
|---|---|---|---|---|
| 0 | 41 ± 2 * | 44.9 ± 1 | 0.89 | 0.98 |
| 1 | 43 ± 0.4 * | 49.3 ± 0.4 * | 0.94 | 1.07 |
| 3 | 41.4 ± 1.4 * | 48.7 ± 0.5 * | 0.9 | 1.06 |
| 7 | 41 ± 2.3 * | 47.6 ± 0.5 * | 0.89 | 1.04 |
| control | 45.8 ± 0.9 | | 1 | |

Serial No 140
Protein name: Neuromedin U receptors (NMUR1)

| Compound | AP-TGFa release (%) 1 mM | 1 μM | Normalized to control 1 mM | 1 μM |
|---|---|---|---|---|
| 0 | 48.4 ± 1.4 * | 51.9 ± 0.4 | 0.91 | 0.97 |
| 1 | 48 ± 0.3 * | 53.6 ± 2.3 | 0.9 | 1.01 |
| 3 | 50.3 ± 1.7 * | 55 ± 1.5 | 0.94 | 1.03 |
| 7 | 47.1 ± 2.7 * | 52.2 ± 2.9 | 0.88 | 0.98 |
| control | 53.3 ± 1.6 | | 1 | |

| Serial No | 141 | | | |
|---|---|---|---|---|
| Protein name | Class A orphan (Mrgb1/Mrgprx2) | | | |
| | AP-TGFa release (%) | | Normalized to control | |
| Compound | 1 mM | 1 µM | 1 mM | 1 µM |
| 0 | 60.5 ± 1.5 * | 61.2 ± 1.8 * | 0.93 | 0.94 |
| 1 | 57.1 ± 1.8 * | 61.3 ± 0.7 * | 0.88 | 0.95 |
| 3 | 59.3 ± 2.2 * | 62.3 ± 2 | 0.92 | 0.96 |
| 5 | 60.1 ± 2.5 * | 65.1 ± 1 | 0.93 | 1 |
| control | 64.8 ± 2.2 | | 1 | |

| Serial No | 142 | | | |
|---|---|---|---|---|
| Protein name | Class A orphan (Mrga1) | | | |
| | AP-TGFa release (%) | | Normalized to control | |
| Compound | 1 mM | 1 µM | 1 mM | 1 µM |
| 1 | 53.7 ± 1.6 * | 57.6 ± 2.1 | 0.94 | 1.01 |
| 3 | 51.2 ± 0.4 * | 56.8 ± 1.6 | 0.9 | 1 |
| 5 | 53.8 ± 1.5 * | 56.8 ± 2.2 | 0.94 | 1 |
| control | 57 ± 1.9 | | 1 | |

| Serial No | 143 | | | |
|---|---|---|---|---|
| Protein name | Neuropeptide Y receptors (NPY2R) | | | |
| | AP-TGFa release (%) | | Normalized to control | |
| Compound | 1 mM | 1 µM | 1 mM | 1 µM |
| 0 | 42.1 ± 0.5 * | 45 ± 0.4 * | 0.91 | 0.98 |
| 1 | 43.8 ± 0.9 * | 48.5 ± 2 | 0.95 | 1.05 |
| 3 | 43.5 ± 0.9 * | 48.4 ± 1.9 | 0.95 | 1.05 |
| 5 | 43.5 ± 0.5 * | 48 ± 0.9 | 0.95 | 1.04 |
| 7 | 38.9 ± 3.1 * | 45.5 ± 1.3 | 0.85 | 0.99 |
| control | 46 ± 1 | | 1 | |

| Serial No | 144 | | | |
|---|---|---|---|---|
| Protein name | Neuropeptide Y receptors (NPY5R) | | | |
| | AP-TGFa release (%) | | Normalized to control | |
| Compound | 1 mM | 1 µM | 1 mM | 1 µM |
| 1 | 37.9 ± 1.8 * | 44.4 ± 1.6 | 0.91 | 1.06 |
| 3 | 36 ± 0.4 * | 42.5 ± 0.7 | 0.86 | 1.02 |
| 7 | 36.4 ± 0.7 * | 42 ± 1.4 | 0.87 | 1.01 |
| control | 41.7 ± 2 | | 1 | |

| Serial No | 145 | | | |
|---|---|---|---|---|
| Protein name | Neuropeptides B and W receptor (NPBWR2) | | | |
| | AP-TGFa release (%) | | Normalized to control | |
| Compound | 1 mM | 1 µM | 1 mM | 1 µM |
| 0 | 38.2 ± 0.7 * | 45.5 ± 0.4 | 0.87 | 1.03 |
| 1 | 39.3 ± 1.1 * | 44.8 ± 3.1 | 0.89 | 1.02 |
| 3 | 38.1 ± 1 * | 43 ± 2.1 | 0.86 | 0.97 |
| 5 | 39.3 ± 1.5 * | 44.6 ± 2.4 | 0.89 | 1.01 |
| 7 | 37.2 ± 1.3 * | 40.6 ± 1.1 * | 0.84 | 0.92 |
| control | 44.1 ± 1.3 | | 1 | |

| Serial No | 146 | | | |
|---|---|---|---|---|
| Protein name | Class A orphan (Mrga2a) | | | |
| | AP-TGFa release (%) | | Normalized to control | |
| Compound | 1 mM | 1 µM | 1 mM | 1 µM |
| 1 | 35.3 ± 0.9 * | 37.8 ± 1.1 | 0.92 | 0.99 |
| 3 | 35.4 ± 1.1 * | 37.8 ± 0.7 | 0.92 | 0.99 |
| 7 | 32.1 ± 2.2 * | 35.3 ± 1.6 * | 0.84 | 0.92 |
| control | 38.3 ± 0.7 | | 1 | |

| Serial No | 147 | | | |
|---|---|---|---|---|
| Protein name | Class A orphan (Mrgb3) | | | |
| | AP-TGFa release (%) | | Normalized to control | |
| Compound | 1 mM | 1 µM | 1 mM | 1 µM |
| 0 | 42.7 ± 2.9 * | 47.3 ± 2 | 0.9 | 1 |
| 1 | 42.1 ± 2.2 * | 46.5 ± 1.9 | 0.89 | 0.98 |
| 3 | 42.4 ± 1.6 * | 45.2 ± 0.2 | 0.89 | 0.95 |
| 5 | 43.2 ± 0.4 * | 45.4 ± 0.9 | 0.91 | 0.96 |
| 7 | 41.3 ± 1.2 * | 44.2 ± 0.7 | 0.87 | 0.93 |
| control | 47.5 ± 2.9 | | 1 | |

| Serial No | 148 | | | |
|---|---|---|---|---|
| Protein name | Melanocortin receptors (MC5R) | | | |
| | AP-TGFa release (%) | | Normalized to control | |
| Compound | 1 mM | 1 µM | 1 mM | 1 µM |
| 1 | 40 ± 2.7 * | 42.7 ± 2 | 0.87 | 0.93 |
| 3 | 39.6 ± 2.3 * | 42.9 ± 2.4 | 0.87 | 0.94 |
| 5 | 38.7 ± 0.9 * | 40.6 ± 1.2 * | 0.85 | 0.89 |
| 7 | 36.5 ± 4 * | 41.1 ± 3.3 | 0.8 | 0.9 |
| control | 45.7 ± 3.4 | | 1 | |

| Serial No | 149 | | | |
|---|---|---|---|---|
| Protein name | Melanocortin receptors (MC3R) | | | |
| | AP-TGFa release (%) | | Normalized to control | |
| Compound | 1 mM | 1 µM | 1 mM | 1 µM |
| 0 | 41 ± 1.4 * | 48.4 ± 2.3 | 0.82 | 0.97 |
| 1 | 42.8 ± 0.9 * | 47.1 ± 1.8 | 0.86 | 0.95 |
| 3 | 43.8 ± 1 * | 48.2 ± 0.9 | 0.88 | 0.97 |
| 5 | 44.5 ± 1.4 * | 48.1 ± 0.9 | 0.89 | 0.97 |
| 7 | 39.4 ± 1.1 * | 47.1 ± 2.4 | 0.79 | 0.95 |
| control | 49.8 ± 1.6 | | 1 | |

| Serial No | 150 | | | |
|---|---|---|---|---|
| Protein name | Neuropeptide FF receptors (NPFFR1) | | | |
| | AP-TGFa release (%) | | Normalized to control | |
| Compound | 1 mM | 1 µM | 1 mM | 1 µM |
| 0 | 60.4 ± 1.7 * | 63.5 ± 1.6 | 0.94 | 0.99 |
| 1 | 59.4 ± 0.4 * | 62.8 ± 1.4 | 0.93 | 0.98 |
| 3 | 60.1 ± 1.8 * | 66.2 ± 2.8 | 0.94 | 1.03 |
| 5 | 60.4 ± 1 * | 66.1 ± 0.5 | 0.94 | 1.03 |
| 7 | 58.2 ± 2.8 * | 66.3 ± 2.3 | 0.91 | 1.03 |
| control | 64.1 ± 1.6 | | 1 | |

| Serial No | 151 | | | |
|---|---|---|---|---|
| Protein name | Melanin-concentrating hormone receptors (MCHR2) | | | |
| | AP-TGFa release (%) | | Normalized to control | |
| Compound | 1 mM | 1 µM | 1 mM | 1 µM |
| 1 | 42.8 ± 1.8 * | 46.4 ± 1 | 0.89 | 0.97 |
| 7 | 43.9 ± 2 * | 46.1 ± 1.6 | 0.91 | 0.96 |
| control | 48 ± 1.4 | | 1 | |

| Serial No | 152 | | | |
|---|---|---|---|---|
| Protein name | Class A Orphans (Mrgb4) | | | |
| | AP-TGFa release (%) | | Normalized to control | |
| Compound | 1 mM | 1 µM | 1 mM | 1 µM |
| 1 | 58.1 ± 1.7 * | 62.8 ± 1.8 | 0.91 | 0.99 |
| 5 | 60.5 ± 0.8 * | 63.5 ± 1 | 0.95 | 1 |
| 7 | 58.7 ± 0.5 * | 61.6 ± 3.3 | 0.92 | 0.97 |
| control | 63.7 ± 2.1 | | 1 | |

| Serial No | 153 | | | |
|---|---|---|---|---|
| Protein name | Class A Orphans (Mrgb5) | | | |
| | AP-TGFa release (%) | | Normalized to control | |
| Compound | 1 mM | 1 µM | 1 mM | 1 µM |
| 0 | 63.7 ± 1.5 * | 66.8 ± 2.6 | 0.93 | 0.98 |
| control | 68.4 ± 2 | | 1 | |

| Serial No | 154 | | | |
|---|---|---|---|---|
| Protein name | Class A Orphans (MRGD) | | | |
| | AP-TGFa release (%) | | Normalized to control | |
| Compound | 1 mM | 1 µM | 1 mM | 1 µM |
| 0 | 49.5 ± 1.4 * | 55.3 ± 3.8 | 0.92 | 1.02 |
| 1 | 49.4 ± 1.1 * | 53.9 ± 1.5 | 0.92 | 1 |
| control | 54 ± 2.6 | | 1 | |

| Serial No | 155 | | | |
|---|---|---|---|---|
| Protein name | Class A Orphans (Mrgb2) | | | |
| | AP-TGFa release (%) | | Normalized to control | |
| Compound | 1 mM | 1 µM | 1 mM | 1 µM |
| 0 | 61.8 ± 0.5 * | 64.2 ± 2.3 | 0.93 | 0.97 |
| 1 | 61 ± 2.1 * | 64.1 ± 1.7 * | 0.92 | 0.97 |
| control | 66.4 ± 0.9 | | 1 | |

| Serial No | 156 | | | |
|---|---|---|---|---|
| Protein name | Class A Orphans (Mrgh) | | | |
| | AP-TGFa release (%) | | Normalized to control | |
| Compound | 1 mM | 1 µM | 1 mM | 1 µM |
| 0 | 60.9 ± 2.2 * | 62.6 ± 3.1 | 0.95 | 0.97 |
| 1 | 57.7 ± 3.2 * | 62.3 ± 5.5 | 0.9 | 0.97 |
| 3 | 59.7 ± 1.4 * | 61.8 ± 2.5 | 0.93 | 0.96 |
| 4 | 60.8 ± 0.7 * | 63.8 ± 3.2 | 0.94 | 0.99 |
| 5 | 61.3 ± 2.5 * | 64.2 ± 3.5 | 0.95 | 1 |
| control | 64.4 ± 1.1 | | 1 | |

| Serial No | 157 | | | |
|---|---|---|---|---|
| Protein name | Neuropeptides B and W receptor (NPBWR1) | | | |
| | AP-TGFa release (%) | | Normalized to control | |
| Compound | 1 mM | 1 µM | 1 mM | 1 µM |
| 0 | 33 ± 1.6 * | 37.4 ± 0.9 | 0.89 | 1 |
| 1 | 31.4 ± 1.8 * | 37.8 ± 1.1 | 0.84 | 1.02 |
| 3 | 32.6 ± 2 * | 36 ± 3.1 | 0.87 | 0.97 |
| 5 | 33.3 ± 2.3 * | 36.5 ± 0.5 | 0.9 | 0.98 |
| 7 | 29.6 ± 1.1 * | 35.5 ± 1 * | 0.8 | 0.96 |
| control | 37.2 ± 0.9 | | 1 | |

| Serial No | 158 | | | |
|---|---|---|---|---|
| Protein name | Class A Orphans (Mrge) | | | |
| | AP-TGFa release (%) | | Normalized to control | |
| Compound | 1 mM | 1 µM | 1 mM | 1 µM |
| 0 | 39.6 ± 1.4 * | 42.7 ± 1.9 | 0.89 | 0.96 |
| 1 | 40.3 ± 3.2 * | 43.2 ± 1.3 | 0.91 | 0.97 |
| 3 | 40.2 ± 0.5 * | 42.8 ± 2.4 | 0.9 | 0.96 |
| 7 | 37.2 ± 0.3 * | 40.1 ± 1.9 * | 0.84 | 0.9 |
| control | 44.5 ± 1.7 | | 1 | |

| Serial No | 159 | | | |
|---|---|---|---|---|
| Protein name | Melanin-concentrating hormone receptors (MCHR1) | | | |
| | AP-TGFa release (%) | | Normalized to control | |
| Compound | 1 mM | 1 µM | 1 mM | 1 µM |
| 0 | 36.9 ± 1.7 * | 43 ± 1.7 | 0.87 | 1.02 |
| 3 | 38.1 ± 0.6 * | 44.7 ± 1.2 | 0.9 | 1.06 |
| 5 | 38.1 ± 0.8 * | 43 ± 1 | 0.9 | 1.02 |
| 7 | 37.2 ± 1.9 * | 42.3 ± 1 | 0.88 | 1 |
| control | 42.3 ± 1.4 | | 1 | |

| Serial No | 160 | | | |
|---|---|---|---|---|
| Protein name | Class A Orphans (Mrga4) | | | |
| | AP-TGFa release (%) | | Normalized to control | |
| Compound | 1 mM | 1 µM | 1 mM | 1 µM |
| 1 | 56.6 ± 0.8 * | 60.2 ± 1.3 | 0.94 | 1 |
| control | 60 ± 1.3 | | 1 | |

| Serial No | 161 | | | |
|---|---|---|---|---|
| Protein name | Class A Orphans (MAS1L) | | | |
| | AP-TGFa release (%) | | Normalized to control | |
| Compound | 1 mM | 1 µM | 1 mM | 1 µM |
| 0 | 36 ± 0.5 * | 39.6 ± 2.6 | 0.88 | 0.97 |
| 1 | 37.3 ± 0.6 * | 40.9 ± 2.7 | 0.91 | 1 |
| 3 | 32.5 ± 1.9 * | 37.8 ± 0.5 * | 0.79 | 0.92 |
| 5 | 34.2 ± 0.4 * | 38.8 ± 1.9 | 0.84 | 0.95 |
| 7 | 32.4 ± 1 * | 36.1 ± 1.5 * | 0.79 | 0.88 |
| control | 40.9 ± 1.9 | | 1 | |

| Serial No | 162 | | | |
|---|---|---|---|---|
| Protein name | Class A Orphans (Mrga7) | | | |
| | AP-TGFa release (%) | | Normalized to control | |
| Compound | 1 mM | 1 µM | 1 mM | 1 µM |
| 1 | 61.4 ± 1.2 * | 66.4 ± 2 | 0.93 | 1.01 |
| 3 | 62.7 ± 0.4 * | 67.5 ± 1.8 | 0.95 | 1.03 |
| 5 | 60.6 ± 2.7 * | 65.7 ± 4.6 | 0.92 | 1 |
| 7 | 61.6 ± 2.1 * | 63.2 ± 5.1 | 0.94 | 0.96 |
| control | 65.7 ± 2.1 | | 1 | |

| Serial No | 163 | | | |
|---|---|---|---|---|
| Protein name | Class A Orphans (MRGX3) | | | |
| | AP-TGFa release (%) | | Normalized to control | |
| Compound | 1 mM | 1 µM | 1 mM | 1 µM |
| 0 | 40.5 ± 3 * | 45.7 ± 0.5 | 0.86 | 0.97 |
| 1 | 42.2 ± 0.2 * | 45.7 ± 2 | 0.9 | 0.97 |
| 3 | 40.8 ± 0.9 * | 44.3 ± 2.1 * | 0.87 | 0.95 |
| 5 | 42.9 ± 0.3 * | 42.7 ± 3.1 * | 0.92 | 0.91 |
| 7 | 39.9 ± 0.8 * | 42.9 ± 1.7 * | 0.85 | 0.92 |
| control | 46.9 ± 1.1 | | 1 | |

| Serial No | 164 | | | |
|---|---|---|---|---|
| Protein name | Melatonin receptors (MTTR) | | | |
| | AP-TGFa release (%) | | Normalized to control | |
| Compound | 1 mM | 1 µM | 1 mM | 1 µM |
| 0 | 44.7 ± 2.2 * | 50.2 ± 1.2 * | 0.83 | 0.93 |
| 1 | 42.7 ± 2.2 * | 51.7 ± 1.9 | 0.79 | 0.95 |
| 3 | 46.2 ± 1.9 * | 48.5 ± 3.8 * | 0.85 | 0.9 |
| 5 | 47.8 ± 2.4 * | 49.9 ± 3.6 | 0.88 | 0.92 |
| 7 | 45.8 ± 1 * | 48.5 ± 2.4 * | 0.85 | 0.9 |
| control | 54.1 ± 1.5 | | 1 | |

| Serial No | 165 | | | |
|---|---|---|---|---|
| Protein name | Melanocortin receptors (MC4R) | | | |
| | AP-TGFa release (%) | | Normalized to control | |
| Compound | 1 mM | 1 µM | 1 mM | 1 µM |
| 0 | 36 ± 2.1 * | 41 ± 3.2 | 0.83 | 0.95 |
| 1 | 36.3 ± 1.6 * | 41.1 ± 1.7 | 0.84 | 0.95 |
| 3 | 35.1 ± 1 * | 38.7 ± 1.1 * | 0.81 | 0.89 |
| 5 | 39 ± 0.8 * | 40.1 ± 1.7 * | 0.9 | 0.92 |
| 7 | 36.3 ± 0.7 * | 39.9 ± 2.6 * | 0.84 | 0.92 |
| control | 43.3 ± 1.2 | | 1 | |

| Serial No | 166 | | | |
|---|---|---|---|---|
| Protein name | Melanocortin receptors (MC1R) | | | |
| | AP-TGFa release (%) | | Normalized to control | |
| Compound | 1 mM | 1 μM | 1 mM | 1 μM |
| 0 | 38.4 ± 1.8 * | 41.3 ± 2.5 * | 0.87 | 0.93 |
| 1 | 40.4 ± 2.9 * | 43.4 ± 0.2 | 0.91 | 0.98 |
| 5 | 42.1 ± 0.9 * | 43.5 ± 2.2 | 0.95 | 0.99 |
| 7 | 39.1 ± 3.2 * | 40.4 ± 1.4 * | 0.89 | 0.91 |
| control | 44.1 ± 1.2 | | 1 | |

| Serial No | 167 | | | |
|---|---|---|---|---|
| Protein name | Class A Orphans (MRGF) | | | |
| | AP-TGFa release (%) | | Normalized to control | |
| Compound | 1 mM | 1 μM | 1 mM | 1 μM |
| 1 | 26.4 ± 1.3 * | 31.4 ± 3.4 | 0.83 | 0.99 |
| 3 | 27.7 ± 0.3 * | 33.7 ± 1.9 | 0.87 | 1.06 |
| 5 | 28.4 ± 0.7 * | 32.6 ± 3.7 | 0.89 | 1.02 |
| 7 | 27.8 ± 1 * | 29.8 ± 1.5 | 0.88 | 0.94 |
| control | 31.8 ± 2.1 | | 1 | |

| Serial No | 168 | | | |
|---|---|---|---|---|
| Protein name | Class A Orphans (MC2R) | | | |
| | AP-TGFa release (%) | | Normalized to control | |
| Compound | 1 mM | 1 μM | 1 mM | 1 μM |
| 0 | 37.4 ± 1.1 * | 44.3 ± 3.1 | 0.8 | 0.95 |
| 1 | 41.7 ± 1.4 * | 42.8 ± 3.8 | 0.89 | 0.91 |
| 3 | 41.8 ± 1.4 * | 44.9 ± 1.4 | 0.89 | 0.96 |
| 5 | 39.9 ± 2.7 * | 45.4 ± 0.6 | 0.85 | 0.97 |
| 7 | 38.6 ± 3.6 * | 41.7 ± 1.5 * | 0.82 | 0.89 |
| control | 46.9 ± 2.7 | | 1 | |

| Serial No | 169 | | | |
|---|---|---|---|---|
| Protein name | Chemokine receptors (XCR1) | | | |
| | AP-TGFa release (%) | | Normalized to control | |
| Compound | 1 mM | 1 μM | 1 mM | 1 μM |
| 0 | 52.5 ± 0.9 * | 63.8 ± 1.7 | 0.85 | 1.04 |
| 7 | 53.8 ± 1.8 * | 63 ± 1.6 | 0.88 | 1.03 |
| control | 61.4 ± 3 | | 1 | |

| Serial No | 170 | | | |
|---|---|---|---|---|
| Protein name | Olfactory receptors (OR1G1) | | | |
| | AP-TGFa release (%) | | Normalized to control | |
| Compound | 1 mM | 1 μM | 1 mM | 1 μM |
| 0 | 43.3 ± 0.7 * | 50.3 ± 0.3 | 0.85 | 0.99 |
| 1 | 45.4 ± 0.8 * | 50.9 ± 0.9 | 0.89 | 1 |
| 7 | 44.2 ± 1.3 * | 52 ± 1.3 | 0.87 | 1.02 |
| control | 50.7 ± 2.4 | | 1 | |

| Serial No | 171 | | | |
|---|---|---|---|---|
| Protein name | Leukotriene receptors (OXER1) | | | |
| | AP-TGFa release (%) | | Normalized to control | |
| Compound | 1 mM | 1 μM | 1 mM | 1 μM |
| 0 | 51.9 ± 3.2 * | 60.2 ± 2.3 | 0.82 | 0.95 |
| 1 | 56.1 ± 1.2 * | 60.4 ± 3 | 0.89 | 0.96 |
| 3 | 56.3 ± 2.3 * | 62 ± 2.3 | 0.89 | 0.98 |
| 5 | 57.6 ± 1.8 * | 61 ± 2.1 | 0.91 | 0.97 |
| 7 | 52.2 ± 2.7 * | 61.7 ± 0.3 | 0.83 | 0.98 |
| control | 63 ± 2.8 | | 1 | |

| Serial No | 172 | | | |
|---|---|---|---|---|
| Protein name | Opsin receptors (RGR) | | | |
| | AP-TGFa release (%) | | Normalized to control | |
| Compound | 1 mM | 1 μM | 1 mM | 1 μM |
| 0 | 39.8 ± 1.1 * | 49.9 ± 3 | 0.8 | 1 |
| 1 | 45.7 ± 2.7 * | 52.6 ± 2.8 | 0.92 | 1.05 |
| 7 | 42 ± 1.3 * | 49.6 ± 0.8 | 0.84 | 0.99 |
| control | 49.9 ± 1.2 | | 1 | |

| Serial No | 173 | | | |
|---|---|---|---|---|
| Protein name | Lysophospholipid (S1P) receptors (S1P4) | | | |
| | AP-TGFa release (%) | | Normalized to control | |
| Compound | 1 mM | 1 μM | 1 mM | 1 μM |
| 0 | 62 ± 1.3 * | 74.5 ± 0.6 * | 0.9 | 1.09 |
| 5 | 64.2 ± 1 * | 71 ± 9.6 * | 0.94 | 1.04 |
| 7 | 63.3 ± 1.5 * | 70 ± 2 * | 0.92 | 1.02 |
| control | 68.6 ± 1.6 | | 1 | |

| Serial No | 174 | | | |
|---|---|---|---|---|
| Protein name | Prokineticin receptors (PROKR2) | | | |
| | AP-TGFa release (%) | | Normalized to control | |
| Compound | 1 mM | 1 μM | 1 mM | 1 μM |
| 0 | 46 ± 3.4 * | 52.7 ± 0.3 | 0.87 | 1 |
| 1 | 48.6 ± 0.2 * | 53.1 ± 1.3 | 0.92 | 1.01 |
| 5 | 49.5 ± 1.2 * | 53.8 ± 1.5 | 0.94 | 1.02 |
| 7 | 46.3 ± 3.9 * | 54.4 ± 3.8 | 0.88 | 1.03 |
| control | 52.9 ± 1.8 | | 1 | |

| Serial No | 175 | | | |
|---|---|---|---|---|
| Protein name | Somatostatin receptors (SSTR1) | | | |
| | AP-TGFa release (%) | | Normalized to control | |
| Compound | 1 mM | 1 μM | 1 mM | 1 μM |
| 0 | 47.6 ± 2.2 * | 53.8 ± 0.4 | 0.88 | 1 |
| 7 | 47 ± 1.9 * | 56.2 ± 3.5 | 0.87 | 1.04 |
| control | 53.9 ± 1.9 | | 1 | |

| Serial No | 176 | | | |
|---|---|---|---|---|
| Protein name | Prostanoid receptors (TP iso2) | | | |
| | AP-TGFa release (%) | | Normalized to control | |
| Compound | 1 mM | 1 μM | 1 mM | 1 μM |
| 0 | 50.4 ± 2.6 * | 57.9 ± 1.5 | 0.89 | 1.02 |
| 7 | 53.6 ± 0.8 * | 59.2 ± 2.4 | 0.95 | 1.05 |
| control | 56.6 ± 1.7 | | 1 | |

| Serial No | 177 | | | |
|---|---|---|---|---|
| Protein name | Chemokine receptors (CCR2) | | | |
| | AP-TGFa release (%) | | Normalized to control | |
| Compound | 1 mM | 1 μM | 1 mM | 1 μM |
| 0 | 52.4 ± 3.9 * | 58 ± 1.4 | 0.89 | 0.99 |
| 1 | 53.7 ± 2.3 * | 58.9 ± 1.6 | 0.91 | 1 |
| 7 | 50.6 ± 0.6 * | 57.1 ± 2.7 | 0.86 | 0.97 |
| control | 58.7 ± 2.1 | | 1 | |

| Serial No | 178 | | | |
|---|---|---|---|---|
| Protein name | Chemokine receptors (CCBP2) | | | |
| | AP-TGFa release (%) | | Normalized to control | |
| Compound | 1 mM | 1 μM | 1 mM | 1 μM |
| 0 | 44.3 ± 0.2 * | 55.2 ± 2.3 | 0.82 | 1.02 |
| 7 | 42.3 ± 1.2 * | 52.7 ± 2.1 | 0.78 | 0.97 |
| control | 54 ± 2.9 | | 1 | |

| Serial No | 179 | | | |
|---|---|---|---|---|
| Protein name | class A orphans (RABGAP(GPR21)) | | | |
| | AP-TGFa release (%) | | Normalized to control | |
| Compound | 1 mM | 1 μM | 1 mM | 1 μM |
| 0 | 45.7 ± 1.5 * | 53.9 ± 1 | 0.87 | 1.03 |
| 1 | 48.5 ± 1.8 * | 54 ± 0.7 | 0.92 | 1.03 |
| 7 | 48.4 ± 2.1 * | 54.3 ± 0.8 | 0.92 | 1.04 |
| control | 52.5 ± 2.5 | | 1 | |

| Serial No | 180 | | | |
|---|---|---|---|---|
| Protein name | Somatostatin receptors (SSTR5) | | | |
| | AP-TGFa release (%) | | Normalized to control | |
| Compound | 1 mM | 1 μM | 1 mM | 1 μM |
| 0 | 58.8 ± 3.8 * | 64.7 ± 1.3 | 0.88 | 0.97 |
| 1 | 59.2 ± 1.7 * | 64.9 ± 2.3 | 0.88 | 0.97 |
| 7 | 61.2 ± 2.6 * | 65.5 ± 0.9 | 0.91 | 0.98 |
| control | 66.9 ± 1.9 | | 1 | |

| Serial No | 181 | | | |
|---|---|---|---|---|
| Protein name | Prolactin-releasing peptide receptors (PRLHR) | | | |
| | AP-TGFa release (%) | | Normalized to control | |
| Compound | 1 mM | 1 μM | 1 mM | 1 μM |
| 5 | 58.4 ± 0.9 * | 63.4 ± 2.2 | 0.94 | 1.02 |
| 7 | 55.4 ± 1 * | 63.7 ± 3.3 | 0.89 | 1.02 |
| control | 62.2 ± 1.9 | | 1 | |

| Serial No | 182 | | | |
|---|---|---|---|---|
| Protein name | Adrenergic receptors (β2) | | | |
| | AP-TGFa release (%) | | Normalized to control | |
| Compound | 1 mM | 1 μM | 1 mM | 1 μM |
| 0 | 41.1 ± 3.3 * | 50.6 ± 3.9 | 0.84 | 1.04 |
| 5 | 41.4 ± 3 * | 49.6 ± 4.9 | 0.85 | 1.02 |
| 7 | 41.3 ± 1.1 * | 49.4 ± 3.1 | 0.85 | 1.01 |
| control | 48.7 ± 2.2 | | 1 | |

| Serial No | 183 | | | |
|---|---|---|---|---|
| Protein name | Proteinase-activated receptors (PAR2) | | | |
| | AP-TGFa release (%) | | Normalized to control | |
| Compound | 1 mM | 1 μM | 1 mM | 1 μM |
| 0 | 46.1 ± 2.8 | 51.8 ± 0.9 | 0.91 | 1.02 |
| 1 | 47.9 ± 1.3 | 50.8 ± 2.1 | 0.95 | 1.01 |
| 3 | 46.7 ± 1.4 | 51.5 ± 0.9 | 0.92 | 1.02 |
| 7 | 42.8 ± 5.8 | 46.4 ± 3.3 * | 0.85 | 0.92 |
| control | 50.5 ± 1.5 | | 1 | |

| Serial No | 184 | | | |
|---|---|---|---|---|
| Protein name | Class A Orphans (TAAR5) | | | |
| | AP-TGFa release (%) | | Normalized to control | |
| Compound | 1 mM | 1 μM | 1 mM | 1 μM |
| 0 | 46.6 ± 4 * | 55 ± 1 | 0.87 | 1.03 |
| 7 | 50.4 ± 2.6 * | 51.6 ± 0.7 | 0.94 | 0.96 |
| control | 53.5 ± 1.5 | | 1 | |

| Serial No | 185 | | | |
|---|---|---|---|---|
| Protein name | Relaxin family peptide receptors (RXFP3) | | | |
| | AP-TGFa release (%) | | Normalized to control | |
| Compound | 1 mM | 1 μM | 1 mM | 1 μM |
| 0 | 53.3 ± 0.5 * | 64.8 ± 4.1 | 0.88 | 1.06 |
| 1 | 57.2 ± 1.6 | 63.8 ± 2.6 | 0.94 | 1.05 |
| 5 | 57.4 ± 0.9 * | 61.8 ± 2 | 0.94 | 1.01 |
| 7 | 52.8 ± 0.8 * | 61.9 ± 0.4 | 0.87 | 1.02 |
| control | 60.9 ± 1.9 | | 1 | |

| Serial No | 186 | | | |
|---|---|---|---|---|
| Protein name | Relaxin family peptide receptors (RXFP4) | | | |
| | AP-TGFa release (%) | | Normalized to control | |
| Compound | 1 mM | 1 μM | 1 mM | 1 μM |
| 0 | 44.2 ± 1.1 * | 50.5 ± 1.1 * | 0.8 | 0.92 |
| 1 | 49.5 ± 1 * | 51.1 ± 0.9 * | 0.9 | 0.93 |
| 7 | 49.3 ± 1.6 * | 55.3 ± 2 | 0.9 | 1.01 |
| control | 55.1 ± 1.8 | | 1 | |

| Serial No | 187 | | | |
|---|---|---|---|---|
| Protein name | Class A Orphans (TAAR2) | | | |
| | AP-TGFa release (%) | | Normalized to control | |
| Compound | 1 mM | 1 μM | 1 mM | 1 μM |
| 0 | 47.9 ± 0.5 * | 57.7 ± 3 | 0.85 | 1.02 |
| 7 | 48.7 ± 0.9 * | 55.3 ± 0.5 | 0.86 | 0.98 |
| control | 56.5 ± 3 | | 1 | |

| Serial No | 188 | | | |
|---|---|---|---|---|
| Protein name | Somatostatin receptors (SSTR2) | | | |
| | AP-TGFa release (%) | | Normalized to control | |
| Compound | 1 mM | 1 μM | 1 mM | 1 μM |
| 0 | 41.4 ± 0.8 * | 47.1 ± 2.4 | 0.83 | 0.94 |
| 1 | 43.2 ± 2.3 * | 47.5 ± 1.3 | 0.86 | 0.95 |
| 7 | 42.7 ± 1.5 * | 49 ± 0.3 | 0.85 | 0.98 |
| control | 50.1 ± 1.8 | | 1 | |

| Serial No | 189 | | | |
|---|---|---|---|---|
| Protein name | Opsin receptors (OPN1LW) | | | |
| | AP-TGFa release (%) | | Normalized to control | |
| Compound | 1 mM | 1 μM | 1 mM | 1 μM |
| 0 | 54.4 ± 2.6 * | 62.7 ± 2.2 * | 0.82 | 0.94 |
| 1 | 59.7 ± 0.4 * | 63.9 ± 0.2 | 0.9 | 0.96 |
| 4 | 71.2 ± 1.1 * | 64 ± 2.1 | 1.07 | 0.96 |
| 7 | 61.4 ± 1.1 * | 62.5 ± 2.1 * | 0.92 | 0.94 |
| control | 66.6 ± 2.4 | | 1 | |

| Serial No | 190 | | | |
|---|---|---|---|---|
| Protein name | Opsin receptors (OPN1MW) | | | |
| | AP-TGFa release (%) | | Normalized to control | |
| Compound | 1 mM | 1 μM | 1 mM | 1 μM |
| 0 | 46 ± 1 * | 52.7 ± 2.2 | 0.87 | 0.99 |
| 1 | 46.4 ± 1.8 | 52.6 ± 2.5 | 0.87 | 0.99 |
| 7 | 48.4 ± 0.3 * | 54.5 ± 1.4 | 0.91 | 1.03 |
| control | 53.2 ± 2.5 | | 1 | |

| Serial No | 191 | | | |
|---|---|---|---|---|
| Protein name | 5-Hydroxytryptamine receptors (5-HT5A) | | | |
| | AP-TGFa release (%) | | Normalized to control | |
| Compound | 1 mM | 1 μM | 1 mM | 1 μM |
| 0 | 49.8 ± 0.5 * | 66.5 ± 6.5 | 0.81 | 1.09 |
| 1 | 52.8 ± 0.8 * | 63.3 ± 0.6 | 0.86 | 1.04 |
| 7 | 55.9 ± 1.5 * | 58.9 ± 0.3 | 0.91 | 0.96 |
| control | 61.1 ± 1.9 | | 1 | |

| Serial No | 192 | | | |
|---|---|---|---|---|
| Protein name | Olfactory receptors (OR51E2) | | | |
| | AP-TGFa release (%) | | Normalized to control | |
| Compound | 1 mM | 1 μM | 1 mM | 1 μM |
| 0 | 46.5 ± 1.1 * | 54.7 ± 2.3 | 0.84 | 0.98 |
| 1 | 51.4 ± 0.6 * | 55.3 ± 1.7 | 0.92 | 1 |
| 7 | 49.8 ± 1 * | 56.9 ± 2.1 | 0.9 | 1.02 |
| control | 55.6 ± 1.9 | | 1 | |

| Serial No | 193 | | | |
|---|---|---|---|---|
| Protein name | Class A Orphans (TAAR6) | | | |
| | AP-TGFa release (%) | | Normalized to control | |
| Compound | 1 mM | 1 μM | 1 mM | 1 μM |
| 0 | 42.9 ± 1.5 * | 52.7 ± 1.6 | 0.86 | 1.06 |
| control | 49.7 ± 4.4 | | 1 | |

| Serial No | 194 | | | |
|---|---|---|---|---|
| Protein name | Putative pheromone receptors (VN1R1) | | | |
| | AP-TGFa release (%) | | Normalized to control | |
| Compound | 1 mM | 1 μM | 1 mM | 1 μM |
| 0 | 39.6 ± 1.1 * | 49.6 ± 2.7 | 0.81 | 1.01 |
| 1 | 44.3 ± 0.5 * | 50.3 ± 0.8 | 0.9 | 1.03 |
| 3 | 43.9 ± 0.2 * | 49.9 ± 3.3 | 0.9 | 1.02 |
| 7 | 41.5 ± 0.8 * | 50.9 ± 3 | 0.85 | 1.04 |
| control | 48.9 ± 1.7 | | 1 | |

| Serial No | 195 | | | |
|---|---|---|---|---|
| Protein name | Chemokine receptors (CXCR6) | | | |
| | AP-TGFa release (%) | | Normalized to control | |
| Compound | 1 mM | 1 µM | 1 mM | 1 µM |
| 0 | 41.5 ± 1.3 * | 49.6 ± 1.9 * | 0.79 | 0.95 |
| 1 | 47.7 ± 1.8 * | 48.9 ± 0.8 * | 0.91 | 0.93 |
| 3 | 45.4 ± 1.3 * | 50.8 ± 2.3 | 0.87 | 0.97 |
| 7 | 43.9 ± 0 * | 49.9 ± 1.7 * | 0.84 | 0.95 |
| control | 52.3 ± 0.8 | | 1 | |

| Serial No | 196 | | | |
|---|---|---|---|---|
| Protein name | Olfactory receptors (OR3A2) | | | |
| | AP-TGFa release (%) | | Normalized to control | |
| Compound | 1 mM | 1 µM | 1 mM | 1 µM |
| 0 | 49.3 ± 1.1 * | 56 ± 0.4 | 0.82 | 0.94 |
| 1 | 48.7 ± 0.6 * | 56.3 ± 1.6 | 0.82 | 0.94 |
| 3 | 53.6 ± 1.7 * | 57 ± 1.8 | 0.9 | 0.95 |
| 7 | 51.7 ± 1 * | 57.6 ± 2.7 | 0.87 | 0.96 |
| control | 59.8 ± 4 | | 1 | |

| Serial No | 197 | | | |
|---|---|---|---|---|
| Protein name | Somatostatin receptors (SSTR3) | | | |
| | AP-TGFa release (%) | | Normalized to control | |
| Compound | 1 mM | 1 µM | 1 mM | 1 µM |
| 0 | 44.3 ± 2.8 * | 54.5 ± 1.8 | 0.84 | 1.03 |
| 3 | 47.1 ± 1.9 * | 51.9 ± 1.3 | 0.89 | 0.98 |
| 7 | 45.7 ± 0.6 * | 50.1 ± 2.5 | 0.87 | 0.95 |
| control | 52.8 ± 3.1 | | 1 | |

| Serial No | 198 | | | |
|---|---|---|---|---|
| Protein name | Prostanoid receptors (EP3 (iso5)) | | | |
| | AP-TGFa release (%) | | Normalized to control | |
| Compound | 1 mM | 1 µM | 1 mM | 1 µM |
| 7 | 36.8 ± 1.1 * | 41.8 ± 0.7 | 0.9 | 1.03 |
| control | 40.7 ± 2.5 | | 1 | |

| Serial No | 199 | | | |
|---|---|---|---|---|
| Protein name | Visual pigment-like receptors peropsin (RRH) | | | |
| | AP-TGFa release (%) | | Normalized to control | |
| Compound | 1 mM | 1 µM | 1 mM | 1 µM |
| 0 | 45.7 ± 1.7 * | 52.6 ± 3.1 | 0.87 | 1 |
| 7 | 45.6 ± 4.2 * | 49.7 ± 2 | 0.87 | 0.95 |
| control | 52.4 ± 3.9 | | 1 | |

| Serial No | 200 | | | |
|---|---|---|---|---|
| Protein name | Class A Orphans (TAAR9) | | | |
| | AP-TGFa release (%) | | Normalized to control | |
| Compound | 1 mM | 1 µM | 1 mM | 1 µM |
| 0 | 42.3 ± 0.4 * | 50.9 ± 2.4 | 0.79 | 0.95 |
| 1 | 43.4 ± 1.4 * | 49.3 ± 2 * | 0.81 | 0.92 |
| 3 | 45.4 ± 0.9 * | 50.1 ± 1.6 | 0.84 | 0.93 |
| 5 | 48.1 ± 1.7 * | 49.6 ± 2.7 | 0.89 | 0.92 |
| 7 | 43.1 ± 1.1 * | 49.5 ± 0.9 * | 0.8 | 0.92 |
| control | 53.7 ± 2.6 | | 1 | |

| Serial No | 201 | | | |
|---|---|---|---|---|
| Protein name | Class A Orphans (TAAR8) | | | |
| | AP-TGFa release (%) | | Normalized to control | |
| Compound | 1 mM | 1 µM | 1 mM | 1 µM |
| 0 | 42.9 ± 2.4 * | 54.2 ± 1.1 | 0.83 | 1.05 |
| 1 | 46.9 ± 2.1 * | 49.5 ± 3.2 | 0.91 | 0.96 |
| 3 | 46 ± 2 * | 50.3 ± 3.2 | 0.89 | 0.97 |
| 5 | 46.1 ± 3 * | 50 ± 1.7 | 0.89 | 0.97 |
| 7 | 42.2 ± 3 * | 46.1 ± 0.4 * | 0.82 | 0.89 |
| control | 51.6 ± 2.3 | | 1 | |

| Serial No | 202 | | | |
|---|---|---|---|---|
| Protein name | Class A Orphans (GPR84) (= Serial No. 35) | | | |
| | AP-TGFa release (%) | | Normalized to control | |
| Compound | 1 mM | 1 µM | 1 mM | 1 µM |
| 14 | 55 ± 1.2 * | 62 ± 2.9 | 0.92 | 1.04 |
| control | 59.5 ± 2.9 | | 1 | |

| Serial No | 203 | | | |
|---|---|---|---|---|
| Protein name | Vasopressin receptors (V2) (= Serial No. 12) | | | |
| | AP-TGFa release (%) | | Normalized to control | |
| Compound | High | Low | High | Low |
| 14 | 48.2 ± 2.3 * | 57.7 ± 3.4 | 0.87 | 1.04 |
| control | 55.5 ± 4.3 | | 1 | |

| Serial No | 204 | | | |
|---|---|---|---|---|
| Protein name | P2Y receptors (P2Y14) (= Serial No. 31) | | | |
| | AP-TGFa release (%) | | Normalized to control | |
| Compound | High | Low | High | Low |
| 13 | 61 ± 4.4 * | 68.4 ± 2 | 0.89 | 1 |
| 14 | 56.1 ± 6.1 * | 71.8 ± 4.3 | 0.82 | 1.05 |
| control | 68.5 ± 4.4 | | 1 | |

| Serial No | 205 | | | |
|---|---|---|---|---|
| Protein name | Class A Orphans (GPR156) | | | |
| | AP-TGFa release (%) | | Normalized to control | |
| Compound | High | Low | High | Low |
| 12 | 48.2 ± 2.9 * | 57.9 ± 4 | 0.9 | 1.08 |
| control | 53.7 ± 3.1 | | 1 | |

| Serial No | 206 | | | |
|---|---|---|---|---|
| Protein name | Bradykinin receptors (B1) (= Serial No. 69) | | | |
| | AP-TGFa release (%) | | Normalized to control | |
| Compound | High | Low | High | Low |
| 12 | 45.9 ± 2.2 * | 53.4 ± 6.6 * | 0.79 | 0.92 |
| control | 57.8 ± 3.2 | | 1 | |

| Serial No | 207 | | | |
|---|---|---|---|---|
| Protein name | Free fatty acid receptors (FFA3) (= Serial No. 32) | | | |
| | AP-TGFa release (%) | | Normalized to control | |
| Compound | High | Low | High | Low |
| 11 | 47.3 ± 1.4 * | 42.9 ± 2.2 * | 0.84 | 0.76 |
| 12 | 44.9 ± 2.1 * | 40.3 ± 3.7 * | 0.8 | 0.72 |
| control | 56.2 ± 3.4 | | 1 | |

| Serial No | 208 | | | |
|---|---|---|---|---|
| Protein name | P2Y receptors (P2Y6) (= Serial No. 10) | | | |
| | AP-TGFa release (%) | | Normalized to control | |
| Compound | High | Low | High | Low |
| 13 | 64.9 ± 0.6 * | 66.2 ± 2.2 | 0.93 | 0.95 |
| control | 70.1 ± 3 | | * 1 | |

Data are given as mean value (±standard deviation) with triplicate

CLASS A GPCR-BINDING COMPOUND MODIFIER

TECHNICAL FIELD

The present invention relates to class-A GPCR antagonists or a method for designing or producing a class-A GPCR antagonist, etc.

BACKGROUND ART

The conformations of class-A (also called rhodopsin-family) G-protein coupled receptors (GPCRs) are modulated by extra- and intracellular molecules, such as agonists, inverse agonists, allosteric modulators, G-proteins, lipids, and sodium ion (Non-Patent Literatures 1 and 2). For example, G-protein coupling to a GPCR allosterically shifts the conformational equilibrium of the GPCR to the high-affinity agonist binding state, as compared with the uncoupled state of the receptor. The allosteric ligand binds to a different site from the orthosteric binding site of the GPCR, and positively or negatively modulates the binding affinity and/or the signaling efficacy of the orthosteric agonist and GPCR system. A sodium ion also acts as a negative allosteric modulator for the GPCR activity.

Allosteric modulatory action by a sodium ion has been observed for a variety of GPCRs. First, a physiological or higher sodium ion concentration favors the antagonist activity for a GPCR. Sodium ion decreased the dissociation rates of antagonists (Non-Patent Literatures 3-5) and improved their binding affinities (Non-Patent Literature 6-8) but lowered the agonist binding affinity (Non-Patent Literature 9). In addition to the effect on the ligand binding affinity, sodium ion reduced the G-protein signal efficacy. Sodium ion reduced the GTPγS-binding activity of G-protein by GPCRs with (Non-Patent Literatures 10, 11) or without agonist-stimulation (Non-Patent Literature 10, 12-14). The overall effect of sodium ion is the negative modulation of agonist-GPCR activity, with the lowering of the agonist affinity and the reduction in the G-protein efficacy, including the attenuation of the agonist-independent basal signal activity. In contrast, the antagonist-GPCR activity is positively modulated by sodium ion.

The interaction between a sodium ion and the highly conserved $Asp^{2.50}$ (Ballesteros-Weinstein residue numbering [Non-Patent Literature 15]) was considered to contribute to the mechanism underlying the modulatory action of the sodium ion, based on mutation studies (Non-Patent Literature 4, 5). However, the recently solved high-resolution crystal structures of inactive-state GPCRs and active-state GPCRs with a bound agonist and G-protein revealed the modulatory mechanism of the sodium ion. In the inactive-state GPCRs, $A_{2A}$ adenosine receptor ($A_{2A}AR$) (Non-Patent Literature 16), $β_1$ adrenergic receptor ($β_1AR$) (Non-Patent Literature 17), protease activated receptor 1 (PAR1) (Non-Patent Literature 18), and δ-opioid receptor (δ-OR) (Non-Patent Literature 19), the sodium ion was found to bind to the highly conserved residues in the middle of the trans-membrane helix bundle. The sodium ion binds to $Asp^{2.50}$ and $Ser^{3.39}$ in common, and additionally to $Asn^{3.35}$ in δ-OR and $Asn^{7.49}$ in PAR1. The bound sodium ion organizes a water cluster that interacts with several residues, including $Trp^{6.48}$, $Asn^{7.45}$, $Ser^{7.46}$, and $Asn^{7.49}$, and stabilizes the inactive-state GPCR structure. Among 273 class-A human GPCRs, the residues involved in the sodium ion-centered water cluster are well conserved (Table 2), and the cluster is considered to exist in most class-A GPCRs in the inactive state in common. In contrast, in the agonist- and G-protein (or G-protein mimicking nanobody)-bound active-state GPCRs, the sodium ion-centered water cluster should be collapsed with the sodium ion ejected from the binding site, due to the decrease in the cavity volume of the sodium ion-binding site, induced by the structural change of the GPCR accompanied by the agonist binding and G-protein coupling (Non-Patent Literature 20-23). In other words, the GPCR structure stabilized by the sodium ion-centered water cluster as the inactive state is competent for the antagonist binding but is not suitable for the G-protein coupling and agonist binding. These structural results illustrated why the bound sodium ion serves as a positive and negative modulator of the antagonist and agonist/G-protein bound states of GPCRs, respectively.

In addition, the $Na^+$-water cluster binding site of each class-A GPCR has a well-conserved amino acid sequence to form a similar structure (Non-Patent Literatures 16 to 19) and is located close to its orthosteric binding site (where amino acid residues are versatile and the structure of which varies depending on each GPCR).

CITATION LIST

Non-Patent Literature

[Non-Patent Literature 1] Canals, M. et al., Trends Biochem. Sci. 36, 663-672 (2011)
[Non-Patent Literature 2] Mahoney, J. P et al., Curr. Opin. Struct. Biol. 41, 247-254 (2016)
[Non-Patent Literature 3] Gao, Z. G. et al., Biochem. Pharmacol. 65, 525-534 (2003a)
[Non-Patent Literature 4] Gao, Z. G. et al., Mol. Pharmacol. 63, 1021-1031 (2003b)
[Non-Patent Literature 5] Ceresa, B. P. et al., J. Biol. Chem. 269, 29557-29564 (1994)
[Non-Patent Literature 6] Neve, K. A. et al., Mol. Pharmacol. 60, 373-381 (2001)
[Non-Patent Literature 7] Horstman, D. A. et al., J. Biol. Chem. 265, 21590-21595 (1990)
[Non-Patent Literature 8] Wilson, M. H. et al., Mol. Pharmacol. 59, 929-938(2001)
[Non-Patent Literature 9] Ardati, A. et al., Mol. Pharmacol. 51, 816-824 (1997)
[Non-Patent Literature 10] Selley, D. E. et al., Br. J. Pharmacol. 130, 987-996 (2000)
[Non-Patent Literature 11] Kleemann, P. et al., Naunyn Schmiedebergs Arch Pharmacol. 378, 261-274 (2008)
[Non-Patent Literature 12] Vosahlikova, M. et al., Naunyn Schmiedebergs Arch Pharmacol. 387, 487-502 (2014)
[Non-Patent Literature 13] Nickl, K. et al., Neurosci. Lett. 447, 68-72 (2008)
[Non-Patent Literature 14] Schnell, D. et al., Neurosci. Lett. 472, 114-118 (2010)
[Non-Patent Literature 15] Ballesteros, J. A. et al., "Integrated methods for the construction of three-dimensional models and computational probing of structure-function relations in G protein-coupled receptors." In Methods in Neurosciences, C. S. Stuart, ed. (Academic Press), pp. 366-428 (1995)
[Non-Patent Literature 16] Liu, W. et al., Science 337, 232-236 (2012)
[Non-Patent Literature 17] Miller-Gallacher, J. L. et al., PLoS One 9, e92727 (2014)
[Non-Patent Literature 18] Zhang, C. et al., Nature 492, 387-392 (2012)

[Non-Patent Literature 19] Fenalti, G. et al., Nature 506, 191-196 (2014)

[Non-Patent Literature 20] Rasmussen, S. G. et al., Nature 477 (2011) 549-555

[Non-Patent Literature 21] Carpenter, B. et al., Nature 536 (2016) 104-107

[Non-Patent Literature 22] Kruse, A. C. et al., Nature 504 (2013a) 101-106

[Non-Patent Literature 23] Huang, W. et al., Nature 524 (2015) 315-321

[Non-Patent Literature 24] Birke, F. W. et al., J. Pharmacol. Exp. Ther. 297 (2001) 458-466

[Non-Patent Literature 25] Yokomizo, T. et al., Nature 387 (1997) 620-624

SUMMARY OF INVENTION

Technical Problem

Meanwhile, to date, no method for efficiently engineering a class-A GPCR antagonist (inverse agonist) has been reported. In addition, there was no report about a binding ligand that interacts with the $Na^+$-water cluster binding site of each class-A GPCR. Thus, it has been conventionally impossible to rationally design a class-A GPCR-targeting drug.

The present invention has been made in view of the above situations. The purpose of the present invention is to provide, based on the rational design protocol, a class-A GPCR antagonist, a novel method for producing a class-A GPCR antagonist, a novel class-A GPCR antagonist, or a novel compound that interacts with the $Na^+$-water cluster binding site of a class-A GPCR, etc.

Solution to Problem

The present inventors conducted crystallography and are the first to reveal the crystal structure of BLT1 (leukotriene B4 (LTB4) receptor, a class-A GPCR) (Non-Patent Literature 25) bound to an antagonist BIIL260 (Non Patent Literature 24) (see Example 1). This crystallographic analysis results show that a benzamidine (hereinafter, sometimes referred to as "amidinylphenyl") moiety of BIIL260 binds to the $Na^+$-water cluster binding site of BLT1 to mimic the sodium ion-centered water cluster. Here, particularly unexpected results are that the benzamidine moiety having a hydrophobic benzene ring is included in the water cluster binding site.

Then, the present inventors examined a function of a compound generated by linking a benzamidine moiety to a known class-A GPCR (other than BLT1) (e.g., an adrenergic receptor)-binding compound (e.g., carazolol). As a result, the compound generated specifically bound to the class-A GPCR and exhibited antagonistic activity or inverse agonistic activity (see Example 2). This result may be because (i) the $Na^+$-water cluster binding site of each class-A GPCR is structurally conserved (see, for example, Table 2 and Non-Patent Literatures 16 to 19), so that the benzamidine moiety can bind to class-A GPCRs other than BLT1; and (ii) the benzamidine moiety replaces the $Na^+$-water cluster to exert an antagonistic action or inverse agonistic action.

Further, the present inventors created benzamidine derivatives and investigated the inverse agonistic activity thereof on 202 different class-A GPCRs (e.g., prostaglandin receptors) (see Example 3). The results show that the benzamidine derivatives exerted inverse agonistic activity on each class-A GPCR. This result may be because (i) the $Na^+$-water cluster binding site of each class-A GPCR is structurally conserved (see, for example, Table 2 and Non-Patent Literatures 16 to 19), so that each benzamidine derivative can bind to each class-A GPCR; and (ii) each benzamidine derivative replaces the $Na^+$-water cluster to exert an inverse agonistic action.

The above results have revealed that a novel class-A GPCR antagonist can be created by linking a known class-A GPCR ligand with a functional group (e.g., a benzamidine moiety or a derivative thereof) that can bind to the $Na^+$-water cluster binding site of the class-A GPCR.

Specifically, an aspect of the present invention provides a compound or a salt thereof comprising a structure comprising a class-A GPCR-binding compound linked to a functional group that can bind to a $Na^+$-water cluster binding site of the class-A GPCR. Use of the compound or salt thereof makes it possible to inhibit a function of the class-A GPCR.

Another aspect of the present invention provides a compound or a salt thereof comprising a structure comprising a class-A GPCR-binding compound linked to at least one functional group selected from the group consisting of benzamidine moieties or derivatives thereof, phenyl-substituted protonated amine groups, and phenyl-substituted unprotonated amine groups. Use of the compound or salt thereof makes it possible to inhibit a function of the class-A GPCR.

Another aspect of the present invention provides a composition for an antagonist of a class-A GPCR, comprising a compound or a salt thereof having a functional group that can bind to a $Na^+$-water cluster binding site of the class-A GPCR. Use of the composition makes it possible to inhibit a function of the class-A GPCR due to the antagonistic action.

Another aspect of the present invention provides a method for producing a class-A GPCR antagonist, comprising the step of linking one compound with another compound that can bind to a $Na^+$-water cluster binding site of the class-A GPCR. Use of this production method makes it possible to generate a class-A GPCR antagonist.

Another aspect of the present invention provides a material for creating a class-A GPCR antagonist, comprising a compound that can bind to a $Na^+$-water cluster binding site. Use of this material makes it possible to create a class-A GPCR antagonist by linking a class-A GPCR-binding compound with a compound that binds to the $Na^+$-water cluster binding site.

Another aspect of the present invention provides a binding molecule that specifically binds to an inactive leukotriene receptor, an inactive adrenergic receptor, an inactive opioid receptor, or an inactive histamine receptor. Use of this binding molecule makes it possible to detect an inactive leukotriene receptor, an inactive adrenergic receptor, an inactive opioid receptor, or an inactive histamine receptor.

Another aspect of the present invention provides a binding molecule that specifically binds to a complex comprising: a class-A GPCR; and a compound or a salt thereof having a functional group that can bind to a $Na^+$-water cluster binding site of the class-A GPCR. Use of this binding molecule makes it possible to detect an inactive class-A GPCR.

BRIEF DESCRIPTION OF DRAWINGS

FIG. 1 shows the results of analyzing the crystal structure of BLT1 bound to an antagonist BIIL260 (A) Simulated annealing $mF_o$-$DF_c$ omit maps of BIIL260, contoured at $2.0\sigma$ with BIIL260 viewed from two directions. (B) Simulated annealing $mF_o$-$DF_c$ omit map contoured at $2.0\sigma$ for the residues specifically involved in BIIL260 binding. The corresponding residues were replaced with glycine to calculate the omit map. (C) Overall structure of the BLT1-BIIL260 complex. BIIL260 and the $D66^{2.50}$ side chain are represented by sphere models, colored salmon (carbon atoms of BIIL260), magenta (carbon atoms of $D66^{2.50}$), red (oxygen atoms), and blue (nitrogen atoms). (D) Comparison of the locations of the bound GPCR ligands. All GPCR crystal structures were superimposed on BLT1-BIIL260, and all of the bound ligands are represented by stick models (light yellow). (E) Comparison of the structures of BLT1 (cyan and ECL2 in blue) and CXCR4 (light yellow and ECL2 in orange) depicted by cartoon models, viewed from the extracellular side. (F) Surface representation of the extracellular region of BLT1. The surface was calculated without the BIIL260 molecule and represented in the same viewpoint as (E).

FIG. 2 shows how the binding of BIIL260 to BLT1 looks. (A) Structure of the BIIL260-binding site. BIIL260 and the BLT1 side chains within 4 Å from BIIL260 are represented by stick models, and transmembrane helices are depicted by thin ribbons. Sulfur atoms are colored gold. (B) Schematic representation of the BLT1-BIIL260 interaction. Intermolecular forces such as the salt bridge, hydrogen bonding, π-to-edge, CH-to-π, and hydrophobic interactions are indicated in red, blue, orange, violet, and green, respectively. The three non-identical residues in human BLT1 and BLT2, a cognate receptor of BLT1, are highlighted in green shaded boxes, and the corresponding residues of human BLT1 and BLT2 (hBLT1 and hBLT2, respectively) are also presented. (C) Competition binding assays of BIIL260 to 0.5 nM $^3$H-LTB$_4$, using the membrane fractions of HEK293 cells expressing the mutant and wild-type BLT1s. The mutations were introduced at the residues involved in the specific BIIL260 binding. Each point (±s.e.m.) indicates the mean value of two independent experiments, each with triplicate reactions. NS is non-specific binding measured with 0.5 μM LTB$_4$. The binding constants are summarized in Table 1.

FIG. 3 shows the effects of benzamidine on BLT1-LTB$_4$ binding and LTB$_4$-mediated signal transduction. (A) Competition binding assay of benzamidine and NaCl to 0.5 nM $^3$H-LTB$_4$, using the membrane fraction of HEK293 cells expressing the wild-type BLT1. Each point (±s.e.m.) indicates the mean value of three independent experiments, each with triplicate reactions. (B) Saturation assay of $^3$H-LTB$_4$ and BLT1 with various concentrations of benzamidine. Each point (±s.e.m.) indicates the mean value of three independent experiments, each with triplicate reactions. (C and D) Effects of benzamidine on G-protein activation by LTB$_4$, measured by the TGFα shedding assay with Gq/il (C) and G16 (D). Each point (±s.e.m.) indicates the mean value of triplicate reactions. All pharmacological parameters are summarized in Table 1.

FIG. 4 is diagrams illustrating the structure of the benzamidine moiety-binding site of BLT1, which structure is compared to that of $A_{2A}$ adenosine receptor in the inactive state. (A) Interactions of BLT1 around the benzamidine moiety in the BIIL260-binding site. Residues involved in the salt bridge are indicated, and hydrogen bonds are represented by cyan dotted lines. (B) BLT1 (cyan carbon atoms) was superimposed on the inactive-state $A_{2A}$ adenosine receptor ($A_{2A}$R, light yellow carbons, PDB code: 4EIY). The interactions of $A_{2A}$R with similar interactions present or absent in BLT1-BIIL260 are represented by black and white dotted lines, respectively. The receptors were superimposed using pair fitting of the Cα atoms of residues 2.49-2.51, 3.38-3.40, and 7.45-7.47. The sodium ion and waters w1 and w4 of $A_{2A}$R are within van der Waals distances from the benzamidine moiety of BIIL260. (C) The benzamidine moiety and the bound sodium ion and water molecules in (B) are depicted as spheres and dots, respectively.

FIG. 5 is diagrams illustrating how the bound benzamidine moiety affects agonist-induced activation of BLT1. (A, B) Comparison of the structures of transmembrane helices 2, 3, and 7 among BLT1 and the agonist-bound GPCRs (left panel) and the corresponding inactive-state GPCRs (right panel) around the benzamidine moiety binding site. The agonist-bound states of BLT1, β$_2$ adrenergic receptor (PDB code: 3SN6), $A_{2A}$ adenosine receptor (5G53), μ-opioid receptor (5C1M), M$_2$ muscarinic receptor (4MQS), US28 (4XT1), and rhodopsin (3PQR) are compared. The inactive states of BLT1, β$_2$ adrenergic receptor (2RH1), $A_{2A}$ adenosine receptor (4EIY), μ-opioid receptor (4DKL), M$_2$ muscarinic receptor (3UON), rhodopsin (1U19), CXCR4 (3OUU), CCR2 (5T1A), CCR5 (4MBS), and CCR9 (5LWE) are compared. All GPCRs were superimposed with BLT1 using pair fitting of the Cα atoms of residues 2.49-2.51, 3.38-3.40 and 7.45-7.47. The molecules are viewed from the membrane side as the side view (A) and from the cytoplasmic side as the bottom view (B). In the agonist-bound state, the side chains of residues 3.39 and 7.46 are within van der Waals distances to the amidine group of benzamidine (indicated by the red arrows).

FIG. 6 is diagrams about amino acid conservation of the benzamidine binding site and the orthosteric binding site among GPCRs. (A, B) Amino acid conservation of class-A GPCRs, depicted with the BLT1 structure. The side chains constituting the orthosteric binding and the benzamidine binding sites are presented and colored according to the standard deviation of conservation of each residue among the 273 GPCRs (A). In (B), the side chains are colored as in (A), but the residues are classified according to four characteristics, negatively charged (D and E), positively charged (K and R), hydrophilic (C, H, N, Q, S, T, and Y), and hydrophobic residues (A, F, G, I, L, M, P, V, and W). For example, when a residue is completely conserved in all 273 GPCRs, the standard deviation values are 61 (A) and 137 (B), respectively. A higher standard deviation value reflects the higher conservation of the amino acid residue. The residues constituting the orthosteric binding site are not conserved, but those of the benzamidine binding site are conserved among the 273 GPCRs. (C) Superimposition of representative bound GPCR ligands. β$_2$ adrenergic receptor (β$_2$AR, PDB code: 2RH1), $A_{2A}$ adenosine receptor ($A_{2A}$R, 2YDO), δ-opioid receptor (δ-OR, 4N6H), and cannabinoid receptor (CB1, 3PQR), CCR5 chemokine receptor (4MBS), and BLT1 are compared. Each receptor was superimposed by pair-fitting of the Cα atoms of residues 2.49-2.51, 3.38-3.40, and 7.45-7.47, and only the bound ligands are presented. In BLT1, only the benzamidine moiety is depicted. The molecules are represented in the same viewpoint as in (A and B). All of the ligands were located near the benzamidine moiety, indicating that the bound benzamidine moiety is adjacent to the orthosteric binding site. In CCR5, since maraviroc is an allosteric modulator, the benzamidine moiety is near the allosteric site.

FIG. 7 shows expression constructs and illustrates LTB$_4$ binding and thermostability. (A) Expression construct represented by a snake model. The expression region included residues 15-348 of gpBLT1, with the N-terminal α factor prepro-signal sequence of Saccharomyces cerevisiae followed by the FLAG tag, the C-terminal PreScission site and His$_6$ tag, and T4 lysozyme (T4L) fused at ICL3. As shown in (B), twelve BLT1-T4L chimeras were constructed with different fusion sites, and the construct with the solved structure (ICL3-10) and others are shown with solid and dashed lines, respectively. The three mutations (H83G/K88G/V212A) introduced to increase the thermostability of gpBLT1 are indicated in red. The experimental result obtained with the newly introduced V212A mutation is shown in FIG. 8A. The S309A mutation was also introduced in this construct, to avoid phosphorylation. The signal sequence was digested with the endogenous yeast protease during expression, and the His$_6$ tag was removed with HRV 3C protease in the purification step. The N-terminal FLAG tag, the C-terminal residues 288-348 including part of the PreScission site, and residues T254 and L255 (colored grey) are not included in the refined structure, since their electron densities were unclear. Twelve residues in BLT1 (colored green) and 8 residues in T4L were replaced by alanine in the crystal structure, due to ambiguous electron densities. (B) Fusion positions of BLT1-T4L. T4L was introduced within ICL3, at the N-terminal or at both the N-terminal and ICL3 of BLT1. In the fusion at ICL3, T4L was fused between the C-terminal of transmembrane helix 5 (TM5) (R211, A212, or R213) and the N-terminal of TM6 (R214, F215, or H216), with linker residues colored cyan. Note that V212 was replaced with alanine, based on the results shown in FIG. 8A. The number of residues in ICL3 of BLT1 is the same as that of CXCR4, and the construct ICL3-1 has T4L at the same position in the linkers with the same lengths as those of CXCR4-T4L (PDB code: 3ODU). Crystals appeared for constructs ICL3-1 and ICL3-10 under similar crystallization conditions, and the structure was solved only for construct ICL3-10.

FIG. 8 is graphs illustrating the results of characterizing various BLT1 thermostability mutants and respective T4 lysozyme chimeras. (A) (left graph) LTB$_4$ binding and thermostability assays of the BLT1 mutants expressed in COS-7 cells. Point mutations were introduced according to the consensus method, to stabilize BLT1. The parent construct (parent 1) was the mutant BLT1 with the N-terminal residues 1-14 deleted, two previously confirmed thermostabilizing H83G and K88G mutations, and the phosphorylation-site S309A mutation. RA is the remaining activity, calculated by the following equation: RA=(Total binding (50° C. pre-heat treatment)−NS binding (1 μM LTB$_4$))/(Total binding (20° C. pre-heat treatment)−NS binding (1 μM LTB$_4$)). (right graph) LTB$_4$ binding and thermostability assays of BLT1-T4L chimeras listed in (B), expressed by *Pichia pastoris*. The parent construct (parent 2) is the H83G/K88G/V212A/S309A mutant with residues 1-14 deleted. (B and C) Saturation (B) and competition binding (C) assays of BLT1-T4L (ICL3-10 construct).

FIG. 9 illustrates the results of the purification, crystallization, electron density map, and crystal packing of BLT1-T4L. (A) Final results of gel filtration on a Superose-6 column. (B) Crystals of the BLT1-T4L-BIIL260 complex, obtained by the lipidic cubic phase method. The picture was taken using circularly polarized light. (C) BLT1-T4L molecules with 2 mF$_o$-DF$_c$ electron density. (D) Lattice packing of BLT1-T4L. BLT1 and T4L are colored cyan and magenta, respectively. There are no BLT1-BLT1 intermolecular interactions. The crystal lattices are presented with arrows. (E) The chemical structures of LTB$_4$, and BIIL260.

FIG. 10 shows the features of the structure of BLT1. (A) Cartoon representation. BLT1 is represented by a rainbow-colored cartoon model, and BIIL260 is represented by light pink (carbon), red (oxygen), and blue (nitrogen) spheres. Transmembrane helices 3, 4, and 5 near the extracellular region adopt a relatively open structure, as indicated in the oval. (B) Surface representation viewed from the same direction as in (A). The surface was calculated without BIIL260 The BIIL260 molecule is not visible from any direction in the surface model, except for the extracellular view, as shown in FIG. 1F. (C) Superimposition of BLT1 and the inactive-state nociceptin/orphanin FQ (N/OFQ) peptide receptor (NOP, PDB code: 4EA3), viewed from the cytoplasmic side. The structures were superimposed using pair fitting for 95 Cα atoms of residues 1.50-1.60, 2.39-2.50, 3.39-3.55, 4.39-4.50, 5.50-5.68, 6.34-6.48, and 7.45-7.53, the inner halves of the transmembrane helices (TMs). In the right panel, the root mean square deviation (r.m.s.d.) values for the backbone atoms of the corresponding inner TM residues of γ-branch GPCRs are listed. GPCRs indicated with asterisks are in the active form. (D) Cytoplasmic interhelical hydrogen bonding interactions. The BLT1 backbone is represented by a rainbow-colored ribbon model. The residues involved in the interhelical interactions are shown in stick models, and their interactions are indicated with black dashed lines.

FIG. 11 is diagrams illustrating structural comparison between BLT1 and GPCRs with the bound sodium ion. (A, C, E) BLT1 and GPCRs in which the sodium ion was observed are superimposed, as in FIG. 4B. (A) β$_1$ acetylcholine receptor (β$_1$AR, PDB code: 4BVN), (C) δ-opioid receptor (δ-OR, PDB code: 4N6H), and (E) protease activated receptor 1 (PAR1, PDB code: 3VW7). Each receptor was superimposed by pair fitting of the Cα atoms of residues 2.49-2.51, 3.38-3.40, and 7.45-7.47. The carbon atoms of BLT1, the benzamidine moiety of the bound BIIL260, and other GPCRs are colored cyan, salmon, and light yellow, respectively. The salt bridge and hydrogen bonding interactions within the BLT1-BIIL260 complex are indicated with cyan dashed lines. In GPCRs other than BLT1, the interactions with or without corresponding interactions in the BLT1-BIIL260 complex are indicated with orange and grey dashed lines, respectively. (B, D, F) The benzamidine moiety and the bound sodium ion and water molecules in (A, C, E) respectively are depicted as spheres and dots, respectively.

FIGS. 12(A) and (B) show the candidate structures of modified class-A GPCR binding compounds. Modified Class-A GPCR binding compound candidates for the selected four A$_{2A}$AR, β$_1$AR, δ-OR and histamine receptor were tentatively constructed with varying linker type, length and composition.

FIGS. 13(A) to (D) are diagrams illustrating the results of modeling studies on how each GPCR interacts with a modified class-A GPCR-binding compound. (A) shows the modeling of A$_{2A}$ adenosine receptor (A$_{2A}$AR) and adenosine-linker-benzamidine, (B) shows the modeling of β$_1$ adrenergic receptor (β$_1$AR) and carazolol-linker-benzamidine, (C) shows the modeling of δ-opioid receptor (δ-OR) and TIPP-linker-benzamidine, (D) shows the modeling of H$_1$ histamine receptor (H$_1$HR) and histamine-linker-benzamidine.

Panel (a) shows the structure of GPCR with the benzamidine-ligand was refined by the program CNS. There is no conflict between the ligand and GPCRs. In each GPCR, the two modeling results with the different linker length were depicted. Panel (b) shows the schematic drawing of the ligand-linker-benzamidine. The ligand and benzamidine molecule are linked with the click chemistry. Panel (c) shows the structure before the energy minimization procedure by the program CNS. The benzamidine moiety of BLT1-BIIL260 was docked to the target GPCRs, after the BLT1-BIIL260 structure and the corresponding GPCR were overlaid each other. The initial position of the linker moiety linked to each ligand was arbitrary as indicated with dashed line ellipse.

FIGS. 14(A) to (D) are charts illustrating the results of checking physical properties (e.g., NMR, MS) of compound 1 synthesized in Example 2.

FIGS. 15(A) to (H) are charts illustrating the results of checking physical properties (e.g., NMR, MS) of compound 2 synthesized in Example 2.

FIGS. 16(A) to (G) are charts illustrating the results of checking physical properties (e.g., NMR, MS) of compound 3 synthesized in Example 2.

FIGS. 17(A) to (H) are charts illustrating the results of checking physical properties (e.g., NMR, MS) of compound 4 synthesized in Example 2.

FIGS. 18(A) to (F) are graphs illustrating the results of examining how each GPCR activity was suppressed by a compound comprising a structure comprising a class-A GPCR-binding compound linked to the benzamidine moiety. The ability of each compound to suppress G-protein activity was measured by TGFα shedding assay. (1) $β_1$ and $β_2$ adrenaline receptors; (2) $A_{2A}$ adenosine receptor; and (3) $H_1$, $H_2$, and $H_4$ histamine receptors. • and ○: Compounds comprising a structure comprising a class-A GPCR-binding compound linked to the benzamidine moiety. The reaction was triplicate in each experiment and each point (±standard error of the mean (s.e.m)) indicates a mean.

FIG. 19 shows the structures of protonated benzamidine hydrochloride hydrate and benzamidine derivatives used in Example 3.

FIGS. 20(A) to (P) are tables illustrating the results of measuring, by TGFα shedding assay, the ability of each benzamidine derivative to suppress a corresponding class-A GPCR-mediated G-protein activity in the absence of an agonist.

DESCRIPTION OF EMBODIMENTS

Hereinafter, embodiments of the present invention will be described in detail. Note that substantially the same description is omitted so as to avoid redundancy.

The present inventors have found that the inhibitory activity of BIIL260 to BLT1 critically depends on its benzamidine moiety. The structural and pharmacological results revealed that the benzamidine moiety mimics the sodium ion-centered water cluster located at the bottom of the orthosteric binding site inside the transmembrane helix bundle, and negatively modulates the $BLT1-LTB_4$ system. The amidine group of benzamidine forms a salt bridge and hydrogen bonds with the residues $D66^{2.50}$, $S106^{3.39}$, and $S276^{7.45}$, and the phenyl rings form CH-to-π (and edge-to-π (interactions with the residues of $V69^{2.53}$ and $W236^{6.48}$, respectively. These interactions truly reproduce the sodium ion-centered water cluster observed in GPCRs (Liu et al., 2012, supra; Miller-Gallacher et al., 2014, supra; Zhang et al., 2012, supra; Fenalti et al., 2014, supra), and should keep BLT1 in an inactive state (Liu et al., 2012, supra). Moreover, the bulky benzamidine moiety inhibits the agonist-induced structural change of the transmembrane helices by steric hindrance. Furthermore, the benzamidine molecule by itself suppressed the $BLT1-LTB_4$ binding more potently than the sodium ion, by one order of magnitude (FIG. 3A). This phenomenon should occur because the bulkier benzamidine molecule bound to BLT1 would be much more difficult to remove, as compared with the sodium ion, which thus prevents the receptor from undergoing the agonist-induced structural change (Liu et al., 2012, supra; Miller-Gallacher et al., 2014, supra; Zhang et al., 2012, supra; Fenalti et al., 2014, supra). Taken together, the bound benzamidine moiety should function to selectively maintain BLT1 in the inactive state.

The amino acid residues that interact with the benzamidine moiety of BIIL260 are highly conserved among GPCRs (Table 2). In fact, the benzamidine molecule, by itself, can serve as a negative allosteric modulator for an agonist $LTB_4$ activity on BLT1 (FIGS. 3C and 3D). Thus, the benzamidine molecule can also function as an allosteric modulator of another GPCR. Benzamidine (120 Da) is smaller than amiloride (230 Da) (Gutierrez-de-Teran, H. et al., Structure 21 (2013) 2175-2185). In view of the structure illustrated in the below-described Examples, the bound benzamidine hardly competes for the orthosteric binding site.

According to the results obtained by the present inventors, it is possible to design each class-A GPCR-specific, benzamidine moiety-containing inverse agonist for a wide range of class-A GPCRs. To date, there has been no reported benzamidine moiety-containing inverse agonist for any class-A GPCRs. Meanwhile, it is possible to use, as effective inverse agonists, compounds designed to comprise a benzamidine moiety, as a modulator portion, and another moiety that specifically and tightly binds to a class-A GPCR. In order to make each compound functional, it is important that the benzamidine binding site is adjacent to the orthosteric binding site (FIGS. 6A and 6B). For example, when each receptor and BLT1 are superimposed (FIG. 6C), the distance between the closest atoms of benzamidine and bound carazolol is 4.4 Å in the case of $β_2$-adrenergic receptor (PDB code: 2RH1) (Rosenbaum, D. M. et al., Science 318 (2007) 1266-1273). This distance is 2.3 Å in the case of δ-opioid receptor (with naltrindole; PDB code: 4N6H) (Fenalti et al., 2014, supra). In addition, amino acid sequence analysis has demonstrated that residues of the benzamidine binding site are conserved among class-A GPCRs (FIGS. 6A and 6B and Table 2). Based on the above results and discussion, an embodiment of the present invention provides a method for rationally designing a novel inverse agonist specific to each GPCR. Conventionally, inverse agonists of GPCRs have been discovered unintentionally by random screening using a large-scale chemical library. In view of this fact, the present inventors' findings are a critical breakthrough in GPCR-targeting drug discovery.

An embodiment of the present invention provides a novel compound. This compound, for instance, includes a compound or a salt thereof comprising a structure comprising a class-A GPCR-binding compound linked to a functional group that can bind to a Na+-water cluster binding site of the class-A GPCR. Use of the compound or salt thereof makes it possible to inhibit a function of the class-A GPCR as demonstrated in the below-described Examples. Another embodiment of the present invention provides a compound or a salt thereof comprising a structure comprising a class-A GPCR-binding compound linked to at least one functional group selected from the group consisting of benzamidine moieties or derivatives thereof, phenyl-substituted protonated amine groups, and phenyl-substituted unprotonated amine groups. Use of the compound or salt thereof makes it possible to inhibit a function of the class-A GPCR as demonstrated in the below-described Examples. Another embodiment of the present invention includes a compound or a salt thereof structured by linking a class-A GPCR-binding compound and a compound that can bind to a $Na^+$-water cluster binding site of the class-A GPCR. Use of the compound or salt thereof makes it possible to inhibit a function of the class-A GPCR as demonstrated in the below-described Examples.

In an embodiment of the present invention, examples of the "class-A GPCR" include the following family members: (1) amine receptors (e.g., adrenoceptors (α1A, α1B, α1D, α2A, α2B, α2C, β1, β2, β3), serotonin receptors (5-HT1A, 5-HT1B, 5-HT1D, 5-HT1E, 5-HT1F, 5-HT2A, 5-HT2B, 5-HT2C, 5-HT4, 5-HT5A, 5-HT5B, 5-HT6, 5-HT7), muscarinic acetylcholine receptors (M1, M2, M3, M4, M5), dopamine receptors (D1, D2, D3, D4, D5), histamine receptors (H1, H2, H3, H4), trace amine receptors (TAAR1)); (2) nucleic acid receptors (e.g., adenosine receptors (A1, A2A, A2B, A3), P2Y receptors (P2Y1, P2Y2, P2Y4, P2Y6, P2Y11, P2Y12, P2Y13, P2Y14)); (3) lipid receptors (e.g., bile acid receptors (GPBA), cannabinoid receptors (CB1, CB2), estrogen receptors (GPER), free fatty acid receptors (FFA1, FFA2, FFA3, FFA4, GPR42), leukotriene receptors (BLT1, BLT2, CysLT1, CysLT2, OXE, FPR2/ALX), platelet activating factor receptor (PAFR), prostanoid receptors (DP1, DP2/GPR44, EP1, EP2, EP3, EP4, FP, IP, TP), lysophosphatidic acid receptors (LPA1, LPA2, LPA3, LPA4, LPA5, LPA6), sphingosine-1-phosphate receptors (S1P1, S1P2, S1P3, S1P4, SIP5)); (4) low-molecular-weight compound receptors (e.g., hydroxy carboxylic acid receptors (HCA1, HCA2, HCA3), melanin receptors (MT1, MT2), oxoglutaric acid receptor (OXGR1), succinic acid receptor (SUCNR1)); (5) peptide receptors (e.g., angiotensin receptors (AT1, AT2), apelin receptor (APLNR), bombesin receptors (BB1, BB2, BB3), bradykinin receptors (B1, B2), chemerin receptors (CMKKLR1, GPR1), cholecystokinin receptors (CCK1, CCK2), endothelin receptors (ETA, ETB), formyl peptide receptors (FPR1, FPR2/ALX, FPR3), galanin receptors (GAL1, GAL2, GAL3), ghrelin receptor (GHSR), kisspeptin receptor (KISS1R), melanin-concentrating hormone receptors (MCH1, MCH2), melanocortin receptors (MC1, MC2, MC3, MC4, MC5), motilin receptor (MTLR), neuromedin U receptors (NMU1, NMU2), neuropeptide FF receptors (NPFF1, NPFF2), neuropeptide S receptor (NPS), neuropeptide BW receptors (NPBW1, NPBW2), neuropeptide Y receptors (Y1, Y2, Y3, Y4, Y5, Y6), neurotensin receptors (NTS1, NTS2), opioid receptors (δOR, κOR, μOR, NOP), orexin receptors (OX1, OX2), prokineticin receptors (PKR1, PKR2), prolactin releasing peptide receptor (PrRP), QRFP receptor (QRFPR), relaxin family peptide receptors (RXFP1, RXFP2, RXFP3, RXFP4), somatostatin receptors (SST1, SST2, SST3, SST4, SST5), tachykinin receptors (NK1, NK2, NK3), thyrotropin-releasing hormone receptors (TRH1, TRH2), urotensin receptor (UTS2R), vasopressin receptors (V1A, V1B, V2), oxytocin receptor (OT)); (6) protein receptors (e.g., chemokine receptors (CCR1, CCR2, CCR3, CCR4, CCR5, CCR6, CCR7, CCR8, CCR9, CCR10, CXCR1, CXCR2, CXCR3, CXCR4, CXCR5, CXCR6, CX3CR1, XCR1, ACKR1, ACKR2, ACKR3, ACKR4, CCRL2), complement receptors (C3a, C5a1, C5a2), glycoprotein hormone receptors (FSH, LH, TSH), gonadotropin-releasing hormone receptors (GnRH1, RnRH2), parathyroid hormone receptors (PTH1, PTH2), protease receptors (PAR1, PAR2, PAR3, PAR4)); (7) rhodopsin receptors (e.g., OPN1LW, OPN1MW, OPN1SW, Rhodopsin, OPN3, OPN4, OPN5); (8) olfactory receptors (e.g., OR1G1, OR51E2, OR3A2); and (9) class-A orphan GPCRs, an artificial ligand of which has been identified (e.g., GPR119, G2A, EBI2, GPR84GPR17, GPR61, GPR52, GPR37, GPR32, GPR55, GPR75, GPR83, GPR18, LGR5, GPR142, GPR139, GPR182, GPR35, MRGX2, MRGD, MAS1, TAAR5, TAAR2). Meanwhile, each class-A GPCR may have a Na$^+$-water cluster binding site and an orthosteric binding site that are adjacent to each other. Examples of species of each class-A GPCR include a human, a monkey, a mouse, and a rat.

Class A GPCRs are also known to be classified into four groups: α-group, β-group, γ-group and δ-group (Frederiksson, R. et al., Mol Pharmacol 63 (2003) 1256-1272).

It is known that various class-A GPCRs exhibit a varied degree of basal or constitutive activity (that is, exhibit activity in the absence of an agonist). In an embodiment of the present invention, the class-A GPCRs include GPCRs that exhibit basal or constitutive activity. Examples include, but are not limited to, adrenoceptors, histamine receptors, adenosine receptors, glycoprotein hormone receptors (TSHR, LHR, FSHR), bradykinin receptors, 5-hydroxytryptamine receptors, melanin-concentrating hormone receptors, dopamine receptors, acetylcholine receptors, angiotensin receptors, prostanoid receptors, cannabinoid receptors, lysophospholipid (S1P) receptors, opioid receptors, thyroid stimulating hormone releasing hormone receptor, formyl peptide receptors, complement peptide receptors, platelet activating factor receptors, chemokine receptors, tachykinin receptors, neurotensin receptors, vasopressin and oxytocin receptors, cholecystokinin receptors, P2Y receptors, melanocortin receptors, and orexin receptors (Seifert, R. et al., Naunyn-Schmiedeberg's Arch Pharmacol (2002) 381-416; Khilnani, G. et al., Indian J Pharmacol (2011) 492-501; Stoy, H. et al., Genes & Diseases (2015) 108-132; Drug Bank (https://www.drugbank.ca/)).

From the viewpoints of strong inverse agonistic action or antagonistic action exerted by the above compound(s) according to an embodiment of the present invention, preferable examples of the class-A GPCRs include the following. Note that the numbers in parentheses each indicate an accession number of the UniProtKB/Swiss-Prot. EP1 (P34995), OXGR1 (Q96P68), GPR119 (Q8TDV5), CysLT1 (Q9Y271), FFAT2 (O15552), G2A (Q9UNW8), P2Y2 (P41231), P2Y4 (P51582), NK2 (P21452), P2Y6 (Q15077), PAR1 (P25116), V2 (P30518), DP (Q13258), FP (P43088), 5-HT2A (P28223), EP2 (P43116), EP4 (P35408), V1B (P47901), V1A (P37288), α1A (P35348), 5-HT4 (Q13639), CB2 (P34972), EBI2 (P32249), BLT2 (Q9NPC1), 5-HT1A (P08908), 5-HT1D (P28221), α1D (P25100), PAR3 (O00254), P2Y13 (Q9BPV8), P2Y12 (Q9H244), P2Y14 (Q15391), FFA3 (O14843), NOP (P41146), 5-HT1E (P28566), GPR84 (Q9NQS5), PAR4 (Q96RI0), κOR (P41145), D5 (P21918), A3 (P0DMS8), H2 (P25021), FPR1 (P21462), D1 (P21728), FFA4 (Q5NUL3), EP3 (iso8) (P43115-8), AGTR2 (P50052), 5-HT1F (P30939), β1 (P08588), CCR1 (P32246), CCR8 (P51685), CCR6 (P51684), CCR5 (P51681), HCRTR2(OX2R) (O43614), GPR81 (Q9BXC0), GPR85 (P60893), GNRHR (P30968), GPR149 (Q86SP6), GPR17 (Q13304), GPR61 (Q9BZJ8), GALR3 (O60755), GALR2 (O43603), GPR1 (P46091), GPR62 (Q9BZJ7), GPR52 (Q9Y2T5), GPR37 (O15354), GPR32 (O75388), M5 (P08912), GPR55 (Q9Y2T6), PAFR (P25105), B1 (P46663), OT (P30559), CysLT2 (Q9NS75), FFA1 (O14842), AT1 (P30556), B2 (P30411), M1 (P11229), P2Y11 (Q96G91), NK3 (P29371), P2Y1 (P47900), A2B (P29275), A2A (P29274), SIP5(Q9H228), IP (P43119), 5-HT6 (P50406), 5-HT2B (P41595), S1P3 (Q99500), α1B (P35368), TP (P21731), D3 (P35462), S1P1 (P21453), H4 (Q9H3N8), S1P2 (O95136), 5-HT1B (P28222), ETB (Q24530), M4 (P08173), EP3 (P43115), M2 (P08172), H3 (Q9Y5N1), 5-HT7 (P34969), D2 (P14416), D4 (P21917), CB1 (P21554), ETA (P25101), δ-OR (P41143), A1 (P30542), FPR2 (P25090), α2C (P18825), α2A (P08913), α2B (P18089), BLT1 (Q15722), FPR3 (P25089), C3AR1 (Q16581), CCR3 (P51677), CMKLR1 (Q99788), C5AR1 (P21730), β3 (P13945), CCR7 (P32248), EP3 (iso6) (P43115-6), CCR4 (P51679), CXCR5 (P32302), DARC (Q16570), CCKBR (P32239), GPR109A (Q8TDS4), GRPR (P30550), GPR75 (O95800), GPER (Q99527), GPR173 (Q9NS66), GPR18 (Q14330), GPR101 (Q96P66), LGR5 (O75473), GPR142 (Q7Z601), GPR146 (Q96CH1), GHSR (Q92847), GALR1 (P47211), GPR161 (Q8N6U8), GPR44/DP2 (Q9Y5Y4), GPR139 (Q6DWJ6), GPR182 (O15218), MRGX2 (Q96LB1), NPFFR2 (Q9Y5X5), NMUR1 (Q9HB89), Mrgb1/Mrgprx2 (Q96LB1), Mrga1 (Q91WW), NPY2R (P49146), NPYSR (Q99463), NPBWR2 (P48146), Mrga2a (Q91WW4), Mrgb3 (Q91ZC1), MCSR (P33032), MC3R (P41968), NPFFR1 (Q9GZQ6), MCHR2 (Q969V1), MRGE (Q86SM8), Mrgb4 (Q91ZC0), Mrgb5 (Q91ZB9), MRGD (Q8TDS7), Mrgb2 (Q3KNA1), Mrgh (Q99MT8), NPBWR1 (P48145), MCHR1 (Q99705), Mrga4 (Q91WW2), MAS1L (P35410), Mrga7 (Q91ZC5), MRGX3 (Q96LB0), MT1R (P48039), MC4R (P32245), MC1R (Q01726), MRGF (Q96AM1), MC2R (Q01718), XCR1 (P46094), OR1G1 (P47890), OXER1 (Q8TDS5), RGR (P47804), S1P4 (O95977), PROKR2 (Q8NFJ6), SSTR1 (P30872), TP (iso2) (P21731-2), CCR2 (P41597), CCBP2 (O00590), RABGAP (GPR21), SSTRS (P35346), PRLHR (P49683), β2 (P07550), PAR2 (P55085), TAAR5 (O14804), RXFP3 (Q9NSD7), RXFP4 (Q8TDU9), TAAR2 (Q9P1P5), SSTR2 (P30874), OPN1LW (P04000), OPN1MW (P04001), 5-HTSA (P47898), OR51E2 (Q9H255), TAAR6 (Q96RI8), VN1R1 (Q9GZP7), CXCR6 (O00574), OR3A2 (P47893), SSTR3 (P32745), EP3 (iso5) (P43115-5), RRH (O14718), TAAR9 (Q96RI9), or TAAR8 (Q969N4).

Each class-A GPCR may be a mutant containing one or more mutations in the amino acid sequence of wild-type class-A GPCR. The mutations include those caused by a variation in the DNA sequence among individuals.

As used herein, the "inverse agonists" include those that can inhibit and decrease basal or constitutive activity of GPCR to a level lower than a normal level. The basal or constitutive activity involves endogenous activity or activity in the absence of an agonist (or when an agonist is not in contact).

As used herein, the "antagonists" include compounds that can inhibit a function of a receptor molecule. The antagonists include inverse agonists.

An embodiment of the present invention provides a modified class-A GPCR-binding compound, wherein a class-A GPCR binding compound is modified by covalent linkage with a functional group that will bind in the pocket of the GPCR composed of Amino Acid$^{2.50}$, Amino Acid$^{3.39}$, Amino Acid$^{6.48}$ and Amino Acid$^{7.45}$ specified by the Ballesteros-Weinstein numbering scheme (Ballesteros, J. A. et al., Methods Neurosci (1995) 366-428).

The Ballesteros-Weinstein numbering scheme is well-known in the art, which applies herein to all class-A GPCRs.

In an embodiment of the present invention, the "modified class-A GPCR-binding compound" may be orthosteric, allosteric, syntopic, or bitopic with respect to the class-A GPCR because of the modification and examples include compounds with inverse agonistic activity or partial inverse agonistic activity.

As used herein, the "class-A GPCR-binding compounds" include compounds that exhibit class-A GPCR-binding activity. In addition, the class-A GPCR-binding compounds include compounds before modification with a functional group that enters the above pocket of class-A GPCR. Such compounds (e.g., chemical compounds, ligands, drugs) may be inverse agonists, agonists, partial agonists, partial inverse agonists, antagonists, partial antagonists, or modulators, or may not exert any effects on the corresponding class-A GPCRs. Each class-A GPCR-binding compound may have an organic or inorganic moiety. Each class-A GPCR-binding compound may be referred to as a "ligand". Each class-A GPCR-binding compound may be bonded via a linker. The class-A GPCR-binding compounds include compounds that can each bind to the orthosteric binding site of GPCR. The class-A GPCR-binding compounds include polypeptides (e.g., chemokines).

In addition, examples of the class-A GPCR compounds include class-A GPCR ligands. Examples of the class-A GPCR ligands include amine receptor ligands, nucleic acid receptor ligands, lipid receptor ligands, low-molecular-weight compound receptor ligands, peptide receptor ligands, protein receptor ligands, and ligands for class-A orphan GPCRs, an artificial ligand of which has been identified. More specific examples of the class-A GPCR ligands may include the following ligands. Note that the members in parentheses each indicate a corresponding receptor example.

Examples of the amine receptor ligands include: adrenaline (adrenoceptor), noradrenaline (adrenoceptor), serotonin (serotonin receptor), acetylcholine (muscarinic acetylcholine receptor), dopamine (dopamine receptor), histamine (histamine receptor), tyramine (trace amine receptor), carazolol (adrenoceptor), carvedilol (adrenoceptor), CGP 12177 (adrenoceptor), and isoprenaline (adrenoceptor).

Examples of the nucleic acid receptor ligands include: adenosine (adenosine receptor), ADP (P2Y receptor), ATP (P2Y receptor), UTP (P2Y receptor), UDP (P2Y receptor), UDP-glucose (P2Y receptor), CGS21680 (adenosine receptor), NECA (adenosine receptor), apadenoson (adenosine receptor), and piclidenoson (adenosine receptor).

Examples of the lipid receptor ligands include: chenodeoxycholic acid (bile acid receptor), cholic acid (bile acid receptor), deoxycholic acid (bile acid receptor), lithocholic acid (bile acid receptor), anandamide (cannabinoid receptor), 2-arachidonoyl glycerol (cannabinoid receptor), 17β-estradiol (estrogen receptor), free fatty acid (free fatty acid receptor), leukotriene B4 (leukotriene receptor), 12-hydroxyheptadecatrienoic acid (leukotriene receptor), leukotriene C4, leukotriene D4 (leukotriene receptor), leukotriene E4 (leukotriene receptor), 5-oxo-ETE (leukotriene receptor), 5-oxo-ODE (leukotriene receptor), lysophosphatidic acid (lysophosphatidic acid receptor), sphingosine-1-phosphate (sphingosine-1-phosphate receptor) HU-210 (cannabinoid receptor), CP55940 (cannabinoid receptor), AM1241 (cannabinoid receptor), JWH-133 (cannabinoid receptor), and SR144528 (cannabinoid receptor).

Examples of the low-molecular-weight compound receptor ligands include: lactic acid (hydroxy-carboxylic acid receptor) 3-hydroxy-butyric acid (hydroxy carboxylic acid receptor), 3-hydroxy-octanoic acid (hydroxy-carboxylic acid receptor), melanin (melanin receptor), oxo-glutaric acid (oxo-glutaric acid receptor), and succinic acid (succinic acid receptor).

Examples of the peptide receptor ligands include: angiotensin II (angiotensin receptor), angiotensin III (angiotensin receptor), apelin-13 (apelin receptor), apelin-17 (apelin receptor), apelin-36 (apelin receptor), gastrin releasing peptide (bombesin receptor), neuromedin B (bombesin receptor), bradykinin (bradykinin receptor), kallidin (bradykinin receptor), chemerin (chemerin receptor), resolvin E1 (chemerin receptor), CCK-4 (cholecystokinin receptor), CCK-8 (cholecystokinin receptor), CCK-33 (cholecystokinin receptor), gastrin (cholecystokinin receptor), endothelin-1 (endothelin receptor), endothelin-2 (endothelin receptor), endothelin-3 (endothelin receptor), annexin (formyl peptide receptor, leukotriene receptor), cathepsin (formyl peptide receptor), lipoxin A4 (formyl peptide receptor, leukotriene receptor), resolvin D (formyl peptide receptor, leukotriene receptor), F2L (formyl peptide receptor), humanin (formyl peptide receptor), galanin (galanin receptor), galanin-like peptide (galanin receptor), ghrelin (ghrelin receptor), kisspeptin (kisspeptin receptor), melanin-concentrating hormone (melanin-concentrating hormone receptor), motilin (motilin receptor), neuromedin-23 (neuromedin U receptor), neuromedin-25 (neuromedin U receptor), neuromedin-33 (neuromedin U receptor), neuromedin-35 (neuromedin U receptor), neuropeptide FF (neuropeptide FF receptor), neuropeptide AF (neuropeptide FF receptor), neuropeptide SF (neuropeptide FF receptor), RFamide-Related Peptide-1 (neuropeptide FF receptor), RFamide-Related Peptide-3 (neuropeptide FF receptor), neuropeptide S (neuropeptide S receptor), DADLE (opioid receptor), TIPP (opioid receptor), DAMGO (opioid receptor), and enadoline (opioid receptor).

Examples of the protein receptor ligands include: chemokine (chemokine receptor), Ca3 (complement receptor), Ca5 (complement receptor), thyroid stimulating hormone (glycoprotein hormone receptor), follicle stimulating hormone (glycoprotein hormone receptor), luteinizing hormone (glycoprotein hormone receptor), human chorionic gonadotropin (glycoprotein hormone receptor), gonadotropin releasing hormone (glycoprotein hormone receptor), Maraviroc (chemokine receptor), isothiourea-1t (chemokine receptor), and X4P-001 (chemokine receptor).

Examples of the ligands for class-A orphan GPCRs, an artificial ligand of which has been identified, include: N-oleoylethanolamide (GPR119), lysophospholipid (G2A), dihydroxycholesterol (EBI2), hydroxycholesterol (EBI2), fatty acid (GPR84), cysteinyl-leukotrienes (GPR17), uracil nucleotide (GPR17), 5-nonyloxytryptamine (GPR61), compound 7a (GPR52), pro-saponin (GPR37), resolvin D1 (GPR32), lipoxin A4 (GPR32), lysophosphatidylinositol (GPR55), CCL5 (GPR75), proprotein convertase subtilisin/kexin type 1 inhibitor (GPR83), N-arachidonoylglycin (GPR18), R-spongin (LGR5), tryptophan (GPR142), JNJ-63533054 (GPR139), adrenomedullin (GPR182), 2-oleoyl-lysophosphatidic acid (GPR35), PAMP-12 (MRGX2), β-alanine (MRGD), angiotensin-(1-7) (MAS1I), trimethylamine (TAAR5), and β-phenylethylamine (TAAR2).

In addition, examples of the class-A GPCR-binding compounds include compounds having affinity to a corresponding GPCR, such as a dissociation constant $(K_d)(M)$ of $1 \times 10^{-2}$ M or less. This value may be, for example, $1 \times 10^{-2}$, $1 \times 10^{-3}$, $1 \times 10^{-4}$, $1 \times 10^{-5}$, $1 \times 10^{-6}$, $1 \times 10^{-7}$, $1 \times 10^{-8}$, $1 \times 10^{-9}$, $1 \times 10^{-10}$, $1 \times 10^{-11}$ M or less or may be between two of the values. The affinity may be measured by TGFα shedding assay. When the affinity of each of a plurality of compounds is measured, high-throughput screening may be utilized.

Examples of the class-A GPCR-binding compounds include compounds with a molecular weight of 130 or higher. This molecular weight may be 130, 150, 100, 200, 300, 400, 500, 600, 700, 800, 900, 1000, 10000, 30000, or higher or may be between two of the values. From the viewpoints of strong antagonistic action exerted by the above compound(s) according to an embodiment of the present invention, this molecular weight is preferably from 150 to 1000 and more preferably from 200 to 600. In addition, each class-A GPCR-binding compound may be a compound other than compounds having a functional group that can bind to a $Na^+$-water cluster binding site.

Each class-A GPCR-binding compound may have, for example, a hydroxyl group, an amino group, or a thiol group. The number of substituents per group may be, for example, 1, 2, 3, 4, 5, or more or may be between two of the numbers.

Examples of the modification include chemical structure modification with below-described functional groups. The GPCR pocket, including amino acid$^{2.50}$, amino acid$^{3.39}$, amino acid$^{6.48}$, and amino acid$^{7.45}$ as specified by Ballesteros-Weinstein numbering scheme, is highly conserved among class-A GPCRs, and contributes to binding between a class-A GPCR and each modified GPCR-binding compound. The class-A GPCR-binding compounds may be each modified with a moiety (e.g., a benzamidine moiety) that enters the pocket of class-A GPCR so as to reinforce the class-A GPCR-binding activity. As described below, an amidine group of the benzamidine moiety interacts, through intermolecular force, with a carboxyl group of D66$^{2.50}$ and interacts, through intermolecular force, with hydroxyl groups of S106$^{3.39}$ and S276$^{7.45}$, thereby contributing mainly to formation of tight binding. Thus, each class-A GPCR-binding compound modified by a group selected from amidinyl, N-hydroxyamidinyl, guanidyl, amidinyl-substituted guanidyl, ethylamino, methylamino, amino, amidyl, amide, and NHCH$_3$ can bind more strongly to a corresponding GPCR than the original compound without modification using such a group.

As used herein, examples of the "intermolecular force" include salt bridges, hydrogen bonds, π-to-edge interactions, CH-to-π (interactions, and hydrophobic interactions. As used herein, examples of the "link" include covalent bonds, intermolecular force-mediated binding, and linker-mediated bonds.

In an embodiment of the present invention, the above $Na^+$-water cluster binding site contains, for instance, amino acid$^{2.50}$, $^{3.39}$, $^{6.48}$ or $^{7.45}$ as specified by Ballesteros-Weinstein numbering scheme. In addition, the above $Na^+$-water cluster binding site may contain an amino acid(s) listed in Table 2.

In an embodiment of the present invention, the amino acid of the Amino Acid$^{2.50}$ is a negative-charged amino acid. Preferably, the amino acid of the Amino Acid$^{2.50}$ is Asp, Glu or Asn.

In an embodiment of the present invention, the amino acid of the Amino Acid$^{3.39}$ is a hydrophilic amino acid. Preferably, the amino acid of the Amino Acid$^{3.39}$ is Ser, Thr, Gln or Gly.

In an embodiment of the present invention, the amino acid of the Amino Acid$^{6.48}$ is a hydrophobic amino acid. Preferably, the amino acid of the Amino Acid$^{6.48}$ is Trp, Phe, Ala, Ile, Met, Tyr or Val.

In an embodiment of the present invention, the amino acid of the Amino Acid$^{7.45}$ is a hydrophilic amino acid. Preferably, the amino acid of the Amino Acid$^{7.45}$ is Asn, Ser or Thr.

In an embodiment of the present invention, the above functional group may have a structure accommodated in a GPCR pocket comprising amino acids$^{2.50}$, $^{3.39}$, $^{6.48}$ and $^{7.45}$ as specified by the Ballesteros-Weinstein numbering scheme. In addition, the above functional group may also have a structure that can replace a $Na^+$-water cluster at the $Na^+$-water cluster binding site of class-A GPCR. In addition, the functional group that binds to the $Na^+$-water cluster binding site may be a compound that can bind to the $Na^+$-water cluster binding site. The functional group may be bonded via a linker.

The structure of the above compound according to an embodiment of the present invention may be represented by a formula: G-A-B or G-L-A-B. In the formula, G may mean the structure of a class-A GPCR-binding compound; L may mean a linker; and -A-B may mean a functional group (including a functional group that binds to the Na⁺-water cluster binding site of class-A GPCR, a benzamidine moiety or a derivative thereof, a phenyl-substituted protonated amine group, or a phenyl-substituted unprotonated amine group). Also, in the formula, the "-" may mean a covalent bond.

From the viewpoint of strong antagonistic activity on a class-A GPCR, the above functional group preferably has the following structure:

A-B wherein

A is a 3-to-6-membered saturated or unsaturated carbon ring group or heterocyclic group;

a heteroatom of the heterocyclic group is at least one selected from the group consisting of N, O, and S;

the carbon ring group or heterocyclic group is optionally substituted by at least one group selected from the group consisting of halogen, methyl, hydroxyl, amino, nitro, and $N_3$; and B is amidinyl, N-hydroxyamidinyl, guanidyl, amidinyl-substituted guanidyl, ethylamino, methylamino, amino, amidyl, amide, or $NHCH_3$.

From the viewpoint of strong antagonistic activity on a class-A GPCR, the above functional group is more preferably selected from the following groups:

benzamidine or derivatives thereof (e.g., 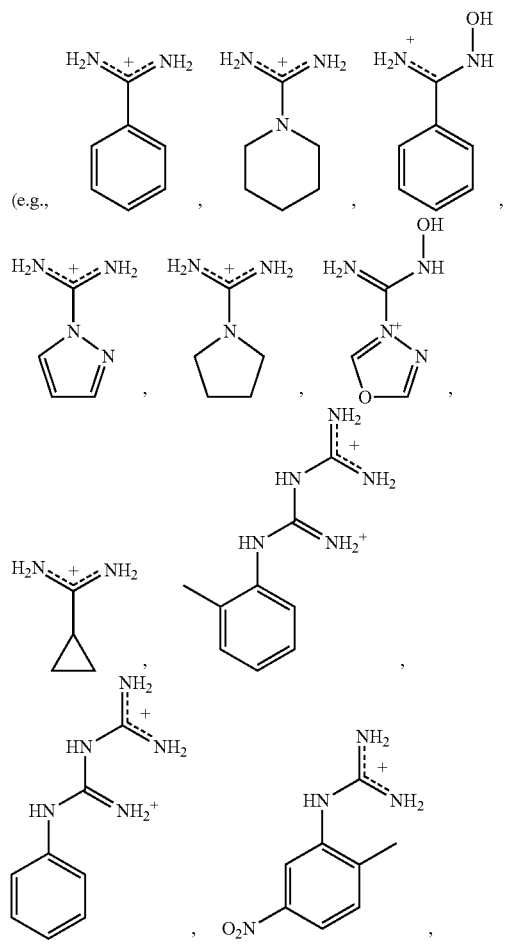

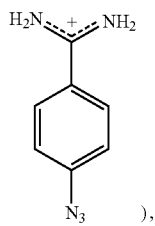

), phenyl-substituted protonated amine groups (e.g., 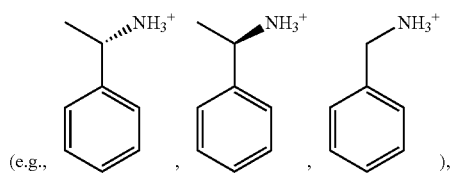 ), and phenyl-substituted unprotonated amine groups (e.g., 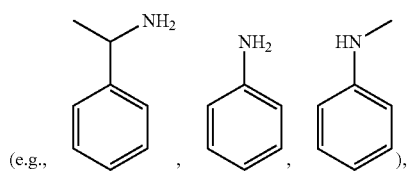 ), The above benzamidine or derivatives thereof may have, for instance, the following structure:

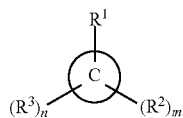

wherein ring C is a 3-to-6-membered saturated or unsaturated carbon ring group or heterocyclic group;

$R^1$ is amidinyl, N-hydroxyamidinyl, guanidyl, amidinyl-substituted guanidyl, ethylamino, methylamino, amino, amidyl, amide, or $NHCH_3$;

$R^2$ and $R^3$ are the same or different and are H, methyl, halogen, hydroxyl, amino, nitro, or $N_3$; and m and n are the same or different and are each an integer of 0 to 11.

The above benzamidine or derivatives thereof may have, for instance, a structure selected from the following groups:

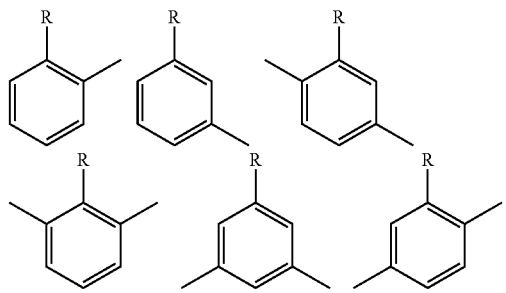

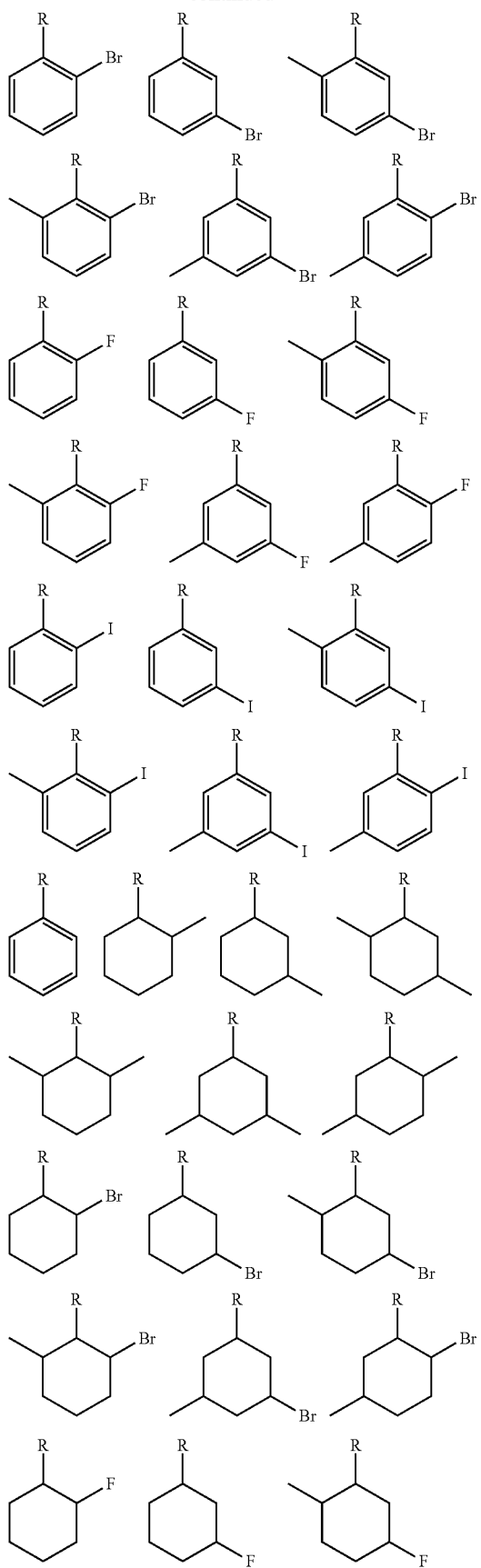

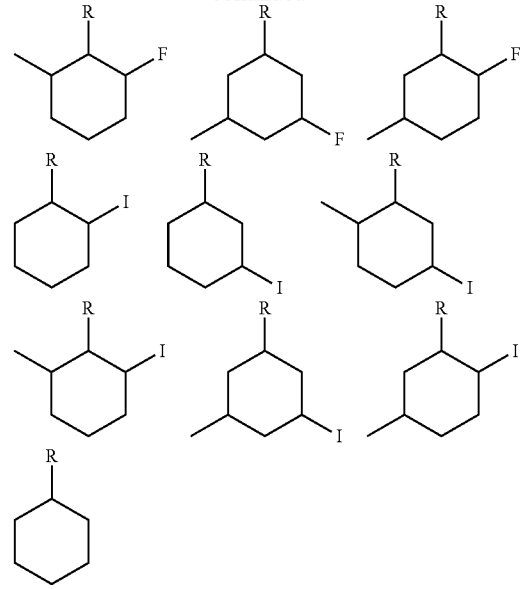

wherein R is selected from the following groups:

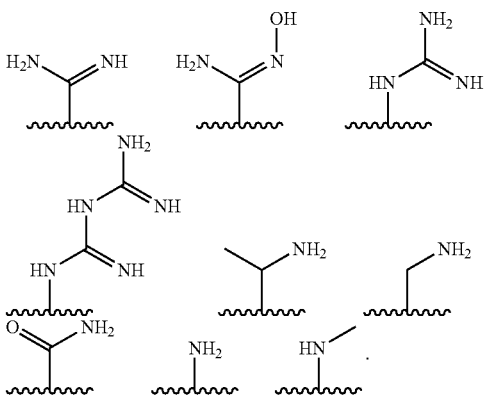

As long as the above functional group can bind to the Na$^+$-water cluster binding site of class-A GPCR, the functional group may have a structure defined by including the following ranges: in the above -A-B structure, the number of heteroatoms may be 1 to 3; when the position of B bonded to A is defined as position 1, the class-A GPCR-binding compound may be bonded at position 2, 3, 4, 5, or 6; the number of N atoms included in B may be 1, 2, 3, 4, 5, 6, 7, 8, 9, 10, or more or may be between two of the numbers; the number of C atoms included in B may be 3, 4, 5, 6, 7, 8, 9, 10, 11, 12, or more or may be between two of the numbers; the number of H atoms included in B may be 4, 5, 6, 7, 8, 9, 10, 11, 12, 14, 16, 18, 20, or more or may be between two of the numbers; the number of atoms (e.g., O), other than N, C, and H, included in B may be 1, 2, 3, 4, 5, or more or may be between two of the numbers; the number of the above substituents may be from 1 to 5; and when the position of B bonded to A is defined as position 1, the substituent may be substituted at position 2, 3, 4, 5, or 6. Here, the number of atoms and the bonding position in the above-described structure -A-B can apply to a formula including the above R$^{1-3}$ and ring C (in this case, A may be read as ring C and R$^{2-3}$, and B as R$^1$). When the position of R$^1$ bonded to ring C is defined as position 1, the class-A GPCR-binding compound may be bonded at position 2, 3, 4, 5, or 6. When the bonding position of $R^1$ is defined as position 1, $R^2$ or $R^3$ may be bonded at position 2, 3, 4, 5, or 6. Example of the above halogen include F, Cl, Br, and I. In an embodiment of the present invention, the "functional group" or "compound" specified using a particular structural formula include those in which part of the structural formula (e.g., an amino group) is protonated.

Examples of the above functional group include compounds with a molecular weight of 80 or higher. This molecular weight may be 80, 90, 150, 100, 200, 250, 300, 400, 500, 600, 700, 800, 900, 1000, or higher or may be between two of the values. From the viewpoint of strong antagonistic activity on a class-A GPCR, the molecular weight is preferably from 80 to 300 and more preferably from 100 to 200. In addition, each class-A GPCR-binding compound may be a compound other than compounds having a functional group that can bind to a $Na^+$-water cluster binding site.

From the viewpoint of strong antagonistic activity on a class-A GPCR, the above functional group is preferably linked to, for instance, a hydroxyl group, an amino group, or a thiol group of the class-A GPCR-binding compound.

From the viewpoint of strong antagonistic activity on a class-A GPCR, the above functional group is most preferably amidinylphenyl.

In an embodiment of the present invention, the modified class-A GPCR-binding compound is an inverse agonist of a class-A GPCR.

An embodiment of the present invention includes a modified class-A GPCR-binding compound wherein a class-A GPCR-binding compound is covalently bonded to a functional group having the following structure:

A-B wherein
A is a 3-to-6-membered saturated or unsaturated carbon ring group or heterocyclic group;
a heteroatom of the heterocyclic group is at least one selected from the group consisting of N, O, and S;
the carbon ring group or heterocyclic group is optionally substituted by at least one group selected from the group consisting of halogen, methyl, hydroxyl, amino, nitro, and $N_3$; and
B is amidinyl, N-hydroxyamidinyl, guanidyl, amidinyl-substituted guanidyl, ethylamino, methylamino, amino, amidyl, amide, or $NHCH_3$.

In an embodiment of the present invention, whether the functional group or compound can bind to the $Na^+$-water cluster binding site may be evaluated by, for instance, crystallography or mutagenesis experiment. For example, if a mutant, in which an amino acid (amino acid$^{2.50}$, $^{3.39}$, $^{6.48}$, or $^{7.45}$ as specified by Ballesteros-Weinstein numbering scheme) of the $Na^+$-water cluster binding site is mutated, has a significantly lower strength of binding to the functional group or compound than the wild-type, it may be determined that the functional group or compound can bind to the $Na^+$-water cluster binding site. The decreased binding strength may be, for instance, 80, 70, 60, 50, 40, 30, 20, 10, or 0% of the original one or may be between two of the values. When the binding strength of each of a plurality of compounds should be evaluated, high-throughput screening may be utilized. $K_d$ between the wild-type and the functional group or compound may include $K_d$ between the class-A GPCR and the above class-A GPCR-binding compound.

An embodiment of the present invention includes a method for preparing a modified class-A GPCR-binding compound, the method comprising the step of covalently linking a class-A GPCR-binding compound with a functional group that can bind to a GPCR pocket including amino acid$^{2.50}$, amino acid$^{3.39}$, amino acid$^{6.48}$, and amino acid$^{7.45}$ as specified by Ballesteros-Weinstein numbering scheme.

In the present specification, amino acids are occasionally abbreviated with 3 letters or 1 letter. Such abbreviations are well-known in the art and have the same meaning as used in the art. For example, aspartic acid can be abbreviated as Asp or D and, Asp$^{2.50}$ and D$^{2.50}$ can have the same meaning.

In an embodiment of the present invention, when a function of a class-A GPCR is inhibited (including the case where basal or constitutive activity is inhibited), the activity may be inhibited by 5, 10, 15, 20, 25, 30, 40, 50, 60, 70, 75, 80, 85, 90, 95%, or 100% than when the activity is not inhibited. This inhibition percentage may be between two of the values. Note that the case where the activity is inhibited includes a case of the presence of a modified class-A GPCR-binding compound or a case of the presence of a compound structured by linking a class-A GPCR-binding compound with a functional group that can bind to a $Na^+$-water cluster binding site of the class-A GPCR. The case where the activity is not inhibited includes a case of the absence of such an inhibitory substance.

In an embodiment of the present invention, the class-A GPCR-binding compound and the functional group that can bind to a $Na^+$-water cluster binding site of the class-A GPCR may be linked directly or via a linker. The class-A GPCR-binding compound, the linker, and the functional group that can bind to a $Na^+$-water cluster binding site of the class-A GPCR may be coupled using click chemistry. For the click chemistry, technologies (e.g., Hou J et al., Expert Opin Drug Discov. 2012 Jun. 7(6): 489-501; Bonnet D et al., Bioconjug Chem. 2006 November-December, 17(6): 1618-23) may be utilized.

As used herein, examples of the "linker" include compounds positioned between two compounds while the two compounds are linked. Examples of the linker include alkyl chain linkers, PEG linkers, and triazole linkers having an alkyl chain. From the viewpoint of production efficiency, the linker is preferably a triazole linker having an alkyl chain(s). The triazole linker having an alkyl chain(s) may be structured such that an alkyl chain is attached to each of N and C or either N or C of the triazole. The above triazole may be 1,2,3-triazole. The triazole linker may be structured such that an alkyl chain is attached to N at position 1 or C at position 4 of 1,2,3-triazole.

Synthesis of various linkers or compounds with a linker or a linker-mediated coupling of compounds may be outsourced to a service company or reagent manufacturer such as Funakoshi Co., Ltd., TOKYO CHEMICAL INDUSTRY CO., LTD., Shinsei Chemical Company Ltd., or WAK-ENYAKU CO., LTD. The linker may be structured such that one end or both ends are bonded to, for instance, —CO—. The linker may be substituted by, for example, halogen, methyl, hydroxyl, amino, nitro, or $N_3$. Examples of the linker include those through which two target compounds are linked and the activities (including binding activity) of two compounds are then not substantially lost. Examples of the linker include those, by themselves, having substantially no activity of binding to a class-A GPCR. As long as the linker does not cause loss of antagonistic activity of a compound structured by linking a class-A GPCR-binding compound with a functional group that can bind to a $Na^+$-water cluster binding site of the class-A GPCR, the linker may have a structure defined by including the following ranges. Examples of the linker include linkers with a molecular weight of 10 or higher. The molecular weight may be 10, 20, 30, 40, 50, 60, 70, 80, 90, 100, 150, 200, 300, 400, 500, 1000, or higher or may be between two of the values. The number of carbon atoms of the above alkyl chain may be, for instance, 1, 2, 3, 4, 5, 6, 7, 8, 9, 10, 11, 12, or more or may be between two of the numbers. The linker may be coupled, for instance, via O, N, or S, to a compound to be linked.

An embodiment of the present invention includes a composition comprising a compound or a salt thereof comprising a structure comprising a class-A GPCR-binding compound linked to the above functional group. This composition may be a composition for an antagonist, a composition for an inverse agonist, a composition for causing equilibrium between an active state and an inactive state of a class-A GPCR to be shifted to the inactive state, or a composition for stabilizing a class-A GPCR in an inactive form. This composition may contain a pharmaceutically acceptable carrier. An embodiment of the present invention includes use of a compound or a salt thereof comprising a structure comprising a class-A GPCR-binding compound linked to the above functional group.

An embodiment of the present invention includes a method for causing an inverse agonistic effect on a class-A GPCR, comprising the step of causing the class-A GPCR to contact a compound or a salt thereof structured by linking a class-A GPCR-binding compound and the above functional group. Another embodiment of the present invention includes a method for causing an antagonistic effect, a method for causing equilibrium between an active state and an inactive state of a class-A GPCR to be shifted to the inactive state, or a method for stabilizing a class-A GPCR in an inactive form, each method comprising the above step.

An embodiment of the present invention includes a composition for an inverse agonist of a class-A GPCR, comprising a compound or a salt thereof having a functional group that can bind to a $Na^+$-water cluster binding site of the class-A GPCR.

An embodiment of the present invention includes a method for producing a class-A GPCR antagonist, comprising the step of linking one compound with another compound that can bind to a $Na^+$-water cluster binding site of the class-A GPCR. From the viewpoint of binding stability or strong antagonistic activity on a class-A GPCR, the one compound is preferably a class-A GPCR-binding compound. The antagonist may be an inverse agonist. The above production method may comprise the step of coupling a linker to the one compound or the other compound that binds to the $Na^+$-water cluster binding site. The above production method may comprise the step of linking, via a linker, the one compound and the other compound that binds to the $Na^+$-water cluster binding site.

An embodiment of the present invention includes a method for designing a class-A GPCR antagonist, comprising the step of linking one compound with another compound that can bind to a $Na^+$-water cluster binding site of the class-A GPCR.

In an embodiment of the present invention, the compound structured by linking a class-A GPCR-binding compound with a functional group that can bind to a $Na^+$-water cluster binding site of the class-A GPCR does not include all the compound comprising a functional group (e.g., a benzamidine moiety) that binds to the $Na^+$-water cluster binding site. It is important that the compound of interest comprises a class-A GPCR-binding compound in addition to the functional group that binds to the $Na^+$-water cluster binding site. For instance, examples of the compound structured by linking a class-A GPCR-binding compound and a functional group that can bind to a $Na^+$-water cluster binding site of the class-A GPCR do not include compounds: BIIL260, BIIL284, DW-1350, and CGS-25019C. In addition, examples of the compound structured by linking a class-A GPCR-binding compound and a functional group that can bind to a $Na^+$-water cluster binding site of the class-A GPCR do not include manufacturable benzamidine moiety-containing compounds among compounds described in the following literatures: JP4334016(B2), JP4288299(B2), JP4288299 (B2), JP4215278(B2), JP4047275(B2), JP3917516(B2), JP2931410(B2), JP2007536299(A), JP2007513068(A), JP2006508992(A), JP2005529085(A), JP2005502630(A), JP2004513100(A), Nakayama et al., Bioorg Med Chem. 1997 May 5(5): 971-85, Marie et al., J Biol Chem. 2001 Nov. 2, 276(44): 41100-11, Anat et al., PLoS One. 2011, 6(11): e27990, and Kruse et al., Mol Pharmacol. 2013 October, 84(4): 528-40.

In an embodiment of the present invention, the "compound" or "modified compound" includes salt forms. In an embodiment of the present invention, the "salt" is not particularly limited and examples include anionic salts having any acidic (e.g., carboxyl) group or cationic salts having any basic (e.g., amino) group. Examples of salts include inorganic salts and organic salts and include salts described in "Berge S M et al., J Pharm Sci. 1977 January, 66(1): 1-19". Examples include metal salts, ammonium salts, organic base salts, inorganic acid salts, organic acid salts, and basic or acidic amino acid salts.

In an embodiment of the present invention, the "compound" or "modified compound" includes solvate forms. For instance, examples of the compound structured by linking a class-A GPCR-binding compound with a functional group that can bind to a Na+-water cluster binding site of the class-A GPCR include solvates of the compound. As used herein, the "solvates" include compounds formed by using a solute and a solvent. Regarding the solvate, one can consult, for instance, "J. Honig et al., The Van Nostrand Chemist's Dictionary P650 (1953)". When the solvent is water, the solvate formed is a hydrate. The solvent is not limited and examples include water and organic solvents (e.g., ethanol, acetic acid, or DMSO). The solvate is hygroscopic when being in contact with the air or recrystallized. In some cases, examples include those having hygroscopic water or those that become hydrates.

An embodiment of the present invention includes a binding molecule that specifically binds to an inactive class-A GPCR. This binding molecule may be, for instance, an antibody or an aptamer. Use of this binding molecule makes it possible to specifically detect, for instance, an inactive class-A GPCR. In addition, an inactive class-A GPCR, for instance, can be detected to diagnose a disease caused by an inactivated class-A GPCR.

An embodiment of the present invention includes a binding molecule that specifically binds to a complex comprising: a class-A GPCR; and a compound or a salt thereof having a functional group that can bind to a $Na^+$-water cluster binding site of the class-A GPCR. This binding molecule may be an antibody or an aptamer. Use of this binding molecule makes it possible to specifically detect, for instance, an inactive class-A GPCR. In addition, an inactive class-A GPCR, for instance, can be detected to diagnose a disease caused by an inactivated class-A GPCR.

An embodiment of the present invention includes an antigen comprising a complex comprising: a class-A GPCR; and a compound or a salt thereof having a functional group that can bind to a Na$^+$-water cluster binding site of the class-A GPCR. An embodiment of the present invention is an antigen comprising: a class-A GPCR; and a compound or a salt thereof having a functional group that can bind to a Na$^+$-water cluster binding site of the class-A GPCR. An embodiment of the present invention is a method for producing an antibody, comprising the step of immunizing an organism with the above antigen.

As used herein, the "antibody" includes molecules that can specifically bind to a specific epitope(s) on an antigen or a population thereof. In addition, the antibody may be a polyclonal or monoclonal antibody. The form of the antibody is not particularly limited and examples include at least one form selected from the group consisting of full-length antibodies (antibodies having a Fab region and a Fc region), Fv antibodies, Fab antibodies, F(ab')$_2$ antibodies, Fab' antibodies, single-chain antibodies (e.g. scFv), antigen-binding peptides, antibody-like molecules, chimeric antibodies, mouse antibodies, chicken antibodies, humanized antibodies, human antibodies, and equivalents thereof. In addition, examples of the antibody include modified antibodies and unmodified antibodies. In each modified antibody, an antibody and, for example, each molecule such as polyethylene glycol may be conjugated. The modified antibody may be produced by chemically modifying the antibody by using a known technique. The amino acid sequence, class or subclass of the antibody may be those derived from a human or a non-human mammal (e.g., a rat, a mouse, a rabbit, a cow, a monkey). The antibody class is not particularly limited and examples may include IgM, IgD, IgG, IgA, IgE, and IgY. The antibody sub-class is not particularly limited and examples may include IgG1, IgG2, IgG3, IgG4, IgA1, and IgA2. In addition, examples of the antibody include isolated antibodies, purified antibodies, and recombinant antibodies. Also, the antibody may be used, for instance, in vitro or in vivo.

As used herein, the "polyclonal antibody" may be generated by immunizing, for instance, a mammal (e.g., a rat, a mouse, a rabbit, a cow, a monkey) with an immunogen containing an antigen of interest. The immunogen may be injected with one or more immunizing agents or adjuvant. The adjuvant may be used for enhancing immune response and may contain, for instance, Freund's adjuvant (complete or incomplete), mineral gel (e.g., aluminum hydroxide), or a surfactant (e.g., lysolecithin). The immunization protocol is known in the art and may be implemented by any method in which an immune response is induced depending on a selected host organism (Protein Experiment Handbook, YODOSHA CO., LTD., (2003): 86-91).

As used herein, the "monoclonal antibody" includes antibodies where individual antibodies constituting a population react with substantially the same epitope. Alternatively, the "monoclonal antibody" may be antibodies where individual antibodies constituting a population are substantially the same (provided that a naturally occurring mutation(s) is permitted). The monoclonal antibody is highly specific and differs from a regular polyclonal antibody, which typically contains different antibodies with different epitopes. How to create a monoclonal antibody is not particularly limited and the monoclonal antibody may be generated by the same method as the hybridoma protocol described in, for instance, "Kohler G, Milstein C., Nature. 1975 Aug. 7, 256(5517): 495-497". Alternatively, the monoclonal antibody may be generated by the same method as the recombinant method described in U.S. Pat. No. 4,816,567. In addition, the monoclonal antibody may be isolated from a phage antibody library by using the same method as the technique described in "Clackson et al., Nature. 1991 Aug. 15, 352(6336): 624-628" or "Marks et al., J Mol Biol. 1991 Dec. 5, 222(3): 581-597". Further, the monoclonal antibody may be prepared by the method described in "Protein Experiment Handbook, YODOSHA CO., LTD., (2003): 92-96".

In an embodiment of the present invention, the "aptamer" includes nucleic acid (DNA or RNA) aptamers or peptide aptamers that can specifically bind to a specific molecule. The nucleic acid aptamers may be created by, for instance, an in vitro selection method or SELEX protocol (Darmostuk M et al., Biotechnol Adv. 2015 Nov. 1, 33 (6 Pt 2): 1141-61). The peptide aptamers may be generated by, for instance, techniques such as yeast two-hybrid method or phage display (Reverdatto S et al., Curr Top Med Chem. 2015, 15(12): 1082-101).

As used herein, the "significant" may mean a state of $p<0.05$ or $p<0.01$ after the statistically significant difference is evaluated by using the Student's t-test (one-tailed or two-tailed).

The "or" is herein used when "at least one" is applicable to the matters listed in the text. The same applies to the "or".

Hereinabove, the embodiments of the present invention have been mentioned, but the embodiments are just examples of the present invention. Accordingly, various other configurations may be employed. In addition, the configurations described in the above embodiments may be combined and adopted.

EXAMPLES

Hereinafter, the present invention is further described by using Examples, but is not limited to them.

Example 1

1.1 Expression of BLT1 Mutants for Characterization of BLT1

For the evaluation of the thermostabilities of guinea pig BLT1 mutants designed by the consensus method (FIG. 8A), point mutations were introduced using a QuikChange kit (Agilent) to the previously constructed thermostabilized BLT1 mutant cDNA (residues 1-14 deleted, H83G/K88G/S309A mutations, and an N-terminal FLAG-tag) in the pcDNA3 vector (Hori, T. et al., Protein Expr. Purif. 72 (2010) 66-74; Hori, T. et al., Biochem. Biophys. Rep. 4 (2015) 243-249). The expression vectors encoding the BLT1 mutants were transfected into COS-7 cells with Lipofectamine 2000. For the analysis of the BIIL260 binding residues of BLT1, point mutations were introduced, using the In-Fusion enzyme (Clontech), into the wild-type BLT1 cDNA with the N-terminal FLAG-tag in the pcDNA3 vector. The expression vectors were transfected into HEK293 cells, using polyethyleneimine. For the benzamidine competition assay, the pcDNA3 vector encoding the wild-type BLT1 with the N-terminal FLAG-tag was transfected into HEK293 cells, using polyethyleneimine. The BLT1 mutants were transiently expressed for three days at 37° C. The cells were washed with PBS, harvested with PBS-EDTA, disrupted with a sonicator, and centrifuged at 800×g for 5 min. The supernatant was further ultra-centrifuged at 100,000×g for 60 min, and the precipitate was collected.

For the ligand binding assay of BLT1-T4Ls, the T4L cDNA was integrated into the cDNA, encoding the newly generated thermostable BLT1 mutant with the additional mutation V212A, by the consensus method (residues 1-14 deleted and H83G/K88G/V212A/S309A mutations), with the α-factor PrePro signal sequence and the FLAG tag at the N-terminal, and the PreScission site and the His$_6$ tag at the C-terminal of BLT1 (Hori T. et al., 2010, supra) in the pPIC3.5K vector, using the In-Fusion enzyme (FIG. 7A). The expression vectors were introduced into the yeast *Pichia pastoris* using an EasyComp kit (Thermo Fisher Scientific). BLT1-T4Ls were expressed in 10 ml cultures, and the membrane fraction was prepared as described previously (Hori T. et al., 2010, supra; Hon T. et al., 2015, supra).

1.2 LTB$_4$ Binding Assay and Thermostability Evaluation of BLT1 Mutants

For the evaluation of the ligand-binding activity of the BLT1 mutants and BLT1-T4Ls, a $^3$H-LTB$_4$ binding assay was performed using the BLT1-expressing membrane fractions of COS-7, HEK293, or *P. pastoris* cells, as described previously (Hori T. et al., 2010, supra; Hori T. et al., 2015, supra). For the evaluation of the thermostability, the membrane fraction was heat-treated before the $^3$H-LTB$_4$ binding assay. For the benzamidine or NaCl binding assay, various concentrations of benzamidine or NaCl were incubated with the membrane fraction of HEK293 cells expressing the wild type BLT1 for 60 min at 20° C., before the reaction with $^3$H-LTB$_4$.

1.3 TGFα Shedding Assay for Evaluation of Benzamidine Allosterism

For the evaluation of the effect of benzamidine on BLT1-dependent intracellular signals, a TGFα shedding assay (Inoue, A. et al., Nat. Methods 9 (2012) 1021-1029) was performed.

1.4 Data Analysis of Allosteric Modulation

For all of the pharmacological analyses, nonlinear regression curve fitting was performed using Prism 5 (Graph Pad Software). For the competitive binding assay with benzamidine and NaCl, the curve fitting was performed using "the allosteric modulation titration analysis" with the following equation (Christopoulos, A. et al., Pharmacol. Rev. 54 (2002) 323-374):

$$Y=Y_{max}([A]+K_d)/\{[A]+K_d(1+[B]/K_B)/(1+\alpha[B]/K_B)\}$$

where $Y_{max}$ is the radioligand ($^3$H-LTB$_4$)-specific binding without the allosteric modulator, [A] is the $^3$H-LTB$_4$ concentration, [B] is the concentration of the allosteric modulator (benzamidine or NaCl), $K_d$ is the equilibrium dissociation constant of $^3$H-LTB$_4$, $K_B$ is the equilibrium dissociation constant of the allosteric modulator, and a is a cooperative factor between $^3$H-LTB$_4$ and the modulator.

In the saturation binding assay with various concentrations of benzamidine, the global fitting was performed using "the saturation binding assay analysis with allosteric modulation shift" with the following equation (Christopoulos, A. et al., 2002, supra):

$$Y=B_{max}[A]/\{[A]+K_d(1+[B]/K_B)/(1+\alpha[B]/K_B)\}$$

where $B_{max}$ is the receptor density, and all of the other parameters are as described above.

In the shedding assay with various concentrations of benzamidine, the global fitting was performed using the following equation (Leach, K. et al., Trends Pharmacol. Sci. 28 (2007) 382-389):

$$E=E_m\{\tau_A[A](K_B+\alpha\beta[B])\}^n/\{([A]K_B+K_AK_B+K_A[B]+\alpha[A][B])^n+(\tau_A[A]K_B+\alpha\beta[B]))^n\}$$

where $E_m$ is the maximum possible signal response, $K_A$ is the equilibrium dissociation constant of LTB$_4$, β is a cooperative factor that describes the LTB$_4$-induced efficacy modulation by benzamidine, n is the logistic slope factor, $\tau_A$ is the operational measure of agonist signaling efficacy, and all of the other parameters are as described above. Since the benzamidine did not act as an agonist of BLT1, the parameter TB existing in the original equation was equal to zero ($\tau_B$=0) (Leach, K. et al., 2007, supra). To determine the parameters, three steps of fitting procedures were performed. In the first fitting, the parameters $E_m$ and n were fixed as constant [$E_m$=25 (Gq/il) and 20 (G16), and n=1] and the parameter log $\tau_A$ was determined by the fitting. In the second fitting, the parameters log $\tau_A$ and $E_m$ were fixed [$E_m$=25 (Gq/il) and 20 (G16), and log $\tau_A$=0.8195 (Gq/il) and 0.07596 (G16)] and the parameter n was determined. In the final fitting, the parameters log $\tau_A$ and n were fixed [log $\tau_A$=0.8195 (Gq/il) and 0.07596 (G16), and n=0.8664 (Gq/il) and 0.5451 (G16)] and all of the other parameters were determined.

1.5 Large-Scale Expression, Purification, and Crystallization of BLT1-T4Ls

All BLT1-T4Ls were expressed, purified, and crystallized by the same method (FIG. 7). *P. pastoris* cells stably expressing the BLT1-T4Ls were cultured in 1 L of BMGY medium [1% (w/v) yeast extract, 2% (w/v) peptone, 100 mM potassium phosphate buffer (pH 6.0), 1.34% (w/v) yeast nitrogen base, and 1% (v/v) glycerol] at 30° C. for 20-24 h. The yeast cells were harvested by centrifugation (3,500×g, 20° C., 20 min). The yeast pellet was suspended in 1 liter of BMMY medium [1% (w/v) yeast extract, 2% (w/v) peptone, 100 mM potassium phosphate buffer (pH 6.0), 1.34% (w/v) yeast nitrogen base, and 0.5% (v/v) methanol] and cultured to express BLT1-T4Ls at 30° C. for 18-20 h. The yeast cells were harvested by centrifugation (3,500×g, 4° C., 20 min), washed with water, and stored at −30° C. until use.

The yeast cells were suspended in buffer A [50 mM Tris (pH 8.0), 1 M NaCl, 5% (v/v) glycerol] with a protease inhibitor cocktail (Roche). The yeast cell suspension and glass beads were placed in a bead beater vessel, which was previously chilled in an ice-water bath for at least 2 h before cell disruption. The yeast cells were disrupted for 1 min using a bead beater (Hamilton Beach Brands), and then chilled for 2 min in ice-water. These breaking and chilling procedures were repeated 20 times. The disrupted cell solution was centrifuged (3,500×g, 4° C., 5 min) to remove the cell debris, and the supernatant was ultracentrifuged (100,000×g, 4° C., 1 h). The pellet was suspended in buffer A using a Potter homogenizer, and the suspension was ultracentrifuged again. The pellet was suspended in 5 ml buffer B [50 mM Tris-Cl buffer (pH 8.0), 150 mM NaCl, 5% (v/v) glycerol] and stored at −80° C. until use. The typical suspended pellet volume was 25 ml.

For the purification of BLT1-T4L, the suspended membrane pellet was homogenized with a Potter homogenizer, diluted in 25 ml of buffer B containing 4 mg/ml iodoacetamide, protease inhibitor cocktail, and 80 BIIL260, and incubated for at least 4 h at 4° C. to react BLT1 with BIIL260 For solubilization, 160 ml of buffer C [buffer B containing 1.3% (w/v) lauryl maltose neopentyl glycol (LMNG), 0.013% (w/v) cholesteryl hemi-succinate (CHS)] was added to the BLT1-BIIL260 membrane fraction solution. The final concentrations of BIIL260, LMNG, and CHS were 9.5 μM, 1% (w/v), and 0.001% (w/v), respectively. After a 1-2 h incubation at 4° C., the solution was ultracentrifuged (100, 000×g, 4° C., 1 h), and the supernatant was incubated with 10 ml of TALON resin (Clontech) overnight at 4° C. The resin was packed in a gravity flow column and washed with 20 CV of buffer D [buffer B containing 0.02% (w/v) LMNG, 0.01% (w/v) CHS, and 10 μM BIIL260]. BLT1-T4L was eluted with 3.5 CV of buffer E [buffer D containing 500 mM imidazole (pH 8.0)]. The elution fraction was concentrated using an Amicon Ultra filter (Millipore, 10 kD MWCO), and desalted with a PD10 column (GE Healthcare) equilibrated with buffer D. BLT1-T4L was bound to Ni-Sepharose resin (GE Healthcare, 1 ml), which was washed with 2 CV of buffer D to remove the excess detergent. BLT1-T4L was eluted with 2.5 CV of buffer E. The elution fraction was desalted using a PD10 column equilibrated with buffer D and treated with 25 μl of His-tagged HRV 3C protease (Takara) overnight at 4° C. The reaction solution was applied to Ni-Sepharose resin (1 ml), and the unbound fraction was collected to remove the HRV 3C protease, the $His_6$ tag, and the contaminant proteins. The unbound fraction was concentrated and purified by gel-filtration on a Superose-6 column (once or twice). Typical final gel-filtration results are shown in FIG. 9A. The purified BLT1-T4L was concentrated to 10-50 mg/ml, and 100 μM BIIL260 was added. The sample was frozen in liquid nitrogen and stored at −80° C. until use.

Crystallization was performed by the lipidic cubic phase method. The concentrated BLT1-T4L sample was mixed with monoolein lipid doped with 10% (w/w) cholesterol at the ratio of two to three (w/w), using a syringe mixture device, at 20° C. to form the BLT1-T4L reconstituted cubic phase membrane (Hato, M. et al., J. Phys. Chem. B 113 (2009) 10196-10209; Hato, M. et al., J. Struct. Funct. Genomics 15 (2014) 165-171). For the crystallization setup, a 20-40 nl cubic phase bolus was overlaid with 0.8 μl of precipitation solution on a glass plate and sealed with a thin glass plate using an in-house crystallization machine at 20° C. The initial screening experiment was performed with 576 conditions of a home-made screen, composed of 30% (v/v) PEG400, 96 species of ions (48 ions and 2 concentrations of each ion) and pH 4.0-9.0 (every 1.0 pH unit). The first crystal was observed for the construct ICL3-10 (FIG. 9B) in 100 mM Bicine (pH 9.0), 30% (v/v) PEG400, and 150 mM ammonium phosphate, grown at 20° C. After iterative optimizations of the crystallization conditions, including the crystal growth temperature (20° C. or 4° C.), and evaluation by the X-ray diffraction experiments described below, the final crystallization conditions were 100 mM Bicine buffer (pH 8.5-9.0), 22.5-30% (v/v) PEG300, 50-75 mM ammonium phosphate, 75-100 mM ammonium formate, and 2-4% (v/v) 3-methyl-1,5-heptanediol. The crystals used for structure determination were grown at 4° C. and harvested after 34 days from the crystallization setup. The present inventors attempted the crystallization of all BLT1-T4L chimeric proteins (FIG. 7). Crystals of another construct (ICL3-1) appeared, but a diffraction spot has not been observed in spite of iterative optimizations of the crystallization conditions. The present inventors also performed the expression and attempted the crystallization of BLT1 proteins with a Bril fusion within ICL3 (Bril: thermostabilized apocytochrome, b562 RIL). Among seven BLT1-Bril constructs with different insertion positions of Bril within ICL3 of BLT1, as with the BLT1-T4Ls, crystals appeared for just one BLT1-Bril construct, but only low resolution diffraction has been observed (worse than 10 Å) after iterative optimizations of the crystallization conditions.

1.6 Data Collection and Structural Determination

Crystals were harvested with a MiTeGen cryoloop, and frozen in liquid nitrogen. Since many tiny crystals appeared in the cubic phase bolus (FIG. 9B), the entire 20-40 nl bolus including the crystals and the cubic phase lipid was harvested with one cryoloop, and frozen in liquid nitrogen. The X-ray diffraction experiment was performed with an EIGER X 9M detector at BL32XU of SPring-8, Japan. First, the crystal diffraction was scanned over the whole cubic phase bolus as a still image to determine the crystal position in the cubic phase bolus, using a 5×5 $\mu m^2$ X-ray beam with 0.8 MGy per frame. For crystals in which more than 5 diffraction spots were observed in a low resolution (up to 5 Å) area, five 0.5°-oscillation images were collected from each crystal. The absorbed dose for each wedge was set to ~11 MGy. Data were processed, integrated, scaled, and merged using the KAMO system (https://github.com/keitaroyam/yamtbx), the automated data processing system that utilizes XDS (Kabsch, W. Acta Crystallogr. D Biol. Crystallogr. 66 (2010) 125-132), Pointless (Evans, P. R. Acta Crystallogr. D Biol. Crystallogr. 67 (2011) 282-292), XSCALE (Kabsch, W., 2010, supra), and BLEND (Foadi, J. et al., Acta Crystallogr. D Biol. Crystallogr. 69 (2013) 1617-1632). Finally, 494 wedges (from 494 crystals) were merged. The high resolution limit was determined to be a $CC_{1/2}$ value greater than 50% (Evans, P. R. et al., Acta Crystallogr. D Biol. Crystallogr. 69 (2013) 1204-1214; Karplus, P. A. et al., Science 336 (2012) 1030-1033). Data collection statistics and molecular parameters are summarized in Table 2. The A, C, D, and others in the left column in Table 2 are amino acid one letter codes and the numbers shown on the right side mean how many class-A GPCRs are there. The structure was solved by the molecular replacement method, using Phenix (Adams, P. D. et al., Acta Crystallogr. D Biol. Crystallogr. 66 (2010) 213-221). The starting models for the molecular replacement were the seven transmembrane helix region of the CCR5 structure (PDB code: 4MBS) with the deletion of the loop regions and the T4 lysozyme of the CRFR1-T4L chimera structure (PDB code: 4K5Y), as two independent search models, in which all side chains other than glycine were replaced with alanine. The structure was rebuilt using Coot (Emsley, P. et al., Acta Crystallogr. D Biol. Crystallogr. 66 (2010) 486-501) and refined using Phenix. The BIIL260 coordinates were obtained from the PubChem web site (https://www.ncbi.nlm.nih.gov/pccompound/). Structure validation was performed using MolProbity (Chen, V. B. et al., Acta Crystallogr. D Biol. Crystallogr. 66 (2010) 12-21) in Phaser. In the final BLT1-T4L model, the N-terminal FLAG tag, the C-terminal residues 288-348, including part of the PreScission recognition site, and residues T254 and L255 are not included, and 12 and 8 non-alanine resides of BLT1 and T4L, respectively, are assigned as alanine (FIG. 7A), due to unclear electron density. The dihedral angles of all residues are in either the favored (96.8%) or allowed (3.2%) region.

1.7 Method for the Construction of a Modified Class-A GPCR-Binding Compound

A variety of modified class-A GPCRs-binding compounds can be constructed as shown in the following illustrative methods well-known to those skilled in the art.

In this example, a benzamidine moiety is used as a functional group for the construction of a modified class-A GPCR binding compound ("BENZ-ligand" hereinafter) by covalently linking it with a class-A GPCR binding compound for the following target GPCRs: $H_1$ histamine receptor, $A_{2A}$ adenosine receptor, $\beta_1$ adrenergic receptor, and δ-opioid receptor respectfully.

(1) The crystal structures of BLT1 and the target GPCRs were superimposed by pair fitting of the Ca atoms of residues 2.49-2,51, 3.38-3.40 and 7.45-7.47.

(2) The following four class-A GPCR binding compounds were selected among known class-A GPCR binding compounds for each target GPCRs. Class-A GPCR binding compounds can be easily found in Drug Bank (https://www.drugbank.ca/), IUPHAR/BPS (http://www.guidetopharmacology.org/GRAC/GPCRListForward?class=A) or in related journals. Those of ordinary skill in the art will understand the techniques appropriate for selecting compounds given the information of (1). We selected the following Class A binding compounds:

Histamine for $H_1$ histamine receptor ($H_1$HR).
Adenosine for $A_{2A}$ adenosine receptor ($A_{2A}$AR).
Carazolol for β1 adrenergic receptor ($β_1$AR).
TIPP for δ-opioid receptor (δ-OR).

(3) Virtually, the several BENZ-ligand with the different linker can be constructed by those of ordinary skill in the art, including for example, the alkyl chain linkers with different carbon number, PEG linkers and the triazole linkers with the alkyl chain. In this example, for $A_{2A}$AR, $β_1$AR and δ-OR, BENZ-ligands were designed that have at least three kinds of alkyl chain linkers and the nine triazole linkers with the different length of alkyl chains (FIG. 12). For $H_1$HR, the three triazole linkers with the different length of alkyl chains were designed (FIG. 12). The parameter and topology files for the energy minimization process were constructed by the HIC-UP site (http://xray.bmc.uu.se/hicup/) or The Glyco-BioChem PRODRG2 Server (http://davapc1.bioch.dundee.ac.uk/cgi-bin/prodrg). The force field of the dihedral angle and improper torsion were modified, if necessary.

(4) The each BENZ-ligand designed in (3) was superimposed to the target GPCR in the following way. The position of the benzamidine moiety of BENZ-ligand is that of the bound benzamidine moiety of BLT1, after BLT1 structure is superimposed on the target GPCR structures as mentioned in (1). The position of the ligand moiety of BENZ-ligand is that of the bound ligand of the target GPCR. The linker moiety is linked to the ligand of the target GPCR but the position is arbitrary. Each GPCR with the BENZ-ligands were refined by the program CNS (energy minimization). As for the program CNS (Crystallography and NMR System), see Brunger, A. T. et al., Acta Cryst. D54 (1998) 905-921; Brunger, A. T., Nature Protocols 2 (2007) 2728-2733. As shown in this example, those of ordinary skill in the art can easily determine and select the appropriate length of covalent linkage (linker).

(5) In the structures after the energy minimization, the linkers were selected by which the amidine group can interact with $D^{2.50}$, $S^{3.39}$ and $N^{745}$, and the position of the benzamidine is similar to that of BLT1.

The Modeling Studies of GPCRs and a Modified Class-A GPCR-Binding Compound

Model studies of the constructed BENZ-ligands in above examples with target GPCRs were conducted into demonstrating the effectiveness of selecting appropriate modified class-A GPCR binding compounds by using the process of (1) to (5).

FIG. 13A shows $A_{2A}$ adenosine receptor ($A_{2A}$AR) and adenosine-linker-benzamidine, FIG. 13B shows $β_1$ adrenergic receptor ($β_1$AR) and carazolol-linker-benzamidine, FIG. 13C shows δ-opioid receptor (δ-OR) and TIPP-linker-benzamidine, and FIG. 13D shows $H_1$ histamine receptor ($H_1$HR) and histamine-linker benzamidine.

Panel (a) in FIG. 13 shows the structure of GPCR with the benzamidine-ligand was refined by the program CNS. There is no conflict between the ligand and GPCRs. In each GPCR, the two modeling results with the different linker length were depicted.

Panel (b) in FIG. 13 shows the schematic drawing of the ligand-linker-benzamidine. The ligand and benzamidine molecule are linked with the click chemistry.

Panel (c) in FIG. 13 shows the structure before the energy minimization procedure by CNS. The benzamidine moiety of BLT1-BIIL260 was docked to the target GPCRs, after the BLT1-BIIL260 structure and the corresponding GPCR were overlaid each other. The initial position of the linker moiety linked to each ligand was arbitrary as indicated with dashed line ellipse.

TABLE 1

Summary of assay results, related to FIGS. 2, 3 and 8.

(A) Ligand binding affinity of BLT1-T4L expressed in
*P. pastoris* (ILC3-10 construct, see also FIG. 8B)
Saturation binding of $^3$H-LTB$_4$

| | |
|---|---|
| $K_d$ | 1.2 ± 0.1 nM |
| $B_{max}$ | 106 ± 2 pmol/mg |

Competition assay of ligands

| Ligands | logIC$_{50}$ (K$_i$) |
|---|---|
| BIIL260 | −8.5 ± 0.0 |
| | (K$_i$ = 2.3 nM) |
| BIIL284 | −6.7 ± 0.1 |
| | (K$_i$ = 148 nM) |
| LTB$_4$ | −9.0 ± 0.1 |
| | (K$_i$ = 0.67 nM) |

(B) Competition binding of BIIL260 to BLT1 mutants
involved in BIIL260-specific binding expressed in
HEK293 cells (see also FIG. 2C)

| Mutants | logIC$_{50}$ (IC$_{50}$) |
|---|---|
| D66$^{2.50}$A | No binding |
| V69$^{2.53}$A | −7.5 ± 0.1 |
| | (33 nM) |
| F76$^{2.60}$A | N.D. |
| L80$^{2.64}$A | −7.9 ± 0.2 |
| | (12 nM) |
| S106$^{3.39}$A | −7.9 ± 0.2 |
| | (12 nM) |
| W236$^{6.48}$A | −7.2 ± 0.4 |
| | (62 nM) |
| F274$^{7.43}$A | N.D. |
| S276$^{7.45}$A | −6.9 ± 0.2 |
| | (124 nM) |
| WT | −7.5 ± 0.2 |
| | (30 nM) |

(C) Allosteric modulation of NaCl and Benzamidine
(see also FIG. 3)
Competition binding assay

| | NaCl | Benzamidine |
|---|---|---|
| logα | −1.5 ± 0.7 | −0.82 ± 0.34 |
| | (α = 0.035) | (α = 0.15) |
| logK$_B$ | −0.86 ± 0.11 | −1.6 ± 0.2 |
| | (K$_B$ = 140 mM) | (K$_B$ = 26 mM) |

Saturation binding assay with benzamidine

| | | |
|---|---|---|
| logα | −0.93 ± 0.41 | |
| | (α = 0.12) | |
| logK$_B$ | −1.4 ± 0.2 | |
| | (K$_B$ = 40 mM) | |
| $K_d$ | 0.6 ± 0.0 nM | |

TGF-α shedding assay with benzamidine

| | Gq/i1 | G16 |
|---|---|---|
| logα | 0.00 ± 0.11 | −0.45 ± 0.17 |
| | (α = 1.00) | (α = 0.36) |

TABLE 1-continued

Summary of assay results, related to FIGS. 2, 3 and 8.

| | | |
|---|---|---|
| $\log\beta$ | $-1.9 \pm 0.2$ ($\beta = 0.01$) | $-1.6 \pm 0.2$ ($\beta = 0.03$) |
| $\log K_A$ | $-7.6 \pm 0.0$ ($K_A = 24$ nM) | $-8.0 \pm 0.1$ ($K_A = 9.2$ nM) |
| $\log K_B$ | $-3.4 \pm 0.0$ | $-3.4 \pm 0.1$ |
| $\log\tau_A$ | ($K_B = 0.49$ mM) $0.82 \pm 0.06$ (in $n = 1$, $E_m = 25$) | ($K_B = 0.42$ mM) $0.076 \pm 0.028$ (in $1$, $E_m = 20$) |
| $E_m$ | $26.7 \pm 0.5$ | $27.6 \pm 0.6$ |

TABLE 2

Amino acid conservation of 273 class-A GPCRs.

(A) The number of appearances of residues involved in the benzamidine or sodium ion-centered water cluster

| B. W.[a] | 2.50 | 2.53 | 3.32 | 3.35 | 3.36 | 3.39 | 6.48 | 7.45 | 7.46 | 7.49 |
|---|---|---|---|---|---|---|---|---|---|---|
| gpBLT1 | D66 | V69 | C99 | S102 | M103 | S106 | W236 | S276 | S277 | N280 |
| A | 0 | 18 | 7 | 24 | 4 | 8 | 3 | 7 | 21 | 0 |
| C | 0 | 4 | 2 | 23 | 31 | 4 | 1 | 3 | 34 | 0 |
| D | 258 | 0 | 55 | 0 | 0 | 0 | 0 | 1 | 0 | 57 |
| E | 2 | 3 | 4 | 0 | 0 | 4 | 2 | 0 | 1 | 0 |
| F | 0 | 54 | 40 | 31 | 24 | 0 | 47 | 1 | 2 | 1 |
| G | 4 | 10 | 8 | 18 | 16 | 31 | 6 | 1 | 4 | 3 |
| H | 0 | 3 | 4 | 2 | 0 | 0 | 0 | 23 | 0 | 2 |
| I | 0 | 19 | 16 | 0 | 12 | 0 | 1 | 2 | 1 | 0 |
| K | 0 | 0 | 5 | 0 | 2 | 0 | 0 | 6 | 0 | 3 |
| L | 0 | 47 | 26 | 15 | 39 | 2 | 0 | 6 | 4 | 0 |
| M | 0 | 19 | 21 | 3 | 51 | 0 | 3 | 1 | 1 | 1 |
| N | 8 | 0 | 1 | 75 | 2 | 0 | 1 | 181 | 2 | 194 |
| P | 0 | 0 | 4 | 3 | 2 | 4 | 3 | 3 | 4 | 0 |
| Q | 0 | 2 | 24 | 0 | 5 | 1 | 7 | 0 | 4 | 1 |
| R | 0 | 3 | 4 | 0 | 9 | 0 | 1 | 4 | 1 | 0 |
| S | 0 | 3 | 7 | 61 | 22 | 200 | 7 | 32 | 171 | 6 |
| T | 0 | 6 | 9 | 13 | 13 | 19 | 1 | 1 | 19 | 4 |
| V | 0 | 66 | 15 | 4 | 30 | 0 | 3 | 1 | 4 | 1 |
| W | 0 | 0 | 1 | 0 | 0 | 0 | 181 | 0 | 0 | 0 |
| Y | 1 | 16 | 20 | 1 | 11 | 0 | 6 | 0 | 0 | 0 |
| Negative-charged[b] | 260 | 3 | 59 | 0 | 0 | 4 | 2 | 1 | 1 | 57 |
| Positive-charged[c] | 0 | 3 | 9 | 0 | 11 | 0 | 1 | 10 | 1 | 3 |
| Polar[d] | 9 | 34 | 67 | 175 | 84 | 224 | 23 | 240 | 230 | 207 |
| Hydrophobic[e] | 4 | 233 | 138 | 98 | 178 | 45 | 247 | 22 | 41 | 6 |

(B) Interaction of the benzamidine of BLT1 and the sodium ion-centered water cluster in four GPCRs[f,g]

| B. W. | 2.50 | 2.53 | 3.32 | 3.35 | 3.36 | 3.39 | 6.48 | 7.45 | 7.46 | 7.49 |
|---|---|---|---|---|---|---|---|---|---|---|
| BLT1 | Amidine (D) | Phenyl (V) | | | | Amidine (S) | Phenyl (W) | Amidine (S) | | |
| $A_{2A}AR$ | Na$^+$ (D) | | | | Wat (T) | Na$^+$ (S) | Wat (W) | Wat (N) | | Wat (N) |
| $\beta1AR$ | Na$^+$ (D) | | | | | Na$^+$ (S) | Wat (W) | Wat (N) | Wat (S) | Wat (N) |
| δ-OR | Na$^+$ (D) | | Wat (D) | Na$^+$ (N) | | Na$^+$ (S) | Wat (W) | Wat (N) | Wat (S) | Wat (N) |
| PAR1 | Na$^+$ (D) | | | Wat (N) | | Na$^+$ (S) | | Wat (S) | | Na$^+$ (D) |

(C) The number of appearances of residues involved in binding regions of BIIL260 other than the benzamidine moiety

| B. W. | 1.39 | 2.60 | 2.64 | 3.29 | 6.44 | 7.36 | 7.39 | 7.40 | 7.42 | 7.43 |
|---|---|---|---|---|---|---|---|---|---|---|
| gpBLT1 | L27 | F76 | L80 | H96 | F232 | K267 | I270 | A271 | A273 | F274 |
| A | 8 | 9 | 16 | 26 | 2 | 13 | 9 | 23 | 104 | 12 |
| C | 6 | 1 | 0 | 0 | 2 | 0 | 2 | 30 | 9 | 5 |
| D | 0 | 2 | 16 | 6 | 5 | 21 | 3 | 1 | 1 | 1 |
| E | 4 | 5 | 14 | 8 | 0 | 14 | 17 | 0 | 1 | 4 |
| F | 20 | 93 | 14 | 7 | 221 | 8 | 17 | 20 | 9 | 34 |
| G | 7 | 1 | 2 | 38 | 0 | 1 | 5 | 4 | 51 | 1 |
| H | 4 | 2 | 5 | 11 | 0 | 19 | 14 | 0 | 1 | 6 |
| I | 15 | 18 | 11 | 14 | 1 | 20 | 25 | 15 | 8 | 5 |
| K | 0 | 0 | 2 | 7 | 2 | 12 | 5 | 1 | 0 | 10 |
| L | 61 | 58 | 16 | 29 | 8 | 33 | 56 | 46 | 11 | 12 |
| M | 14 | 7 | 2 | 5 | 1 | 9 | 6 | 6 | 2 | 19 |
| N | 1 | 7 | 13 | 12 | 2 | 15 | 10 | 4 | o | 4 |
| P | 2 | 29 | 3 | 14 | 0 | 15 | 1 | 6 | 4 | 7 |
| Q | 1 | 1 | 10 | 7 | 1 | 18 | 7 | 1 | 1 | 1 |
| R | 0 | 2 | 11 | 13 | 2 | 8 | 13 | 8 | 1 | 0 |
| S | 10 | 6 | 38 | 28 | 3 | 16 | 15 | 19 | 41 | 33 |
| T | 11 | 6 | 16 | 30 | 0 | 16 | 27 | 8 | 20 | 18 |
| V | 7 | 18 | 13 | 10 | 5 | 16 | 28 | 21 | 5 | 6 |
| W | 0 | 4 | 8 | 0 | 0 | 2 | 2 | 57 | 0 | 4 |
| Y | 102 | 4 | 63 | 8 | 18 | 17 | 11 | 3 | 4 | 91 |

TABLE 2-continued

Amino acid conservation of 273 class-A GPCRs.

| Negative-charged | 4 | 7 | 30 | 14 | 5 | 35 | 20 | 1 | 2 | 5 |
|---|---|---|---|---|---|---|---|---|---|---|
| Positive-charged | 0 | 2 | 13 | 20 | 4 | 20 | 18 | 9 | 1 | 10 |
| Polar | 135 | 27 | 145 | 96 | 26 | 101 | 86 | 65 | 76 | 158 |
| Hydrophobic | 134 | 237 | 85 | 143 | 238 | 117 | 149 | 198 | 194 | 100 |

[a]Ballesteros-Weinstein numbering.
[b]D and E.
[c]K and R.
[d]C, H, N, Q, S, T, and Y.
[e]A, F, G, I, L, M, P, V, and W.
[f]Functional groups (amidine and phenyl of benzamidine), Na$^+$, or water that interact are indicated.
[g]Amino acid is indicated in parentheses.

TABLE 3

Data collection and structure refinement statistics

Data collection

| | |
|---|---|
| Number of crystals | 494 |
| Beamline | SPring-8 BL32XU |
| Space group | P2$_1$2$_1$2$_1$ |

Cell Dimensions

| | |
|---|---|
| a, b, c (Å) | 69.6, 77.6, 135.5 |
| α, β, γ (°) | 90, 90, 90 |
| Number of reflections measured | 286,746 |
| Number of unique reflections | 8,291 |
| Resolution (Å) | 48.5 – 3.7 (3.92 – 3.70)* |
| Completeness (%) | 99.9 (100.0) |
| CC$_{1/2}$ | 95.7 (53.5) |
| I/σI | 6.7 (1.1) |
| Redundancy | 34.6 (31.8) |

Refinement

| | |
|---|---|
| Resolution | 48.5 – 3.7 |
| Number of reflections (test set) | 7852 (414) |
| R$_{work}$/R$_{free}$ (%) | 24.8/29.6 |

Number of atoms

| | |
|---|---|
| Protein | 3340 |
| Ligand | 35 |

Average B factors (Å$^2$)

| | |
|---|---|
| BLT1 | 71.9 |
| T4 lysozyme | 63.6 |
| BIIL260 | 79.2 |

Root mean square deviations

| | |
|---|---|
| Bond lengths (Å) | 0.005 |
| Bond angles (°) | 0.801 |

Ramachandran plot

| | |
|---|---|
| Favored (%) | 96.8 |
| Allowed (%) | 3.2 |
| Disallowed (%) | 0 |

*Highest resolution shell is shown in parentheses.

1.8 Results 1.8.1 Structural Determination of the BLT1-BIIL260 Complex

For the structural study, the thermostabilized guinea pig BLT1 mutant (lacking residues 1-14 and with the H83G/K88G/V212A/S309A mutations) (FIGS. 7 and 8), fused with T4 lysozyme at intracellular loop 3 (ICL3), according to the method described in the literature (Rosenbaum D. M. et al., 2007, supra), was expressed by *Pichia pastoris* (Hori T. et al., 2010, supra; Hori T. et al., 2015, supra) and crystallized as the complex with the antagonist BIIL260 by the lipidic cubic phase method (construct ICL3-10, FIGS. 9A-9D). The mutations did not alter the affinities for LTB$_4$ and BIIL260 (FIG. 9E), as compared with the wild-type guinea pig BLT1 expressed by *P. pastoris* (FIGS. 8B and 8C). The structure was determined at 3.7 Å resolution (Table 3). The electron densities of the bound BIIL260 and the surrounding residues were sufficiently clear for interpretation (FIGS. 1A and 1B).

1.8.2 The Structure of Whole BLT1

BLT1 has a typical seven-transmembrane helix structure, the N-terminal of which is located on the extracellular side and the C terminal of which is located on the intracellular side (FIGS. 1C and 10A). The transmembrane helix bundle of the BLT1 structure is similar to those of chemokine GPCRs. The root mean square deviation of the backbone atoms with respect to CXCR4 (Wu, B. et al., Science 330 (2010) 1066-1071) (PDB code: 3OE8; sequence identity: 29% with regard to 207 residues) was 1.6☐ and that with respect to CCR5 (Tan, Q. et al., Science 341 (2013) 1387-1390) (4MBS; 28% with regard to 207 residues) was 1.8☐ (these chemokines belong to γ branch GPCRs (Fredriksson, R. et al., Mol. Pharmacol. 63 (2003) 1256-1272). The benzamidine moiety of BIIL260 interacts with D66$^{25.0}$ which is highly conserved among class-A GPCRs (FIG. 1C and Table 2).

The extracellular loop region of the BLT1 structure adopts the common features of the γ branch GPCRs (Fredriksson, R. et al., 2003, supra): the extracellular loop 2 (ECL2) of BLT1 has a β-hairpin (FIG. 1E), as in the chemokine- and peptide-ligand GPCRs (Zhang, H. et al., Cell 161 (2015) 833-844). The vestibule of BLT1 is open on the extracellular surface (FIG. 1F) and the bound BIIL260 was not visible from the membrane side (FIG. 10B), supporting the proposal that the BLT1 ligands, including BIIL260 and LTB$_4$, may enter and leave the ligand-binding site via the extracellular surface.

The intracellular side of the BLT1 structure has the typical features associated with the inactive GPCR state. The inner half of the transmembrane helix bundle structure of BLT1 is the most similar to that of the nociceptin/orphanin FQ (N/OFQ) peptide receptor (Thompson, A. A. et al., Nature 485 (2012) 395-399) (NOP, PDB code: 4EA3) in the inactive state, with a root mean square deviation of 1.4 Å for the backbone atoms of the inner halves of the transmembrane helices (FIG. 10C). There is an inter-helical hydrogen-bonding network among the transmembrane helices 2, 3, 5, and 6, and ICL2, as also observed in most inactive-state GPCRs (FIG. 10D). The side chains of D116$^{3.49}$ and R117$^{3.50}$ within the DRY motif do not form the salt bridge, designated as the ionic lock, for the inverse agonist-bound inactive-state M1 and M3 muscarinic receptors (Thal, D. M. et al., Nature 531 (2016) 335-340; Kruse, A. C. et al., Nature 482 (2013b) 552-556). The guanidino group of R117$^{3.50}$ interacts with the backbone carbonyl group of G222$^{6.34}$ via the hydroxyl group of Y203$^{5.58}$. This conformation suggests that the BLT1-BIIL260 complex might represent the S2 inactive state with a broken ionic lock (Manglik, A. et al., Cell 161 (2015) 1101-1111).

1.8.3 How the Binding of BIIL260 to BLT1 Looks

BIIL260 does not contact ECL but specifically interacts with 8 residues of the transmembrane helices 1, 2, 3, 6, and 7 of BLT1 (FIGS. 1C and 10A) and also has hydrophobic interactions (FIGS. 2A and 2B). First, a salt bridge is formed between the amidine group of the benzamidine moiety and the carboxyl group of $D66^{2.50}$. Then, hydrogen bonds with the hydroxyl groups of $S106^{3.39}$ and $S276^{7.45}$ are formed. Meanwhile, the imino group thereof is considered to be protonated (pKa of benzamidine is 11.6 (Lam, P. Y. et al., J. Med. Chem. 46 (2003) 4405-4418)). Thus, the present inventors performed a competitive binding assay between BIIL260 and $^3$H-LTB$_4$ so as to analyze the effects of $D66^{2.50}$A and $S276^{7.45}$A mutations. Then, it was actually found that these mutations abrogated and decreased the BIIL260-binding ability (FIG. 2C and Table 1). This indicates that the protonated amidine of the benzamidine moiety interacts with these two residues and is essential for the BLT1-BIIL260 binding. Moreover, an edge-to-π (interaction is formed between the phenyl ring of the benzamidine moiety and the indole ring of $W236^{6.48}$ and an CH-to-π (interaction is formed between the phenyl ring of the benzamidine moiety and the methyl group of $V69^{2.53}$. Regarding other 3 phenyl groups of BIIL260, edge-to-π (interactions with the phenyl groups of $F274^{7.43}$ and $F76^{2.60}$ are formed and an CH-to-π (interaction with the methyl group of $L80^{2.64}$ is formed (FIGS. 2A and 2B).

1.8.4 Allosteric Modulation of LTB$_4$-BLT1 Activity by Benzamidine

The following focuses on the benzamidine moiety-binding site of the BLT1-BIIL260 structure. The benzamidine moiety binds to the same site as of a sodium ion, which broadly functions as a negative allosteric modulator for class-A GPCRs (Katritch, V. et al., Trends Biochem. Sci. 39 (2014) 233-244). In fact, the binding of an agonist LTB$_4$ to BLT1 decreased in a sodium ion concentration-dependent manner (FIG. 3A). The orthosteric binding site for LTB$_4$ seems to have a distance from the sodium ion-binding site of BLT1 in view of the mutation studies (Basu, S. et al., J. Biol. Chem. 282 (2007) 10005-10017; Sabirsh, A. et al., Biochemistry 45 (2006) 5733-5744). Thus, the sodium ion also acts as a negative allosteric modulator of the LTB$_4$-BLT1 binding. Here, the present inventors tested a benzamidine molecule itself. Like the sodium ion, the benzamidine molecule decreased the level of the LTB$_4$-BLT1 binding in a benzamidine concentration-dependent manner (FIG. 3A), lowered the binding affinity of LTB$_4$ toward BLT1 (FIG. 3B), and decreased BLT1-LTB$_4$-mediated Gq/il and G16 activation (FIGS. 3C and 3D). As a whole, the cooperative factor of the binding of LTB$_4$ to BLT1 is α≤1 and the cooperative factor of the LTB$_4$-induced efficacy modulation is β<1.

These results reveal that the benzamidine molecule by itself can serve as a negative allosteric modulator of the LTB$_4$-BLT1 activity, in agreement with the finding that the benzamidine moiety of BIIL260 is essential for BLT1 binding.

1.8.5 the Structural Aspects of the Allosteric Modulation of the LTB$_4$-BLT1 Activity by the Benzamidine Moiety The BLT1-BIIL260 complex structure reveals the mechanism of the negative allosteric modulation of the BLT1-LTB$_4$ activity by the benzamidine moiety. First, the benzamidine moiety of BIIL260 is expected to maintain the inactive state of the BLT1 structure. The $D66^{2.50}$, $V69^{2.53}$, $S106^{3.39}$, $W236^{6.48}$, and $S276^{7.45}$ residues, with side chains that interact specifically with the benzamidine moiety as described above, are highly conserved in the class-A GPCRs (FIG. 4A; Table 2). In common among the high-resolution structures of such GPCRs in the inactive state, a sodium ion is coordinated by the $D66^{2.50}$- and $S106^{3.39}$-corresponding residues, and interacts with the $W236^{6.48}$-, $S276^{7.45}$- and $N280^{7.49}$-corresponding residues via bound water molecules (Liu et al., 2012, supra; Miller-Gallacher et al., 2014, supra; Zhang et al., 2012, supra; Fenalti et al., 2014, supra) (FIGS. 4A, 4B, 11A, 11C, and 11E; Table 2), which are hallmarks of the inactive GPCR state. Therefore, in the absence of BIIL260, the inactive-state BLT1 should bind the sodium ion in the same manner. In contrast, in the present BLT1-BIIL260 structure, the benzamidine moiety has ejected the sodium ion and the surrounding water molecules due to steric hindrance, except for the waters interacting with $N280^{7.49}$. Instead, the benzamidine moiety complements the interactions lost in the absence of the sodium ion and surrounding waters (FIGS. 4A, 4B, 11A, 11C, and 11E; Table 2), by mimicking the sodium ion-centered water cluster through its extensive interactions with BLT1. The dimensions of the benzamidine are comparable to those of the sodium ion-centered water cluster (FIGS. 4C, 11B, 11D, and 11F), as assessed by the superimposition of the BLT1-BIIL260 and other GPCR structures, indicating that the benzamidine can fit into the sodium ion-binding site from both the physical and chemical viewpoints. As the sodium ion-centered water cluster stabilizes GPCRs in the inactive state (Gutierrez-de-Teran, H. et al., 2013, supra), the benzamidine moiety is also considered to stabilize the inactive state of BLT1.

Next, the benzamidine moiety is expected to suppress the structural change of BLT1 to the active state. Based on the crystal structures of agonist-bound GPCRs, the agonist binding is considered to induce structural changes in the sodium ion-binding site, in a G-protein coupling-dependent manner (Rosenbaum D. M. et al., 2007, supra; Rasmussen, S. G. et al., 2011, supra; Rosenbaum, D. M. et al., Nature 469 (2011) 236-240). The approach of transmembrane helix 3 to helices 2 and 7 by the agonist binding ejects the bound sodium ion existing in the inactive state, and enables direct hydrogen bonding between the highly conserved residues 2.50 and 3.39 (Rasmussen, S. G. et al., 2011, supra; Carpenter, B. et al., 2016, supra; Kruse, A. C. et al., 2013a, supra; Huang, W. et al., 2015, supra) (FIG. 5). In the BLT1-BIIL260 complex, the benzamidine moiety prevents $D66^{2.50}$ $S106^{3.39}$, and $S277^{7.46}$ from approaching each other, due to steric hindrance, and disables their direct hydrogen bonding (FIG. 5). Mutations of the corresponding residues in human BLT1 resulted in the loss of ($D^{2.50}$A) or reduction of ($S^{7.45}$A/$S^{7.46}$A/$S^{7.47}$A or $N^{7.49}$A) signaling to G-proteins, without affecting the LTB$_4$-binding affinity (Basu, S. et al., 2007, supra), as also reported for $A_{2A}$AR (Massink, A. et al., Mol. Pharmacol. 87 (2015) 305-313). In view of the above, the benzamidine moiety can prevent transmembrane helices 2, 3, and 7 from getting closer and can prevent direct hydrogen bonds with $D66^{2.50}$, $S106^{3.39}$ and $S277^{7.46}$, thereby inhibiting a BLT1 structural change into the active state. This may disable BLT1-mediated signal transduction.

Example 2

2.1 To Analyze a Function of Compounds Comprising a Structure Comprising a Class-A GPCR-Binding Compound Linked to a Benzamidine Moiety.

2.1.1 Synthesis of Compounds

Synthesized were a compound (Compound 1) comprising a structure comprising carazolol (a ligand of an adrenergic receptor) linked to a benzamidine moiety, a compound (Compound 2) comprising a structure comprising adenosine (a ligand of $A_{2A}$ adrenergic receptor) linked to a benzamidine moiety, and compounds (Compounds 3 and 4) comprising a structure comprising histamine (a ligand of a histamine receptor) linked to a benzamidine moiety. The procedure is as follows. Note that the following Compound 43-28, Compound 42-28, Compound 7-28, and Compound 15-28 correspond to Compound 4, Compound 3, Compound 2, and Compound 1, respectively.

2.1.1.1 Synthesis of Compounds 43-28 and 42-28

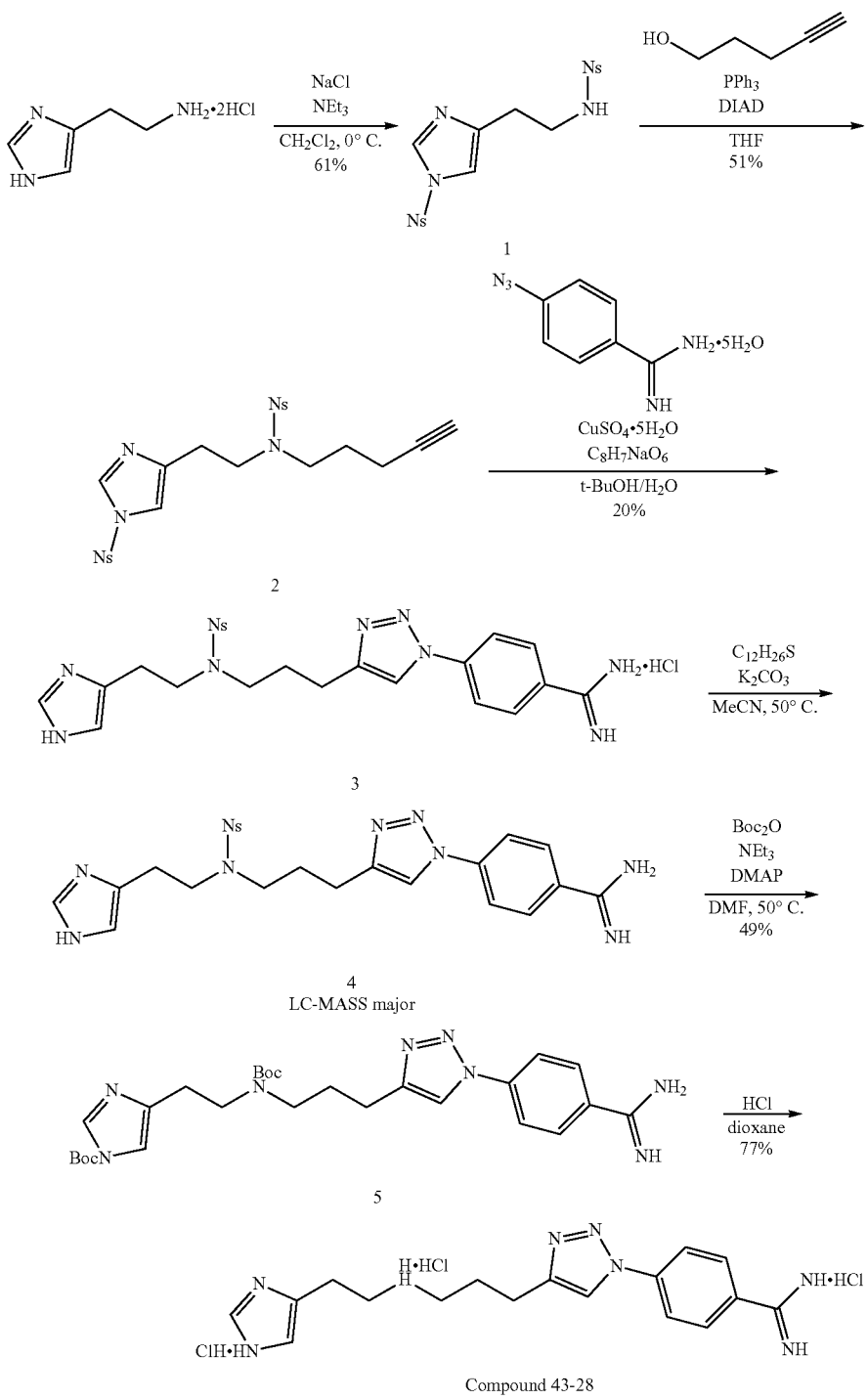

Compound 43-28

Histamine dihydrochloride was nosylated and was subjected to a Mitsunobu reaction. Next, the resulting compound was subjected to a click reaction with amidine, which had been synthesized separately, to synthesize intermediate 3. The nosyl group was then deprotected to synthesize intermediate 4. After that, Boc protection was carried out and the resulting compound was purified. Finally, Compound 43-28 was synthesized under hydrogen chloride-dioxane conditions, in which a target compound was able to be synthesized only by simple posttreatment.

The same intermediate 1 as above was subjected to a Mitsunobu reaction and the resulting compound was subjected to a click reaction with Boc-protected amidine to synthesize intermediate 7. The nosyl group of the intermediate 7 was deprotected to produce Boc-protected intermediate 8. The Boc protection of the intermediate 8, which was able to be easily purified using normal-phase silica gel, was removed at last to synthesize Compound 42-28.

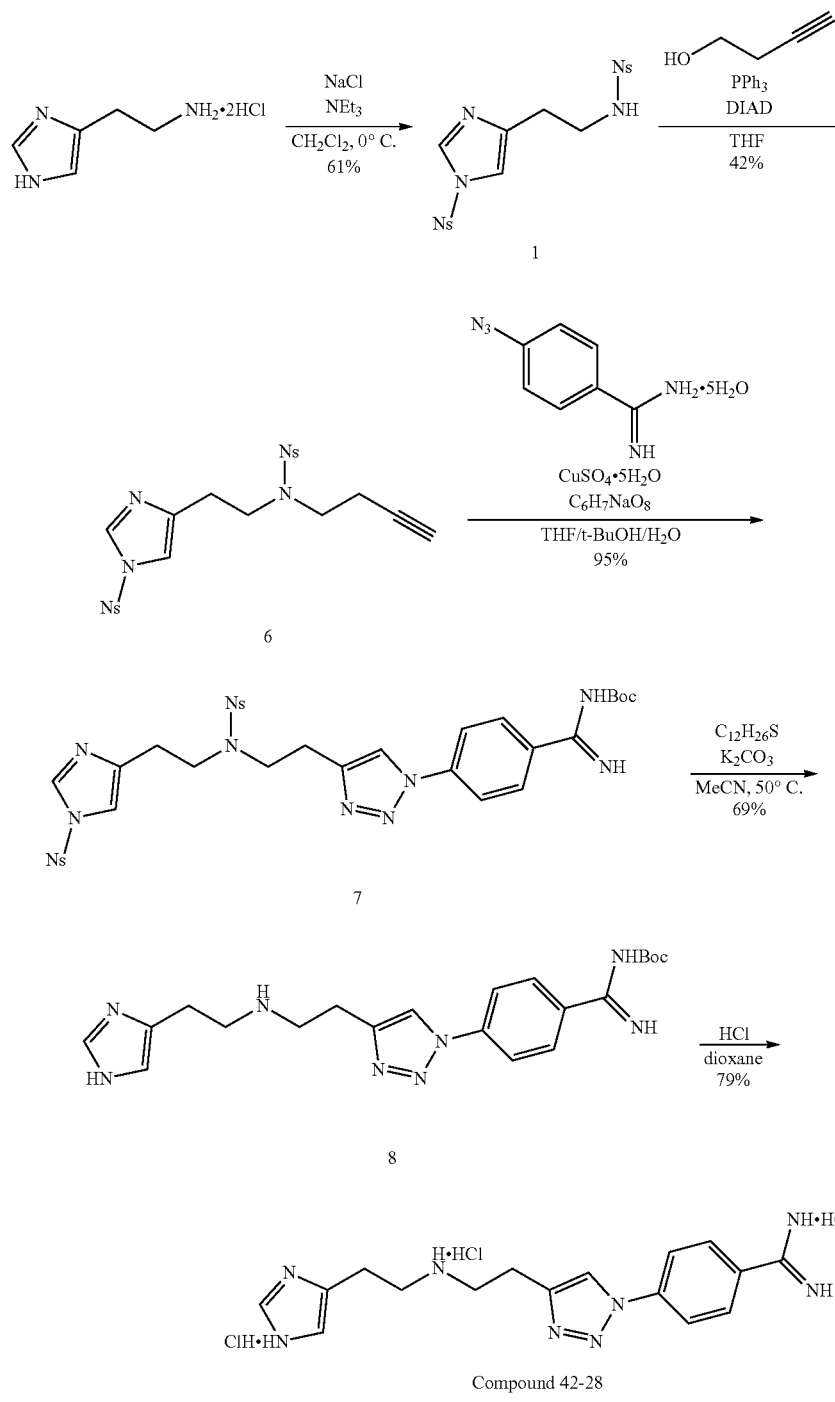

Compound 42-28

2.1.1.2 Synthesis of Compound 7-28

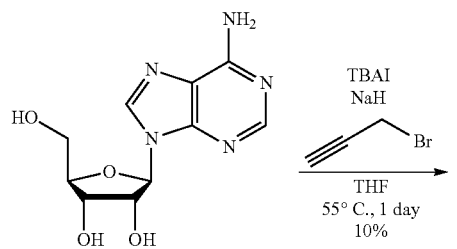

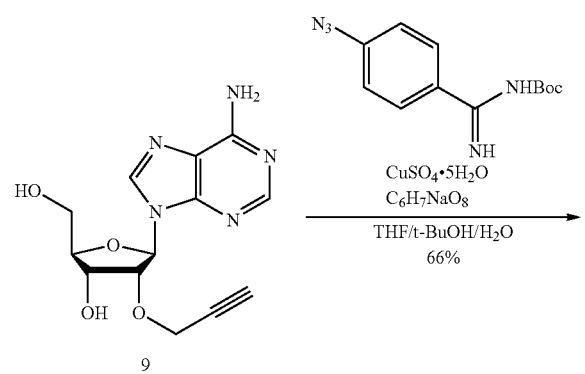

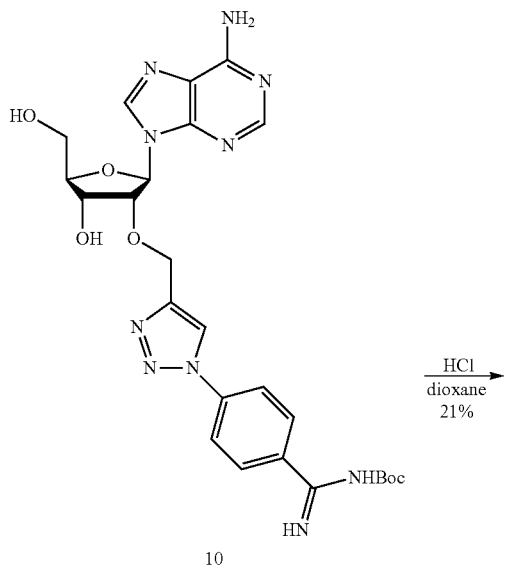

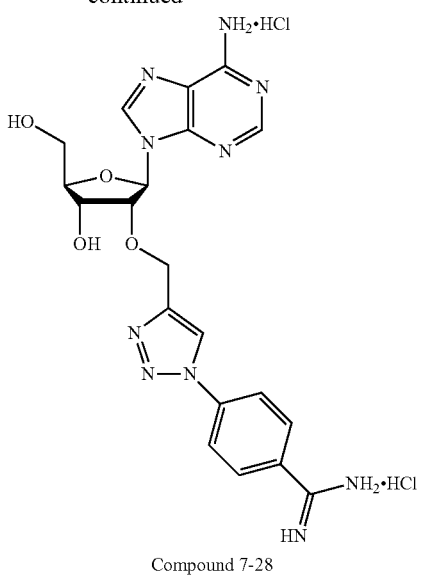

Compound 7-28

Adenosine was reacted with propargyl bromide under basic conditions to synthesize intermediate 9. Next, the intermediate 9 was subjected to a click reaction with Boc-protected amidine. The Boc group of the resulting compound was deprotected to synthesize Compound 7-28.

2.1.1.3 Synthesis of Compound 15-28

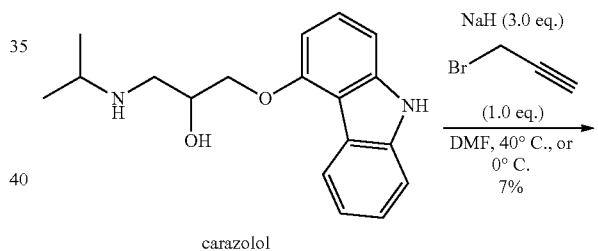

carazolol

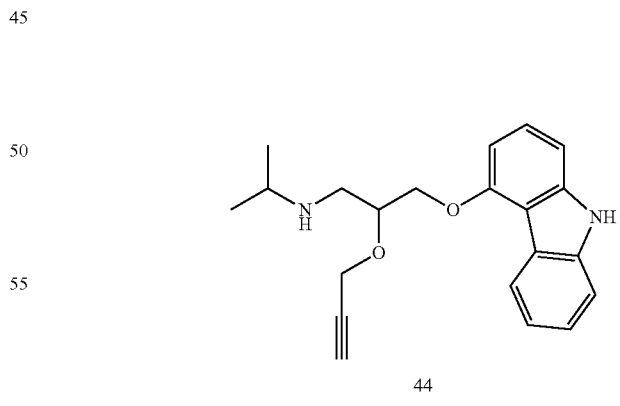

44

Unprotected carazolol was reacted with propargyl bromide under basic conditions. Here, the position at which a propargyl group was introduced was successfully controlled by selecting the kind and amount of a base. Two equivalents or more of sodium hydride were used for generation of a dianion so as to produce intermediate 44.

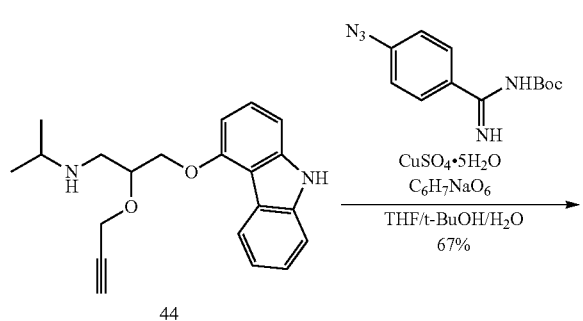

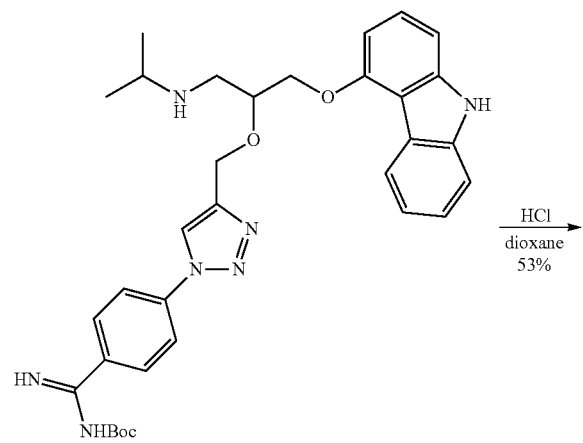

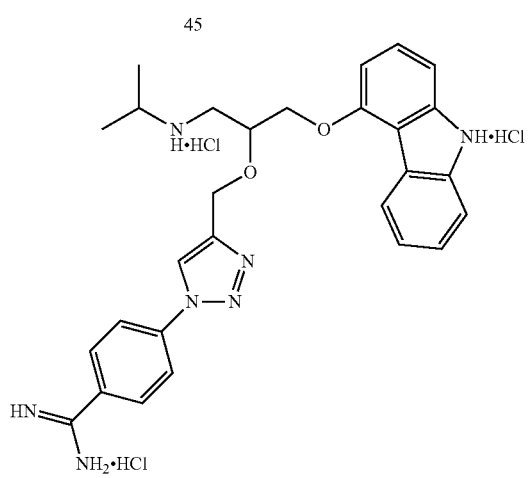

Then, a click reaction for the intermediate 44 proceeded readily. Finally, the Boc group was deprotected to synthesize Compound 15-28.

2.1.1.4 Details of the Synthetic Procedure

More specifically, the above respective compounds were synthesized as follows.

(i) Amidine Used as a Common Source Material in the Click Reaction

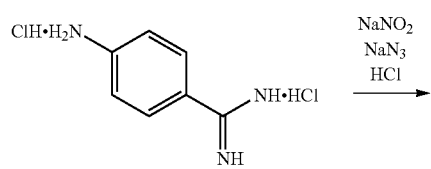

Synthesis of S1

First, the air in a 100-mL three-neck flask equipped with a stirring bar, a thermometer, and a nitrogen line was replaced by nitrogen. Next, 4-aminobenzamidine dihydrochloride (8.32 g, 40 mmol) was suspended in 4 M hydrochloric acid (20 mL) in the flask, and the flask was cooled in an ice bath at 0° C. Subsequently, sodium nitrite (2.90 g, 42 mmol)-containing ultrapure water solution (9 mL) was added dropwise over about 30 min and the mixture, as it was, was stirred for another 30 min. While the resulting orange solution was agitated in the ice bath, a sodium azide (5.20 g, 80 mmol)-containing ultrapure water solution (20 mL) was added dropwise over about 1 h and 30 min. Then, the mixture was stirred for another 20 min. The resulting reaction mixture, which was beige slurry, was added to and dissolved in ultrapure water (150 mL), and was washed twice with methylene chloride (50 mL). After that, 10 M sodium hydroxide aqueous solution (15 mL) was added to the resulting aqueous layer and the mixture was extracted with methylene chloride (100 mL, 50 mL). The combined organic layer was extracted twice with 1 M hydrochloric acid (100 mL). The combined aqueous layer was concentrated under reduced pressure by using a rotary evaporator and vacuum-dried by using a hydraulic vacuum pump to produce S1 (6.91 g, yield 87%) as a pale brown solid.

Synthesis of S2

First, the air in a 300-mL three-neck flask equipped with a stirring bar, a thermometer, and a nitrogen line was replaced by nitrogen. To the flask were added S1 (3.95 g, 20 mmol) and methylene chloride (100 mL). Then, the flask was cooled in an ice bath at 0° C. Subsequently, triethylamine (6.10 mL, 44 mmol) and 4-dimethylaminopyridine (122 mg, 1.0 mmol) were added and di-tert-butyl dicarbonate (5.05 mL, 22 mmol) was then added dropwise. The resulting brown solution was stirred overnight at room temperature, and the reaction solution was then washed with 15% ammonium chloride aqueous solution (100 mL) and was extracted with methylene chloride (50 mL). The combined organic layer was dried over sodium sulfate and subjected to pleated filtration. Then, the filtrate was concentrated under reduced pressure by using a rotary evaporator and vacuum-dried by using a hydraulic vacuum pump to produce an S2 crude material (4.96 g) as a brown solid. This crude material was purified by medium-pressure preparative liquid column chromatography (silica gel: 200 g; hexane/ethyl acetate=90/10 to 70/30) to yield S2 (4.82 g, yield 92%) as a pale gray solid.

(ii) Compound 43-28

Synthesis of Intermediate 1

First, the air in a 300-mL three-neck flask equipped with a stirring bar, a 50-mL dropping funnel, a thermometer, and a nitrogen line was replaced by nitrogen. Next, to the flask were added histamine dihydrochloride (12.9 mL, 72 mmol), methylene chloride (50 mL), 2-nitrobenzenesulfonyl chloride (24.4 g, 110 mmol). Then, the flask was cooled in an ice bath at 0° C. Triethylamine (30.7 mL, 220 mmol) was added dropwise over 4 h and the resulting brown solution was subsequently stirred for 30 min. Ion-exchanged water (100 mL) was added to the reaction solution. The mixture was extracted twice with methylene chloride (10 mL) and the combined organic layer was dried over sodium sulfate. After pleated filtration, the filtrate was concentrated under reduced pressure by using a rotary evaporator and was vacuum-dried by using a hydraulic vacuum pump to produce a crude material 1 (29 g) as a brown oily liquid. This crude material was purified by medium-pressure preparative liquid column chromatography (silica gel: 200 g; methylene chloride/methanol=100/0 to 97/3) to yield a pale yellow viscous solid 1 (14.8 g, yield 61%).

Synthesis of Intermediate 2

First, the air in a 100-mL three-neck flask equipped with a stirring bar, a thermometer, and a nitrogen line was replaced by nitrogen. To the flask were added the solid 1 (4.81 g, 10 mmol), 4-pentyne-1-ol (1.11 mL, 12 mmol), and dehydrated THF (50 mL). Next, the mixture was stirred at room temperature. To the resulting yellow solution was added triphenylphosphine (3.93 g, 15 mmol), and diisopropyl azodicarboxylate (in 40% toluene solution; about 1.9 mol/L) (6.3 mL, 12 mmol) was added dropwise thereto. After reacted overnight at room temperature, the mixture was concentrated under reduced pressure by using a rotary evaporator and was vacuum-dried by using a hydraulic vacuum pump to produce a reaction reagent residue-containing crude material 2. This crude material was purified by medium-pressure preparative liquid column chromatography (silica gel: 200 g; methylene chloride/methanol=97/3) and was then further purified by medium-pressure preparative liquid column chromatography (silica gel: 100 g; hexane/ethyl acetate=90/10 to 40/60) to yield a yellow viscous solid 2 (2.78 g, yield 51%).

Synthesis of Intermediate 3

First, the air in a 100-mL three-neck flask equipped with a stirring bar, a thermometer, and a nitrogen line was replaced by nitrogen. Next, to the flask were added the solid 2 (1.30 g, 2.4 mmol), THF (6.0 mL), and S1 (535 mg, 2.71 mmol). After tert-butanol (3.0 mL) and ion-exchanged water (1.8 mL) were added, copper sulfate pentahydrate (136 mg, 0.55 mmol), which had been dissolved in ion-exchanged water (0.6 mL), was added and sodium L-ascorbate (221 mg, 1.12 mmol), which had been dissolved in ion-exchanged water (0.6 mL), was further added. This brown solution was stirred overnight at room temperature, and ion-exchanged water (18 mL) was then added. Subsequently, the mixture was extracted twice with ethyl acetate (10 mL) and the aqueous layer was concentrated to yield a crude material 3 (0.97 g) as a brown viscous solid. This crude material was purified by flash column chromatography (ODS silica gel: 60 g; ion-exchanged water/methanol=70/30 to 30/70) to yield a yellow viscous solid 3 (263 mg, yield 20%).

Synthesis of Intermediate 4

First, the air in a 200-mL single-neck flask equipped with a stirring bar and a nitrogen line was replaced by nitrogen. Next, to the flask were added the intermediate 3 (86.2 mg, 0.15 mmol), acetonitrile (2.0 mL), and potassium carbonate (102 mg, 0.74 mmol). After 1-dodecanethiol (0.088 mL, 0.37 mmol) was added, the mixture was stirred at 50° C. for 8 h. Subsequently, ion-exchanged water (5.0 mL) was added to the resulting yellow solution. Then, the mixture was extracted twice with ethyl acetate (10 mL) and the aqueous layer was concentrated to yield a crude material 4 (230 mg) as a reaction reagent residue-containing pale yellow solid.

Synthesis of Intermediate 5

First, the air in a 100-mL three-neck flask equipped with a stirring bar, a thermometer, and a nitrogen line was replaced by nitrogen. To the flask were added the crude material 4 (230 mg), dehydrated DMF (2.0 mL), and triethylamine (0.15 mL, 1.05 mmol) and were further added di-tert-butyl dicarbonate (0.12 mL, 0.53 mmol) and 4-dimethylaminopyridine (3.0 mg, 0.025 mmol). After the resulting yellow solution was stirred at 50° C. for 4 h, saturated saline (5.0 mL) was added. Next, the mixture was extracted twice with methylene chloride (5.0 mL). The combined organic layer was dried over sodium sulfate. After pleated filtration, the filtrate was concentrated under reduced pressure by using a rotary evaporator and was vacuum-dried by using a hydraulic vacuum pump to produce a crude material 5 (83.6 mg) as a yellow oily liquid. This crude material was purified by medium-pressure preparative liquid column chromatography (silica gel: 10 g; methylene chloride/methanol=99/1 to 94/6) to yield a yellow oily liquid 5 (46.7 mg, yield 49%).

Synthesis of Compound 43-28

First, the air in a 100-mL three-neck flask equipped with a stirring bar and a nitrogen line was replaced by nitrogen. To the flask were added the intermediate 5 (46.7 mg, 0.0736 mmol) and hydrogen chloride (in about 4 mol/L 1,4-dioxane solution) (0.28 mL, 1.10 mmol), and the mixture was stirred overnight at room temperature. The reaction solution was concentrated under reduced pressure by using a rotary evaporator and vacuum-dried by using a hydraulic vacuum pump to produce Compound 43-28 (19.2 mg, yield 77%) as a yellow solid. FIGS. 17(A) to (H) show the results of checking the physical properties (e.g., NMR, MS).

(iii) Compound 42-28

Synthesis of Intermediate 1

This has been described in the experiment section of Compound 43-28.

Synthesis of Intermediate 6

First, the air in a 300-mL three-neck flask equipped with a stirring bar, a thermometer, and a nitrogen line was replaced by nitrogen. To the flask were added the intermediate 1 (4.81 g, 10 mmol), 3-butyn-1-ol (0.90 mL, 12 mmol), and dehydrated THF (50 mL). Next, the mixture was stirred at room temperature. To the resulting yellow solution was added triphenylphosphine (3.93 g, 15 mmol), and diisopropyl azodicarboxylate (in 40% toluene solution; about 1.9 mol/L) (6.3 mL, 12 mmol) was added dropwise thereto. After reacted overnight at room temperature, the mixture was concentrated under reduced pressure by using a rotary evaporator and was vacuum-dried by using a hydraulic vacuum pump to produce a reaction reagent residue-containing crude material 6. This crude material was purified by medium-pressure preparative liquid column chromatography (silica gel: 200 g; methylene chloride/methanol=99/1 to 98/2) and was then further purified by medium-pressure preparative liquid column chromatography (silica gel: 100 g; hexane/ethyl acetate=60/40 to 30/70) to yield a yellow viscous solid 6 (2.28 g, yield 42%).

Synthesis of Intermediate 7

First, the air in a 200-mL three-neck flask equipped with a stirring bar, a thermometer, and a nitrogen line was replaced by nitrogen. Next, to the flask were added the solid 6 (1.15 g, 2.16 mmol), THF (7.5 mL), and S2 (642 mg, 2.46 mmol). After tert-butanol (3.0 mL) and ion-exchanged water (1.8 mL) were added, copper sulfate pentahydrate (124 mg, 0.50 mmol), which had been dissolved in ion-exchanged water (0.6 mL), was added and sodium L-ascorbate (201 mg, 1.01 mmol), which had been dissolved in ion-exchanged water (0.6 mL), was further added. The reaction solution was stirred overnight at room temperature and was then concentrated under reduced pressure by using a rotary evaporator. Subsequently, methylene chloride (20 mL) was added. The mixture was subjected to a Kiriyama filtration so as to remove a copper reagent residue. After that, the filtrate was concentrated under reduced pressure by using a rotary evaporator and was vacuum-dried by using a hydraulic vacuum pump to produce a crude material 7 (2.13 g) as a yellow solid. This crude material was purified by medium-pressure preparative liquid column chromatography (silica gel: 100 g; methylene chloride/methanol=99/1 to 92/8) to yield a yellow viscous solid 7 (1.63 g, yield 95%).

Synthesis of Intermediate 8

First, the air in a 200-mL three-neck flask equipped with a stirring bar and a nitrogen line was replaced by nitrogen. Next, to the flask were added the intermediate 7 (1.70 g, 2.14 mmol), acetonitrile (25 mL), and potassium carbonate (5.68 g, 41.0 mmol). After 1-dodecanethiol (4.89 mL, 20.5 mmol) was added, the mixture was stirred overnight at 50° C. Ion-exchanged water (25 mL) was added to the resulting yellow solution. The mixture was extracted twice with ethyl acetate (10 mL) and the combined organic layer was dried over sodium sulfate. After pleated filtration, the filtrate was concentrated under reduced pressure by using a rotary evaporator and was vacuum-dried by using a hydraulic vacuum pump to produce a crude material 8 (4.93 g) as a yellow oily liquid. This crude material was purified by medium-pressure preparative liquid column chromatography (silica gel: 30 g; methylene chloride/methanol=99/1 to 92/8) to yield a white viscous solid 8 (625 mg, yield 69%).

Synthesis of Compound 42-28

First, the air in a 30-mL two-neck flask equipped with a stirring bar and a nitrogen line was replaced by nitrogen. To the flask were added the intermediate 8 (100 mg, 0.236 mmol) and hydrogen chloride (in about 4 mol/L 1,4-dioxane solution) (1.18 mL, 4.71 mmol) and the mixture was stirred at room temperature for 1.5 h. The reaction solution was concentrated under reduced pressure by using a rotary evaporator, vacuum-dried by using a hydraulic vacuum pump, and then lyophilized to produce Compound 42-28 (60 mg, yield 79%) as a white solid. FIGS. 16(A) to (G) show the results of checking the physical properties (e.g., NMR, MS).

(iv) Compound 7-28

Synthesis of Intermediate 9

First, the air in a 500-mL three-neck flask equipped with a stirring bar and a nitrogen line was replaced by nitrogen. Adenosine (5.0 g, 19.8 mmol) and anhydrous DMF (200 mL) were added and the mixture was heated and stirred in a water bath at 50° C. so as to dissolve the adenosine. After cooling in an ice bath at 0° C., 60% sodium hydride (1.0 g, 25.8 mmol) was added and the mixture was stirred at 0° C. for 15 min. Next, tetra butyl ammonium iodide (1.5 g, 4.06 mmol) and propargyl bromide (1.67 mL, 22.2 mmol) were further added and the mixture was stirred overnight in a water bath at 55° C. After the reaction solution was returned to room temperature, methanol (20 mL) was added. While the mixture was heated with a rotary evaporator, the pressure was reduced using a hydraulic vacuum pump. In this way, DMF was distilled away to produce a crude material 9 (10 g) as a brown liquid. This crude material was purified by medium-pressure preparative liquid column chromatography (silica gel: 200 g; methylene chloride/methanol=99/1 to 90/10) to yield a brown viscous solid 9 (810 mg). The resulting solid was dissolved in ethanol (10 mL) in a water bath at 70° C., cooled, recrystallized, subjected to a Kiriyama filtration to produce a white solid 9 (551 mg, yield 10%).

Synthesis of Intermediate 10

First, the air in a 100-mL three-neck flask equipped with a stirring bar and a nitrogen line was replaced by nitrogen. Next, to the flask were added the solid 9 (330 mg, 1.08 mmol), THF (3.0 mL), and S2 (322 mg, 1.23 mmol). After tert-butanol (1.5 mL) and ion-exchanged water (0.9 mL) were added, copper sulfate pentahydrate (62.1 mg, 0.25 mmol), which had been dissolved in ion-exchanged water (0.3 mL), was added and sodium L-ascorbate (101 mg, 0.51 mmol), which had been dissolved in ion-exchanged water (0.3 mL), was further added. The reaction solution was stirred at room temperature for 4 h. After that, the reaction solution was concentrated under reduced pressure by using a rotary evaporator and was vacuum-dried by using a hydraulic vacuum pump to produce a crude material 10 (0.84 g) as a yellow viscous solid. This crude material was purified by medium-pressure preparative liquid column chromatography (silica gel: 30 g; methylene chloride/methanol=99/1 to 90/10) to yield a yellow viscous solid 10 (0.40 g, yield 66%).

Synthesis of Compound 7-28

First, the air in a 50-mL two-neck flask equipped with a stirring bar and a nitrogen line was replaced by nitrogen. To the flask were added the intermediate 10 (300 mg, 0.53 mmol) and dioxane (6.0 mL). Then, the flask was cooled in an ice bath at 0° C. To the flask was added hydrogen chloride (in about 4 mol/L 1,4-dioxane solution) (2.5 mL, 10.4 mmol) and the mixture was stirred overnight at room temperature. After that, the reaction solution was concentrated under reduced pressure by using a rotary evaporator and was vacuum-dried by using a hydraulic vacuum pump to produce a Compound 7-28 crude material (345 mg) as a white solid. This crude material was purified by medium-pressure preparative liquid column chromatography (ODS silica gel: 10 g; ion-exchanged water/methanol=95/5 to 80/20) to yield Compound 7-28 (59 mg, yield 21%) as a white solid. FIGS. 15(A) to (H) show the results of checking the physical properties (e.g., NMR, MS).

(v) Compound 15-28

Synthesis of Intermediate 44

First, the air in a 100-mL three-neck flask equipped with a stirring bar and a nitrogen line was replaced by nitrogen. Next, carazolol (1.45 g, 4.86 mmol) and anhydrous DMF (15 mL) were added and dissolved. After cooling in an ice bath at 0° C., 60% sodium hydride (583 mg, 14.6 mmol) was added and the mixture was stirred at 0° C. for 15 min. Then, propargyl bromide (0.37 mL, 4.86 mmol) was further added and the mixture was stirred at room temperature for 1.5 h. After that, saturated saline (30 mL) was added to the reaction solution and the mixture was extracted three times with ethyl acetate (10 mL). The combined organic layer was washed with saturated saline (20 mL) and dried over sodium sulfate. After pleated filtration, the filtrate was concentrated under reduced pressure by using a rotary evaporator and was vacuum-dried by using a hydraulic vacuum pump to produce a crude material 44 (1.93 g). This crude material was purified by medium-pressure preparative liquid column chromatography (silica gel: 100 g; hexane/ethyl acetate=100/0 to 65/35) to yield a pale yellow liquid 44 (114 mg, yield 7%).

Synthesis of Intermediate 45

First, the air in a 100-mL three-neck flask equipped with a stirring bar, a thermometer, and a nitrogen line was replaced by nitrogen. Next, to the flask were added the intermediate 45 (262 mg, 0.78 mmol), THF (10 mL), and S2 (232 mg, 0.89 mmol). After tert-butanol (5.0 mL) and ion-exchanged water (3.0 mL) were added, copper sulfate pentahydrate (44.7 mg, 0.18 mmol), which had been dissolved in ion-exchanged water (1.0 mL), was added and sodium L-ascorbate (72.5 mg, 0.37 mmol), which had been dissolved in ion-exchanged water (1.0 mL), was further added. The pressure of the reaction solution was reduced with a rotary evaporator to remove tert-butanol. Then, the reaction solution was extracted three times with ethyl acetate (20 mL). The combined organic layer was washed with saturated saline (30 mL) and dried over sodium sulfate. After pleated filtration, the filtrate was concentrated under reduced pressure by using a rotary evaporator and was vacuum-dried by using a hydraulic vacuum pump to produce a crude material 45 (451 mg) as a green viscous solid. This crude material was purified by medium-pressure preparative liquid column chromatography (NH silica gel: 30 g; hexane/ethyl acetate=80/20 to 10/90) to yield a white viscous solid 45 (310 mg; yield 67%).

Synthesis of Compound 15-28

First, the air in a 100-mL three-neck flask equipped with a stirring bar and a nitrogen line was replaced by nitrogen. To the flask were added the intermediate 45 (310 mg, 0.52 mmol) and dioxane (10 mL). Then, the flask was cooled in an ice bath at 0° C. To the flask was added hydrogen chloride (in about 4 mol/L 1,4-dioxane solution) (10 mL, 41.5 mmol) and the mixture was stirred at room temperature for 4.5 h. After that, the reaction solution was concentrated under reduced pressure by using a rotary evaporator and was vacuum-dried by using a hydraulic vacuum pump to produce a Compound 15-28 crude material (350 mg) as a white solid. This crude material was purified by medium-pressure preparative liquid column chromatography (ODS silica gel: 10 g; ion-exchanged water/methanol=90/10 to 50/50) to yield Compound 15-28 (166 mg, yield 53%) as a white solid. FIGS. 14(A) to (D) show the results of checking the physical properties (e.g., NMR, MS).

2.1.2 AP-TGFα Shedding Assay

The AP-TGFα shedding assay, which measures antagonistic activity and inverse agonistic activity, was conducted in accordance with the protocol of Inoue and colleagues (Inoue et al. 2012). The protocol is briefly described below. First, $6 \times 10^5$ HEK293 cells were seeded in 10% fetal calf serum-containing DMEM culture medium on a culture plate with a diameter of 3 cm and were cultured overnight at 37° C. Polyethyleneimine was used to transfect the HEK293 cells with expression vectors, each encoding cDNA of AP-TGFα, a class-A GPCR of interest, or the class-A GPCR-coupled G protein. The transfected cells were further cultured overnight. Next, the culture supernatant was removed. Then, the cells were detached, using protease/EDTA solution (TrypLE Express, Thermo), from the culture plate and were washed with HSBB solution (pH 7.4). After that, the cells were suspended in 5 ml of HSBB solution (pH 7.4). Here, 90 μl of the suspended cells were seeded on each well of a 96-well culture plate, which well had been charged with 10 μl of a compound (a compound structured by linking a class-A GPCR-binding compound with a benzamidine moiety; or a benzamidine derivative) at a concentration 10 times higher than the final concentration. The cells were cultured overnight (for about 16 h). Next, 80 μl of the culture supernatant (CM solution) was pipetted into a well of another 96-well plate. To each CM solution or the rest 20 μl of the corresponding cell solution was added 80 μl of a chromogenic solution (10 mM p-Nitrophenyl Phosphate in 120 mM Tris (pH 9.5), 40 mM NaCl, and 10 mM $MgCl_2$). Then, absorbance at 405 nm was measured immediately after the addition and at 1 h after the addition. The AP-TGFα release (%) was calculated using the following equation:

$$\text{AP-TGF}\alpha \text{ release } (\%) = (\Delta OD_{405}\text{Sup}/(\Delta OD_{405}\text{Sup} + \Delta OD_{405}\text{Cell})) \times 125.$$

2.1.3 To Calculate EC50 Values of Compounds Comprising a Structure Comprising a Class-A GPCR-Binding Compound Linked to a Benzamidine Moiety.

Fitting was performed, using a program GraphPad Prism 5, for three parameters of the following equation:

$$Y = \text{Bottom} + (\text{Top} - \text{Bottom})/(1 + 10^{\wedge}((X - \text{Log EC50}))).$$

2.1.4 the Results of Measuring Antagonistic Activity and Inverse Agonistic Activity The above experimental results are shown in FIGS. 18(A) to (F). The antagonistic activity was measured in the presence of an agonist at or near a concentration of EC50 value and the inverse agonistic activity was measured with respect to an ability to inhibit activity in the absence of the agonist. The compounds 1 to 4 were found to exert the antagonistic activity or inverse agonistic activity on $\beta_1$, $\beta_2$-adrenergic receptors, $A_{2A}$ adenosine receptor, $H_1$, $H_2$, and $H_4$ histamine receptors. In addition, the binding affinity toward each receptor was increased by linking a class-A GPCR-binding compound with a benzamidine moiety.

Example 3

3.1 To Analyze a Function of Benzamidine Derivatives
3.1.1 Compounds

Compound 0 (benzamidine hydrochloride hydrate), Compounds 1, 3 to 5, 7, and 11 to 13 (benzamidine derivatives) listed in Table 4 were purchased. The above S1 was used as Compound 14 (a benzamidine derivative). FIG. 19 shows the structure of each protonated compound.

TABLE 4

| No. | Compound name | Where the compound was purchased | Catalog No. |
| --- | --- | --- | --- |
| 0 | Benzamidine hydrochloride hydrate | Sigma-Aldrich | B6506-5 G |
| 1 | 1H-Pyrazole-1-carboxamidine hydrochloride | Sigma-Aldrich | 402516-10 G |
| 3 | pyrrolidine-1-carboximidamide hydroiodide | Sigma-Aldrich | CDS014943-100 MG |
| 4 | Benzamidoxime | Sigma-Aldrich | CDS001188-50 MG |
| 5 | piperidine-1-carboximidamide hydrobromide | Sigma-Aldrich | CDS014887-100 MG |
| 7 | Cyclopropanecarboxamidine Hydrochloride | TOKYO CHEMICAL INDUSTRY | C2344 |
| 11 | 1-(o-Tolyl)biguanide | TOKYO CHEMICAL INDUSTRY | T0314 |
| 12 | Phenylbiguanide | TOKYO CHEMICAL INDUSTRY | P1002 |
| 13 | 1-(2-Methyl-5-nitrophenyl)guanidine Nitrate | TOKYO CHEMICAL INDUSTRY | M2613 |

3.1.2 AP-TGFα Shedding Assay

For the assay, the same protocol as in the above 2.1.2 was repeated except that each compound of interest was replaced by each benzamidine derivative.

3.1.3 to Calculate Inhibition of Activity by Each Benzamidine Derivative.

Experiments on each compound were conducted in triplicate reactions under the same conditions (provided that the reactions were conducted six times under conditions (a basal state) without any reference compound). The mean and standard deviation of the AP-TGFα shedding percentage under the same conditions were calculated. The significant difference between the value (Value A) of the AP-TGFα shedding exerted by each compound on each class-A GPCR and the value (Value B) of the shedding in a basal state of the same class-A GPCR was tested by the t-test where only the condition P<0.05 was used for evaluation. The activity inhibition by each compound was calculated using the following equation:

Activity inhibition=Value $A$/Value $B$.

Inoue, A. et al. TGFα shedding assay: an accurate and versatile method for detecting GPCR activation. Nat. Methods 9, 1021-1029 (2012).

3.1.4 The Results of Measuring Inverse Agonistic Activity

The TGFα shedding assay was used to measure the ability of benzamidine or each benzamidine derivative (Compounds 0, 1, 3 to 5, 7, and 11 to 14) at a final concentration of 1 mM and 1 µM to suppress a corresponding class-A GPCR-mediated G-protein activity in the absence of an agonist. The results are shown in FIGS. 20(A) to (P). In the tables of FIGS. 20(A) to (P), the first row indicates the serial number and the second row indicates the receptor name. The reaction was triplicate in each experiment and the mean and the standard error of the mean were shown. The t-test was used to test whether or not the difference is significant when compared to the conditions (control) without addition of any benzamidine derivative. The case of P<0.05 was indicated by *. Further, the values normalized to the control were also indicated. When the normalized value was 0.85 or lower at the final concentration of 1 mM and 0.95 at the final concentration of 1 µM or when the normalized value was 0.95 or less at the final concentration of 1 mM, it was defined that the G protein activity was inhibited. The above results successfully demonstrated the inhibition of activity of 202 different class-A GPCRs.

The above results have revealed that a novel class-A GPCR antagonist can be created by linking a known class-A GPCR ligand with, for instance, a benzamidine moiety or a derivative thereof, which is a functional group that binds to the Na$^+$-water cluster binding site of the class-A GPCR.

Hereinabove, the Examples have been described. These Examples are just examples. Those skilled in the art can understand that various modifications are allowed and such modifications are within the scope of the present invention.

The contents of documents, scientific literatures, and the like as cited in the present application are incorporated herein by reference in their entirety.

The invention claimed is:

1. A compound or a salt thereof, consisting of a structure of a class-A GPCR-binding compound linked to ring C of a functional group via a triazole linker or a triazole linker having an alkyl chain, wherein the functional group has the following structure (1):

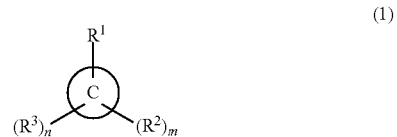

wherein
ring C is a 3-to-6-membered saturated or unsaturated carbon ring group or heterocyclic group;
$R^1$ is amidinyl, N-hydroxyamidinyl, guanidyl, amidinyl-substituted guanidyl, ethylamino, methylamino, or NHCH$_3$;
$R_2$ and $R_3$ are the same or different and are H, methyl, halogen, hydroxyl, nitro, or N$_3$; and
m and n are the same or different and are each an integer of 0 to 11.

2. The compound or salt thereof according to claim 1, wherein the functional group binds to a Na$^+$-water cluster binding site of the class-A GPCR, which comprises amino acid$^{2.50}$ as specified by Ballesteros-Weinstein numbering scheme.

3. The compound or salt thereof according to claim 1, wherein the functional group binds to a Na$^+$-water cluster binding site of the class-A GPCR, which comprises amino acids$^{2.50}$, $^{3.39}$, $^{6.48}$, and $^{7.45}$ as specified by Ballesteros-Weinstein numbering scheme.

4. The compound or salt thereof according to claim 1, wherein the functional group has a structure accommodated in a GPCR pocket comprising amino acids$^{2.50}$, $^{3.39}$, $^{6.48}$, and $^{7.45}$ as specified by Ballesteros-Weinstein numbering scheme.

5. The compound or salt thereof according to claim 1, wherein the functional group has a structure that can replace a Na$^+$-water cluster at the Na$^+$-water cluster binding site of the class-A GPCR.

6. The compound or salt thereof according to claim 1, wherein the functional group is a benzamidine moiety or a derivative thereof, a phenyl-substituted protonated amine group, or a phenyl-substituted unprotonated amine group.

7. The compound or salt thereof according to claim 1, wherein the class-A GPCR-binding compound is a class-A GPCR ligand.

8. The compound or salt thereof according to claim 1, wherein the class-A GPCR-binding compound is a class-A GPCR ligand that can bind to an orthosteric binding site of the class-A GPCR.

9. A binding molecule that specifically binds to a complex consisting of: a class-A GPCR; and a compound or salt thereof of claim 1.

10. The binding molecule according to claim 9, wherein the class-A GPCR included in the complex is an inactive class-A GPCR.

11. The compound or salt thereof according to claim 1, wherein the ring C is a 3, 5, or 6-membered saturated or unsaturated carbon ring group or heterocyclic group, and wherein
when the ring C is 3-membered saturated or unsaturated carbon ring group or heterocyclic group, the 3-membered ring is unsaturated carbon ring group,
when the ring C is 3 or 5-membered saturated or unsaturated carbon ring group or heterocyclic group, $R^2$ and $R^3$ are H, and
when the ring C is 6-membered saturated or unsaturated carbon ring group or heterocyclic group, $R^2$ and $R^3$ are the same or different and are H, methyl, halogen, hydroxyl, nitro, or $N_3$; and m and n are the same or different and are each an integer of 0 to 11.

12. The compound or salt thereof according to claim 11, when the ring C is 6-membered saturated or unsaturated carbon ring group or heterocyclic group, $R^2$ and $R^3$ are the same or different and are H, methyl, halogen, hydroxyl, nitro, or $N_3$; and m and n are each 2.

13. The compound or salt thereof according to claim 11, when the ring C is 5-membered saturated or unsaturated carbon ring group or heterocyclic group, the ring C is saturated or unsaturated heterocyclic group, and when the ring C is 6-membered saturated or unsaturated carbon ring group or heterocyclic group, the ring C is saturated heterocyclic group or unsaturated carbon ring group.

14. The compound or salt thereof according to claim 11, when the ring C is 3-membered saturated or unsaturated carbon ring group or heterocyclic group, the ring C is bonded to the class-A GPCR-binding compound at position 2 or 3 of the ring C when the position of $R^1$ bonded to ring C is defined as position 1, when the ring C is 5-membered saturated or unsaturated carbon ring group or heterocyclic group, the ring C is bonded to the class-A GPCR-binding compound at position 2, 3, 4, or 5 of the ring C when the position of $R^1$ bonded to ring C is defined as position 1, and when the ring C is 6-membered saturated or unsaturated carbon ring group or heterocyclic group, the ring C is bonded to the class-A GPCR-binding compound at position 2, 3, 4, 5, or 6 of the ring C when the position of $R^1$ bonded to ring C is defined as position 1.

\* \* \* \* \*

UNITED STATES PATENT AND TRADEMARK OFFICE
CERTIFICATE OF CORRECTION

| | | |
|---|---|---|
| PATENT NO. | : 12,275,687 B2 | Page 1 of 1 |
| APPLICATION NO. | : 16/613049 | |
| DATED | : April 15, 2025 | |
| INVENTOR(S) | : Yokoyama et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 296 days.

Signed and Sealed this
Thirtieth Day of September, 2025

John A. Squires
*Director of the United States Patent and Trademark Office*